United States Patent
Brown

(10) Patent No.: US 10,150,755 B2
(45) Date of Patent: Dec. 11, 2018

(54) ASK1 INHIBITOR COMPOUNDS AND USES THEREOF

(71) Applicant: Seal Rock Therapeutics, Inc., Seattle, WA (US)

(72) Inventor: Samuel David Brown, Seattle, WA (US)

(73) Assignee: SEAL ROCK THERAPEUTICS, INC., Seattle, WA (US)

( * ) Notice: Subject to any disclaimer, the term of this patent is extended or adjusted under 35 U.S.C. 154(b) by 0 days.

(21) Appl. No.: 15/970,587

(22) Filed: May 3, 2018

(65) Prior Publication Data

US 2018/0291002 A1    Oct. 11, 2018

Related U.S. Application Data

(63) Continuation of application No. PCT/US2018/026134, filed on Apr. 4, 2018.

(60) Provisional application No. 62/482,085, filed on Apr. 5, 2017.

(51) Int. Cl.

| | | |
|---|---|---|
| C07D 401/14 | (2006.01) |
| C07D 417/14 | (2006.01) |
| C07D 487/04 | (2006.01) |
| C07D 498/08 | (2006.01) |
| A61K 31/444 | (2006.01) |
| A61P 1/16 | (2006.01) |

(52) U.S. Cl.
CPC .............. *C07D 401/14* (2013.01); *A61P 1/16* (2018.01); *C07D 417/14* (2013.01); *C07D 487/04* (2013.01); *C07D 498/08* (2013.01)

(58) Field of Classification Search
CPC ........................... C07D 401/14; C07D 417/14
See application file for complete search history.

(56) References Cited

U.S. PATENT DOCUMENTS

| | | |
|---|---|---|
| 2011/0009410 A1 | 1/2011 | Corkey et al. |
| 2013/0150408 A1 | 6/2013 | Liu et al. |
| 2014/0038957 A1 | 2/2014 | Witty et al. |
| 2014/0329850 A1 | 11/2014 | Chang et al. |
| 2016/0067251 A1 | 3/2016 | Witty et al. |

FOREIGN PATENT DOCUMENTS

| | | |
|---|---|---|
| WO | WO-2016049069 A1 | 3/2016 |
| WO | WO-2018133865 A1 | 7/2018 |
| WO | WO-2018133866 A1 | 7/2018 |
| WO | WO-2018148204 A1 | 8/2018 |
| WO | WO-2018149284 A1 | 8/2018 |
| WO | WO-2018151830 | 8/2018 |
| WO | WO-2018157277 A1 | 9/2018 |
| WO | WO-2018157856 | 9/2018 |
| WO | WO-2018157857 | 9/2018 |
| WO | WO-2018160406 A1 | 9/2018 |
| WO | WO-2018183122 A1 | 10/2018 |

OTHER PUBLICATIONS

Ratziu et al. Journal of Hepatology 2015 vol. 62 pp. S65-S75. (Year: 2015).*
Loomba et al. Hepatology, vol. 67, No. 2, 2018 pp. 549-559. (Year: 2018).*
Gibson et al. Structure-based drug design of novel ASK1 inhibitors using an integrated lead optimization strategy. Bioorg Med Chem Lett 27(8):1709-1713 (2017).
Lanier et al. Structure-Based Design of ASK1 Inhibitors as Potential Agents for Heart Failure. ACS Med Chem Lett 8(3):316-320 (2017).
PCT/US2018/26134 International Search Report and Written Opinion dated Jun. 1, 2018.
Banini et al. Current and future pharmacologic treatment of nonalcoholic steatohepatitis. Curr Opin Gastroenterol 33(3):134-141 (2017).
Gilead Presents Data on Multiple Investigational Regimens for the Treatment of Patients With Nonalcoholic Steatohepatitis (NASH)and Advanced Fibrosis at the International Liver Congress™ 2018 Press Release (4 pgs).
Rotman et al. Current and upcoming pharmacotherapy for nonalcoholic fatty liver disease. Gut 66(1):180-190 (2017).

* cited by examiner

*Primary Examiner* — Emily A Bernhardt
(74) *Attorney, Agent, or Firm* — Wilson Sonsini Goodrich & Rosati

(57) ABSTRACT

Described herein are compounds, including pharmaceutically acceptable salts, solvates, metabolites, prodrugs thereof, methods of making such compounds, pharmaceutical compositions comprising such compounds, and methods of using such compounds to treat non-alcoholic steatohepatitis and other diseases characterized by dysfunctional tissue healing and fibrosis.

16 Claims, 1 Drawing Sheet

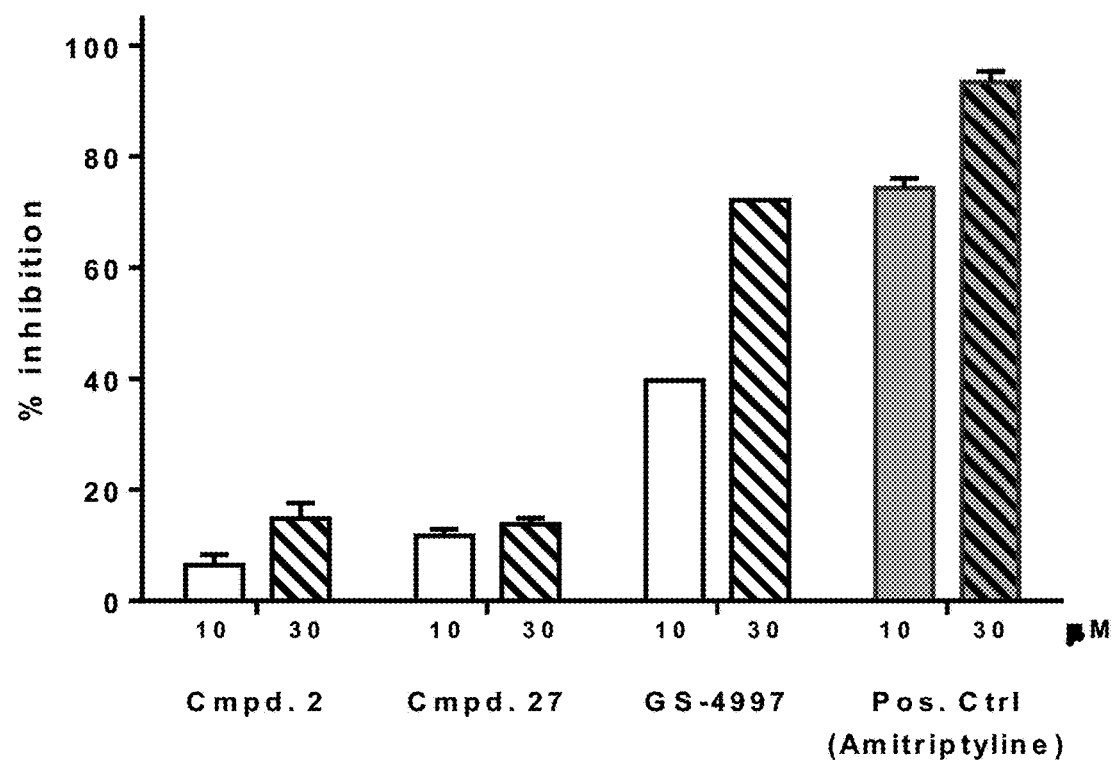

ASK1 INHIBITOR COMPOUNDS AND USES THEREOF

CROSS-REFERENCE

This application is a continuation of International Application No. PCT/US18/26134, filed Apr. 4, 2018, which claims benefit of U.S. Provisional Application No. 62/482,085, filed on Apr. 5, 2017, which is herein incorporated by reference in its entirety.

BACKGROUND OF THE INVENTION

Non-alcoholic steatohepatitis (NASH) is an extreme form of non-alcoholic fatty liver disease (NAFLD), a condition resembling alcohol-induced liver injury associated with obesity and metabolic syndrome rather than alcohol abuse. In NAFLD, triglycerides accumulate within hepatocytes due to alterations in lipid synthesis, storage, movement, or clearance processes causing steatosis. While steatosis typically has no large risk implications on its own, in a subset of NAFLD patients the steatosis progresses to include inflammation (hepatitis), necrosis and fibrosis, a condition known as NASH. These NASH patients have highly elevated risks of both hepatocellular carcinoma (HCC, as high as 7.6% total risk in one study) and cirrhosis (as high as 25% total risk), ultimately leading to liver failure or death.

Current population-based studies indicate that at least 25% of the US population has NAFLD and about 25% of NAFLD patients will go on to develop NASH, making these conditions a significant epidemiologic contributor to organ failure and cancer. As these conditions are associated with obesity and metabolic disease, their prevalence is likely to increase in the future.

SUMMARY OF THE INVENTION

In one aspect, described herein are compounds, or pharmaceutically acceptable salts or solvates thereof that inhibit ASK1.

In one aspect, presented herein are compounds of the structure of Formula I, or a pharmaceutically acceptable salt or solvate thereof:

Formula I wherein

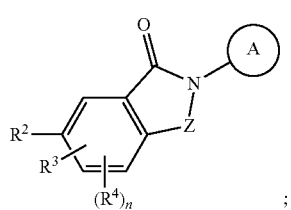

, or

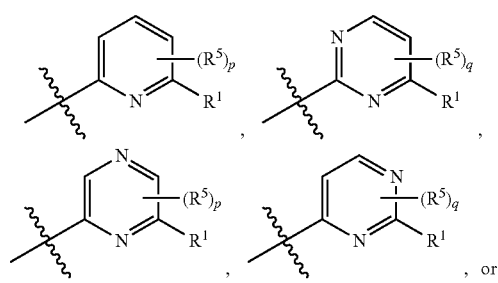

is

Ⓐ

Z is O, S, C(=O), N($R^8$), or C($R^9$)$_2$;

$R^1$ and $R^3$ are each independently selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$ alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;

$R^2$ is selected from a group consisting of hydrogen, halogen, —CN, —OH, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$alkenyl, C$_{2-6}$alkynyl, C$_{3-8}$ cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$; wherein $R^2$ and $R^3$ are not both hydrogen;

each $R^4$ and each $R^5$ are each independently selected from a group consisting of halogen, —CN, and C$_{1-6}$alkyl;

$R^{5a}$ is selected from the group consisting of hydrogen and C$_1$-C$_6$alkyl;

each $R^6$ is independently selected from the group consisting of hydrogen, C$_1$-C$_6$alkyl, —C$_1$-C$_6$alkyl-O—C$_1$-C$_6$alkyl, —C$_1$-C$_6$alkyl-C$_{2-9}$heterocycle, —C$_1$-C$_6$alkyl-C$_{2-9}$heteroaryl, C$_3$-C$_8$cycloalkyl, and C$_{2-9}$heterocycle; or two $R^6$ on the same heteroatom are taken together with that heteroatom to which they are attached to form a C$_{2-9}$heterocycle or a C$_{2-9}$heteroaryl;

each $R^7$ is independently selected from the group consisting of $C_1$-$C_6$alkyl and $C_3$-$C_8$cycloalkyl;

$R^8$ is selected from the group consisting of hydrogen and $C_1$-$C_6$alkyl;

each $R^9$ is independently selected from the group consisting of hydrogen, halogen, and $C_1$-$C_6$alkyl;

each $R^{13}$ is independently selected from the group consisting of hydrogen, $C_1$-$C_6$alkyl, and $C_3$-$C_8$cycloalkyl; or two $R^{13}$ on the same heteroatom are taken together with that heteroatom to which they are attached to form a $C_{2-9}$heterocycle;

each $R^{14}$ is independently selected from the group consisting of $C_1$-$C_6$alkyl and $C_3$-$C_8$cycloalkyl;

n is 0, 1, or 2;

p is 0, 1, 2, or 3; and q is 0, 1, or 2.

In some embodiments, $R^2$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{2-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$ heteroaryl, —C(=O)$R^{14}$, —C(=O)$OR^{13}$, —C(=O)N($R^{13}$)$_2$, —S(=O)$R^{14}$, —S(=O)$_2R^{13}$, S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^2$ is selected from a group consisting of $C_{2-9}$heterocycle and $C_{1-9}$ heteroaryl; wherein $C_{2-9}$heterocycle and $C_{1-9}$heteroaryl are optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)$OR^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^2$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)$OR^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^2$ is selected from a group consisting of pyrazole, imidazole, thiazole, and pyridine; wherein pyrazole, imidazole, thiazole, and pyridine are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)$OR^{13}$, —C(=O)N($R^{13}$)$_2$, —S(=O)$R^{14}$, —S(=O)$_2R^{13}$, —S(=O)$_2$ —N($R^{13}$)$_2$, —N($R^{13}$)C(=O)$R^{14}$, and —N($R^{13}$)S(=O)$_2R^{13}$.

In some embodiments, $R^2$ is selected from a group consisting of pyrazole, imidazole, thiazole, and pyridine; wherein pyrazole, imidazole, thiazole, and pyridine are optionally substituted with one or two substituents selected from the group consisting of halo, $C_{1-6}$alkyl, and $C_{3-8}$cycloalkyl. In some embodiments, $R^2$ is wherein $R^{11}$ is $C_1$-$C_6$alkyl or $C_3$-$C_6$cycloalkyl.

In some embodiments, $R^2$ is wherein $R^{12}$ is halo, $C_1$-$C_6$alkyl, or $C_3$-$C_6$cycloalkyl; and m is 1 or 2.

In some embodiments, $R^2$ is selected from a group consisting of unsubstituted pyrazole, unsubstituted imidazole, unsubstituted thiazole, and unsubstituted pyridine.

In some embodiments, $R^2$ is —C(=O)N($R^6$)$_2$ and each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, $R^2$ is

-continued

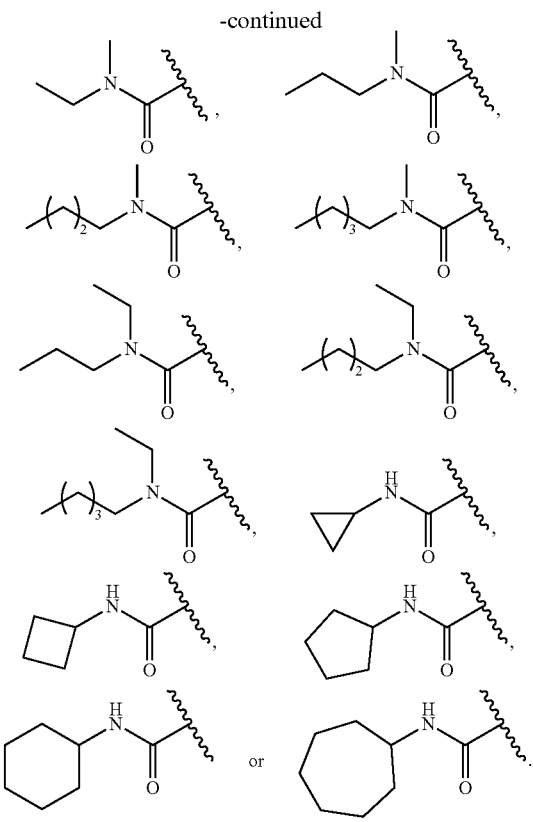

In some embodiments, $R^2$ is

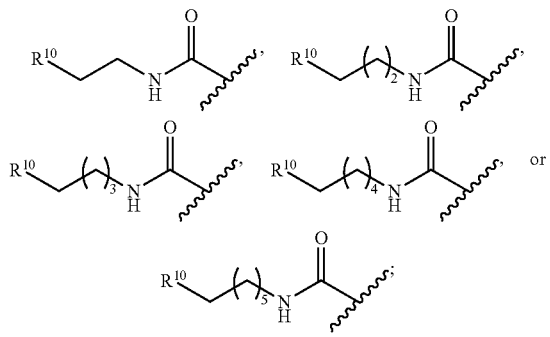

wherein $R^{10}$ is a heteroaryl.

In some embodiments, $R^3$ is hydrogen. In some embodiments, $R^3$ is $C_1$-$C_6$alkyl.

In some embodiments, $R^3$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{2-9}$heteroaryl-cycloalkyl, wherein $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$ heteroaryl, —C(=O)$R^{14}$, —C(=O)O$R^{13}$, —C(=O)N$(R^{13})_2$, —S(=O)$R^{14}$, —S(=O)$_2R^{13}$, S(=O)$_2$—N$(R^{13})_2$, —N$(R^{13})_2$, —N$(R^{13})$C(=O)$R^{14}$, and —N$(R^{13})$S(=O)$_2R^{13}$.

In some embodiments, $R^3$ is selected from a group consisting of $C_{2-9}$heterocycle and $C_{1-9}$ heteroaryl; wherein $C_{2-9}$heterocycle and $C_{1-9}$heteroaryl are optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N$(R^{13})_2$, —S(=O)$R^{14}$, —S(=O)$_2R^{13}$, —S(=O)$_2$—N$(R^{13})_2$, —N$(R^{13})_2$, —N$(R^{13})$C(=O)$R^{14}$, and —N$(R^{13})$S(=O)$_2R^{13}$.

In some embodiments, $R^3$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N$(R^{13})_2$, —S(=O)$R^{14}$, —S(=O)$_2R^{13}$, —S(=O)$_2$—N$(R^{13})_2$, —N$(R^{13})_2$, —N$(R^{13})$C(=O)$R^{14}$, and —N$(R^{13})$S(=O)$_2R^{13}$.

In some embodiments, $R^3$ is selected from a group consisting of pyrazole, imidazole, thiazole, and pyridine; wherein pyrazole, imidazole, thiazole, and pyridine are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N$(R^{13})_2$, —S(=O)$R^{14}$, —S(=O)$_2R^{13}$, —S(=O)$_2$ —N$(R^{13})_2$, —N$(R^{13})_2$, —N$(R^{13})$C(=O)$R^{14}$, and —N$(R^{13})$S(=O)$_2R^{13}$.

In some embodiments, $R^3$ is selected from a group consisting of pyrazole, imidazole, thiazole, and pyridine; wherein pyrazole, imidazole, thiazole, and pyridine are optionally substituted with one or two substituents selected from the group consisting of halo, $C_{1-6}$alkyl, and $C_{3-8}$cycloalkyl.

In some embodiments, $R^3$ is

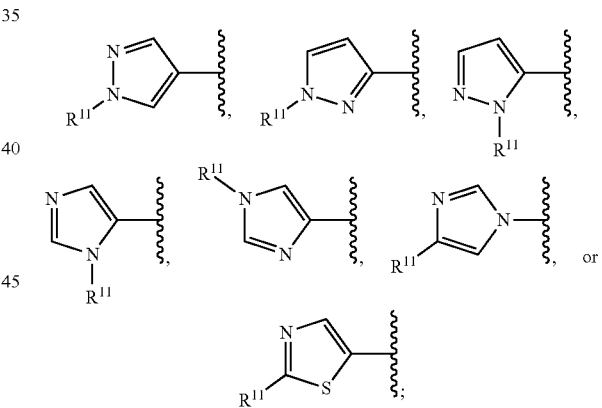

wherein $R^{11}$ is $C_1$-$C_6$alkyl or $C_3$-$C_6$cycloalkyl.

In some embodiments, $R^3$ is

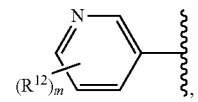

wherein each $R^{12}$ is independently halo, $C_1$-$C_6$alkyl, or $C_3$-$C_6$cycloalkyl; and m is 1 or 2.

In some embodiments, $R^3$ is selected from a group consisting of unsubstituted pyrazole, unsubstituted imidazole, unsubstituted thiazole, and unsubstituted pyridine.

In some embodiments, $R^3$ is —C(=O)N$(R^6)_2$ and each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, $R^3$ is

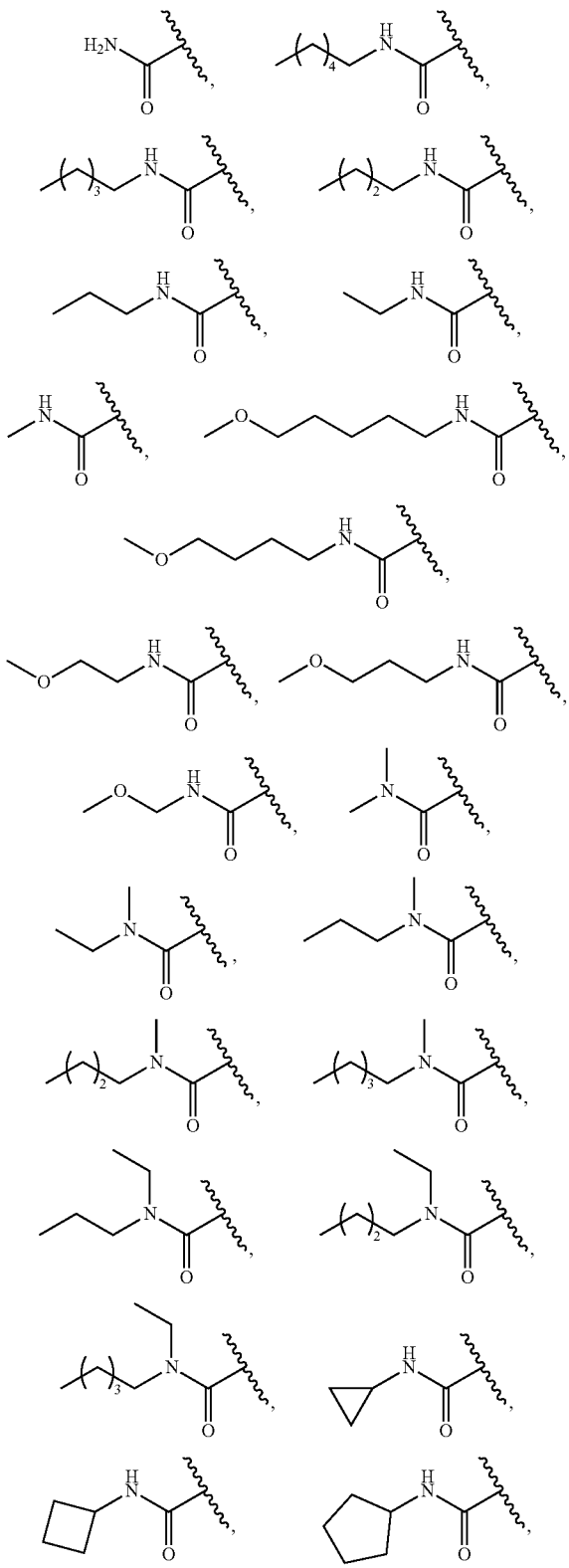

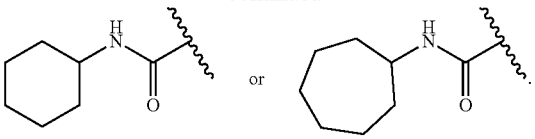

In some embodiments, $R^3$ is

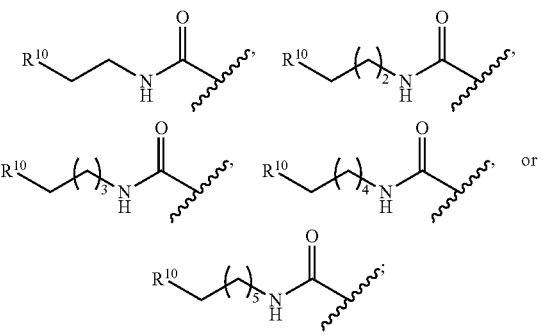

wherein $R^{10}$ is a heteroaryl.

In some embodiments, $R^3$ is —$OR^6$ and $R^6$ is selected from the group consisting of $C_1$-$C_6$alkyl, —$C_1$-$C_6$alkyl-O—$C_1$-$C_6$alkyl, and —$C_1$-$C_6$alkyl-$C_{2-9}$heterocycle. In some embodiments, $R^2$ is hydrogen. In some embodiments, $R^2$ is $C_1$-$C_6$alkyl.

In some embodiments, $R^1$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.

In some embodiments, $R^1$ is selected from a group consisting of a $C_{1-9}$heteroaryl and a fused $C_{5-9}$heteroaryl-cycloalkyl; wherein the $C_{1-9}$heteroaryl and fused $C_{2-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.

In some embodiments, $R^1$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.

In some embodiments, $R^1$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N$(R^{13})_2$, —S(=O)$R^{14}$, —S(=O)$_2R^{13}$, —S(=O)$_2$—N$(R^{13})_2$, —N$(R^{13})_2$, —N$(R^{13})$C(=O)$R^{14}$, and —N$(R^{13})$S(=O)$_2R^{13}$.

In some embodiments, $R^1$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halo, $C_{1-6}$alkyl, and $C_{3-8}$cycloalkyl.

In some embodiments, $R^1$ is

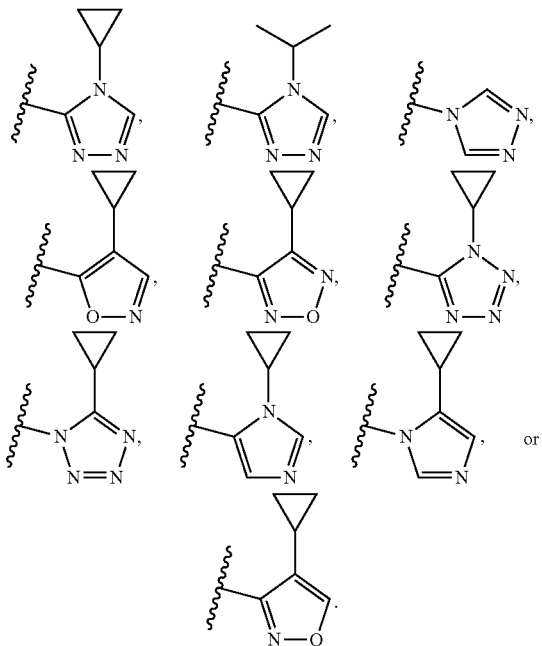

In some embodiments, $R^1$ is

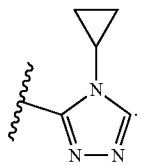

In some embodiments, $R^1$ is

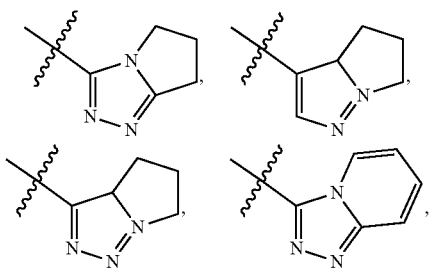

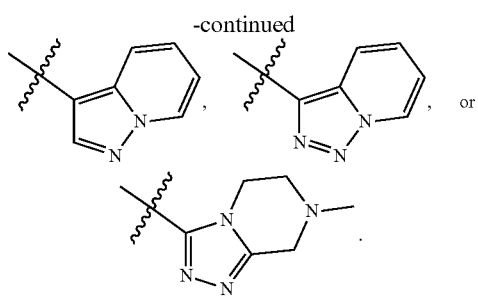

In another aspect described herein are compounds of Formula II, or a pharmaceutically acceptable salt or solvate thereof:

Formula II

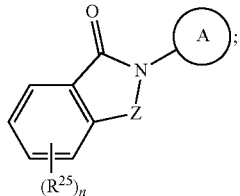

wherein

A is

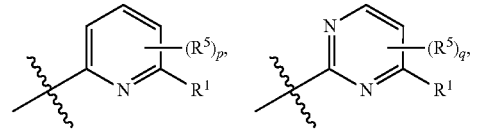

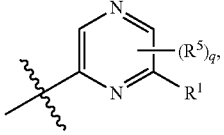

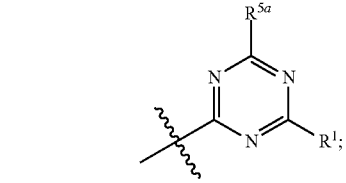

$R^1$ is

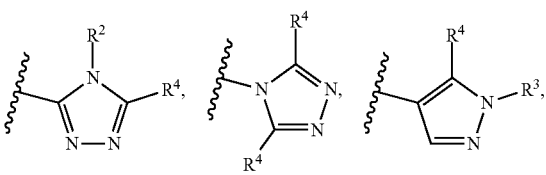

-continued

Z is O, S, C(=O), N($R^8$), or C($R^9$)$_2$;
X is O or S;
$R^2$ is $C_{3-6}$cycloalkyl;
$R^3$ is selected from a group consisting of hydrogen, $C_{1-6}$alkyl, and $C_{3-6}$cycloalkyl; each $R^4$ is independently selected from a group consisting of hydrogen, halo, $C_{1-6}$alkyl, and $C_{3-6}$ cycloalkyl;
or one $R^4$ and another $R^2$, $R^3$, or $R^4$, together with the atoms to which they are attached, form a 5- or 6-membered ring that is optionally containing one or two heteroatoms selected from O, N, and S; wherein the 5- or 6-membered ring is saturated, unsaturated, or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$ $R^{13}$;
each $R^5$ is independently selected from a group consisting of halogen and $C_{1-6}$alkyl;
$R^{5a}$ is selected from the group consisting of hydrogen and $C_1$-$C_6$alkyl;
$R^{25}$ is selected from a group consisting of halogen, —CN, —OH, —O$R^6$, —S$R^6$, —S(=O)$R^7$, —NO$_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —N$R^6$C(=O)N($R^6$)$_2$, —N$R^6$C(=O)$R^7$, —N$R^6$C(=O)O$R^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl;
each $R^7$ is independently selected from the group consisting of $C_1$-$C_6$alkyl and $C_3$-$C_8$cycloalkyl;
$R^8$ is selected from the group consisting of hydrogen and $C_1$-$C_6$alkyl;
each $R^9$ is independently selected from the group consisting of hydrogen, halogen, and $C_1$-$C_6$alkyl;
each $R^{13}$ is independently selected from the group consisting of hydrogen, $C_1$-$C_6$alkyl, and $C_3$-$C_8$cycloalkyl; or two $R^{13}$ on the same heteroatom are taken together with that heteroatom to which they are attached to form a $C_{2-9}$heterocycle;
each $R^{14}$ is independently selected from the group consisting of $C_1$-$C_6$alkyl and $C_3$-$C_8$cycloalkyl;
n is 0, 1, 2, 3, or 4;
p is 0, 1, 2, or 3; and
q is 0, 1, or 2.

In another aspect described herein are compounds of Formula III, or a pharmaceutically acceptable salt or solvate thereof:

Formula III wherein (A) is $R^1$ is

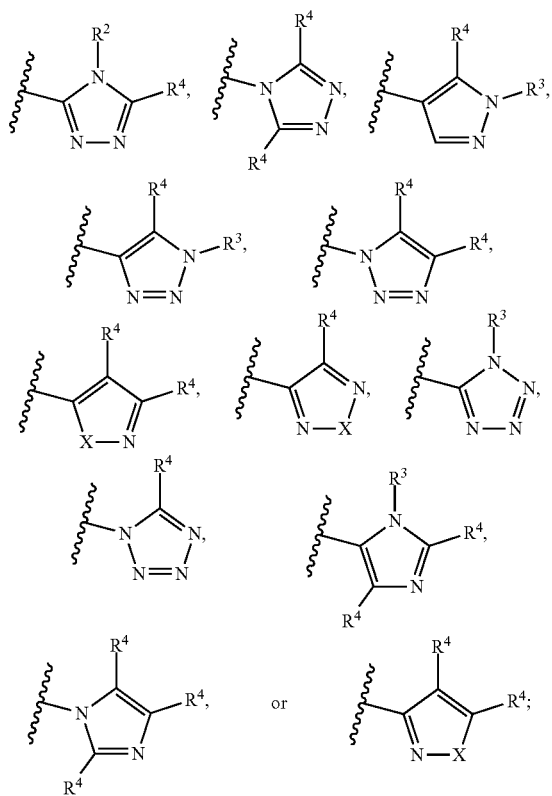

Z is O, S, C(=O), N($R^8$), or C($R^9$)$_2$;
X is O or S;
$R^2$ is $C_{3-6}$cycloalkyl;
$R^3$ is selected from a group consisting of hydrogen, $C_{1-6}$alkyl, and $C_{3-6}$cycloalkyl;
each $R^4$ is independently selected from a group consisting of hydrogen, halo, $C_{1-6}$alkyl, and $C_{3-6}$cycloalkyl;
or one $R^4$ and another $R^2$, $R^3$, Or $R^4$, together with the atoms to which they are attached, form a 5- or 6-membered ring that is optionally containing one or two heteroatoms selected from O, N, and S; wherein the 5- or 6-membered ring is saturated, unsaturated, or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$ $R^{13}$;
each $R^5$ is independently selected from a group consisting of halogen and $C_{1-6}$alkyl;
$R^{5a}$ is selected from the group consisting of hydrogen and $C_1$-$C_6$alkyl;
each $R^{25}$ is independently selected from a group consisting of halogen, —CN, —OH, —O$R^6$, —S$R^6$, —S(=O)$R^7$, —NO$_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —N$R^6$C(=O)N($R^6$)$_2$, —N$R^6$C(=O)$R^7$, —N$R^6$C(=O)O$R^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$ $R^{13}$;
each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, —$C_3$-$C_8$cycloalkyl-phenyl, and $C_{2-9}$heterocycle, wherein $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, —$C_3$-$C_8$cycloalkyl-phenyl, and $C_{2-9}$heterocycle are optionally substituted with one, two, or three substituents selected from the group consisting of halo, —O$R^8$, —S$R^8$, —N($R^{13}$)$_2$, —$C_{1-6}$alkyl, —O—$C_{1-6}$alkyl, —C(=O)$R^{14}$, —C(=O)O$R^{13}$, and —N($R^{13}$)C(=O)$R^{14}$; or two $R^6$ on the same heteroatom are taken together with that heteroatom to which they are attached to form a $C_{2-9}$heterocycle or a $C_{2-9}$heteroaryl, wherein $C_{2-9}$heterocycle or $C_{2-9}$heteroaryl are optionally substituted with one, two, or three substituents selected from the group consisting of halo, —O$R^8$, —S$R^8$, —N($R^8$)$_2$, —$C_{1-6}$alkyl, —O—$C_{1-6}$alkyl, —C(=O)$R^{14}$, —C(=O)O$R^{13}$, and —N($R^{13}$)C(=O)$R^{14}$;
each $R^7$ is independently selected from the group consisting of $C_1$-$C_6$alkyl, $C_3$-$C_8$cycloalkyl, and $C_{2-9}$heterocycle, wherein $C_3$-$C_8$cycloalkyl and $C_{2-9}$heterocycle are optionally substituted with one, two, or three substituents selected from the group consisting of halo, oxo, —O$R^8$, —S$R^8$, —N($R^8$)$_2$, —$C_{1-6}$alkyl, —O—$C_{1-6}$alkyl, —C(=O)$R^{14}$, —C(=O)O$R^{13}$, and —N($R^{13}$)C(=O)$R^{14}$;
each $R^8$ is independently selected from the group consisting of hydrogen and $C_1$-$C_6$alkyl;
each $R^9$ is independently selected from the group consisting of hydrogen, halogen, and $C_1$-$C_6$alkyl;
each $R^{13}$ is independently selected from the group consisting of hydrogen, $C_1$-$C_6$alkyl, and $C_3$-$C_8$cycloalkyl; or two $R^{13}$ on the same heteroatom are taken together with that heteroatom to which they are attached to form a $C_{2-9}$heterocycle;
each $R^{14}$ is independently selected from the group consisting of $C_1$-$C_6$alkyl and $C_3$-$C_8$cycloalkyl;
n is 0, 1, 2, 3, or 4;
p is 0, 1, 2, or 3; and
q is 0, 1, or 2.

In some embodiments, $R^{25}$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{5-9}$heteroaryl-cycloalkyl, wherein $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$ heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^{25}$ is selected from a group consisting of $C_{2-9}$heterocycle and $C_{1-9}$ heteroaryl; wherein $C_{2-9}$heterocycle and $C_{1-9}$heteroaryl are optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^{25}$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^{25}$ is selected from a group consisting of pyrazole, imidazole, thiazole, and pyridine; wherein pyrazole, imidazole, thiazole, and pyridine are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$ —N($R^{13}$)$_2$, —N($R^{13}$)$_2$, —N($R^{13}$)C(=O)$R^{14}$, and —N($R^{13}$)S(=O)$_2R^{13}$.

In some embodiments, $R^{25}$ is selected from a group consisting of pyrazole, imidazole, thiazole, and pyridine; wherein pyrazole, imidazole, thiazole, and pyridine are optionally substituted with one or two substituents selected from the group consisting of halo, $C_{1-6}$alkyl, and $C_{3-8}$cycloalkyl.

In some embodiments, $R^{25}$ is

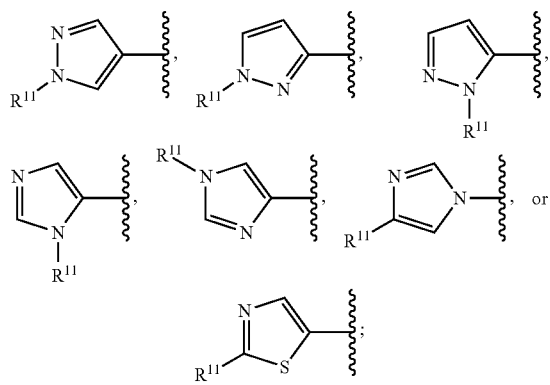

wherein each $R^{11}$ is independently $C_1$-$C_6$alkyl or $C_3$-$C_6$cycloalkyl.

In some embodiments, $R^{25}$ is

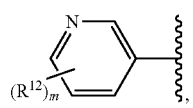

wherein each $R^{12}$ is independently hydrogen, halo, $C_1$-$C_6$alkyl, or $C_3$-$C_6$cycloalkyl; and m is 1 or 2.

In some embodiments, $R^{25}$ is selected from a group consisting of unsubstituted pyrazole, unsubstituted imidazole, unsubstituted thiazole, and unsubstituted pyridine.

In some embodiments, $R^{25}$ is selected from a group consisting of pyrimidine, pyrazine, and pyridazine; wherein pyrimidine, pyrazine, and pyridazine are optionally substituted with one or two substituents selected from the group consisting of halo, $C_{1-6}$alkyl, and $C_{3-8}$cycloalkyl.

In some embodiments, $R^{25}$ is selected from a group consisting of halogen, —OR$^6$, —N(R$^6$)$_2$, $C_{1-6}$alkyl, pyrazole, imidazole, thiazole, and pyridine; wherein pyrazole, imidazole, thiazole, and pyridine are optionally substituted with one or two substituents selected from the group consisting of halo, $C_{1-6}$alkyl, and $C_{3-8}$cycloalkyl.

In some embodiments, $R^{25}$ is selected from a group consisting of halogen, —OR$^6$, —N(R$^6$)$_2$, $C_{1-6}$alkyl, and unsubstituted pyridine.

In some embodiments, $R^{25}$ is —C(=O)N(R$^6$)$_2$ and each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, $R^{25}$ is

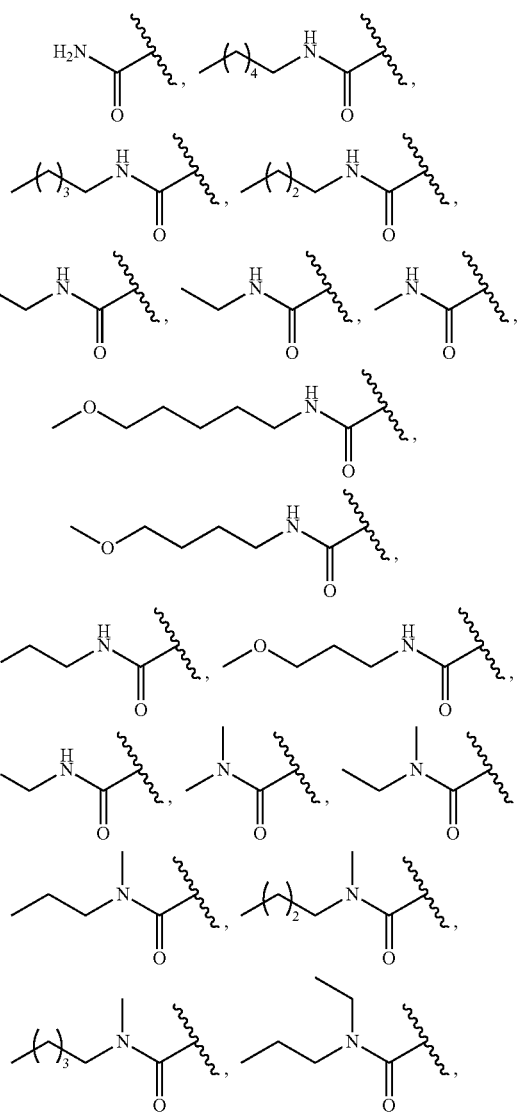

-continued

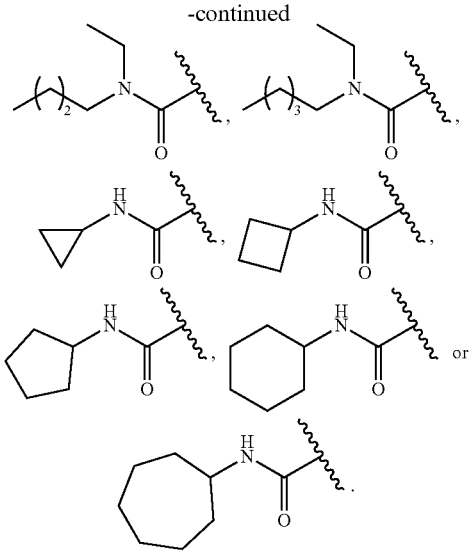

In some embodiments, $R^{25}$ is

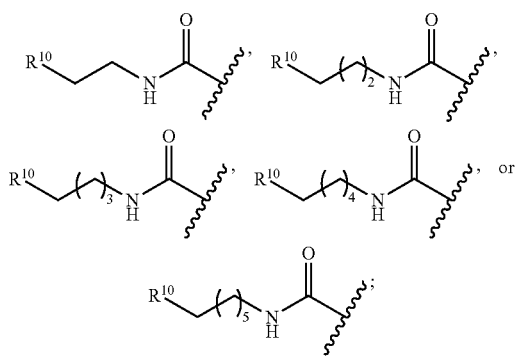

wherein $R^{10}$ is a heteroaryl.

In some embodiments, $R^{25}$ is —C(=O)N($R^6$)$_2$ and two $R^6$ on the same heteroatom are taken together with that heteroatom to which they are attached to form a $C_{2-9}$heterocycle or a $C_{2-9}$heteroaryl, wherein $C_{2-9}$heterocycle or $C_{2-9}$heteroaryl are optionally substituted with one, two, or three substituents selected from the group consisting of halo, —$OR^8$, —$SR^8$, —N($R^8$)$_2$, —$C_{1-6}$alkyl, —O—$C_{1-6}$alkyl, —C(=O)$R^{14}$, —C(=O)$OR^{13}$, and —N$R^{13}$C(=O)$R^{14}$.

In some embodiments, $R^{25}$ is

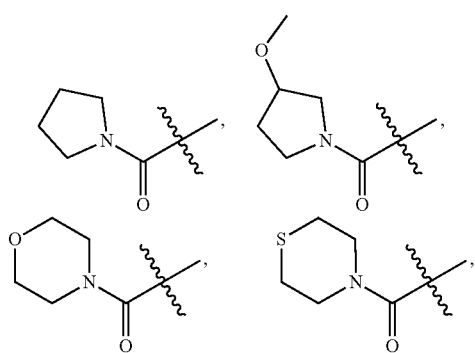

-continued

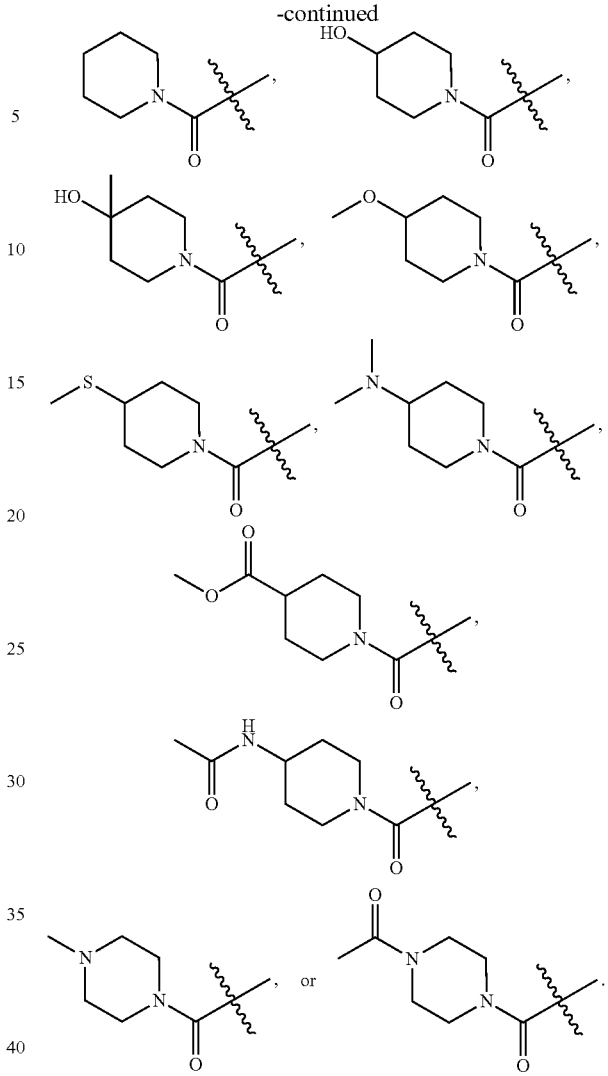

In some embodiments, $R^{25}$ is —C(=O)N($R^6$)$_2$ and two $R^6$ on the same heteroatom are taken together with that heteroatom to which they are attached to form a $C_{2-9}$heterocycle or a $C_{2-9}$heteroaryl.

In some embodiments, $R^{25}$ is —C(=O)N($R^6$)$_2$ and two $R^6$ are taken together with that heteroatom to which they are attached to form a $C_{2-9}$heterocycle or a $C_{2-9}$heteroaryl.

In some embodiments, $R^{25}$ is

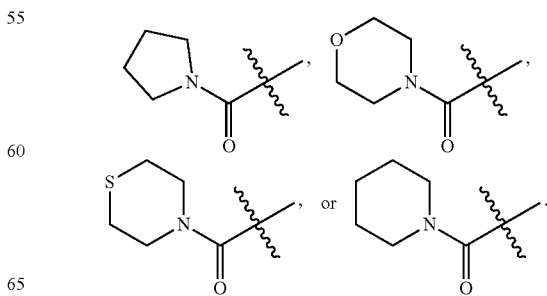

In some embodiments, $R^{25}$ is —$OR^6$ and $R^6$ is selected from the group consisting of $C_1$-$C_6$alkyl, —$C_1$-$C_6$alkyl-O—$C_1$-$C_6$alkyl, and —$C_1$-$C_6$alkyl-$C_{2-9}$heterocycle.
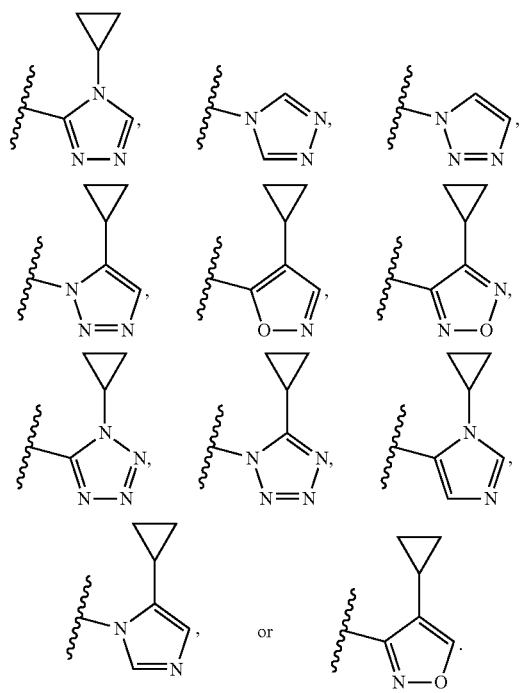
In some embodiments, $R^1$ is
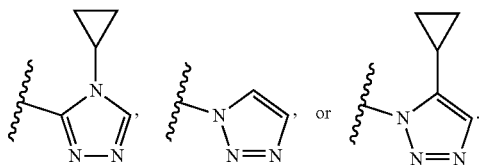
In some embodiments, $R^1$ is
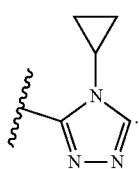
In some embodiments, $R^1$ is
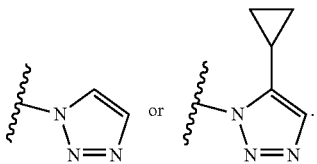 [SMILES: *n1ccnn1 ; *n1nncc1C1CC1]
In some embodiments, $R^1$ is
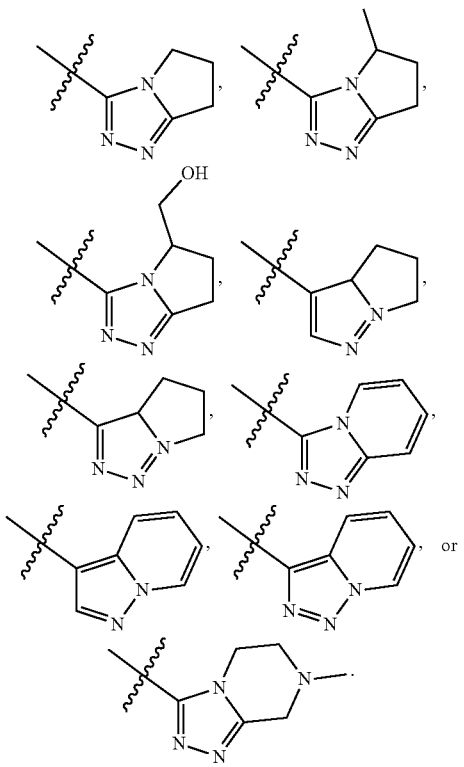
In some embodiments,
is
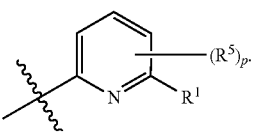
In some embodiments, p is 0.
In some embodiments,
is
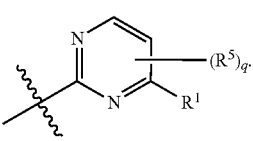

In some embodiments, 

is

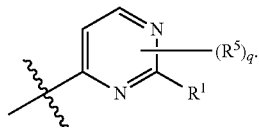

In some embodiments, q is 0.

In some embodiments, n is 0. In some embodiments, n is 1. In some embodiments, n is 2. In some embodiments, Z is $C(R^9)_2$. In some embodiments, $R^9$ is H.

In a further aspect described herein are pharmaceutical compositions comprising a compound of Formula I, Formula II, or Formula III, or a pharmaceutically acceptable salt or solvate thereof, and at least one pharmaceutically acceptable excipient.

In another aspect described herein are methods of treating non-alcoholic steatohepatitis in a subject in need thereof, comprising administering to the subject a therapeutically effective amount of a compound of Formula I, Formula II, or Formula III, or a pharmaceutically acceptable salt or solvate thereof. In another aspect described herein are methods of treating non-alcoholic steatohepatitis in a subject in need thereof, comprising administering to the subject a therapeutically effective amount of a pharmaceutical composition comprising a compound of Formula I, Formula II, or Formula III, or a pharmaceutically acceptable salt or solvate thereof, and at least one pharmaceutically acceptable excipient.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing of which:

FIG. 1 shows a graph comparing the inhibition of the hERG potassium channel between compound 2 and compound 27 described herein (cmpd. 2 and cmpd. 27, respectively), ASK1 inhibitor GS-4997, and positive control Amitriptyline.

DETAILED DESCRIPTION OF THE INVENTION

ASK1 is a membrane-proximal MAP3K (MAP-kinase-kinase-kinase) upstream of pathways which play important roles in the cellular response to environmental stresses (e.g. the c-Jun and p38 pathways, which are known to be responsive to UV and oxidative damage), is a promising therapeutic target for NASH. A positive regulator of mitochondrial apoptosis, ASK1 is tightly regulated and activated by cellular damage signals as diverse as receptor-acting inflammatory cytokines (e.g. TNFa and LPS), calcium and intracellular r sensors (e.g. the redox sensor thioredoxin, and the ER-stress-responsive IRE1).

Consistent with this role as an effector of stress signals, ASK1 has been shown as an important mediator of pathological stress-induced hepatic tissue remodeling. In a mouse model of non-alcoholic liver injury, ASK1 null mice show resistance to diet-induced steatohepatitis and subsequent fibrosis. Human data is consistent with this role in directing responses to diet-induced liver damage; ASK1 inhibitors (e.g. the small molecule selonsertib/GS-4997 in clinical trial NCT02466516) have recently shown utility in phase II trials against non-alcoholic steatohepatitis (NASH) in affected patients, and NASH patients show upregulation of ASK1 activity in separate molecular analyses.

In addition to its apparent role in NASH, recent studies have produced evidence that ASK1 may be critical in diseases of stress-induced tissue remodeling generally. Cardiac-targeted deletion of ASK1 improves resistance to ischemia-, angiotensin II-, and pressure-induced pathologic tissue remodeling. Further, the ubiquitous expression of the molecule combined with its central place upstream in stress-induced signaling cascades suggests inhibitors of this molecule may be broadly useful for counteracting diseases of dysfunctional tissue healing and fibrosis.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl moiety may be branched or straight chain. The "alkyl" group may have 1 to 15 carbon atoms (whenever it appears herein, a numerical range such as "1 to 15" refers to each integer in the given range; e.g., "1 to 15 carbon atoms" means that the alkyl group may consist of 1 carbon atom, 2 carbon atoms, 3 carbon atoms, etc., up to and including 15 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, and the like.

The term "alkenyl" refers to a type of alkyl group in which at least one carbon-carbon double bond is present. In one embodiment, an alkenyl group has the formula —C(R)

=CR$_2$, wherein R refers to the remaining portions of the alkenyl group, which may be the same or different. In some embodiments, R is H or an alkyl. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkynyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a C$_3$-C$_6$cycloalkyl.

The term "aromatic" refers to a planar ring having a delocalized π-electron system containing 4π+2π electrons, where n is an integer. Aromatics are optionally substituted. The term "aromatic" includes both cycloalkyl aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "aryl" refers to an aromatic ring wherein each of the atoms forming the ring is a carbon atom. Aryl groups are optionally substituted. Depending on the structure, an aryl group can be a monoradical or a diradical (i.e., an arylene group).

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

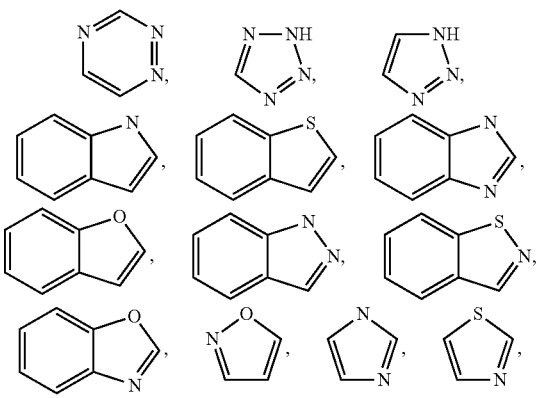

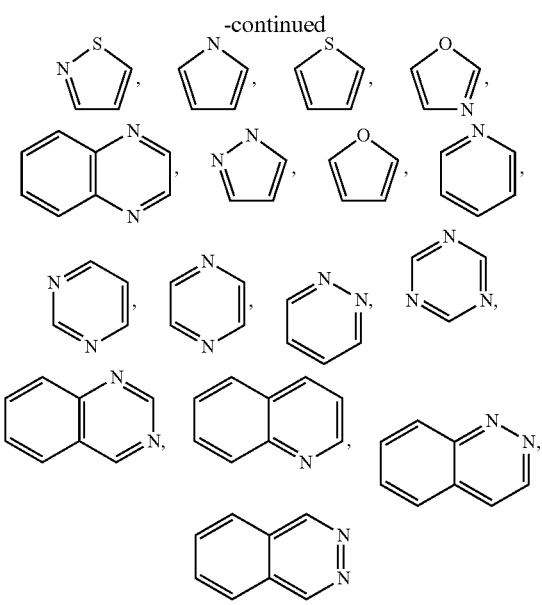

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a C$_1$-C$_9$heteroaryl. In some embodiments, monocyclic heteroaryl is a C$_1$-C$_5$heteroaryl. In some embodiments, monocyclic heteroaryl is a 5-membered or 6-membered heteroaryl. In some embodiments, bicyclic heteroaryl is a C$_6$-C$_9$heteroaryl. Depending on the structure, a heteroaryl group can be a monoradical or a diradical (i.e., a heteroarylene group).

A "heterocycle" or "heterocycloalkyl" group refers to a cycloalkyl group wherein at least one of the carbon atoms of the cycloalkyl is replaced with nitrogen (unsubstituted or substituted, e.g. —NH—, —N(alkyl)-), oxygen (—O—), or sulfur (e.g. —S—, —S(=O)— or —S(=O)$_2$—). The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a C$_2$-C$_{10}$heterocycloalkyl. In another aspect, a heterocycloalkyl is a C$_4$-C$_{10}$heterocycloalkyl. In some embodiments, a heterocycloalkyl contains 0-3 N atoms in the ring. In some embodiments, a heterocycloalkyl contains 0-3 N atoms, 0-3 O atoms and 0-1 S atoms in the ring.

The term "halo" or, alternatively, "halogen" or "halide" means fluoro (F), chloro (Cl), bromo (Br) or iodo (I). The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, halogen is F or C$_1$. In some embodiments, halogen is F.

The methods and formulations described herein include the use of N-oxides (if appropriate), crystalline forms (also known as polymorphs), or pharmaceutically acceptable salts of compounds having the structure of Formula I, Formula II, or Formula III, as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula I, Formula II, or Formula III, or a pharmaceutically acceptable salt thereof, and a co-agent, are both administered to a patient simultaneously in the form of a single entity or dosage. The term "non-fixed combination" means that the active ingredients, e.g. a compound of Formula I, Formula II, or Formula III, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Compounds

In one aspect, presented herein are compounds of the structure of Formula I, or a pharmaceutically acceptable salt or solvate thereof:

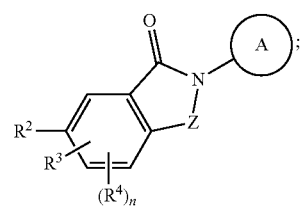

Formula I wherein

is

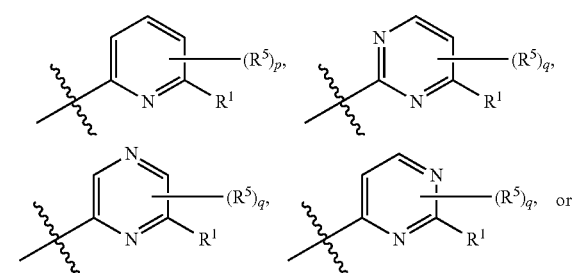

-continued

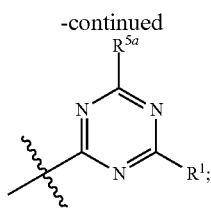

Z is O, S, C(=O), N(R$^8$), or C(R$^9$)$_2$;

R$^1$ and R$^3$ are each independently selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$ alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;

R$^2$ is selected from a group consisting of hydrogen, halogen, —CN, —OH, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$ cycloalkyl, C$_{2-9}$heterocycle, C$_{6-10}$aryl, C$_{1-9}$heteroaryl, and fused C$_{5-9}$heteroaryl-cycloalkyl; wherein C$_{1-6}$alkyl, C$_{2-6}$alkenyl, C$_{2-6}$alkynyl, C$_{3-8}$ cycloalkyl, C$_{2-9}$heterocycle, C$_{6-10}$aryl, C$_{1-9}$heteroaryl, and fused C$_{2-9}$heterocycle-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$; wherein R$^2$ and R$^3$ are not both hydrogen;

each R$^4$ and each R$^5$ are each independently selected from a group consisting of halogen, —CN, and C$_{1-6}$alkyl;

R$^{5a}$ is selected from the group consisting of hydrogen and C$_1$-C$_6$alkyl;

each R$^6$ is independently selected from the group consisting of hydrogen, C$_1$-C$_6$alkyl, —C$_1$-C$_6$alkyl-O—C$_1$-C$_6$alkyl, —C$_1$-C$_6$alkyl-C$_{2-9}$heterocycle, —C$_1$-C$_6$alkyl-C$_{2-9}$heteroaryl, C$_3$-C$_8$cycloalkyl, and C$_{2-9}$heterocycle; or two R$^6$ on the same heteroatom are taken together with that heteroatom to which they are attached to form a C$_{2-9}$heterocycle or a C$_{2-9}$heteroaryl;

each R$^7$ is independently selected from the group consisting of C$_1$-C$_6$alkyl and C$_3$-C$_8$cycloalkyl;

R$^8$ is selected from the group consisting of hydrogen and C$_1$-C$_6$alkyl;

each R$^9$ is independently selected from the group consisting of hydrogen, halogen, and C$_1$-C$_6$alkyl;

each R$^{13}$ is independently selected from the group consisting of hydrogen, C$_1$-C$_6$alkyl, and C$_3$-C$_8$cycloalkyl; or two R$^{13}$ on the same heteroatom are taken together with that heteroatom to which they are attached to form a C$_{2-9}$heterocycle;

each R$^{14}$ is independently selected from the group consisting of C$_1$-C$_6$alkyl and C$_3$-C$_8$cycloalkyl;

n is 0, 1, or 2;

p is 0, 1, 2, or 3; and q is 0, 1, or 2.

In some embodiments, R$^2$ is selected from a group consisting of C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{3-8}$cycloalkyl, C$_{2-9}$heterocycle, C$_{6-10}$aryl, C$_{1-9}$heteroaryl, and fused C$_{2-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$ heteroaryl, —C(=O)R$^{14}$, —C(=O)OR$^{13}$, —C(=O)N(R$^{13}$)$_2$, —S(=O)R$^{14}$, —S(=O)$_2$R$^{13}$, S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^2$ is selected from a group consisting of C$_{2-9}$heterocycle and C$_{1-9}$ heteroaryl; wherein C$_{2-9}$heterocycle and C$_{1-9}$heteroaryl are optionally substituted with one, two, or three substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^2$ is selected from a group consisting of C$_{2-9}$heterocycle and C$_{1-9}$ heteroaryl; wherein C$_{2-9}$heterocycle and C$_{1-9}$heteroaryl are optionally substituted with one or two substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^2$ is selected from a group consisting of pyrazole, imidazole, thiazole, and pyridine; wherein pyrazole, imidazole, thiazole, and pyridine are optionally substituted with one or two substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^2$ is selected from a group consisting of pyrazole, imidazole, thiazole, and pyridine; wherein pyrazole, imidazole, thiazole, and pyridine are optionally substituted with one or two substituents selected from the group consisting of halo, C$_{1-6}$alkyl, and C$_{3-8}$cycloalkyl.

In some embodiments, R$^2$ is

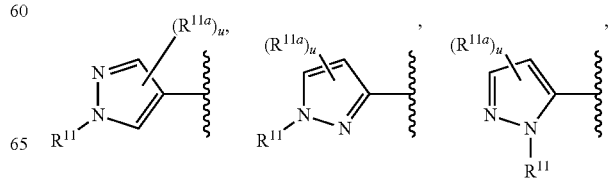

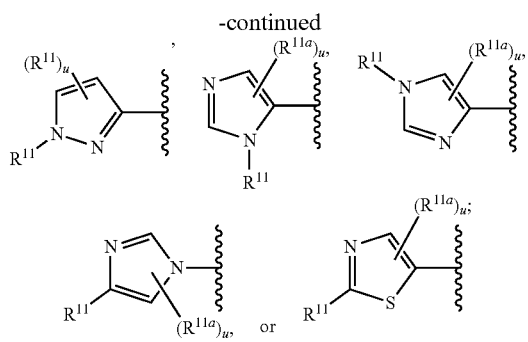
each $R^{11}$ is $C_1$-$C_6$alkyl or $C_3$-$C_6$cycloalkyl; $R^{11a}$ is —CN, —OH, $C_1$-$C_6$alkyl, or $C_3$-$C_6$cycloalkyl; and u is 0, 1 or 2.
In some embodiments, $R^2$ is
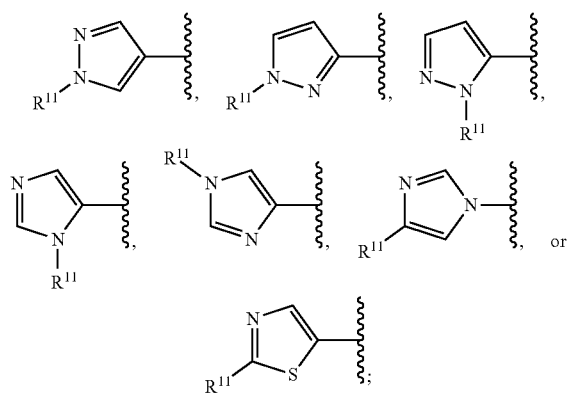
wherein $R^{11}$ is $C_1$-$C_6$alkyl or $C_3$-$C_6$cycloalkyl.
In some embodiments, $R^2$ is
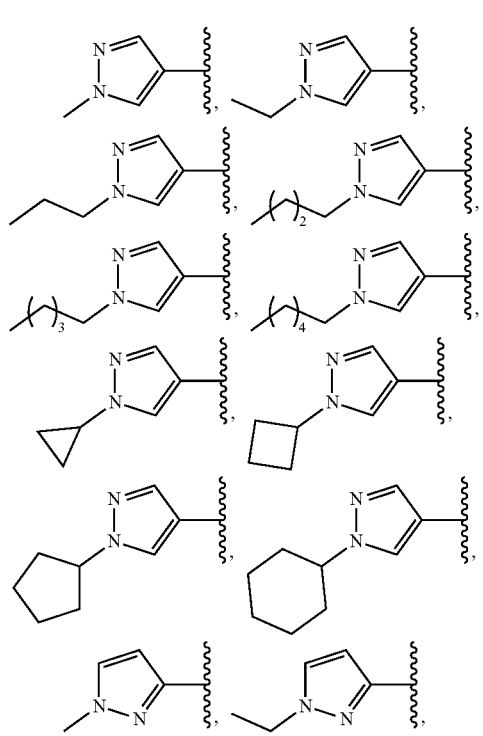
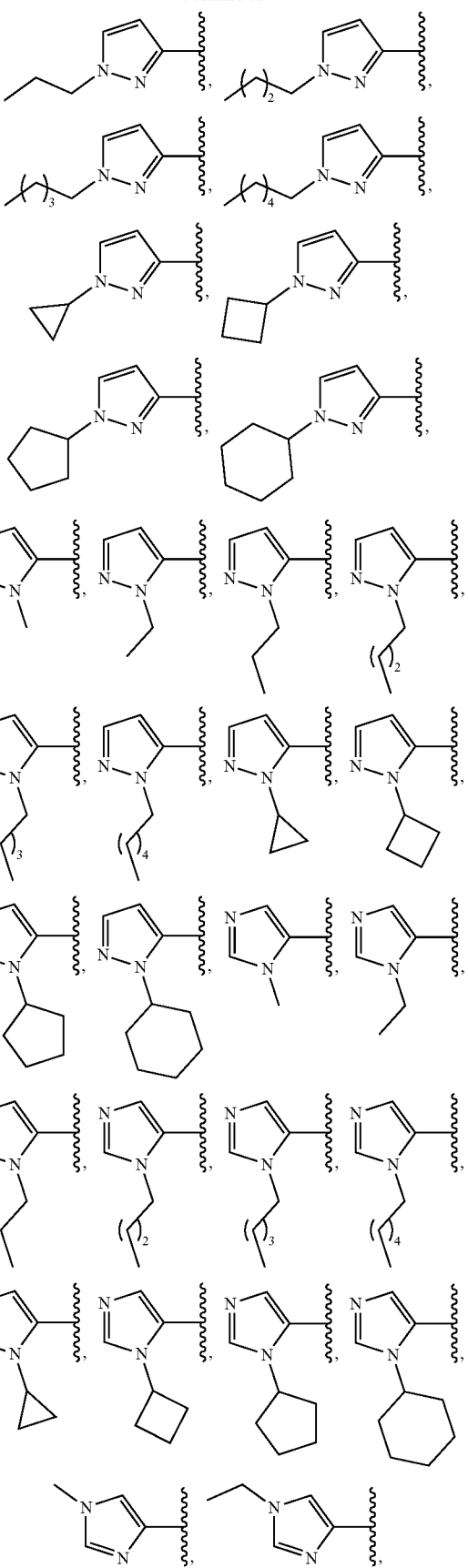

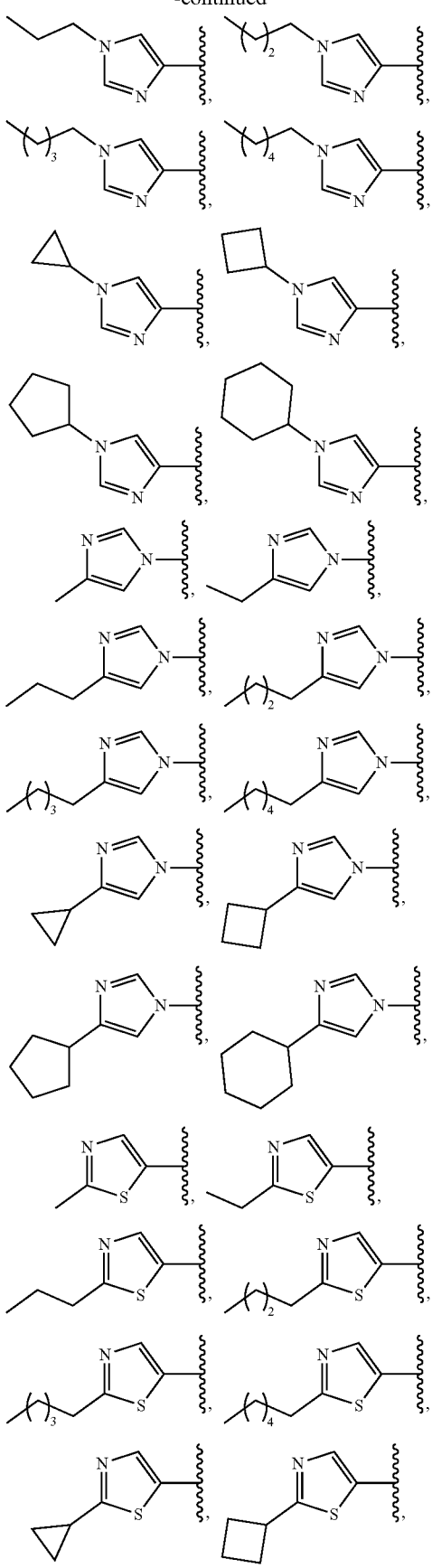

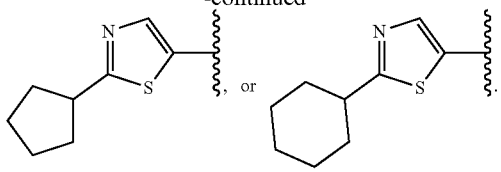

In some embodiments, $R^2$ is

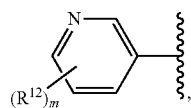

wherein each $R^{12}$ is independently halo, $C_1$-$C_6$alkyl, or $C_3$-$C_6$cycloalkyl; and m is 1 or 2.

In some embodiments, $R^2$ is selected from a group consisting of unsubstituted pyrazole, unsubstituted imidazole, unsubstituted thiazole, and unsubstituted pyridine.

In some embodiments, $R^2$ is —C(=O)N($R^6$)$_2$ and each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, $R^2$ is

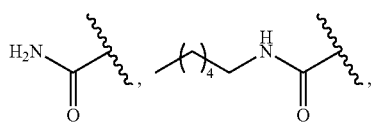

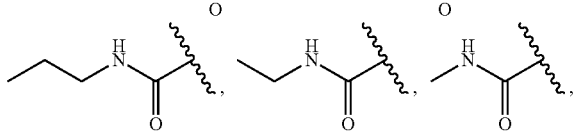

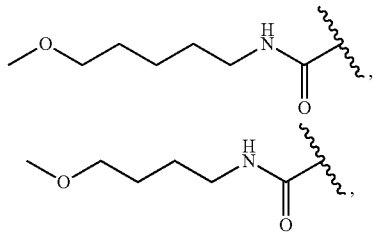

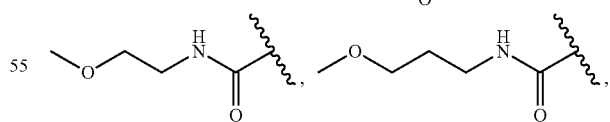

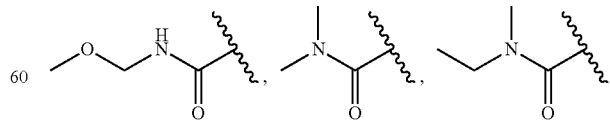

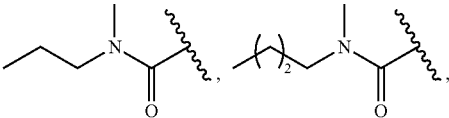

-continued

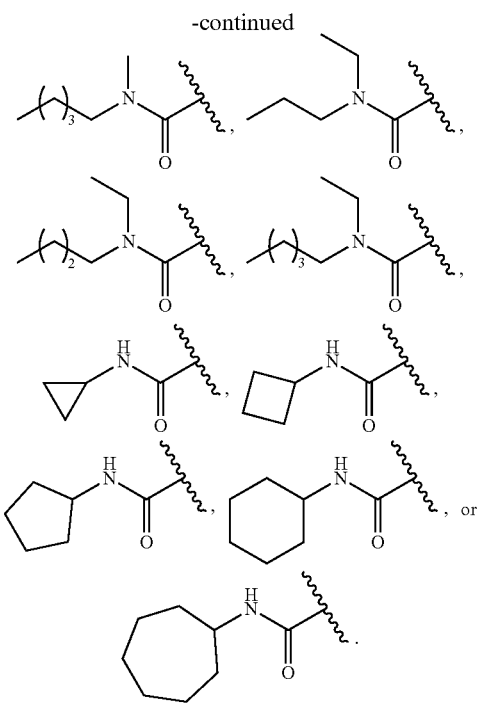

In some embodiments, $R^2$ is

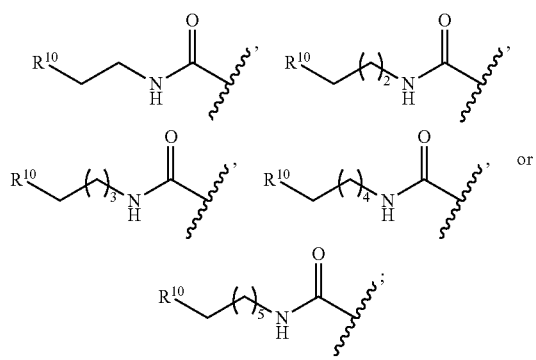

wherein $R^{10}$ is a heteroaryl.

In some embodiments, $R^3$ is hydrogen. In some embodiments, $R^3$ is $C_1$-$C_6$alkyl.

In some embodiments, $R^3$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{2-9}$heteroaryl-cycloalkyl are optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$ heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$ —N($R^{13}$)$_2$, —N($R^{13}$)$_2$, —N($R^{13}$)C(=O)$R^{14}$, and —N($R^{13}$)S(=O)$_2R^{13}$.

In some embodiments, $R^3$ is selected from a group consisting of $C_{2-9}$heterocycle and $C_{1-9}$ heteroaryl; wherein $C_{2-9}$heterocycle and $C_{1-9}$heteroaryl are optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^3$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^3$ is selected from a group consisting of pyrazole, imidazole, thiazole, and pyridine; wherein pyrazole, imidazole, thiazole, and pyridine are optionally substituted with one or two substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$ —N($R^{13}$)$_2$, —N($R^{13}$)$_2$, —N($R^{13}$)C(=O)$R^{14}$, and —N($R^{13}$)S(=O)$_2R^{13}$.

In some embodiments, $R^3$ is selected from a group consisting of pyrazole, imidazole, thiazole, and pyridine; wherein pyrazole, imidazole, thiazole, and pyridine are optionally substituted with one or two substituents selected from the group consisting of halo, $C_{1-6}$alkyl, and $C_{3-8}$cycloalkyl.

In some embodiments, $R^3$ is

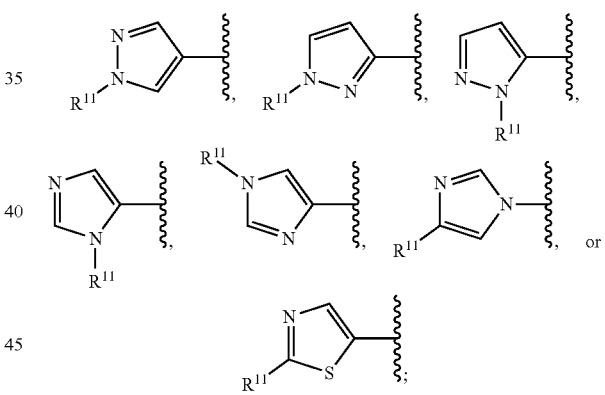

each $R^{11}$ is $C_1$-$C_6$alkyl or $C_3$-$C_6$cycloalkyl; $R^{11a}$ is —CN, —OH, $C_1$-$C_6$alkyl or $C_3$-$C_6$cycloalkyl; and u is 0, 1 or 2.

In some embodiments, $R^3$ is

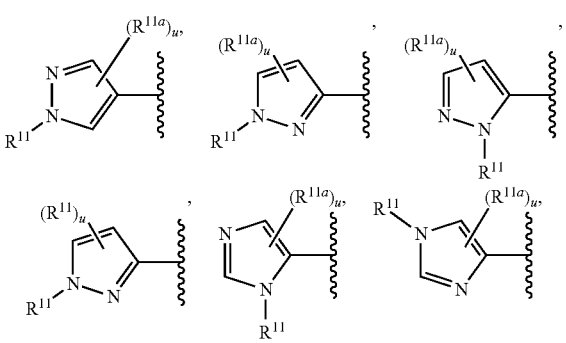

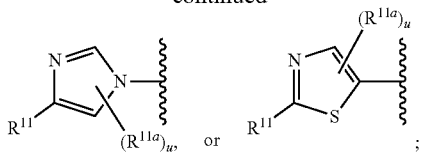
wherein $R^{11}$ is $C_1$-$C_6$alkyl or $C_3$-$C_6$cycloalkyl.
In some embodiments, $R^3$ is
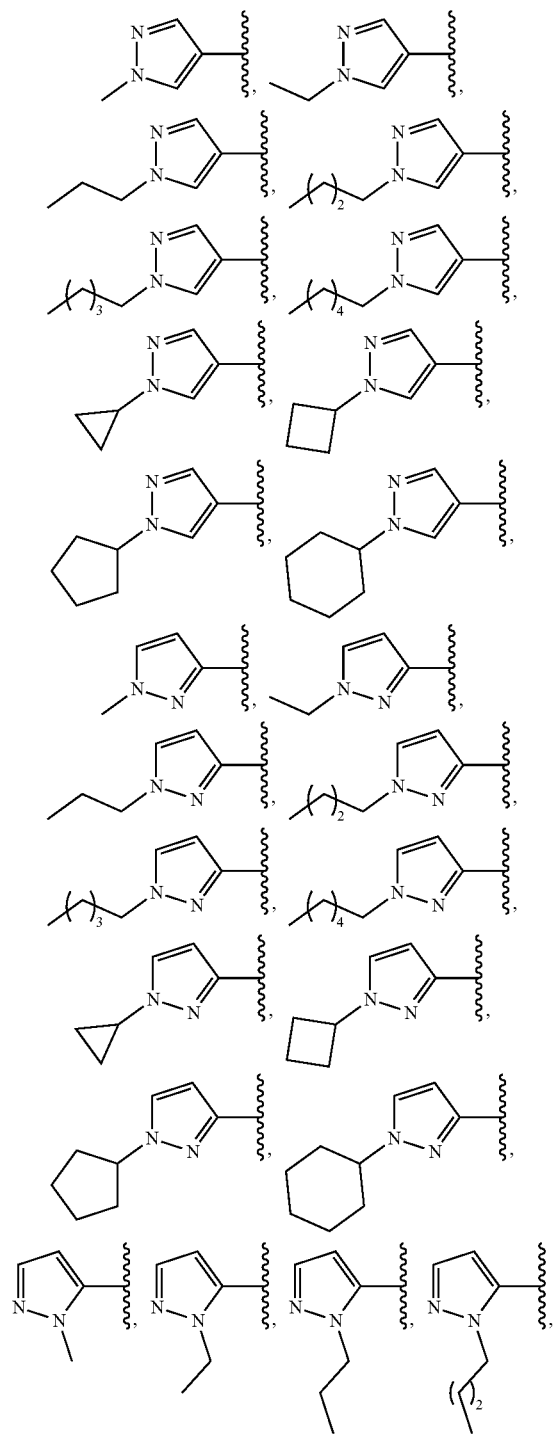
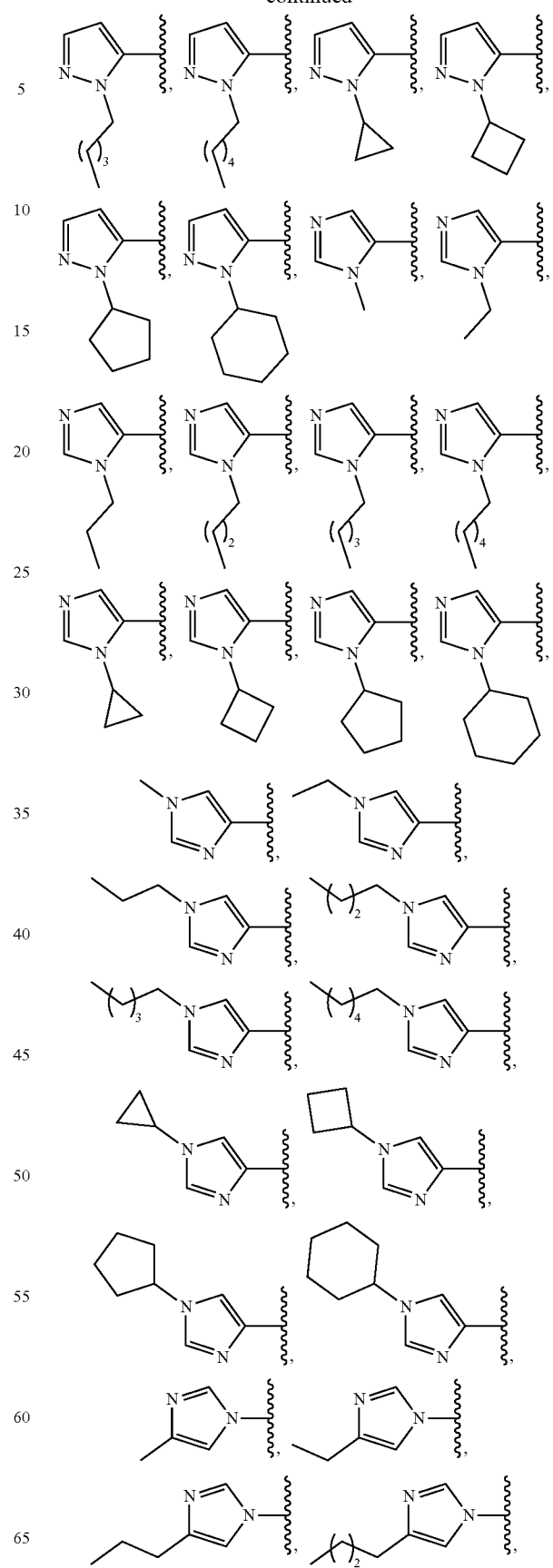

-continued

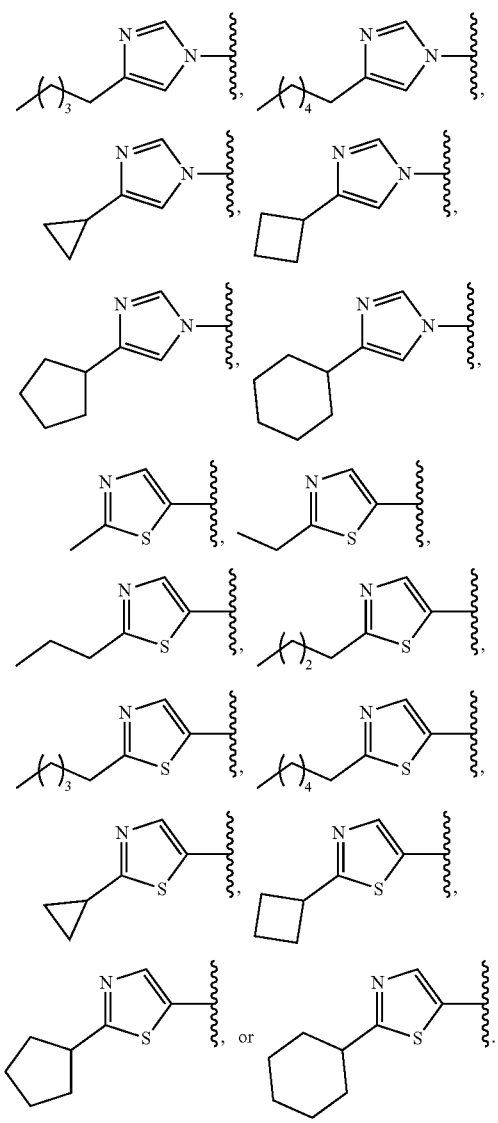

In some embodiments, R³ is

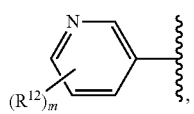

wherein each R¹² is independently halo, $C_1$-$C_6$alkyl, or $C_3$-$C_6$cycloalkyl; and m is 1 or 2.

In some embodiments, R³ is selected from a group consisting of unsubstituted pyrazole, unsubstituted imidazole, unsubstituted thiazole, and unsubstituted pyridine.

In some embodiments, R³ is —C(=O)N(R⁶)₂ and each R⁶ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, R³ is

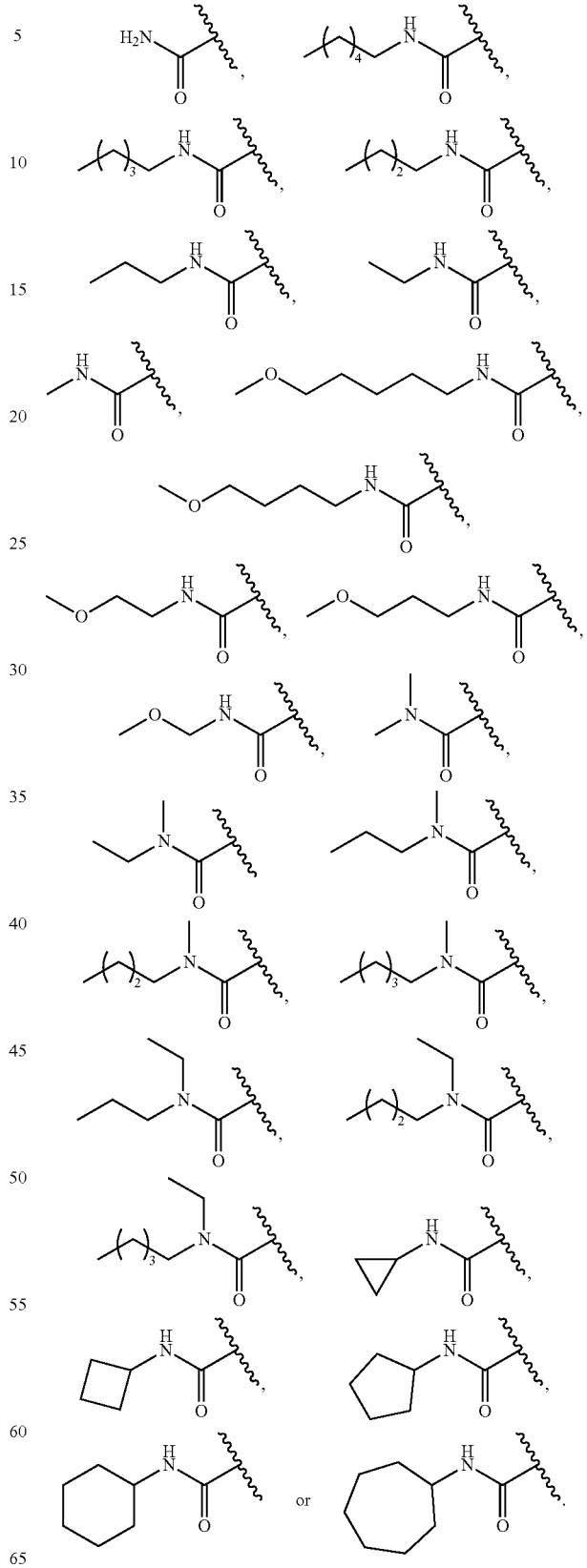

In some embodiments, $R^3$ is

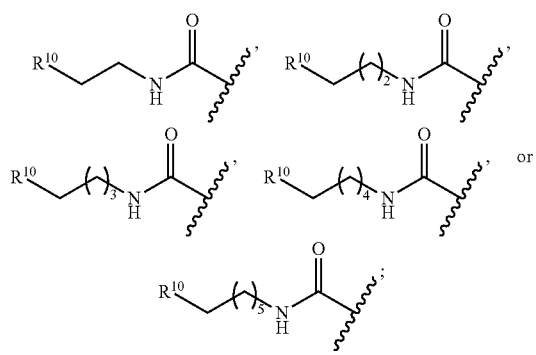

wherein $R^{10}$ is a heteroaryl.

In some embodiments, $R^3$ is $-OR^6$ and $R^6$ is selected from the group consisting of $C_1$-$C_6$alkyl, $-C_1$-$C_6$alkyl-O-$C_1$-$C_6$alkyl, and $-C_1$-$C_6$alkyl-$C_{2-9}$heterocycle. In some embodiments, $R^2$ is hydrogen. In some embodiments, $R^2$ is $C_1$-$C_6$alkyl.

In some embodiments, $R^1$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halo, $-CN$, $C_{1-6}$alkyl, $-C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, $-C(=O)R^{14}$, $-C(=O)OR^{13}$, $-C(=O)N(R^{13})_2$, $-S(=O)R^{14}$, $-S(=O)_2R^{13}$, $-S(=O)_2-N(R^{13})_2$, $-N(R^{13})_2$, $-N(R^{13})C(=O)R^{14}$, and $-N(R^{13})S(=O)_2R^{13}$.

In some embodiments, $R^1$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halo, $-CN$, $C_{1-6}$alkyl, $-C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, $-C(=O)R^{14}$, $-C(=O)OR^{13}$, $-C(=O)N(R^{13})_2$, $-S(=O)R^{14}$, $-S(=O)_2R^{13}$, $-S(=O)_2-N(R^{13})_2$, $-N(R^{13})_2$, $-N(R^{13})C(=O)R^{14}$, and $-N(R^{13})S(=O)_2R^{13}$.

In some embodiments, $R^1$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halo, $-CN$, $C_{1-6}$alkyl, $-C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, $-C(=O)R^{14}$, $-C(=O)OR^{13}$, $-C(=O)N(R^{13})_2$, $-S(=O)R^{14}$, $-S(=O)_2R^{13}$, $-S(=O)_2-N(R^{13})_2$, $-N(R^{13})_2$, $-N(R^{13})C(=O)R^{14}$, and $-N(R^{13})S(=O)_2R^{13}$.

In some embodiments, $R^1$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halo, $C_{1-6}$alkyl, $-C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, $-C(=O)R^{14}$, $-C(=O)OR^{13}$, $-C(=O)N(R^{13})_2$, $-S(=O)R^{14}$, $-S(=O)_2R^{13}$, $-S(=O)_2-N(R^{13})_2$, $-N(R^{13})_2$, $-N(R^{13})C(=O)R^{14}$, and $-N(R^{13})S(=O)_2R^{13}$.

In some embodiments, $R^1$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halo, $C_{1-6}$alkyl, and $C_{3-8}$cycloalkyl.

In some embodiments, $R^1$ is

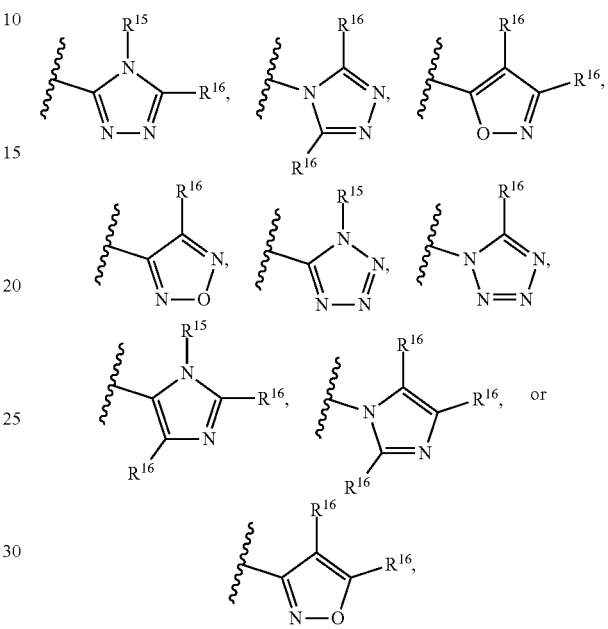

wherein $R^{15}$ is $C_{1-6}$alkyl or $C_{3-8}$cycloalkyl; and $R^{16}$ is hydrogen, halo, $-CN$, $C_{1-6}$alkyl or $C_{3-8}$cycloalkyl.

In some embodiments, $R^1$ is

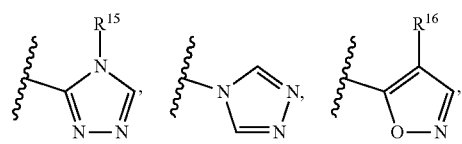

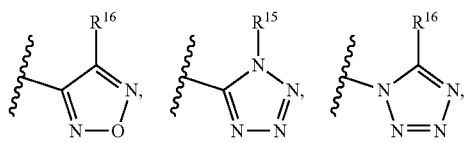

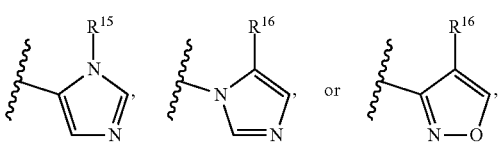

wherein $R^{15}$ is $C_{1-6}$alkyl or $C_{3-8}$cycloalkyl; and $R^{16}$ is halo, $-CN$, $C_{1-6}$alkyl or $C_{3-8}$cycloalkyl.

In some embodiments, R¹ is
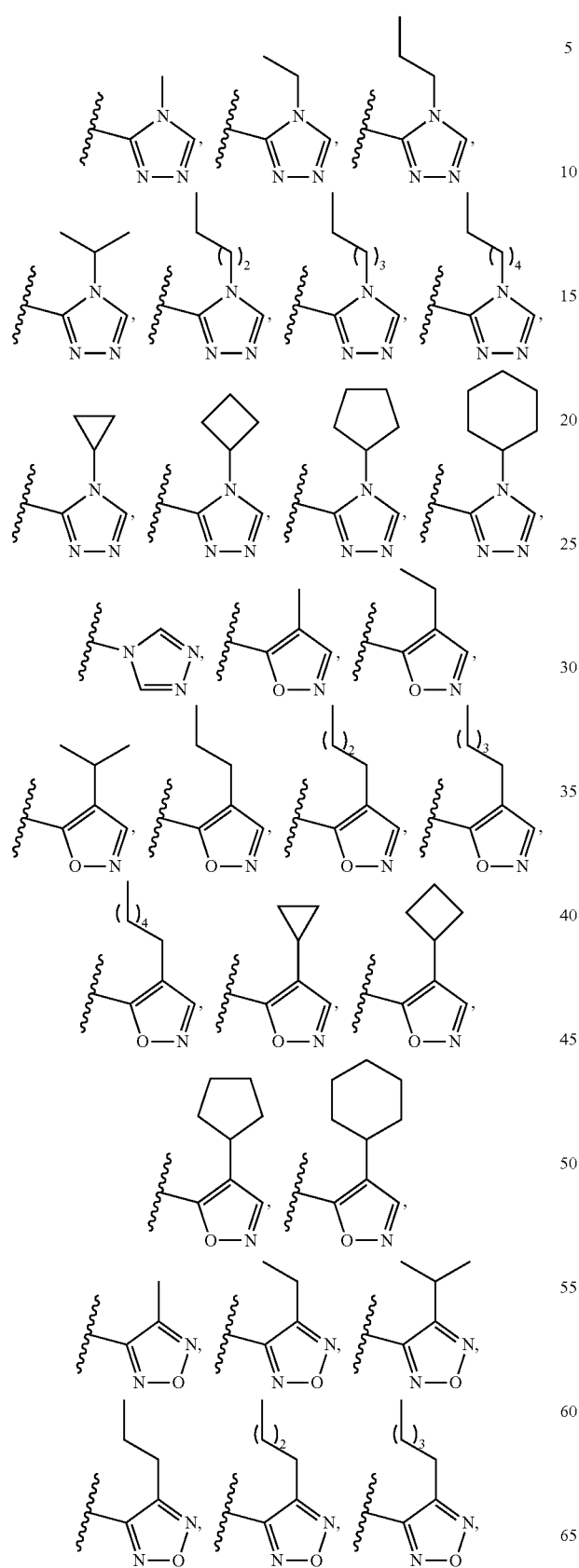
-continued
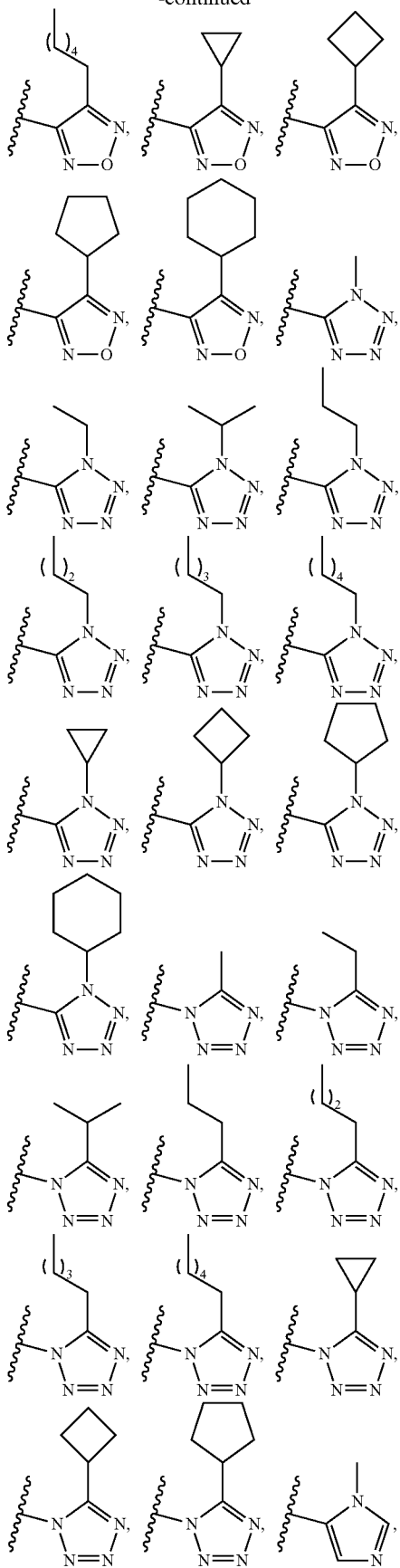

-continued
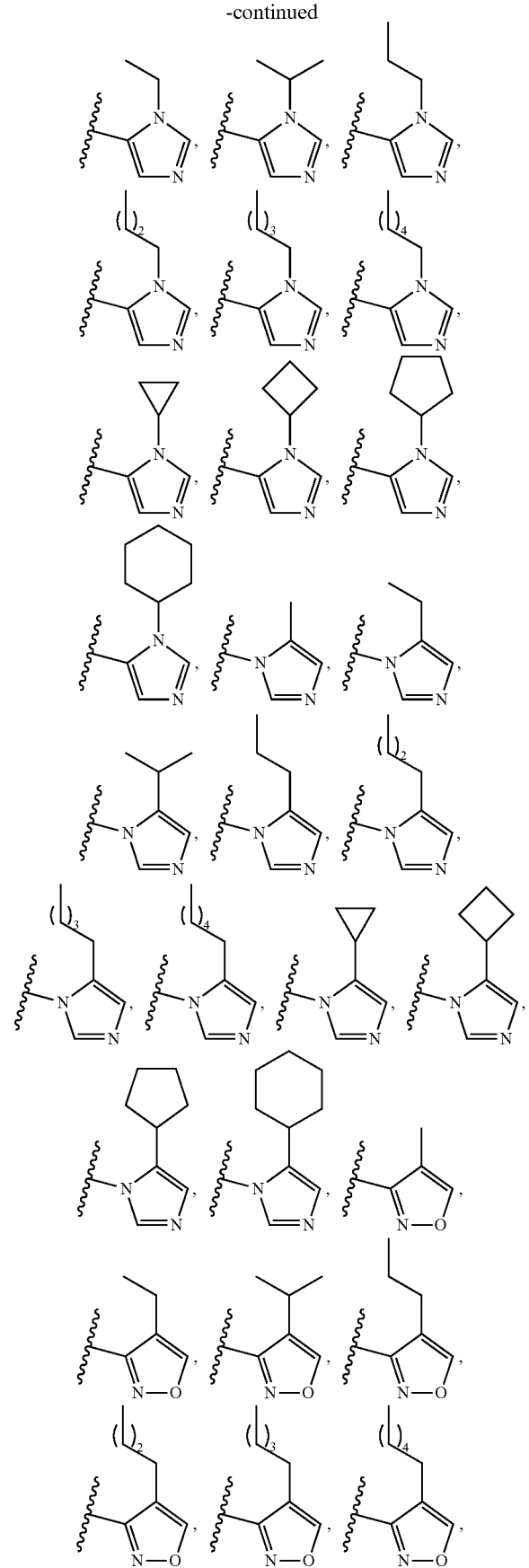
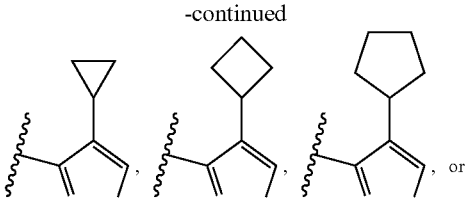
In some embodiments, $R^1$ is
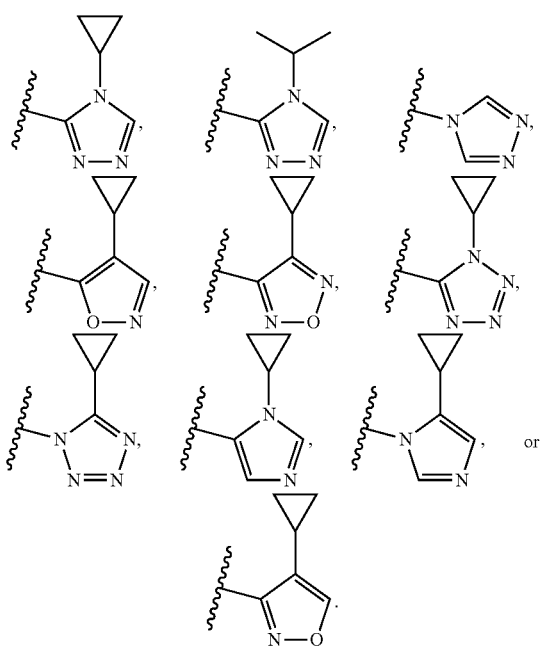
In some embodiments, $R^1$ is
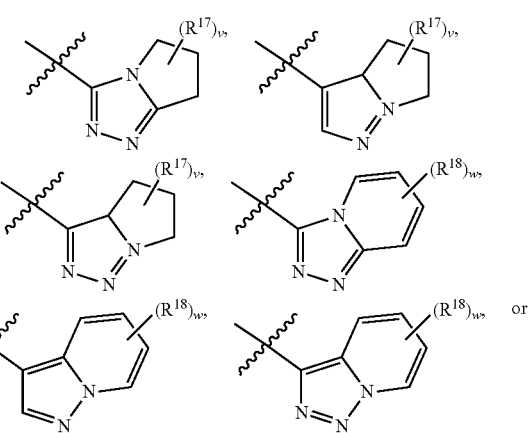

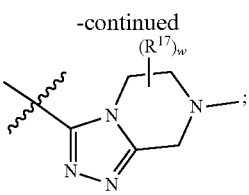

wherein each R$^{17}$ is independently hydrogen, halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$; each R$^{18}$ is independently hydrogen, halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$; v is 0, 1, 2, 3, 4, 5, or 6; and w is 0, 1, 2, 3, or 4. In some embodiments, each R$^{17}$ is independently hydrogen, halo, —CN, C$_{1-6}$alkyl, —C$_{1-6}$alkyl-OH, C$_{1-6}$haloalkyl, or C$_{3-8}$cycloalkyl; each R$^{18}$ is independently hydrogen, halo, —CN, C$_{1-6}$alkyl, —C$_{1-6}$alkyl-OH, C$_{1-6}$haloalkyl, or C$_{3-8}$acycloalkyl.

In some embodiments, each R$^{17}$ is independently hydrogen, halo, —CN, C$_{1-6}$alkyl, —C$_{1-6}$alkyl-OH, or C$_{1-6}$haloalkyl; each R$^{18}$ is independently hydrogen, halo, —CN, C$_{1-6}$alkyl, —C$_{1-6}$alkyl-OH, or C$_{1-6}$ haloalkyl.

In some embodiments, each R$^{17}$ is independently hydrogen, halo, —CN, or C$_{1-6}$alkyl; each R$^{18}$ is independently is hydrogen, halo, —CN, or C$_{1-6}$alkyl.

In some embodiments, R$^1$ is

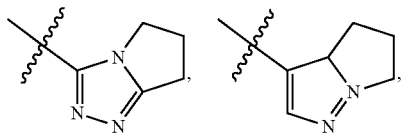

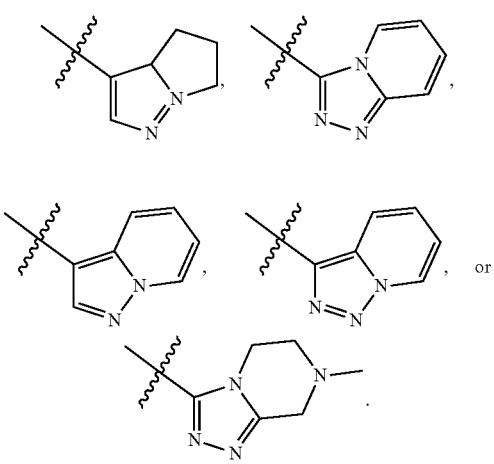

In another aspect described herein are compounds of Formula II, or a pharmaceutically acceptable salt or solvate thereof:

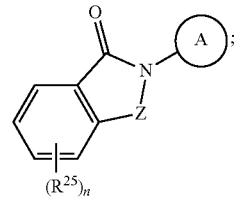

wherein

A is

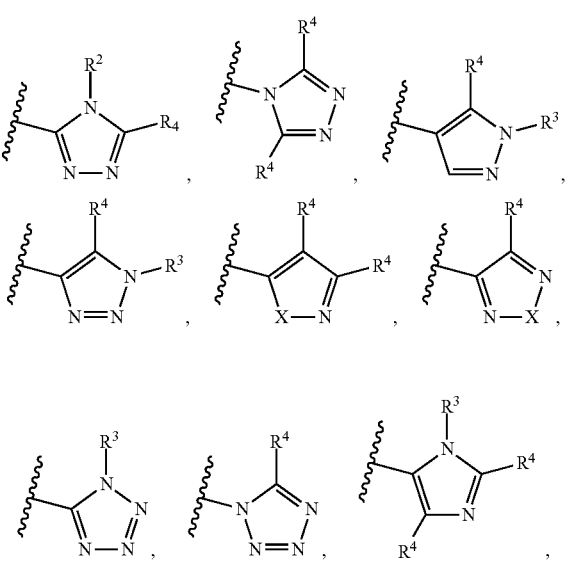

R$^1$ is

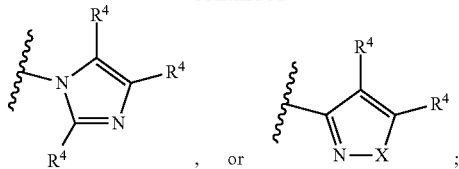

Z is O, S, C(=O), N(R$^8$), or C(R$^9$)$_2$;

X is O or S;

R$^2$ is C$_{3-6}$cycloalkyl;

R$^3$ is selected from a group consisting of hydrogen, C$_{1-6}$alkyl, and C$_{3-6}$cycloalkyl;

each R$^4$ is independently selected from a group consisting of hydrogen, halo, C$_{1-6}$alkyl, and C$_{3-6}$ cycloalkyl;

or one R$^4$ and another R$^2$, R$^3$, or R$^4$, together with the atoms to which they are attached, form a 5- or 6-membered ring that is optionally containing one or two heteroatoms selected from O, N, and S; wherein the 5- or 6-membered ring is saturated, unsaturated, or aromatic; and wherein the 5- or 6-membered ring is optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$ R$^{13}$;

each R$^5$ is independently selected from a group consisting of halogen and C$_{1-6}$alkyl;

R$^{5a}$ is selected from the group consisting of hydrogen and C$_1$-C$_6$alkyl;

R$^{25}$ is selected from a group consisting of halogen, —CN, —OH, —OR$^6$, —SR$^6$, —S(=O)R$^7$, —NO$_2$, —N(R$^6$)$_2$, —S(=O)$_2$R$^7$, —NIHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$ R$^{13}$;

each R$^6$ is independently selected from the group consisting of hydrogen, C$_1$-C$_6$alkyl, —C$_1$-C$_6$alkyl-O—C$_1$-C$_6$alkyl, —C$_1$-C$_6$alkyl-C$_{2-9}$heterocycle, —C$_1$-C$_6$alkyl-C$_{2-9}$heteroaryl, C$_3$-C$_8$cycloalkyl, and C$_{2-9}$heterocycle; or two R$^6$ on the same heteroatom are taken together with that heteroatom to which they are attached to form a C$_{2-9}$heterocycle or a C$_{2-9}$heteroaryl;

each R$^7$ is independently selected from the group consisting of C$_1$-C$_6$alkyl and C$_3$-C$_8$cycloalkyl;

R$^8$ is selected from the group consisting of hydrogen and C$_1$-C$_6$alkyl;

each R$^9$ is independently selected from the group consisting of hydrogen, halogen, and C$_1$-C$_6$alkyl;

each R$^{13}$ is independently selected from the group consisting of hydrogen, C$_1$-C$_6$alkyl, and C$_3$-C$_8$cycloalkyl; or two R$^{13}$ on the same heteroatom are taken together with that heteroatom to which they are attached to form a C$_{2-9}$heterocycle;

each R$^{14}$ is independently selected from the group consisting of C$_1$-C$_6$alkyl and C$_3$-C$_8$cycloalkyl;

n is 0, 1, 2, 3 or 4;

p is 0, 1, 2, or 3; and q is 0, 1, or 2.

In some embodiments, R$^{25}$ is selected from a group consisting of C$_{3-8}$cycloalkyl, C$_{2-9}$ heterocycle, C$_{6-10}$aryl, C$_{1-9}$heteroaryl, and a fused C$_{5-9}$heteroaryl-cycloalkyl; wherein C$_{3-8}$cycloalkyl, C$_{2-9}$heterocycle, C$_{6-10}$aryl, C$_{1-9}$heteroaryl, and fused C$_{5-9}$heteroaryl-cycloalkyl, wherein C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$ heteroaryl, —C(=O)R$^{14}$, —C(=O)OR$^{13}$, —C(=O)N(R$^{13}$)$_2$, —S(=O)R$^{14}$, —S(=O)$_2$R$^{13}$, S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^{25}$ is selected from a group consisting of C$_{2-9}$heterocycle and C$_{1-9}$ heteroaryl; wherein C$_{2-9}$heterocycle and C$_{1-9}$heteroaryl are optionally substituted with one, two, or three substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^{25}$ is selected from a group consisting of C$_{2-9}$heterocycle and C$_{1-9}$ heteroaryl; wherein C$_{2-9}$heterocycle and C$_{1-9}$heteroaryl are optionally substituted with one or two substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^{25}$ is selected from a group consisting of pyrazole, imidazole, thiazole, and pyridine; wherein pyrazole, imidazole, thiazole, and pyridine are optionally substituted with one or two substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$ —N(R$^{13}$)$_2$, —N(R$^{13}$)$_2$, —N(R$^{13}$)C(=O)R$^{14}$, and —N(R$^{13}$)S(=O)$_2$R$^{13}$.

In some embodiments, R$^{25}$ is selected from a group consisting of pyrazole, imidazole, thiazole, and pyridine; wherein pyrazole, imidazole, thiazole, and pyridine are optionally substituted with one or two substituents selected from the group consisting of halo, C$_{1-6}$alkyl, and C$_{3-8}$cycloalkyl.

In some embodiments, R$^{25}$ is

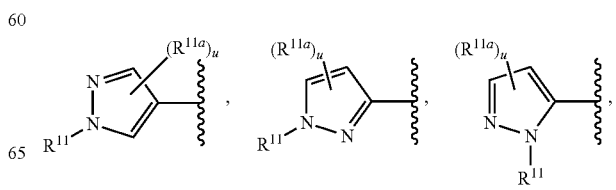

-continued
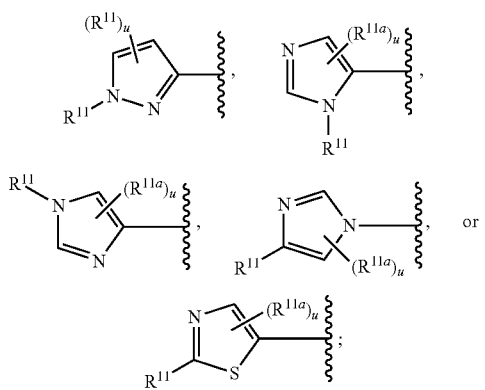
each $R^{11}$ is $C_1$-$C_6$alkyl or $C_3$-$C_6$cycloalkyl; $R^{11a}$ is —CN, —OH, $C_1$-$C_6$alkyl or $C_3$-$C_6$cycloalkyl; and u is 0, 1 or 2.
In some embodiments, $R^{25}$ is
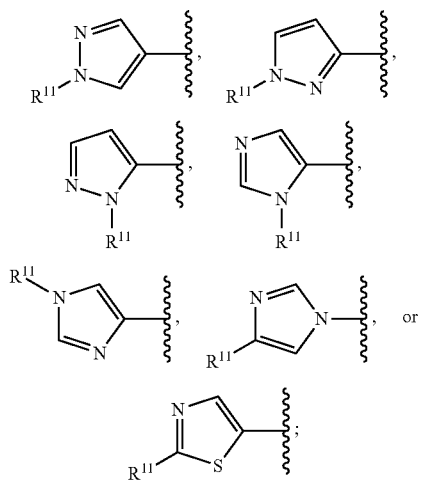
wherein $R^{11}$ is $C_1$-$C_6$alkyl or $C_3$-$C_6$cycloalkyl.
In some embodiments, $R^{25}$ is
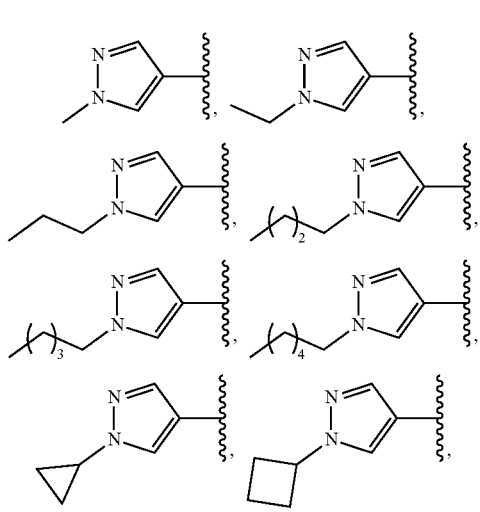
-continued
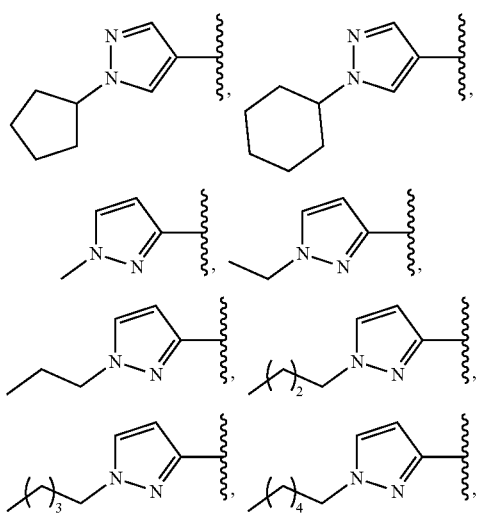
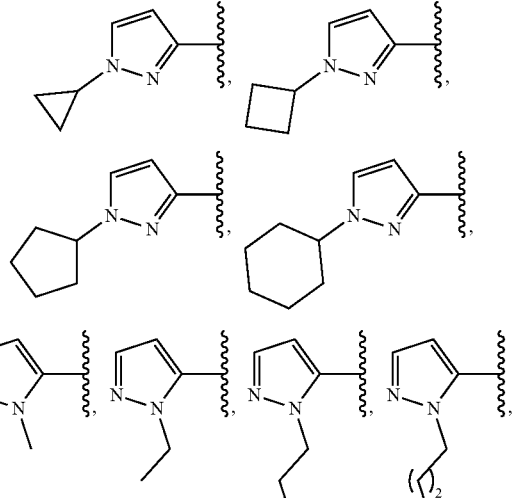
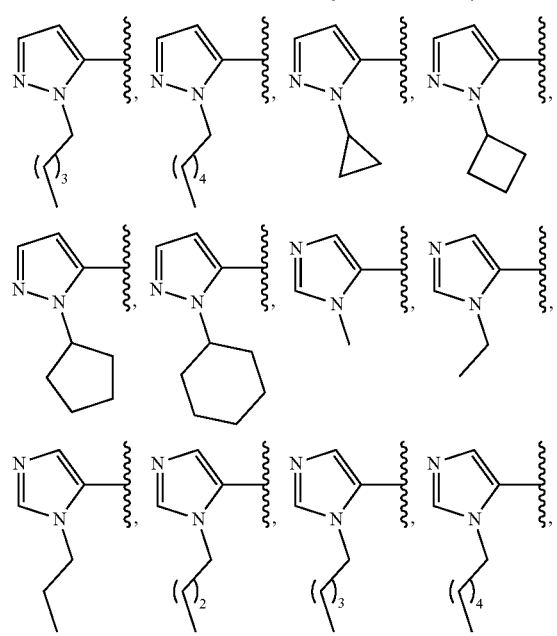

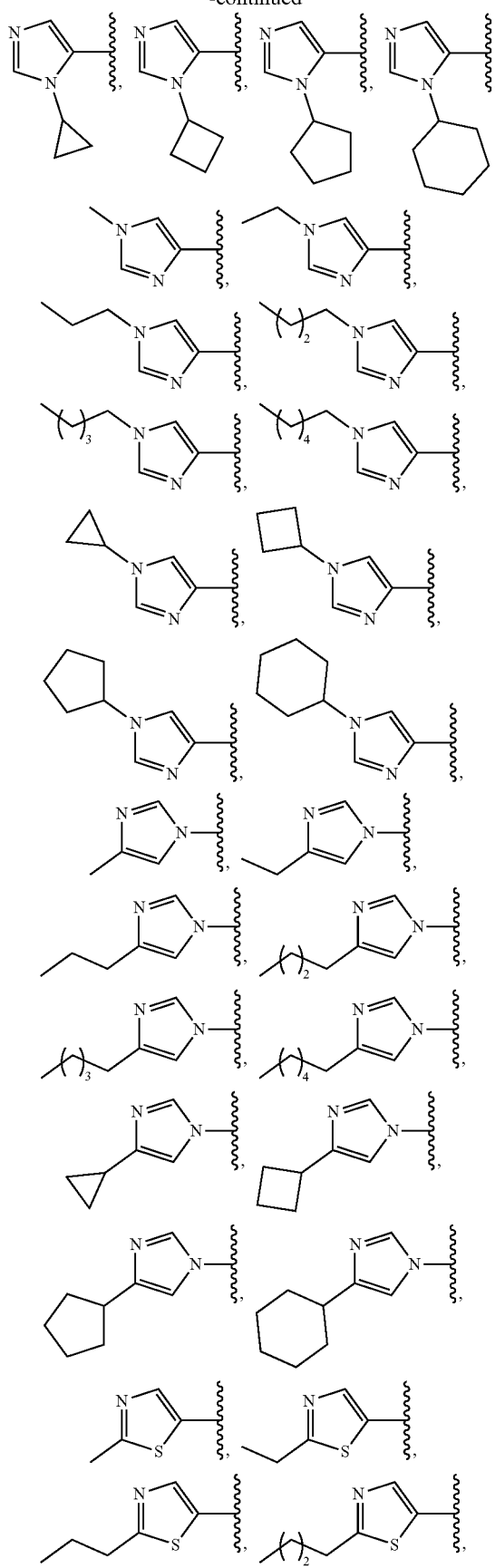

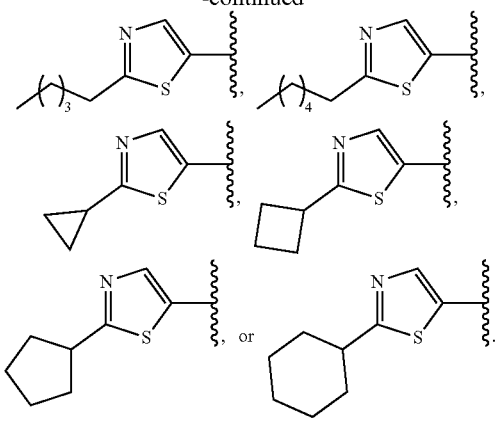

In some embodiments, $R^{25}$ is

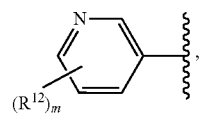

wherein $R^{12}$ is halo, $C_1$-$C_6$alkyl, or $C_3$-$C_6$cycloalkyl; and m is 1 or 2.

In some embodiments, $R^{25}$ is selected from a group consisting of unsubstituted pyrazole, unsubstituted imidazole, unsubstituted thiazole, and unsubstituted pyridine.

In some embodiments, $R^{25}$ is —C(=O)N($R^6$)$_2$ and each $R^6$ is independently selected from the group consisting of hydrogen, $C_1$-$C_6$alkyl, —$C_1$-$C_6$alkyl-O—$C_1$-$C_6$alkyl, —$C_1$-$C_6$alkyl-$C_{2-9}$heterocycle, —$C_1$-$C_6$alkyl-$C_{2-9}$heteroaryl, $C_3$-$C_8$cycloalkyl, and $C_{2-9}$heterocycle.

In some embodiments, $R^{25}$ is

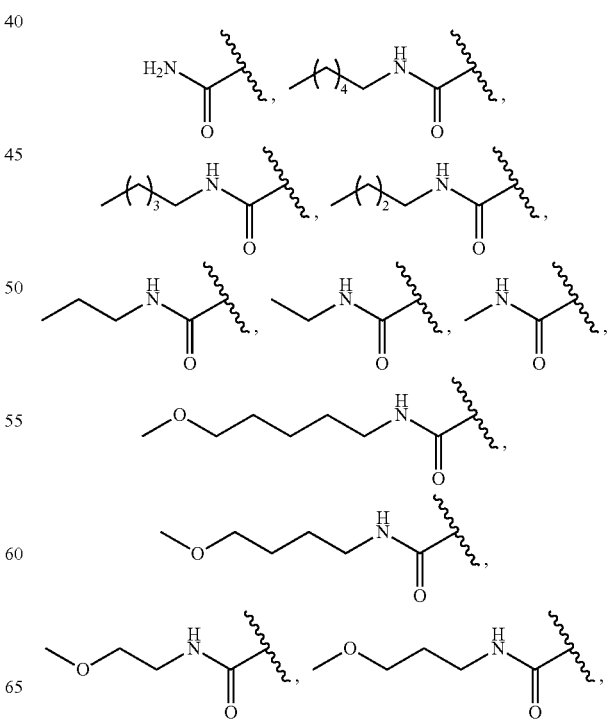

-continued

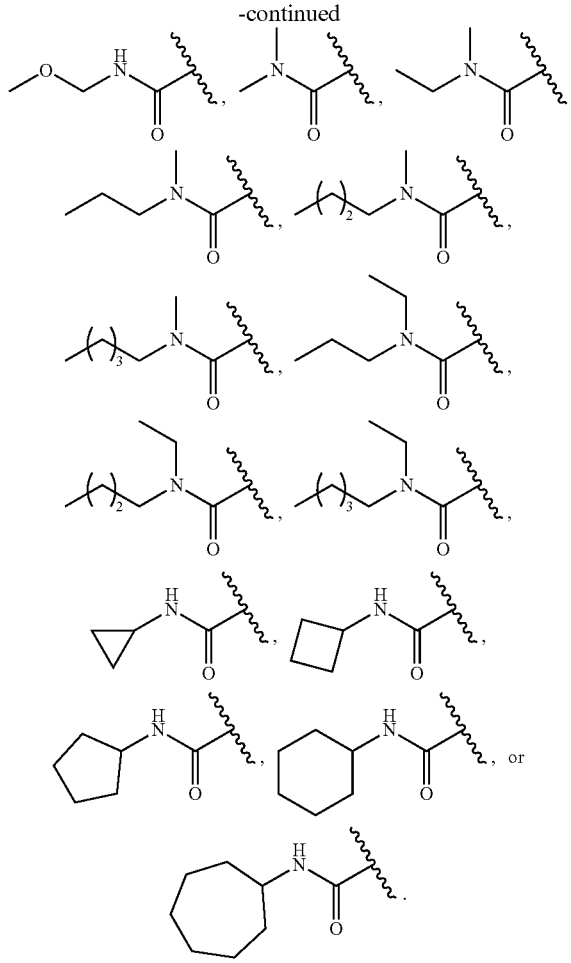

In some embodiments, $R^{25}$ is

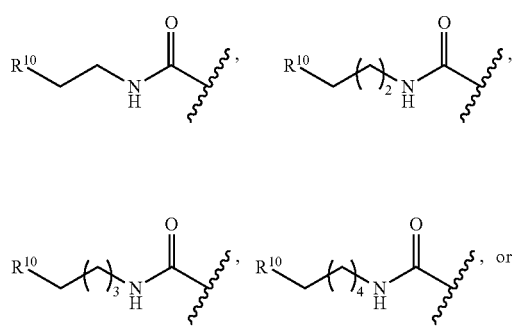

wherein $R^{10}$ is a heteroaryl.

In some embodiments, $R^{25}$ is —C(=O)N($R^6$)$_2$ and two $R^6$ are taken together with that heteroatom to which they are attached to form a $C_{2-9}$heterocycle or a $C_{2-9}$heteroaryl.

In some embodiments, $R^{25}$ is

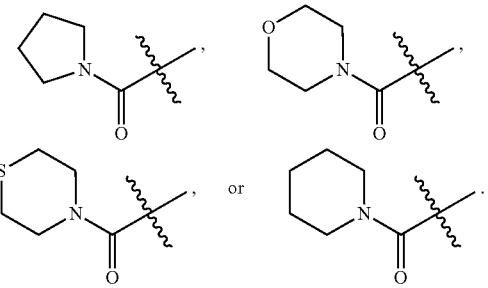

In some embodiments, $R^{25}$ is —O$R^6$ and $R^6$ is selected from the group consisting of $C_1$-$C_6$alkyl, —$C_1$-$C_6$alkyl-O—$C_1$-$C_6$alkyl, and —$C_1$-$C_6$alkyl-$C_{2-9}$heterocycle.

In some embodiments,

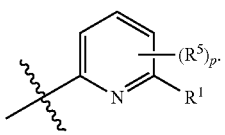

is

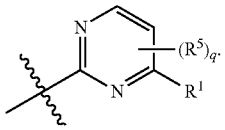

In some embodiments, p is 0.

In some embodiments,

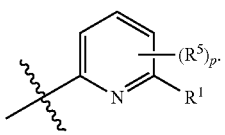

is

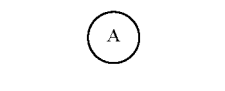

In some embodiments,

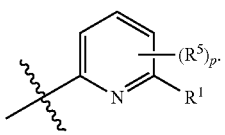

is

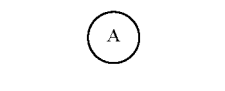

In some embodiments, q is 0.

In some embodiments, n is 0. In some embodiments, n is 1. In some embodiments, Z is $C(R^9)_2$. In some embodiments, $R^9$ is H.

In some embodiments, $R^1$ is

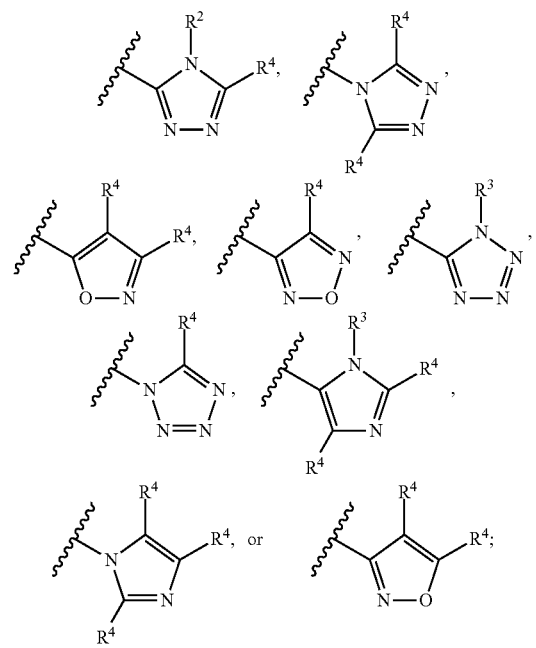

wherein $R^2$ is $C_{3-6}$cycloalkyl; $R^3$ is selected from a group consisting of hydrogen $C_{1-6}$alkyl and $C_{3-6}$cycloalkyl; each $R^4$ is independently selected from a group consisting of hydrogen, halogen, $C_{1-6}$ alkyl, and $C_{3-6}$cycloalkyl; or one $R^4$ and another $R^2$, $R^3$, or $R^4$, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13})_2$, —S(=O)$R^{14}$, —S(=O)$_2R^{13}$, —S(=O)$_2$—N($R^{13})_2$, —N($R^{13})_2$, —N($R^{13}$)C(=O)$R^{14}$, and —N($R^{13}$)S(=O)$_2R^{13}$.

In some embodiments, $R^1$ is

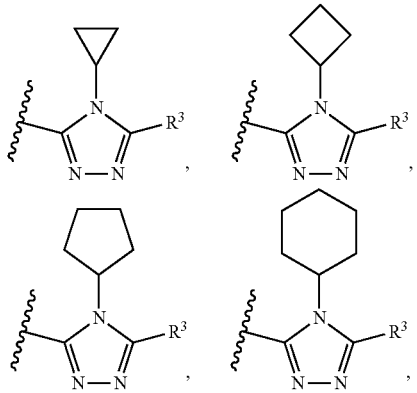

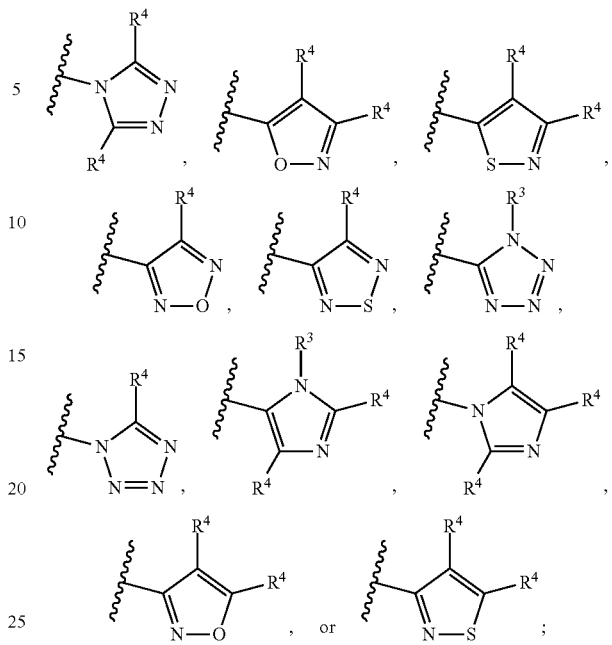

wherein $R^3$ is selected from a group consisting of $C_{1-6}$alkyl and $C_{3-6}$cycloalkyl; and each $R^4$ is independently selected from a group consisting of hydrogen, halogen, $C_{1-6}$alkyl, and $C_{3-6}$cycloalkyl.

In some embodiments, $R^1$ is

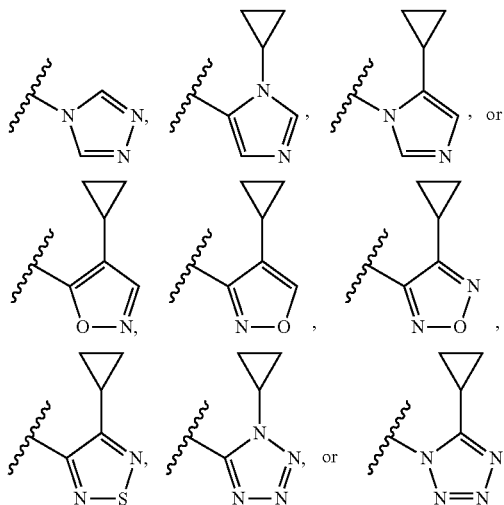

In some embodiments, $R^1$ is

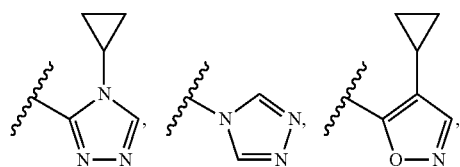

-continued

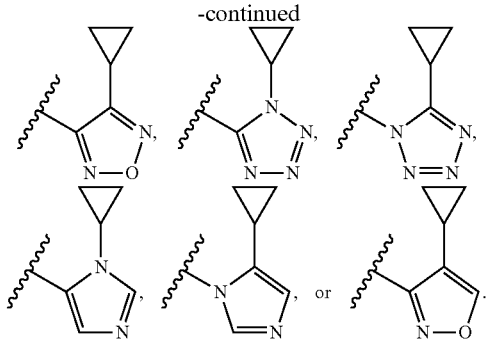

In some embodiments, $R^1$ is

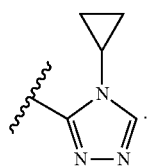 [SMILES: *c1nncn1C1CC1]

In some embodiments, $R^1$ is

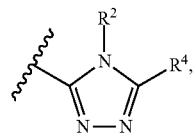

wherein $R^2$ and $R^4$, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^1$ is

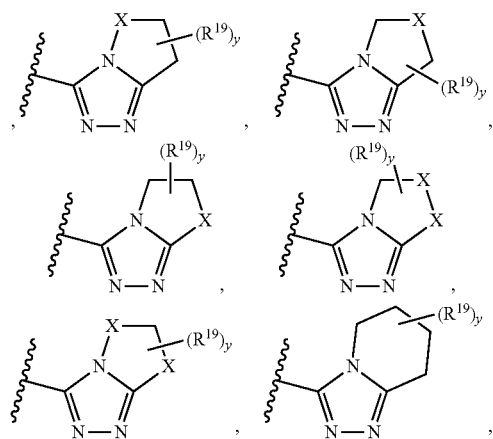

-continued

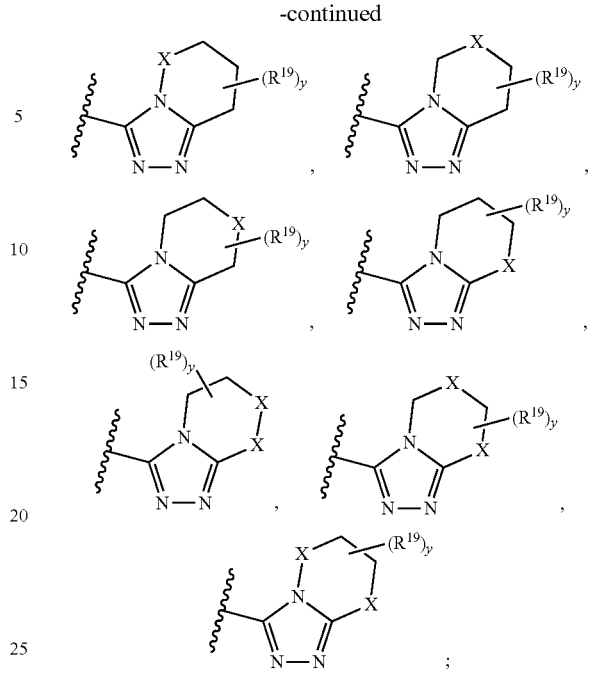

wherein X is O, N or S; each $R^{19}$ is independently halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^4$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$; and y is 0, 1, 2, 3 or 4.

In some embodiments, $R^1$ is

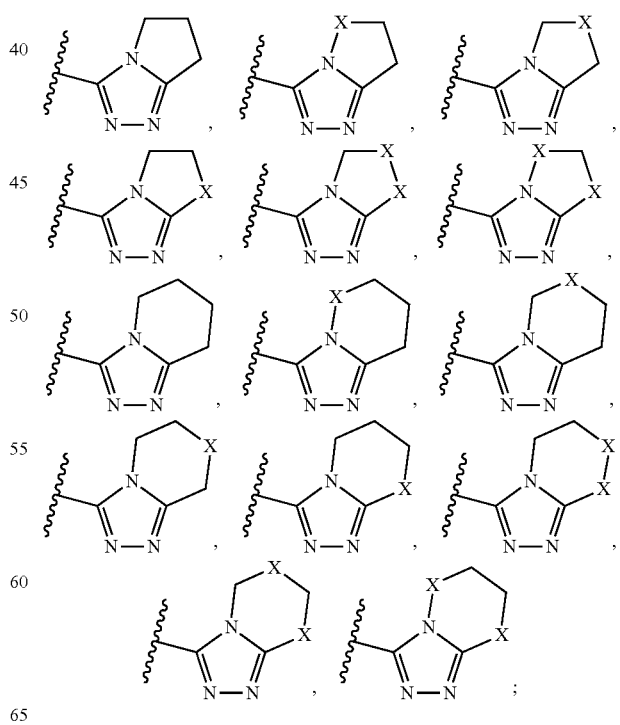

wherein X is O, N or S.

In some embodiments, $R^1$ is

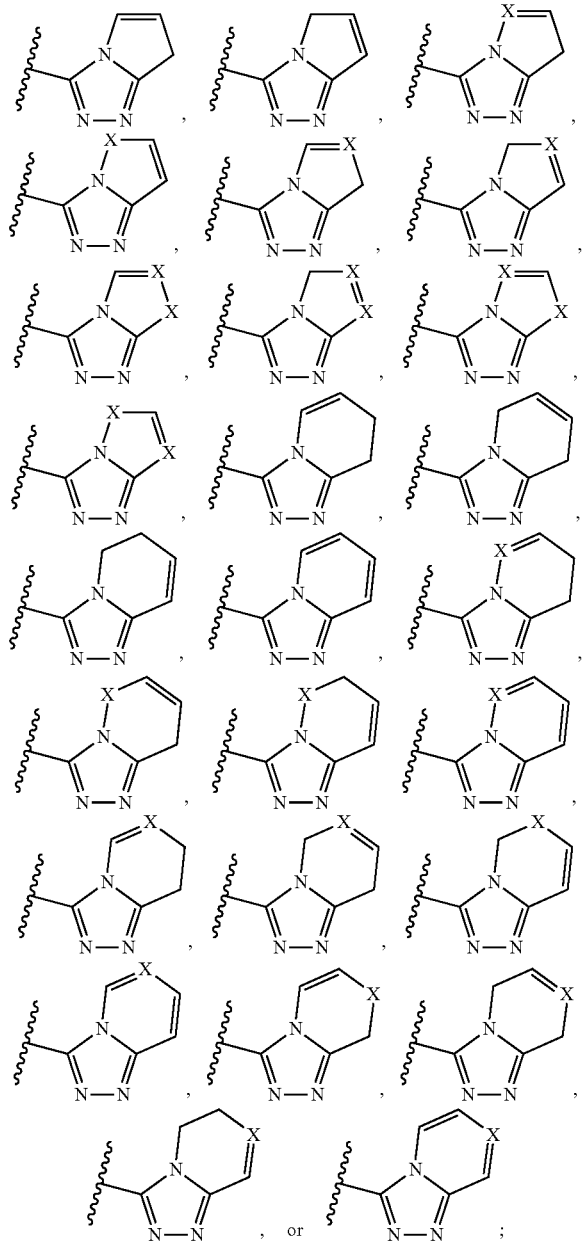

wherein X is N.

In some embodiments, $R^1$ is

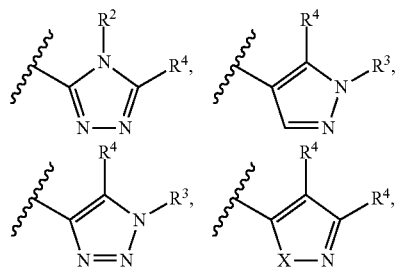

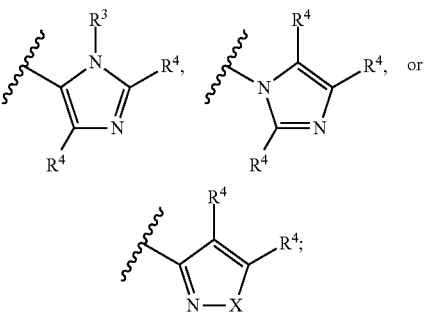

wherein X is O or S; and one $R^4$ and another $R^2$, $R^3$, or $R^4$, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^1$ is

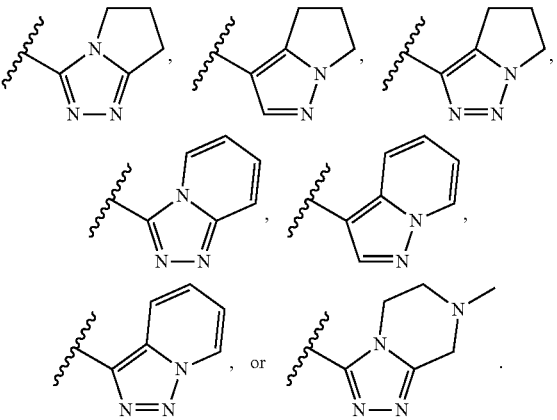

In some embodiments, $R^1$ is

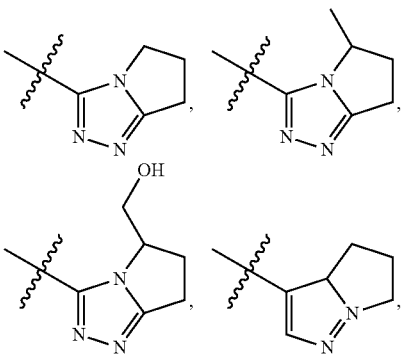

-continued

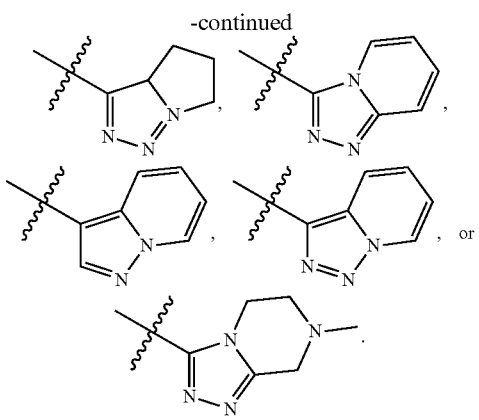

In another aspect described herein are compounds of Formula III, or a pharmaceutically acceptable salt or solvate thereof:

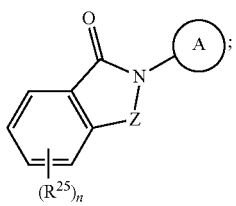

Formula III wherein

A is

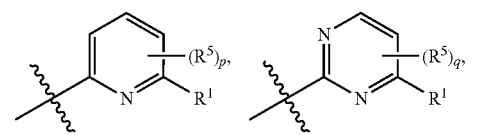

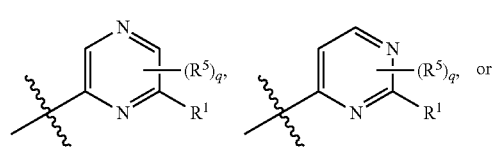

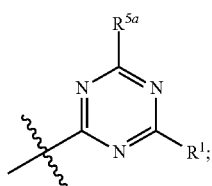

$R^1$ is

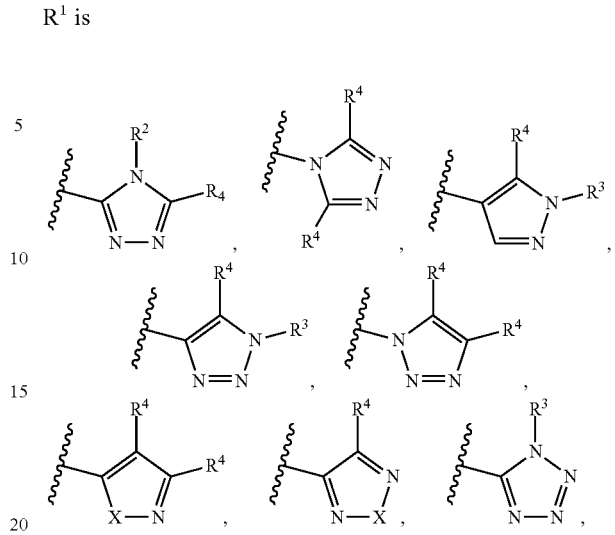

or

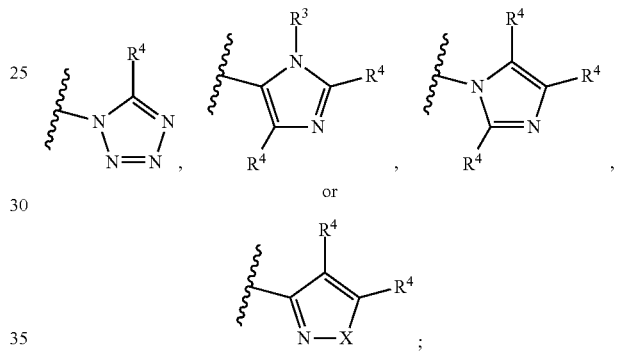

Z is O, S, C(=O), N($R^8$), or C($R^9$)$_2$;
X is O or S;
$R^2$ is $C_{3-6}$cycloalkyl;
$R^3$ is selected from a group consisting of hydrogen, $C_{1-6}$alkyl, and $C_{3-6}$cycloalkyl;
each $R^4$ is independently selected from a group consisting of hydrogen, halo, $C_{1-6}$alkyl, and $C_{3-6}$ cycloalkyl;
or one $R^4$ and another $R^2$, $R^3$, or $R^4$, together with the atoms to which they are attached, form a 5- or 6-membered ring that is optionally containing one or two heteroatoms selected from O, N, and S; wherein the 5- or 6-membered ring is saturated, unsaturated, or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$ $R^{13}$;
each $R^5$ is independently selected from a group consisting of halogen and $C_{1-6}$alkyl;
$R^{5a}$ is selected from the group consisting of hydrogen and $C_1$-$C_6$alkyl;
each $R^{25}$ is independently selected from a group consisting of halogen, —CN, —OH, —O$R^6$, —S$R^6$, —S(=O)$R^7$, —NO$_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —N$R^6$C —C(═O)N(R$^6$)$_2$, —NR$^6$C(═O)R$^7$, —NR$^6$C(═O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$ heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$;

each R$^6$ is independently selected from the group consisting of hydrogen, C$_1$-C$_6$alkyl, —C$_1$-C$_6$alkyl-O—C$_1$-C$_6$alkyl, —C$_1$-C$_6$alkyl-C$_{2-9}$heterocycle, —C$_1$-C$_6$alkyl-C$_{2-9}$heteroaryl, C$_3$-C$_8$cycloalkyl, —C$_3$-C$_8$cycloalkyl-phenyl, and C$_{2-9}$heterocycle, wherein C$_1$-C$_6$alkyl, —C$_1$-C$_6$alkyl-O—C$_1$-C$_6$alkyl, —C$_1$-C$_6$alkyl-C$_{2-9}$heterocycle, —C$_1$-C$_6$alkyl-C$_{2-9}$heteroaryl, C$_3$-C$_8$cycloalkyl, —C$_3$-C$_8$cycloalkyl-phenyl, and C$_{2-9}$heterocycle are optionally substituted with one, two, or three substituents selected from the group consisting of halo, —OR$^8$, —SR$^8$, —N(R)$_2$, —C$_{1-6}$alkyl, —O—C$_{1-6}$alkyl, —C(═O)R$^{14}$, —C(═O)OR$^{13}$, and —N(R$^{13}$)C(═O)R$^{14}$; or two R$^6$ on the same heteroatom are taken together with that heteroatom to which they are attached to form a C$_{2-9}$heterocycle or a C$_{2-9}$heteroaryl, wherein C$_{2-9}$heterocycle or C$_{2-9}$heteroaryl are optionally substituted with one, two, or three substituents selected from the group consisting of halo, —OR$^8$, —SR$^8$, —N(R$^8$)$_2$, —C$_{1-6}$alkyl, —O—C$_{1-6}$alkyl, —C(═O)R$^{14}$, —C(═O)OR$^{13}$, and —N(R$^{13}$)C(═O)R$^{14}$;

each R$^7$ is independently selected from the group consisting of C$_1$-C$_6$alkyl, C$_3$-C$_8$cycloalkyl, and C$_{2-9}$ heterocycle, wherein C$_3$-C$_8$cycloalkyl and C$_{2-9}$heterocycle are optionally substituted with one, two, or three substituents selected from the group consisting of halo, oxo, —OR$^8$, —SR$^8$, —N(R$^8$)$_2$, —C$_{1-6}$alkyl, —O—C$_{1-6}$alkyl, —C(═O)R$^{14}$, —C(═O)OR$^{13}$, and —N(R$^{13}$)C(═O)R$^{14}$;

each R$^8$ is independently selected from the group consisting of hydrogen and C$_1$-C$_6$alkyl;

each R$^9$ is independently selected from the group consisting of hydrogen, halogen, and C$_1$-C$_6$alkyl;

each R$^{13}$ is independently selected from the group consisting of hydrogen, C$_1$-C$_6$alkyl, and C$_3$-C$_8$cycloalkyl; or two R$^{13}$ on the same heteroatom are taken together with that heteroatom to which they are attached to form a C$_{2-9}$heterocycle;

each R$^{14}$ is independently selected from the group consisting of C$_1$-C$_6$alkyl and C$_3$-C$_8$cycloalkyl;

n is 0, 1, 2, 3, or 4;

p is 0, 1, 2, or 3; and q is 0, 1, or 2.

In some embodiments, R$^{25}$ is selected from a group consisting of C$_{3-8}$cycloalkyl, C$_{2-9}$ heterocycle, C$_{6-10}$aryl, C$_{1-9}$heteroaryl, and a fused C$_{5-9}$heteroaryl-cycloalkyl; wherein C$_{3-8}$cycloalkyl, C$_{2-9}$heterocycle, C$_{6-10}$aryl, C$_{1-9}$heteroaryl, and fused C$_{5-9}$heteroaryl-cycloalkyl, wherein C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$ heteroaryl, —C(═O)R$^{14}$, —C(═O)OR$^{13}$, —C(═O)N(R$^{13}$)$_2$, —S(═O)R$^{14}$, —S(═O)$_2$R$^{13}$, S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments, R$^{25}$ is selected from a group consisting of C$_{2-9}$heterocycle and C$_{1-9}$ heteroaryl; wherein C$_{2-9}$heterocycle and C$_{1-9}$heteroaryl are optionally substituted with one, two, or three substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments, R$^{25}$ is selected from a group consisting of C$_{2-9}$heterocycle and C$_{1-9}$ heteroaryl; wherein C$_{2-9}$heterocycle and C$_{1-9}$heteroaryl are optionally substituted with one or two substituents selected from the group consisting of halo, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments, R$^{25}$ is selected from a group consisting of pyrazole, imidazole, thiazole, and pyridine; wherein pyrazole, imidazole, thiazole, and pyridine are optionally substituted with one or two substituents selected from the group consisting of halo, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$ —N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments, R$^{25}$ is selected from a group consisting of pyrazole, imidazole, thiazole, and pyridine; wherein pyrazole, imidazole, thiazole, and pyridine are optionally substituted with one or two substituents selected from the group consisting of halo, C$_{1-6}$alkyl, and C$_{3-8}$cycloalkyl.

In some embodiments, R$^{25}$ is

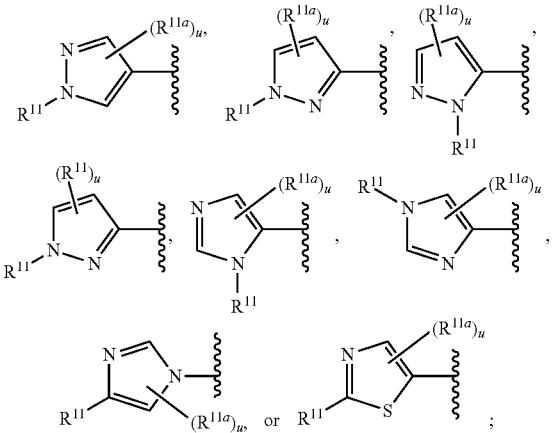

each R$^{11}$ is C$_1$-C$_6$alkyl or C$_3$-C$_6$cycloalkyl; R$^{11a}$ is —CN, —OH, C$_1$-C$_6$alkyl or C$_3$-C$_6$cycloalkyl; and u is 0, 1 or 2.

In some embodiments, R$^{25}$ is

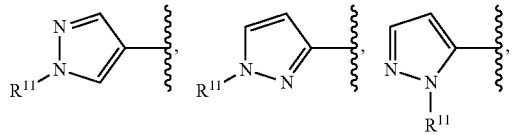

-continued
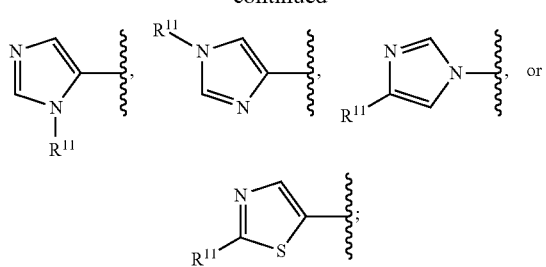
wherein R[11] is $C_1$-$C_6$alkyl or $C_3$-$C_6$cycloalkyl.
In some embodiments, R[25] is
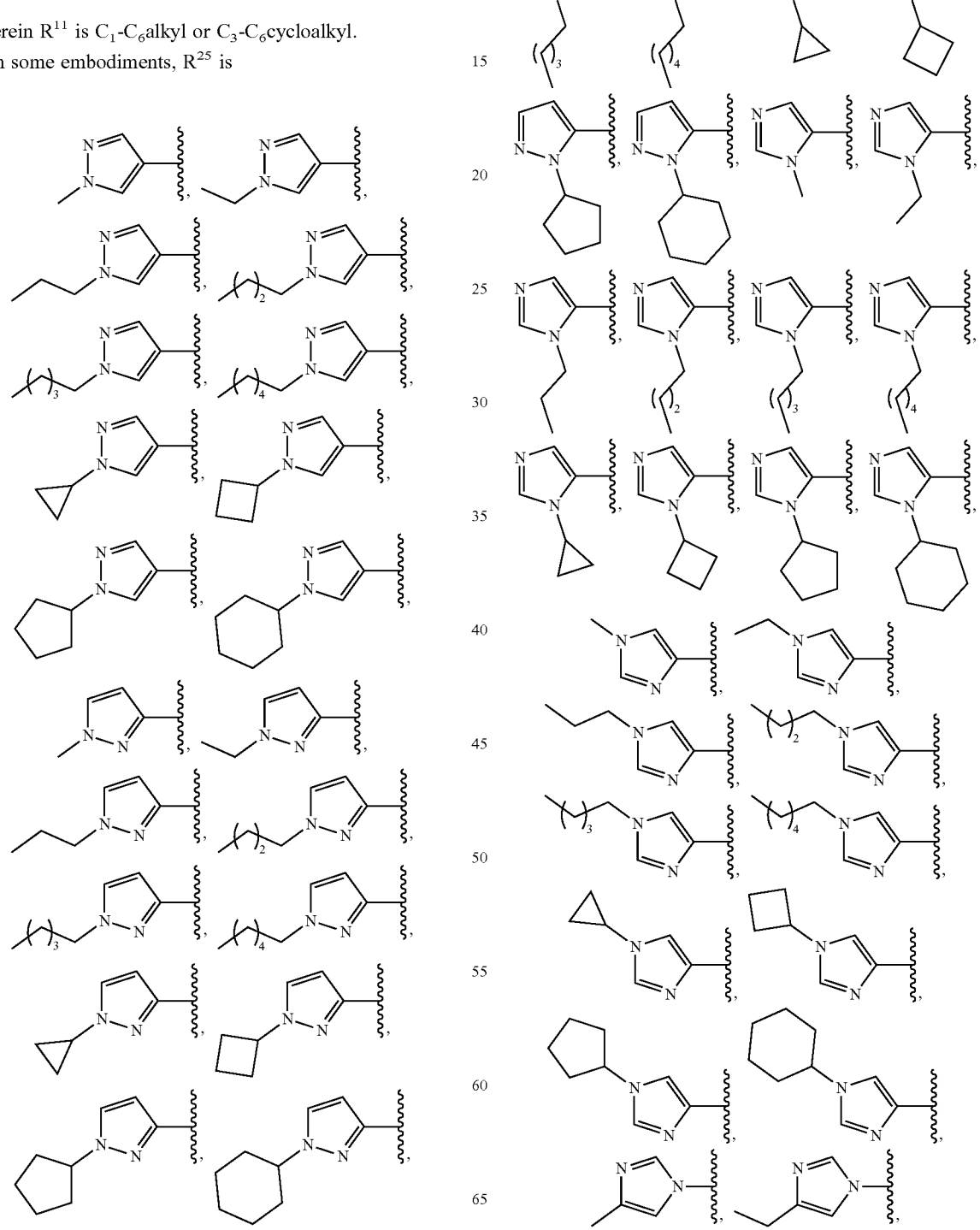

-continued

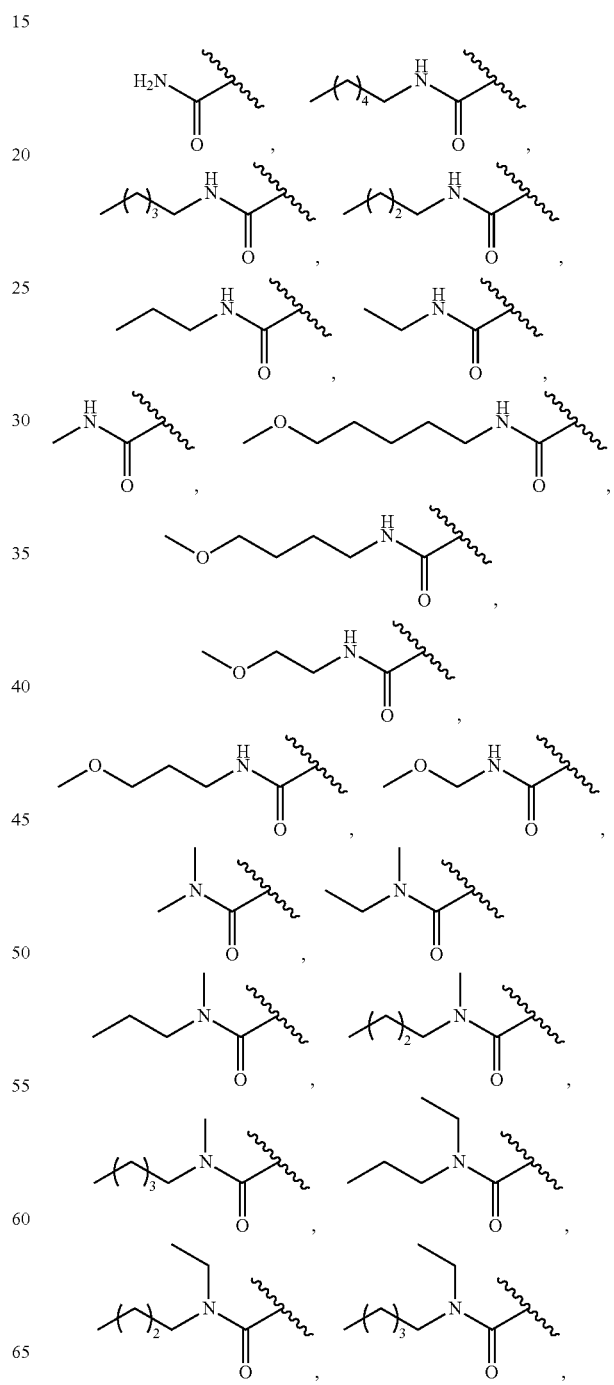

imidazole, thiazole, and pyridine are optionally substituted with one or two substituents selected from the group consisting of halo, $C_{1-6}$alkyl, and $C_{3-8}$cycloalkyl.

In some embodiments, $R^{25}$ is selected from a group consisting of halogen, $—OR^6$, $—N(R^6)_2$, $C_{1-6}$alkyl, and unsubstituted pyridine.

In some embodiments, $R^{25}$ is $—C(=O)N(R^6)_2$ and each $R^6$ is independently selected from the group consisting of hydrogen, $C_1$-$C_6$alkyl, $—C_1$-$C_6$alkyl-O—$C_1$-$C_6$alkyl, $—C_1$-$C_6$alkyl-$C_{2-9}$heterocycle, $—C_1$-$C_6$alkyl-$C_{2-9}$heteroaryl, $C_3$-$C_8$cycloalkyl, and $C_{2-9}$heterocycle.

In some embodiments, $R^{25}$ is

In some embodiments, $R^{25}$ is

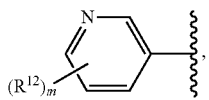

wherein $R^{12}$ is halo, $C_1$-$C_6$alkyl, or $C_3$-$C_6$cycloalkyl; and m is 1 or 2.

In some embodiments, $R^{25}$ is selected from a group consisting of unsubstituted pyrazole, unsubstituted imidazole, unsubstituted thiazole, and unsubstituted pyridine.

In some embodiments, $R^{25}$ is selected from a group consisting of pyrimidine, pyrazine, and pyridazine; wherein pyrimidine, pyrazine, and pyridazine are optionally substituted with one or two substituents selected from the group consisting of halo, $C_{1-6}$alkyl, and $C_{3-8}$cycloalkyl.

In some embodiments, $R^{25}$ is selected from a group consisting of halogen, $—OR^6$, $—N(R^6)_2$, $C_{1-6}$alkyl, pyrazole, imidazole, thiazole, and pyridine; wherein pyrazole, -continued

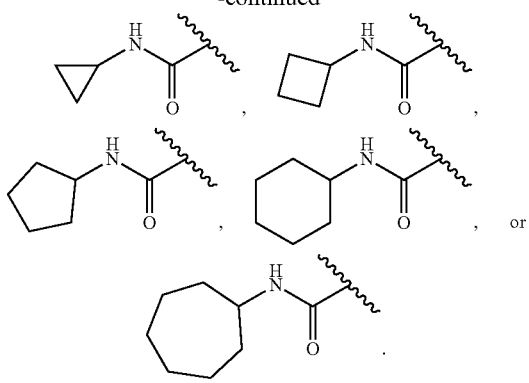

In some embodiments, $R^{25}$ is

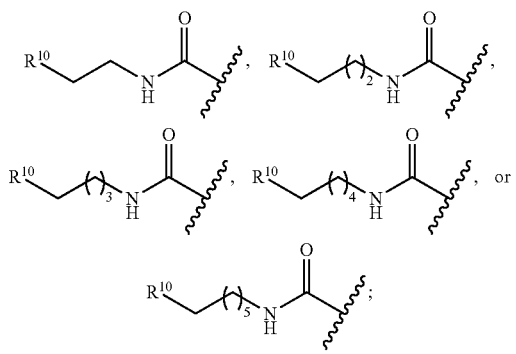

wherein $R^{10}$ is a heteroaryl.

In some embodiments, $R^{25}$ is —C(=O)N($R^6$)$_2$ and two $R^6$ on the same heteroatom are taken together with that heteroatom to which they are attached to form a $C_{2-9}$heterocycle or a $C_{2-9}$heteroaryl, wherein $C_{2-9}$heterocycle or $C_{2-9}$heteroaryl are optionally substituted with one, two, or three substituents selected from the group consisting of halo, —OR$^8$, —SR$^8$, —N(R$^8$)$_2$, —C$_{1-6}$alkyl, —O—C$_{1-6}$alkyl, —C(=O)R$^{14}$, —C(=O)OR$^{13}$, and —N(R$^{13}$)C(=O)R$^{14}$.

In some embodiments, $R^{25}$ is

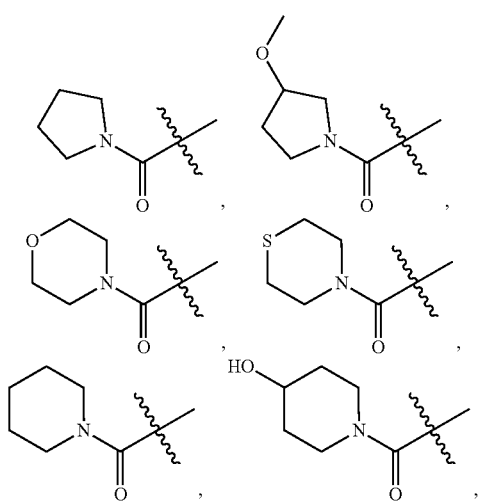

-continued

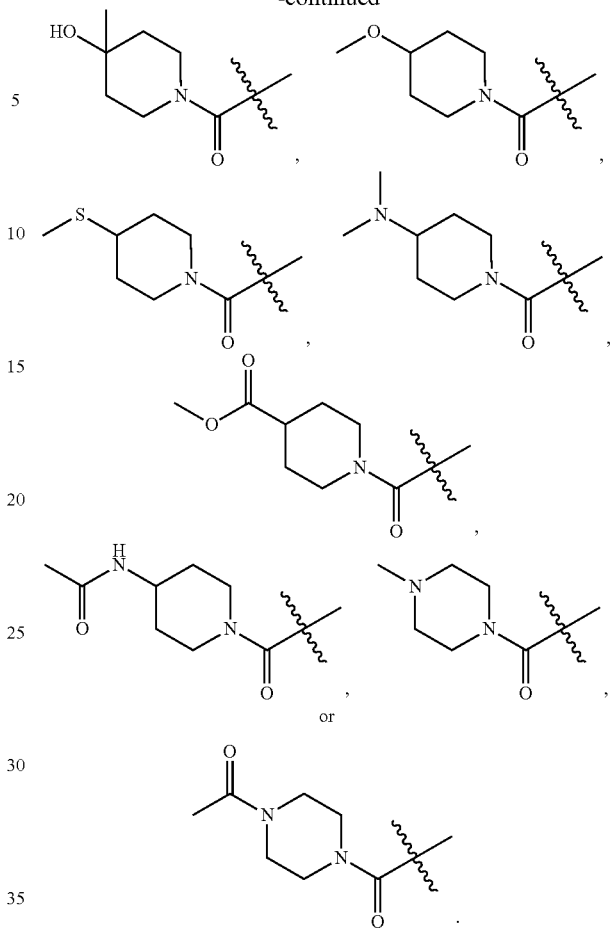

In some embodiments, $R^{25}$ is —C(=O)N($R^6$)$_2$ and two $R^6$ are taken together with that heteroatom to which they are attached to form a $C_{2-9}$heterocycle or a $C_{2-9}$heteroaryl.

In some embodiments, $R^{25}$ is

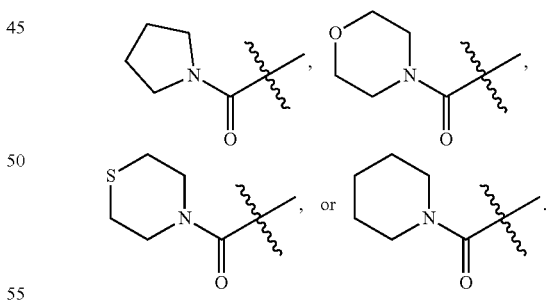

In some embodiments, $R^{25}$ is —OR$^6$ and $R^6$ is selected from the group consisting of $C_1$-$C_6$alkyl, —$C_1$-$C_6$alkyl-O—$C_1$-$C_6$alkyl, and —$C_1$-$C_6$alkyl-$C_{2-9}$heterocycle.

In some embodiments, n is 0. In some embodiments, n is 1. In some embodiments, n is 2.

In some embodiments, Z is C(R$^9$)$_2$. In some embodiments, Z is C(R$^9$)$_2$ and each R$^9$ is H.

In some embodiments, Z is N(R$^8$). In some embodiments, Z is N(R$^8$) and each R$^8$ is H. In some embodiments, Z is N(R$^8$) and each R$^8$ is $C_1$-$C_6$alkyl.

In some embodiments,

is

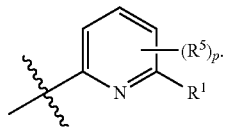

In some embodiments, p is 0.
In some embodiments,

is

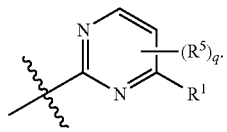

In some embodiments,

is

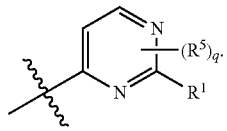

In some embodiments, q is 0.
In some embodiments, R¹ is

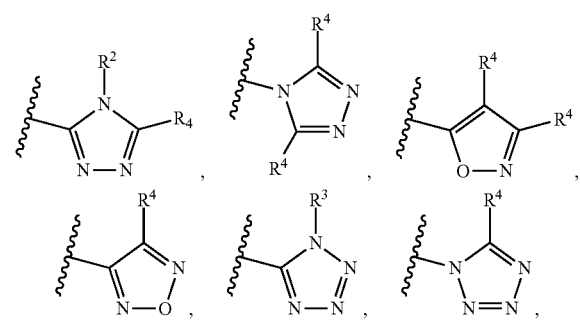

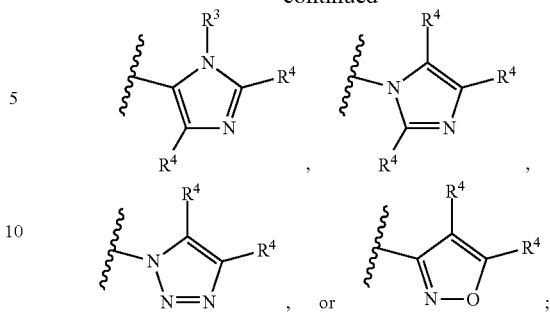

wherein $R^2$ is $C_{3-6}$cycloalkyl; $R^3$ is selected from a group consisting of hydrogen $C_{1-6}$alkyl and $C_{3-6}$cycloalkyl; each $R^4$ is independently selected from a group consisting of hydrogen, halogen, $C_{1-6}$ alkyl, and $C_{3-6}$cycloalkyl; or one $R^4$ and another $R^2$, $R^3$, or $R^4$, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^1$ is

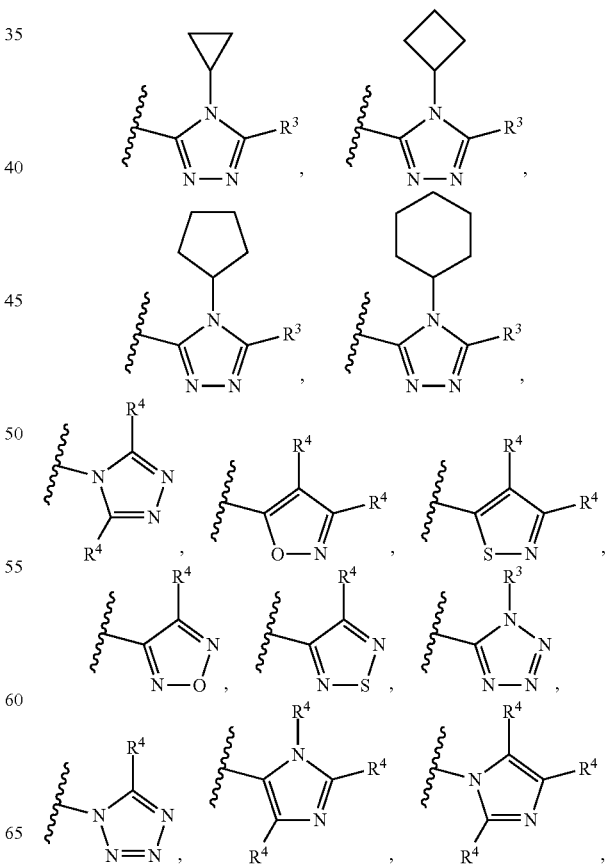

-continued

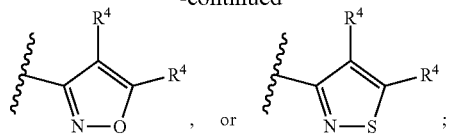, or 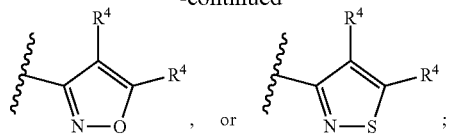;

wherein $R^3$ is selected from a group consisting of $C_{1-6}$alkyl and $C_{3-6}$cycloalkyl; and each $R^4$ is independently selected from a group consisting of hydrogen, halogen, $C_{1-6}$alkyl, and $C_{3-6}$cycloalkyl.

In some embodiments, $R^1$ is

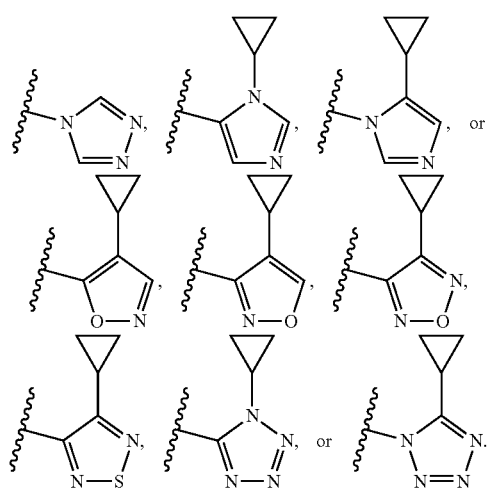

In some embodiments, $R^1$ is

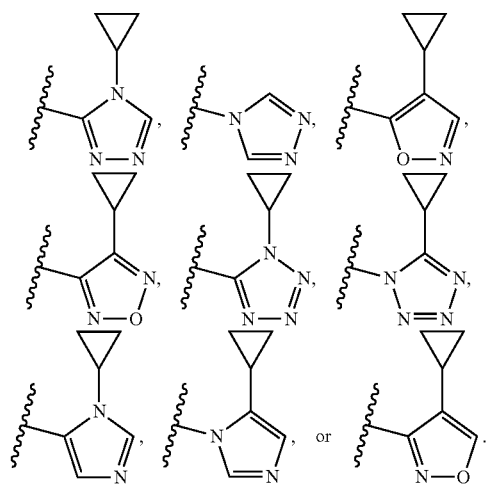

In some embodiments, $R^1$ is

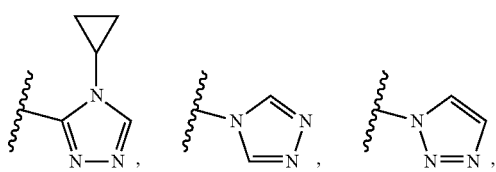

-continued

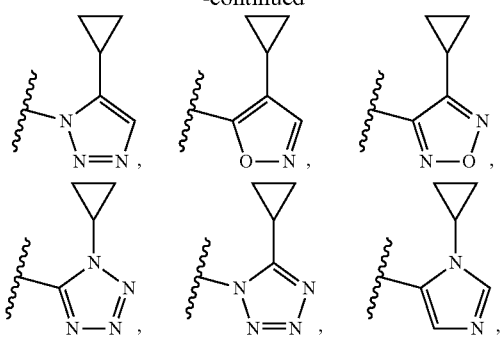

In some embodiments, $R^1$ is

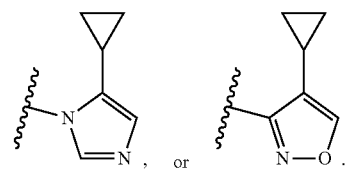

In some embodiments, $R^1$ is

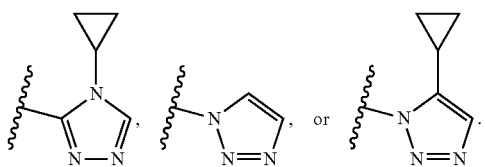

In some embodiments, $R^1$ is

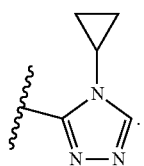 [SMILES: *c1nncn1C1CC1]

In some embodiments, $R^1$ is

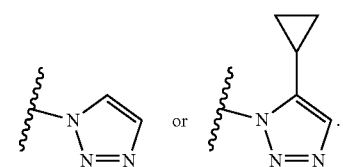 [SMILES: *n1ccnn1 ; *n1nncc1C1CC1]

In some embodiments, $R^1$ is

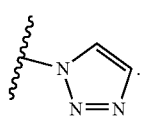

In some embodiments, $R^1$ is

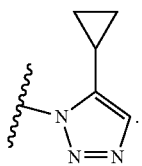 [SMILES: *n1nncc1C1CC1]

In some embodiments, $R^1$ is

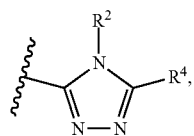

wherein $R^2$ and $R^4$, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments, $R^1$ is

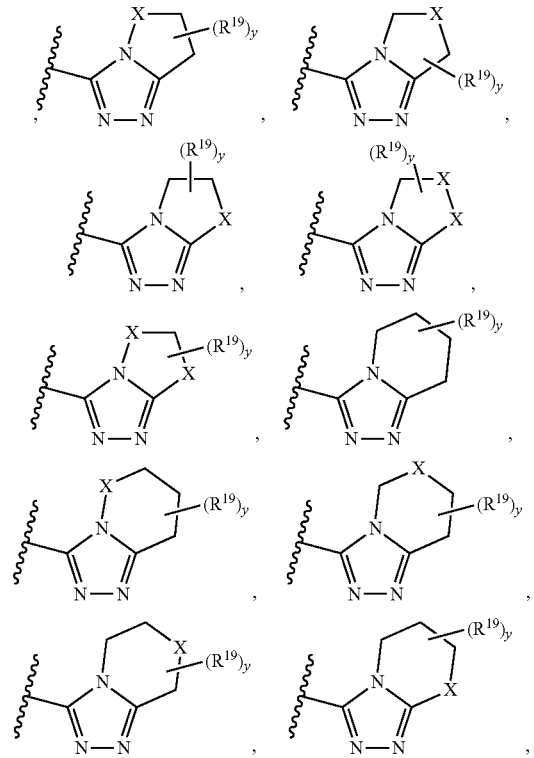

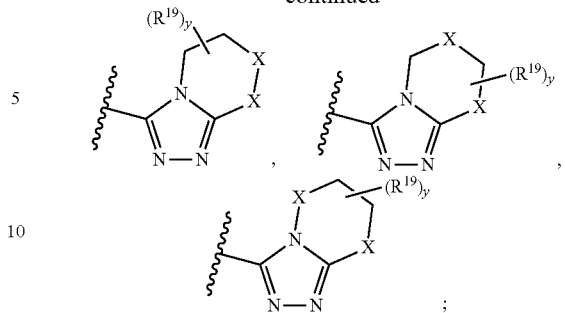

wherein X is O, N or S; each $R^{19}$ is independently halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$; and y is 0, 1, 2, 3 or 4.

In some embodiments, $R^1$ is

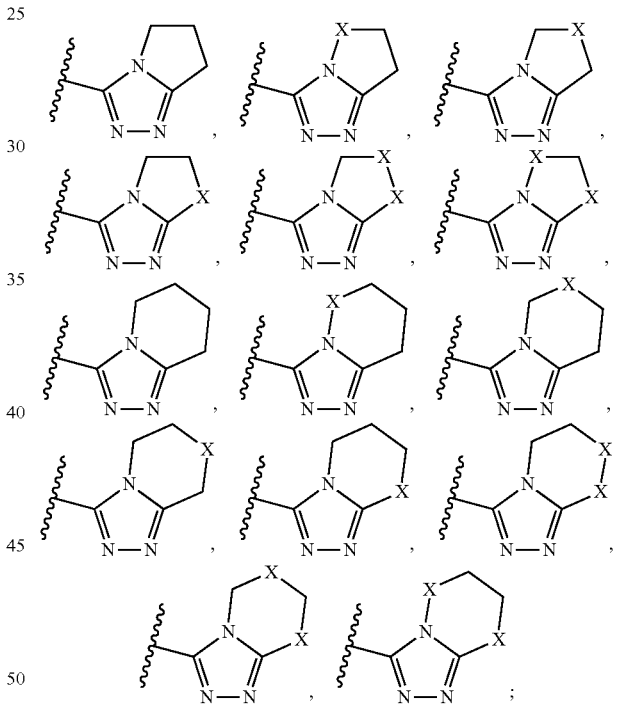

wherein X is O, N or S.

In some embodiments, $R^1$ is

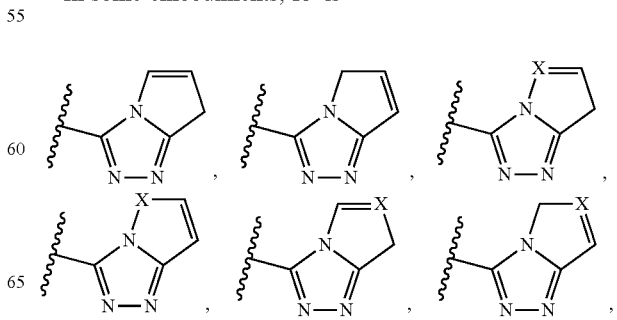

-continued

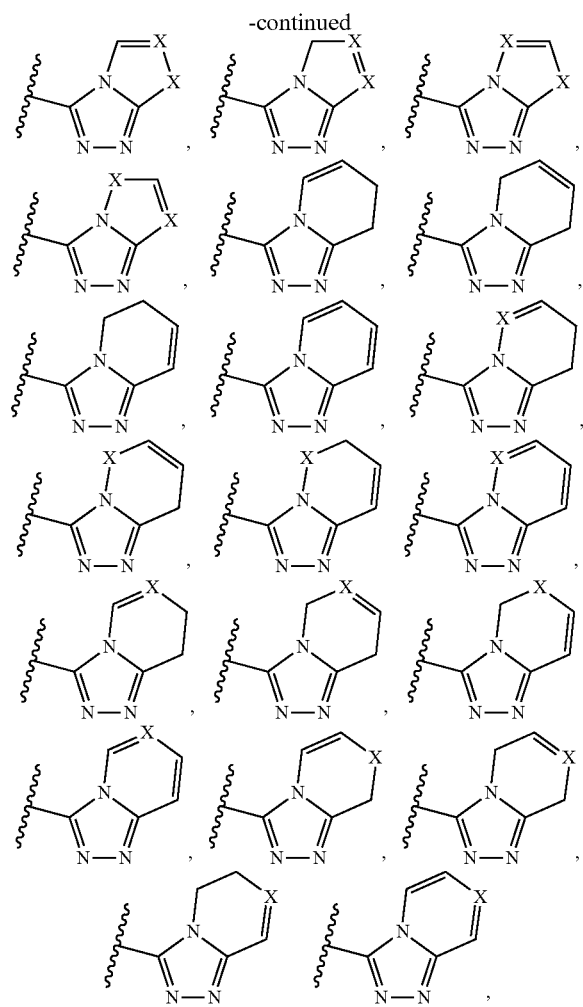

wherein X is N.
In some embodiments, R¹ is

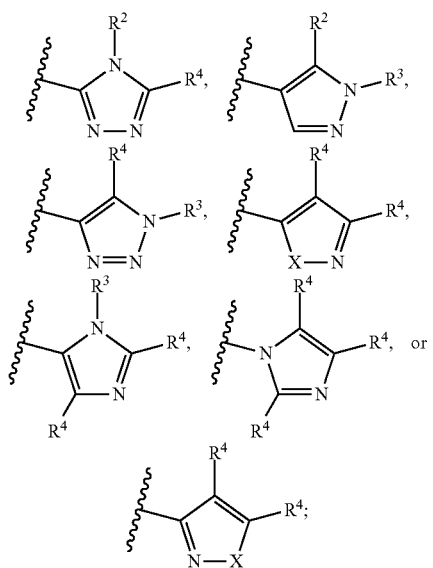

X is O or S; and
one R⁴ and another R², R³, or R⁴, together with the atoms to which they are attached, form a 5- or 6-membered ring that is optionally containing one or two heteroatoms selected from O, N, and S; wherein the 5- or 6-membered ring is saturated, unsaturated or aromatic; and wherein the 5- or 6-membered ring is optionally substituted with one, two, or three substituents selected from the group consisting of halo, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³.

In some embodiments, R¹ is

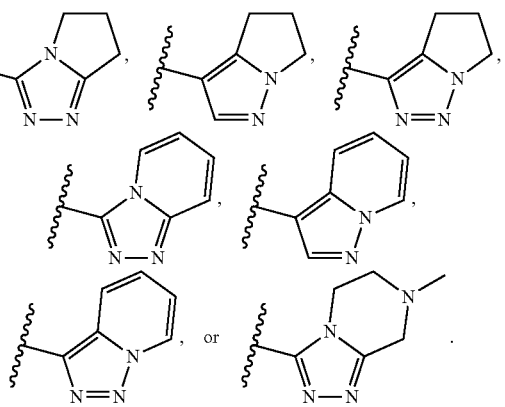

In some embodiments, R¹ is

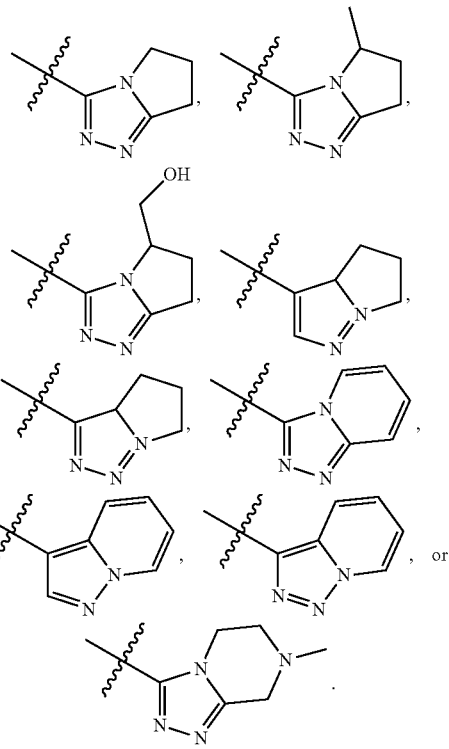

In one aspect, presented herein are pharmaceutical compositions comprising a compound of Formula I, Formula II, or Formula III, or a pharmaceutically acceptable salt or solvate thereof, and at least one pharmaceutically acceptable excipient.

In one aspect, presented herein are methods of treating non-alcoholic steatohepatitis in a subject in need thereof, comprising administering to the subject a therapeutically effective amount of a compound of Formula I, Formula II, or Formula III, or a pharmaceutically acceptable salt or solvate thereof. In some embodiments is a method of treating non-alcoholic steatohepatitis in a subject in need thereof, comprising administering to the subject a therapeutically effective amount of a compound of Formula I, or a pharmaceutically acceptable salt or solvate thereof. In some embodiments is a method of treating non-alcoholic steatohepatitis in a subject in need thereof, comprising administering to the subject a therapeutically effective amount of a compound of Formula II, or a pharmaceutically acceptable salt or solvate thereof. In some embodiments is a method of treating non-alcoholic steatohepatitis in a subject in need thereof, comprising administering to the subject a therapeutically effective amount of a compound of Formula III, or a pharmaceutically acceptable salt or solvate thereof.

In some embodiments, the compound disclosed herein is a compound of any one of Compounds 1-89, or a pharmaceutically acceptable salt or solvate thereof.

In one aspect, the structures of the compounds described herein are selected from Table 1.

TABLE 1

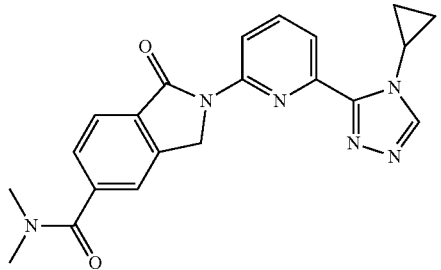 [SMILES: CN(C)C(=O)c1ccc2c(c1)CN(c1cccc(-c3nncn3C3CC3)n1)C2=O]

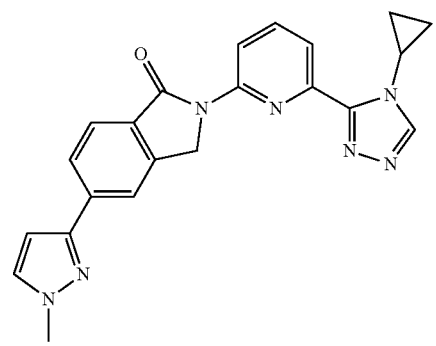 [SMILES: Cn1ccc(-c2ccc3c(c2)CN(c2cccc(-c4nncn4C4CC4)n2)C3=O)n1]

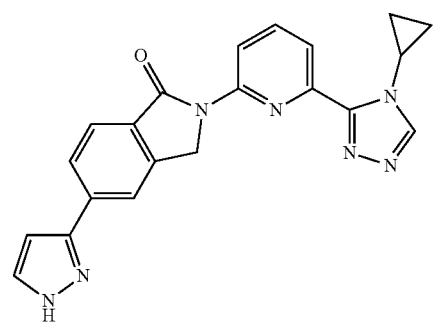 [SMILES: O=C1c2ccc(-c3cc[nH]n3)cc2CN1c1cccc(-c2nncn2C2CC2)n1]

TABLE 1-continued

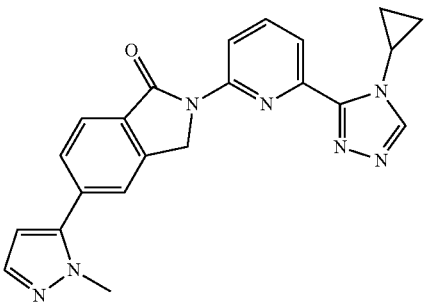 [SMILES: Cn1nccc1-c1ccc2c(c1)CN(c1cccc(-c3nncn3C3CC3)n1)C2=O]

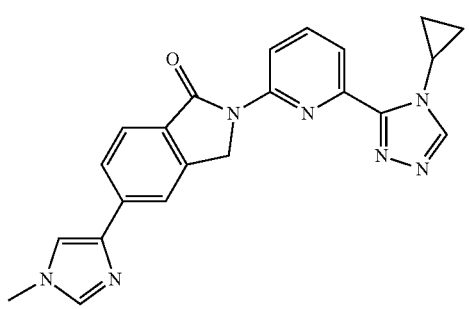 [SMILES: Cn1cnc(-c2ccc3c(c2)CN(c2cccc(-c4nncn4C4CC4)n2)C3=O)c1]

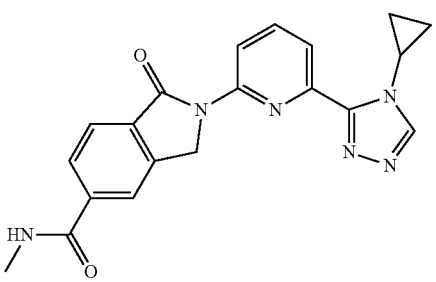 [SMILES: CNC(=O)c1ccc2c(c1)CN(c1cccc(-c3nncn3C3CC3)n1)C2=O]

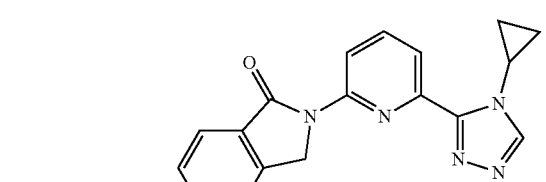

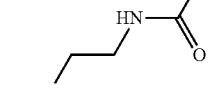

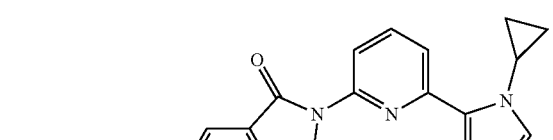

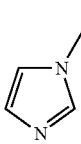

TABLE 1-continued
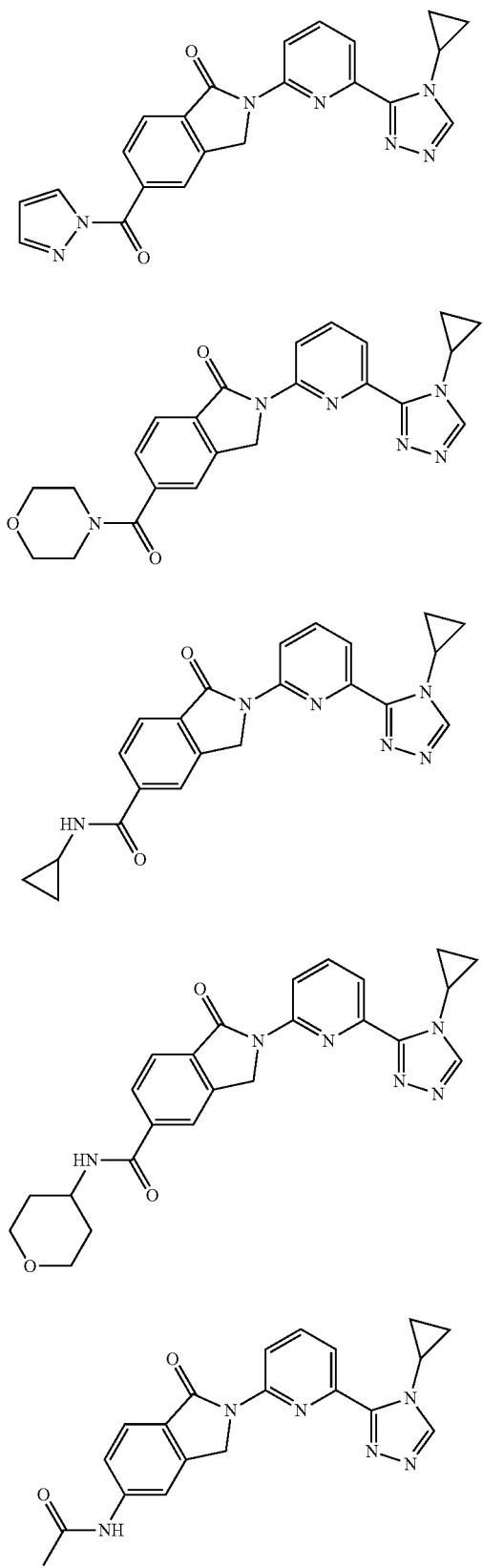
TABLE 1-continued
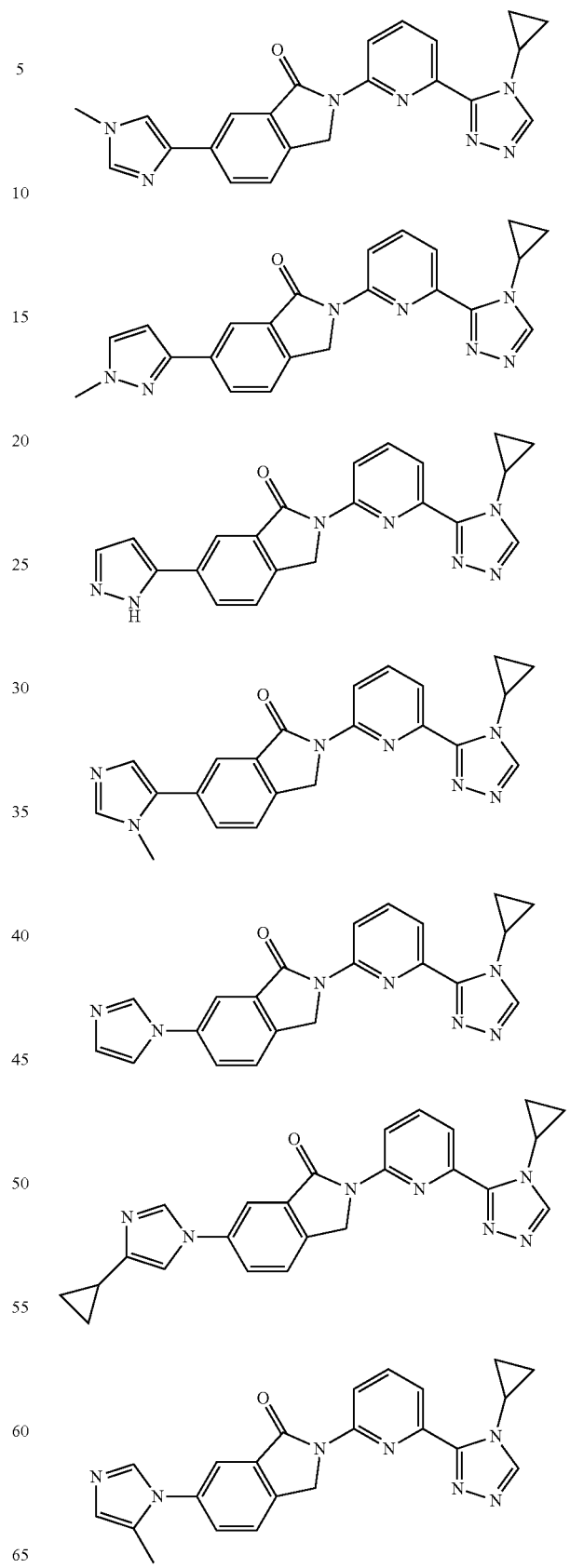

TABLE 1-continued

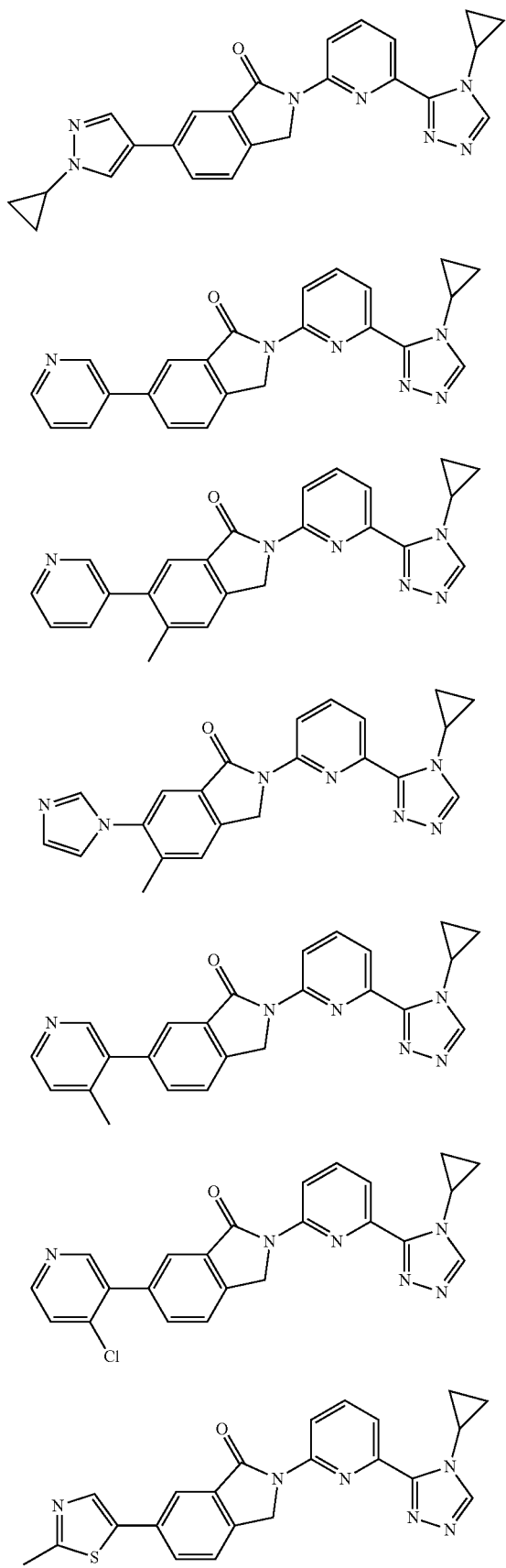

TABLE 1-continued

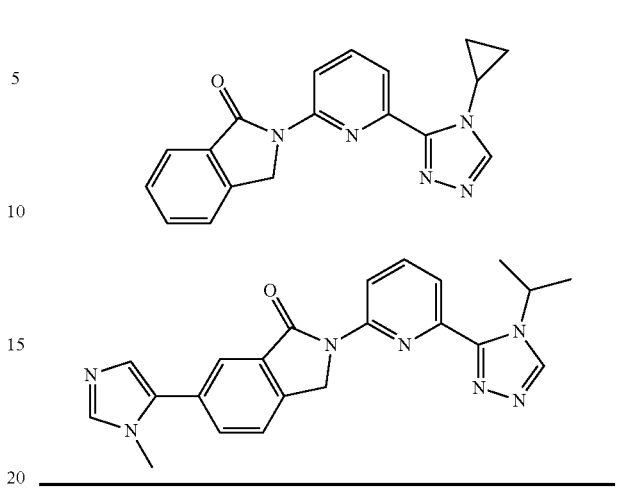

Synthesis of Compounds

Compounds described herein are synthesized using standard synthetic techniques or using methods known in the art in combination with methods described herein. In addition, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, a compound, such as compound 1, is prepared according to the route as shown in Scheme 1.

Scheme 1:

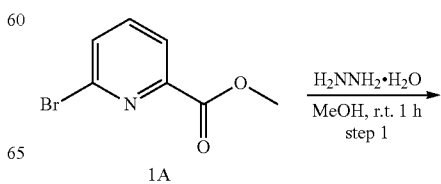

1A

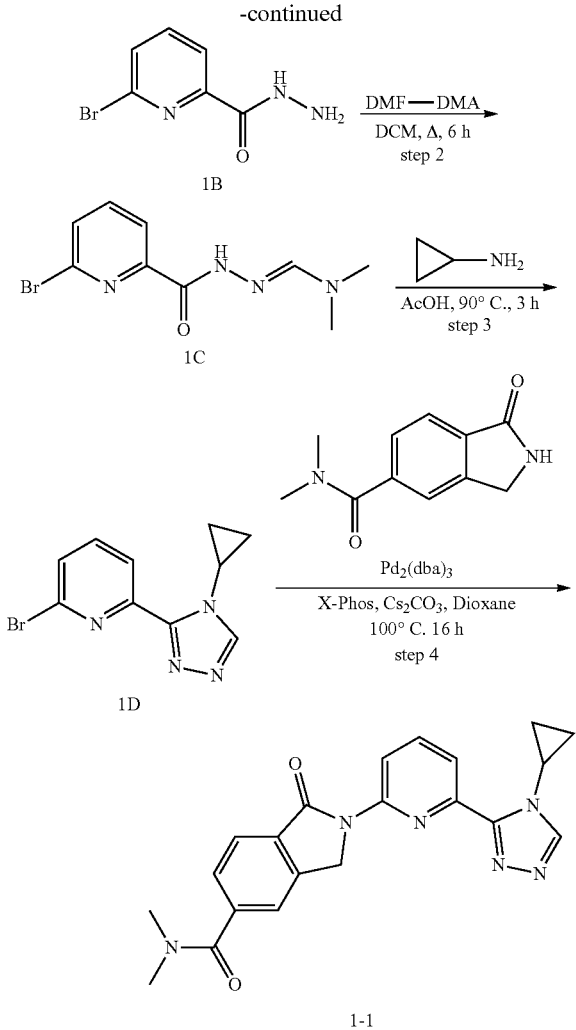

In some embodiments, a phenolic compound, such as 1A, is hydrazinated with a suitable hydrazination reagent, to provide a hydrazide phenolic compound, such as 1B. In some embodiments, the suitable hydrazination reagent is hydrazine hydrate. In some embodiments, the hydrazide phenolic compound, such as 1B, is coupled with an appropriate formamide compound to provide a coupled hydrazide phenolic compound, such as 1C. In some embodiments, the appropriate formamide compound is dimethylformamide dimethylacetal. In some embodiments, the coupled hydrazide phenolic compound, such as 1C, is subjected under suitable reaction conditions to provide a polycyclic compound, such as 1D. In some embodiments, the suitable reaction conditions include treatment with acetic acid. In some embodiments, the polycyclic compound is subjected to suitable reaction conditions to provide a compound, such as compounds 1.

In one aspect, compounds described herein are synthesized as outlined in the Examples. Throughout the specification, groups and substituents thereof are chosen by one skilled in the field to provide stable moieties and compounds.

Further Forms of Compounds

In one aspect, compounds described herein possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis-, trans-, syn-, anti-, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

"Pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein with acids.

Pharmaceutically acceptable salts are also obtained by reacting a compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I, Formula II, or Formula III, or a pharmaceutically acceptable salt thereof, and at least one pharmaceutically acceptable inactive ingredient. In some embodiments is a pharmaceutical composition that includes a compound of Formula I, or a pharmaceutically acceptable salt thereof, and at least one pharmaceutically acceptable excipient. In some embodiments is a pharmaceutical composition that includes a compound of Formula II, or a pharmaceutically acceptable salt thereof, and at least one pharmaceutically acceptable excipient. In some embodiments is a pharmaceutical composition that includes a compound of Formula III, or a pharmaceutically acceptable salt thereof, and at least one pharmaceutically acceptable excipient. In some embodiments, the compounds described herein are administered as pharmaceutical compositions in which a compound of Formula I, Formula II, or Formula III, or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I, Formula II, or Formula III, or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula I, Formula II, or Formula III, or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I, Formula II, or Formula III, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula I, Formula II, or Formula III, or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral dosage forms are prepared by mixing a compound of Formula I, Formula II, or Formula III, or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula I, Formula II, or Formula III, or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula I, Formula II, or Formula III, or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula I, Formula II, or Formula III, or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula I, Formula II, or Formula III, or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula I, Formula II, or Formula III, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula I, Formula II, or Formula III, or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula I, Formula II, or Formula III, or a pharmaceutically acceptable salt thereof, are prepared as transdermal dosage forms. In one embodiment, the transdermal formulations described herein include at least three components: (1) a formulation of a compound of Formula I, Formula II, or Formula III, or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive.

In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula I, Formula II, or Formula III, or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multidose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Combination Treatments

In certain instances, it is appropriate to administer at least one compound of Formula I, Formula II, or Formula III, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula I, Formula II, or Formula III, or a pharmaceutically acceptable salt thereof, is co-administered with a second therapeutic agent, wherein the compound of Formula I, Formula II, or Formula III, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like.

Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula I, Formula II, or Formula III, or a pharmaceutically acceptable salt thereof, is initiated prior to, during, or after treatment with a second agent, and continues until any time during treatment with the second agent or after termination of treatment with the second agent. It also includes treatments in which a compound of Formula I, Formula II, or Formula III, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula I, Formula II, or Formula III, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

For example, in specific embodiments, a compound described herein or a formulation containing the compound is administered for at least 2 weeks, about 1 month to about 5 years.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data. Proton nuclear magnetic resonance spectra were obtained on a Bruker 400 MHz spectrometer. Spectra are given in ppm and coupling constants, J values, are reported in hertz (Hz). Mass spectra analyses were performed on Agilent 6120 Mass Spectrometer in ESI or APCI mode when appropriate. Some abbreviations used herein are as follows:

DCM: dichloromethane
DMAP: 4-dimethylaminopyridine
DMF: dimethyl formamide
DMF-DMA: N,N-dimethylformamide dimethyl acetal
EDCI: 1-ethyl-3-(3-dimethylaminopropyl) carbodiimide
EtOAc: ethyl acetate
EtOH: ethanol
MeOH: methanol
PE: petroleum ether.

Example 1: Preparation of 2-(6-(4-Cyclopropyl-4H-1,2,4-triazol-3-yl)pyridin-2-yl)isoindolin-1-one (compound 1)

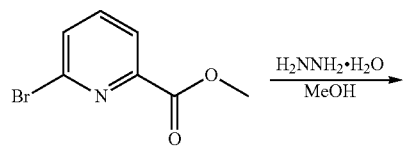

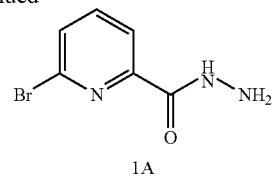

1A

Hydrazine hydrate (1.16 mg, 23.1 mmol, 10 eq) was added to a solution of methyl 6-bromopicolinate (500 mg, 2.31 mmol, 1.0 eq) in MeOH (15 mL) at room temperature, then the reaction was stirred for 1 hour. The reaction mixture was concentrated under reduced pressure to give the desired hydrazide product 1A which was used without further purification: $^1$H NMR (400 MHz, CDCl$_3$) δ 8.84 (s, 1H), 8.12 (d, J=7.5 Hz, 1H), 7.71 (t, J=7.7 Hz, 1H), 7.62 (d, J=7.9 Hz, 1H), 4.10 (br s, 2H).

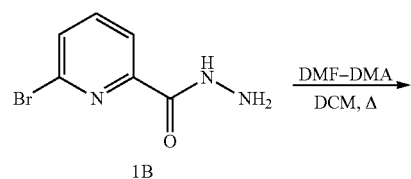

1B

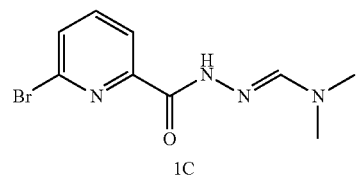

1C

A solution of 1B (500 mg, 2.31 mmol, 1.0 eq) and DMF-DMA (1.38 g, 11.6 mmol, 5.0 eq) in DCM (10 mL) was refluxed for 6 hours. After cooling, the reaction mixture was concentrated under reduced pressure to give the desired product 1C which was used in the subsequent step without any further purification.

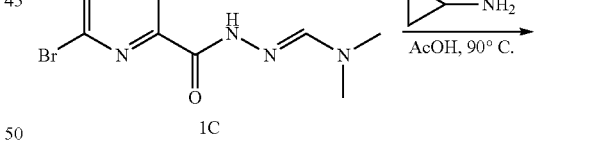

1C

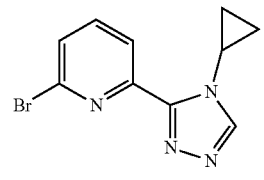

1D

Cyclopropylamine (396 mg, 6.93 mmol, 3.0 eq) was added to a stirred solution of 1C (630 mg, 2.31 mmol, 1.0 equiv) in glacial acetic acid (15 ml) at room temperature. After stirring at 90° C. for 3 hours, the reaction mixture was allowed to cool to room temperature. The solvent was removed under reduced pressure and the residue was purified by column chromatography (30%-100% EtOAc in PE) to give 500 mg of 1D (>85% purity). The partially purified material was then used directly in the next step. ¹H NMR (400 MHz, CDCl₃) δ 8.29 (s, 1H), 8.24 (d, J 7.7 Hz, 1H), 7.70 (t, J 7.8 Hz, 1H), 7.55 (d, J 7.9 Hz, 1H), 3.91-3.83 (m, 1H), 1.20 (q, J 6.9 Hz, 2H), 0.93 (q, J 6.6 Hz, 2H).

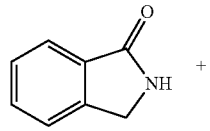

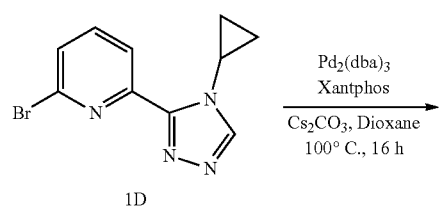

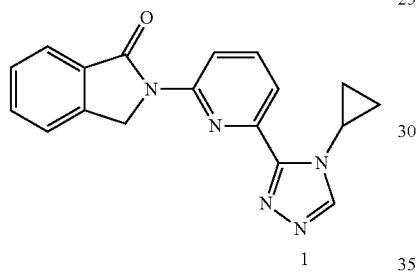

A mixture of isoindolin-1-one (150 mg, 1.13 mmol), 1D (300 mg, 1.13 mmol), Pd₂(dba)₃ (31 mg, 0.034 mmol), Xantphos (20 mg, 0.034 mmol) and Cs₂CO₃ (443 mg, 1.36 mmol) in dioxane (25 mL) was heated to 100° C. for 16 hours under a nitrogen atmosphere. The reaction mixture was allowed to cool to room temperature, filtered and the resulting filtrate was concentrated under reduced pressure. The residue was purified by silica gel chromatography (1-5% MeOH in DCM) to afford compound 1 (270 mg, 75% yield) as an off-white solid: ¹H NMR (400 MHz DMSO-d₆) δ 8.71 (s, 1H), 8.64 (d, J=8.4 Hz, 1H), 8.07 (t, J=8 Hz, 1H), 7.88-7.83 (m, 2H), 7.72 (d, J=8.4 Hz, 2H), 7.59-7.53 (m, 1H), 5.18 (s, 2H), 4.12-4.07 (m, 1H), 1.14-1.09 (m, 2H), 1.0-0.95 (m, 2H); ESI m/z 318.1[M+1]⁺.

Example 2: Preparation of 2-(6-(4-Cyclopropyl-4H-1,2,4-triazol-3-yl)pyridin-2-yl)-N,N-dimethyl-1-oxoisoindoline-5-carboxamide (compound 2)

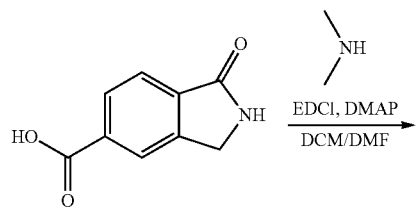

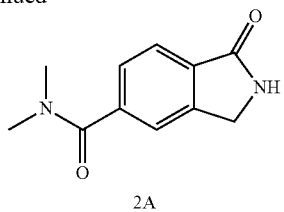

A stirred mixture of 1-oxoisoindoline-5-carboxylic acid (200 mg, 1.13 mmol, 1.0 eq), dimethylamine hydrochloride (138 mg, 1.69 mmol, 1.5 eq), EDCI (324 mg, 1.69 mmol, 1.5 eq), DMAP (276 mg, 2.26 mmol, 2.0 eq) in DMF (20 mL) and DCM (20 mL) was stirred at room temperature overnight under a nitrogen atmosphere. The reaction mixture was concentrated under reduced pressure and purified by silica gel chromatography (30%-100% EtOAc in PE) to give 2A (140 mg, 61% yield): ¹H NMR (400 MHz, CDCl₃) δ 7.91 (d, J=7.8 Hz, 1H), 7.55 (s, 1H), 7.50 (d, J=7.9 Hz, 1H), 6.68 (s, 1H), 4.49 (s, 2H), 3.06 (d, J=65.0 Hz, 6H).

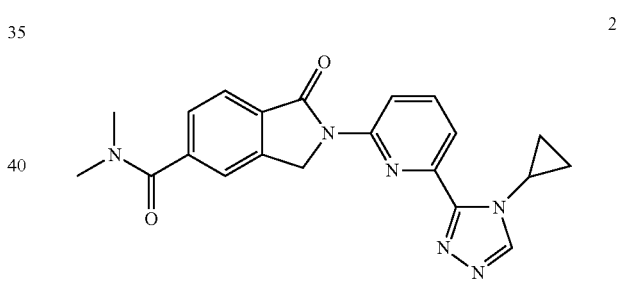

Compound 2 was synthesized according to the procedure for compound 1 substituting intermediate 2A in place of isoindolin-1-one to give the product in 43% yield: ¹H NMR (400 MHz, CDCl₃) δ 8.76 (d, J=8.1 Hz, 1H), 8.37 (s, 1H), 8.03-7.89 (m, 3H), 7.63 (s, 1H), 7.54 (d, J=7.8 Hz, 1H), 5.11 (s, 2H), 4.02-3.91 (m, 1H), 3.07 (d, J=59.0 Hz, 6H), 1.14 (d, J=6.7 Hz, 2H), 0.98 (d, J=2.8 Hz, 2H); ESI m/z 389.2[M+1]⁺.

Compounds 3-25 in Table 2 were synthesized according to the procedure for compound 2 substituting the appropriate amine in place of dimethylamine.

TABLE 2

| Compound | Name | Structure | Characterization |
|---|---|---|---|
| 3 | 2-(6-(4-cyclopropyl-4H-1,2,4-triazol-3-yl)pyridin-2-yl)-N-methyl-1-oxoisoindoline-5-carboxamide | 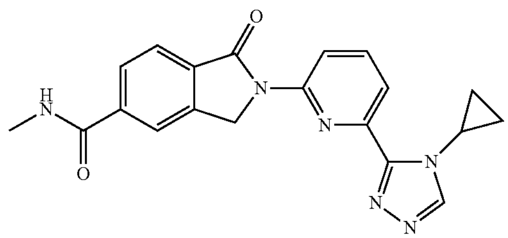 [SMILES: CNC(=O)c1ccc2c(c1)CN(c1cccc(-c3nncn3C3CC3)n1)C2=O] | $^1$H NMR (400 MHz. DMSO-d$_6$) δ 8.72 (s, 1H), 8.68 (d, J = 4.8 Hz, 1H), 8.64 (d, J = 8 Hz, 1H), 8.17 (s, 1H), 8.08 (t, J = 8 Hz, 1H), 7.99 (d, J = 8 Hz, 1H, 7.91 (d, J = 7.6 Hz, 1H), 5.23 (s, 2H), 4.14-4.09 (m, 1H), 2.83 (d, J = 4.4 Hz, 2H), 1.16-1.11 (m, 2H), 1.02-0.96 (m, 2H); ESI m/z 375.1[M + 1]$^+$ |
| 4 | 2-(6-(4-cyclopropyl-4H-1,2,4-triazol-3-yl)pyridin-2-yl)-N-(2-methoxyethyl)-1-oxoisoindoline-5-carboxamide | 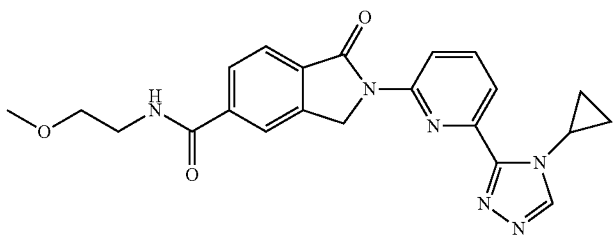 [SMILES: COCCNC(=O)c1ccc2c(c1)CN(c1cccc(-c3nncn3C3CC3)n1)C2=O] | $^1$H NMR (400 MHz, DMSO-d$_6$) δ 8.77 (s, 2H), 8.65 (d, J = 8 Hz, 1H), 8.19 (s, 1H), 8.11-8.07 (m, 1H), 8.01 (d, J = 7.6 Hz, 1H), 7.91 (d, J = 7.6 Hz, 2H), 5.23 (s, 2H), 4.12 (br, 1H), 3.48 (s, 4H), 3.28 (s, 3H) 1.14 (d, J = 6 Hz, 2H), 1.0 (s, 2H); ESI m/z 418.9[M + 1]$^+$ |
| 5 | N-(2-(1H-imidazol-1-yl)ethyl)-2-(6-(4-cyclopropyl-4H-1,2,4-triazol-3-yl)pyridin-2-yl)-1-oxoisoindoline-5-carboxamide | 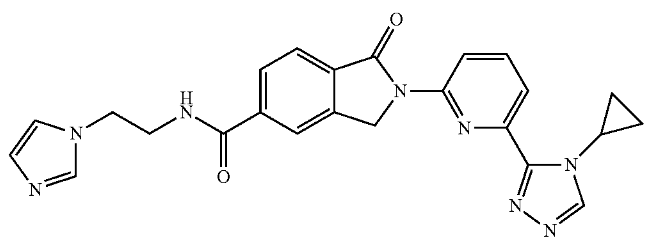 [SMILES: O=C(NCCn1ccnc1)c1ccc2c(c1)CN(c1cccc(-c3nncn3C3CC3)n1)C2=O] | $^1$H NMR (400 MHz, DMSO-d$_6$) δ 9.16 (s, 1H), 8.95-8.92 (m, 1H), 8.78 (s, 1H), 8.65 (d, J = 8.4 Hz. 1H), 8.13-8.08 (m, 2H), 7.96-7.91 (m, 3H), 7.79 (s, 1H), 7.67 (s, 1H), 5.22 (s, 2H), 4.41 (s, 2H), 4.12-4.10 (m, 2H), 3.77-3.76 (m, 2H), 1.13-1.12 (m, 2H), 1.10 (s, 2H); ESI m/z 454.9 [M + 1]$^+$ |
| 6 | 2-(6-(4-cyclopropyl-4H-1,2,4-triazol-3-yl)pyridin-2-yl)-5-(1H-pyrazole-1-carbonyl)isoindolin-1-one | 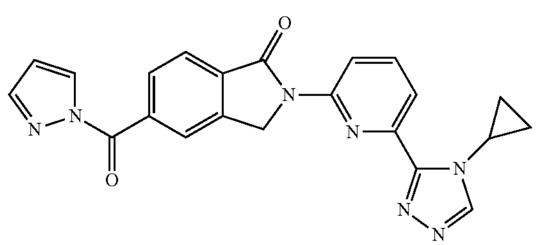 [SMILES: O=C1c2ccc(C(=O)n3cccn3)cc2CN1c1cccc(-c2nncn2C2CC2)n1] | $^1$H NMR (400 MHz, DMSO-d$_6$) δ 8.72 (s, 1H), 8.67-8.65 (m, 2H), 8.34 (s, 1H), 8.5 (d, J = 8 Hz, 1H), 8.10 (t, J = 8 Hz, 1H), 8.01 (t, J = 8 Hz, 2H), 7.92 (d, J = 7.6 Hz, 1H), 6.77-6.76 (m, 1H), 5.23 (s, 2H), 4.15-4.10 (m, 1H), 1.16-1.11 (m, 2H), 1.0-0.96 (m, 2H); ESI m/z 412.1 [M + 1]$^+$ |
| 7 | 2-(6-(4-cyclopropyl-4H-1,2,4-triazol-3-yl)pyridin-2-yl)-5-(morpholine-4-carbonyl)isoindolin-1-one | 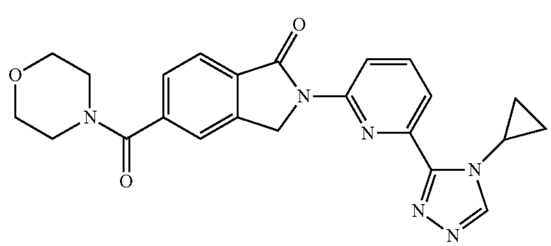 [SMILES: O=C(c1ccc2c(c1)CN(c1cccc(-c3nncn3C3CC3)n1)C2=O)N1CCOCC1] | $^1$H NMR (400 MHz, DMSO-d$_6$) δ 8.71 (s, 1H), 8.64 (d, J = 8 Hz, 1H), 8.08 (t, J = 7.6 Hz, 1H), 7.89 (dd, J = 8 Hz, 2.4 Hz, 2H), 7.76 (s, 1H), 7.57 (d, J = 7.6 Hz, 1H), 5.21 (s. 2H), 4.12-4.06 (m, 1H), 3.66-3.58 (m, 8H), 1.14-1.09 (m, 2H), 1.0-0.96 (m, 2H); ESI m/z 431.1 [M+ 1]$^+$ |
| 8 | N-cyclopropyl-2-(6-(4-cyclopropyl-4H-1,2,4-triazol-3-yl)pyridin-2-yl)-1-oxoisoindoline-5-carboxamide | 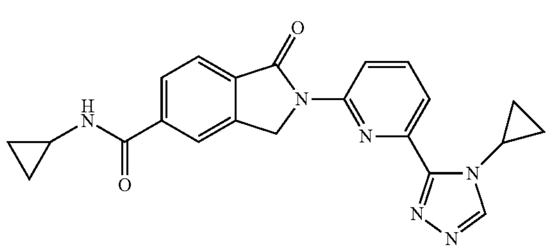 [SMILES: O=C(NC1CC1)c1ccc2c(c1)CN(c1cccc(-c3nncn3C3CC3)n1)C2=O] | $^1$H NMR (400 MHz, DMSO-d$_6$) δ 8.71 (s, 1H), 8.68 (d, J = 4.4 Hz, 1H), 8.63 (d, J = 8.4 Hz, 1H), 8.14 (s, 1H), 8.08 (t, J = 8 Hz, 1H), 7.97 (d, J = 8 Hz, 1H), 7.91-7.88 (m, 2H), 5.21 (s, 2H), 4.13-4.08 (m, 1H), 2.93-2.87 (m, 1H), 1.15-1.10 (m, 2H), 1.01-0.97 (m, 2H), 0.75-0.70 (m, 2H), 0.62-0.58 (m, 2H); ESI m/z 400.2 [M + 1]$^+$ |

TABLE 2-continued

| Compound | Name | Structure | Characterization |
|---|---|---|---|
| 9 | 2-(6-(4-cyclopropyl-4H-1,2,4-triazol-3-yl)pyridin-2-yl)-1-oxo-N-(tetrahydro-2H-pyran-4-yl)isoindoline-5-carboxamide | 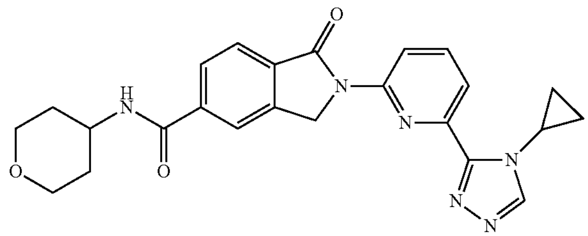 [SMILES: O=C(NC1CCOCC1)c1ccc2c(c1)CN(c1cccc(-c3nncn3C3CC3)n1)C2=O] | $^1$H NMR (400 MHz, DMSO-d$_6$) δ 8.71 (s, 1H), 8.65 (d, J = 8.4 Hz, 1H), 8.57 (d, J = 7.6 Hz, 1H), 8.18 (s, 1H), 8.09 (t, J = 8 Hz, 1H), 8.01 (d, J = 8 Hz, 1H), 7.91 (d, J = 8 Hz, 2H), 5.23 (s, 2H), 4.13-4.03 (m, 2H), 3.90 (d, J = 9.6 Hz, 2H), 3.43-3.38 (m, 2H), 1.80-1.77 (m, 2H), 1.66-1.59 (m, 2H), 1.16-1.12 (m, 2H), 1.02-0.98 (m, 2H); ESI m/z 445.2 [M + 1]$^+$ |
| 10 | 2-(6-(4-cyclopropyl-4H-1,2,4-triazol-3-yl)pyridin-2-yl)-5-(4-methylpiperazine-1-carbonyl)isoindolin-1-one | 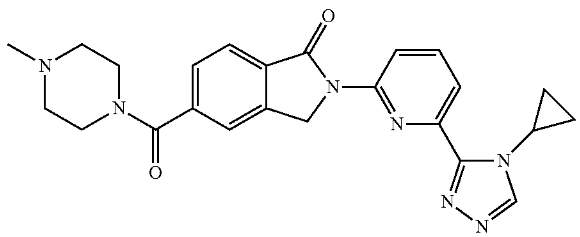 [SMILES: CN1CCN(C(=O)c2ccc3c(c2)CN(c2cccc(-c4nncn4C4CC4)n2)C3=O)CC1] | $^1$H NMR (400 MHz, CDCl$_3$) δ 8.75 (d, J = 8.4 Hz, 1H), 8.24 (s, 1H), 8.00-7.92 (m, 3H), 7.62 (s, 1H), 7.53 (d, J = 8 Hz, 1H), 5.11 (s, 2H), 3.95-3.91 (m, 1H), 3.83 (br, 2H), 3.48-3.44 (m, 2H), 2.52 (br, 2H), 2.37 (d, J = 0.8 Hz, 2H), 2.34 (s, 1H), 1.15-1.10 (m, 2H), 0.98-0.94 (m, 2H); ESI m/z 444.1[M + 1]$^+$ |
| 11 | 2-(6-(4-cyclopropyl-4H-1,2,4-triazol-3-yl)pyridin-2-yl)-5-(piperidine-1-carbonyl)isoindolin-1-one | 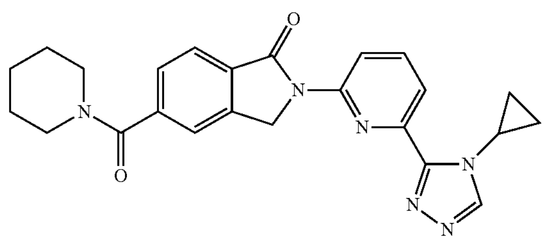 [SMILES: O=C(c1ccc2c(c1)CN(c1cccc(-c3nncn3C3CC3)n1)C2=O)N1CCCCC1] | $^1$H NMR (400 MHz, CDCl$_3$) δ 8.76 (dd, J = 0.8 Hz, 1H), 8.25 (s, 1H), 8.01-7.92 (m, 3H), 7.60 (s, 1H), 7.52-7.50 (m, 1H), 5.11 (s, 2H), 3.96-3.91 (m, 1H), 3.75 (br, 2H), 3.36 (br, 2H), 1.71 (s, 4H), 1.31 (s, 2H), 1.16-1.10 (m, 2H), 0.98-0.94 (m, 2H); ESI m/z 429.1[M + 1]$^+$ |
| 12 | 2-(6-(4-cyclopropyl-4H-1,2,4-triazol-3-yl)pyridin-2-yl)-5-(4-hydroxypiperidine-1-carbonyl)isoindolin-1-one | 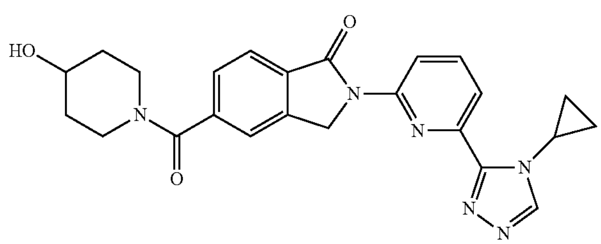 [SMILES: O=C(c1ccc2c(c1)CN(c1cccc(-c3nncn3C3CC3)n1)C2=O)N1CCC(O)CC1] | $^1$H NMR (400 MHz, DMSO-d$_6$) δ 8.71 (s, 1H), 8.64 (d, J = 8.4 Hz, 1H), 8.09 (t, J = 8 Hz, 1H), 7.89 (d, J = 8 Hz, 2H), 7.73 (s, 1H), 7.53 (s, 1H), 5.21 (s, 2H), 4.82 (d, J = 4 Hz, 1H), 4.15-3.98 (m, 2H), 3.81-3.73 (m, 1H), 3.51-3.41 (m, 1H), 3.29-3.20 (m, 1H), 3.19-3.06 (m, 1H), 1.88-1.68 (m, 2H), 1.47-1.29 (m, 2H), 1.16-1.07 (m, 2H), 1.01-0.94 (m, 2H); ESI m/z 445.1 [M + 1]$^+$ |
| 13 | 2-(6-(4-cyclopropyl-4H-1,2,4-triazol-3-yl)pyridin-2-yl)-5-(4-hydroxy-4-methylpiperidine-1-carbonyl)isoindolin-1-one | 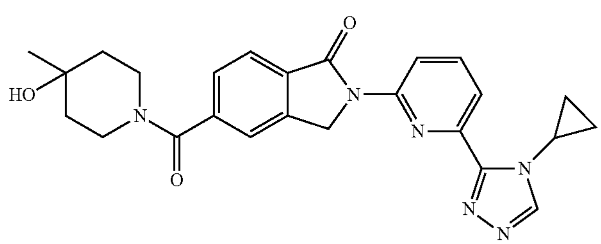 [SMILES: CC1(O)CCN(C(=O)c2ccc3c(c2)CN(c2cccc(-c4nncn4C4CC4)n2)C3=O)CC1] | $^1$H NMR (400 MHz, DMSO-d$_6$) δ 8.71 (s, 1H), 8.64 (d, J = 8.4 Hz, 1H), 8.09 (t, J = 8 Hz, 1H), 7.90 (dd, J = 7.6 Hz, 1.2 Hz, 1H), 7.88 (d, J = 2 Hz, 1H), 7.72 (s, 1H), 7.54 (d. J = 8 Hz, 1H), 5.21 (s, 2H), 4.46 (s, 1H), 4.13-4.06 (m, 2H), 1.60-1.39 (m, 5H), 1.17 (s, 3H), 1.13-1.09 (m, 2H), 1.0-0.96 (m, 2H); ESI m/z 459.1 [M + 1]$^+$ |
| 14 | 2-(6-(4-cyclopropyl-4H-1,2,4-triazol-3-yl)pyridin-2-yl)-5-(4-methoxypiperidine-1-carbonyl)isoindolin-1-one | 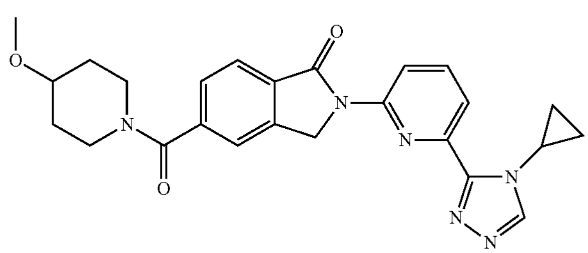 [SMILES: COC1CCN(C(=O)c2ccc3c(c2)CN(c2cccc(-c4nncn4C4CC4)n2)C3=O)CC1] | $^1$H NMR (400 MHz, DMSO-d$_6$) δ 8.71 (s, 1H), 8.64 (d, J = 8.4 Hz, 1H), 8.87 (m, 1H), 7.89 (d, J = 7.6 Hz, 2H), 7.74 (s, 1H), 7.55 (d, J = 8 Hz, 1H), 5.21 (s, 2H), 4.12-4.07 (m, 1H), 3.96 (br, 1H), 3.48-3.44 (m, 2H), 3.39-3.36 (m, 1H), 3.27 (s, 3H), 3.17 (br, 1H), 1.91 (s, 1H), 1.80 (s, 1H), 1.49 (s, 1H), 1.43 (s, 1H), 1.15-1.10 (m, 2H), 1.0-0.96 (m. 2H); ESI m/z 459.1 [M + 1]$^+$ |

TABLE 2-continued

| Compound | Name | Structure | Characterization |
|---|---|---|---|
| 15 | 2-(6-(4-cyclopropyl-4H-1,2,4-triazol-3-yl)pyridin-2-yl)-5-(4-(dimethylamino)piperidine-1-carbonyl)isoindolin-1-one | 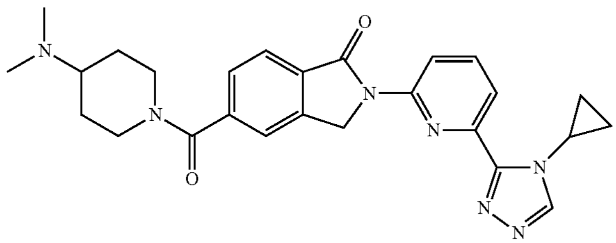 [SMILES: CN(C)C1CCN(C(=O)c2ccc3c(c2)CN(c2cccc(-c4nncn4C4CC4)n2)C3=O)CC1] | ¹H NMR (400 MHz, DMSO-d₆) δ 8.71 (s, 1H), 8.64 (d, J = 8.4 Hz, 1H), 8.09 (t, J = 8 Hz, 1H), 7.89 (d, J = 8 Hz, 2H), 7.73 (s, 1H), 7.54 (d, J = 8.4 Hz, 1H), 5.21 (s, 2H), 4.46 (br, 1H), 4.12-4.06 (m, 1H), 3.60-3.51 (m, 1H), 3.09-3.03 (m, 1H), 2.88-2.83 (m, 1H), 2.39-2.33 (m, 1H), 2.18 (s, 6H), 1.86-1.83 (m, 1H), 1.71-1.68 (m, 1H), 1.39-1.32 (m, 2H), 1.14-1.09 (m, 2H), 1.0-0.95 (m, 2H); ESI m/z 472.2 [M + 1]¹ |
| 16 | 5-(4-acetylpiperazine-1-carbonyl)-2-(6-(4-cyclopropyl-4H-1,2,4-triazol-3-yl)pyridin-2-yl)isoindolin-1-one | 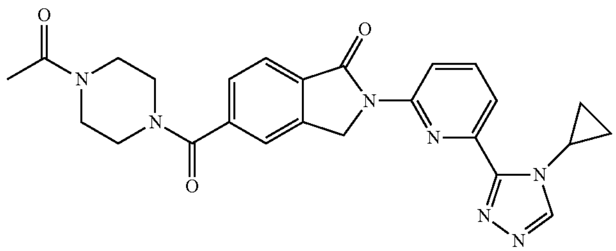 [SMILES: CC(=O)N1CCN(C(=O)c2ccc3c(c2)CN(c2cccc(-c4nncn4C4CC4)n2)C3=O)CC1] | ¹H NMR (400 MHz, DMSO-d₆) δ 8.71 (s, 1H), 8.64 (d, J = 8.4 Hz, 1H), 8.09 (t, J = 8 Hz, 1H), 7.90 (t, J = 6.8 Hz, 2H), 7.77 (s, 1H), 7.59 (d, J = 7.6 Hz, 1H), 5.22 (s, 2H), 4.12-4.06 (m, 1H), 3.69-3.37 (m, 8H), 2.04 (br, 3H), 1.14-1.09 (m, 2H), 1.00-0.96 (m, 2H); ESI m/z 472.1 [M + 1]⁺ |
| 17 | N-(1-(2-(6-(4-cyclopropyl-4H-1,2,4-triazol-3-yl)pyridin-2-yl)-1-oxoisoindoline-5-carbonyl)piperidin-4-yl)acetamide | 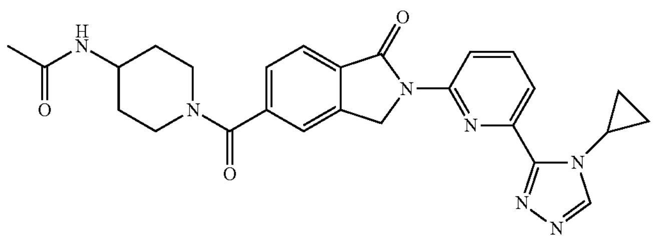 [SMILES: CC(=O)NC1CCN(C(=O)c2ccc3c(c2)CN(c2cccc(-c4nncn4C4CC4)n2)C3=O)CC1] | ¹H NMR (400 MHz, DMSO-d₆) δ 8.71 (s, 1H), 8.64 (d, J = 8.4 Hz, 1H), 8.08 (t, J = 7.6 Hz, 1H), 7.91-7.86 (m, 3H), 7.72 (s, 1H), 7.52 (d, J = 8.4 Hz, 1H), 5.22 (s, 2H), 4.33 (br, 1H), 4.12-4.07 (m, 1H), 3.87-3.78 (m, 1H), 3.645-3.52 (m, 1H), 3.16-3.00 (m, 2H), 1.80 (s, 3H), 1.29-1.24 (m, 4H), 1.14-1.09 (m, 2H), 1.00-0.96 (m, 2H); ESI m/z 486.1 [M + 1]⁺ |
| 18 | 2-(6-(4-cyclopropyl-4H-1,2,4-triazol-3-yl)pyridin-2-yl)-5-(pyrrolidine-1-carbonyl)isoindolin-1-one | 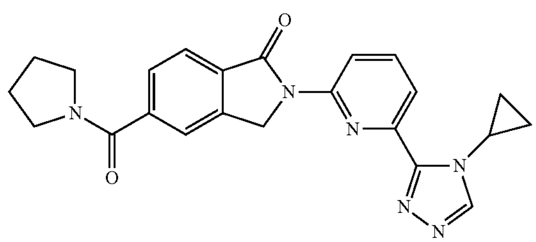 [SMILES: O=C(c1ccc2c(c1)CN(c1cccc(-c3nncn3C3CC3)n1)C2=O)N1CCCC1] | ¹H NMR (400 MHz, CDCl₃) δ 8.72 (s, 1H), 8.64 (d, J = 8.4 Hz, 1H), 8.09 (t, J = 8 Hz, 1H), 7.90-7.87 (m, 2H), 7.85 (s, 1H), 7.67 (d, J = 7.6 Hz, 1H), 5.21 (s, 2H), 4.11-4.07 (m, 1H), 3.50 (t, 6.4 Hz, 2H), 3.40-3.37 (m, 2H), 1.91-1.81 (m 4H), 1.12-1.07 (m 4H), 1.0-0.96 (m, 2H); ESI m/z 415.1 [M + 1]⁺ |
| 19 | 5-(azetidine-1-carbonyl)-2-(6-(4-cyclopropyl-4H-1,2,4-triazol-3-yl)pyridin-2-yl)isoindolin-1-one | 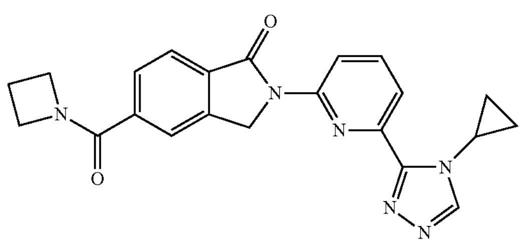 [SMILES: O=C(c1ccc2c(c1)CN(c1cccc(-c3nncn3C3CC3)n1)C2=O)N1CCC1] | ¹H NMR (400 MHz, CDCl₃) δ 8.74 (d, J = 8.4 Hz, 1H), 8.25 (s, 1H), 8.0-7.91 (m, 3H), 7.87 (s, 1H), 7.70 (d, J = 7.6 Hz, 1H), 5.11 (s, 2H), 4.30 (tt, J = 7.6 Hz, 4H), 3.97-3.91 (m, 1H), 2.41 (m, 2H), 1.16-1.11 (m, 2H), 0.98-0.94 (m, 2H); ESI m/z 401.1 [M + 1]⁺ |
| 20 | 2-(6-(4-cyclopropyl-4H-1,2,4-triazol-3-yl)pyridin-2-yl)-5-(3-oxopiperazine-1-carbonyl)isoindolin-1-one | 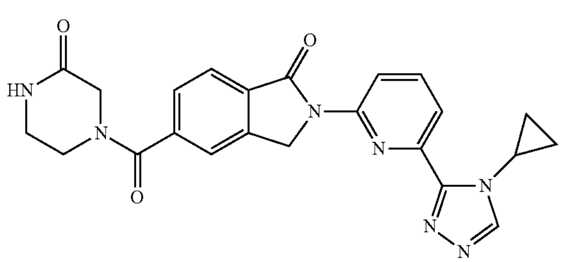 [SMILES: O=C1CN(C(=O)c2ccc3c(c2)CN(c2cccc(-c4nncn4C4CC4)n2)C3=O)CCN1] | ¹H NMR (400 MHz, DMSO-d₆) δ 8.70 (s, 1H), 8.64 (d, J = 8.4 Hz, 1H), 8.14-8.07 (m, 2H), 7.90 (t, J = 8 Hz, 2H), 7.80 (s, 1H), 7.61 (d, J = 8 Hz, 1H), 5.22 (s, 2H), 4.14-4.06 (m, 2H), 3.86 (m, 2H), 3.50 (s, 1H), 3.25 (s, 2H), 1.13-1.09 (m, 2H), 1.00-0.96 (m, 2H); ESI m/z 444.0 [M + 1]⁺ |

TABLE 2-continued

| Compound | Name | Structure | Characterization |
|---|---|---|---|
| 21 | 5-((1R,5S)-8-oxa-3-azabicyclo[3.2.1]octane-3-carbonyl)-2-(6-(4-cyclopropyl-4H-1,2,4-triazol-3-yl)pyridin-2-yl)isoindolin-1-one | 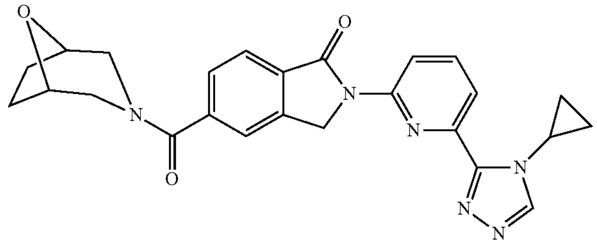 [SMILES: O=C(c1ccc2c(c1)CN(c1cccc(-c3nncn3C3CC3)n1)C2=O)N1CC2CCC(C1)O2] | $^1$H NMR (400 MHz, CDCl$_3$) δ 8.75 (d, J = 8 Hz, 1H), 8.26 (s, 1H), 8.0-7.92 (m, 3H), 7.61 (s, 1H), 7.50 (d, J = 7.6 Hz, 1H), 5.11 (s, 1H), 4.48-4.41 (m, 2H), 4.26 (s, 1H), 3.96-3.91 (m, 1H), 3.52-3.48 (m, 1H), 3.30 (d, J = 12.4 Hz, 1H), 3.18 (d, J = 12.8 Hz, 1H), 1.98 (s, 3H), 1.68 (s, 1H), 1.13 (d, J = 7.2 Hz, 1H), 0.97 (s, 2H); ESI m/z 457.1[M + 1]$^+$ |
| 22 | (R)-2-(6-(4-cyclopropyl-4H-1,2,4-triazol-3-yl)pyridin-2-yl)-5-(3-methoxypyrrolidine-1-carbonyl)isoindolin-1-one | 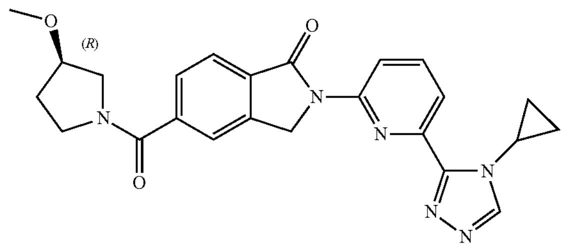 | $^1$H NMR (400 MHz, DMSO-d$_6$) δ 8.72 (s, 1H), 8.64 (d, J = 8.4 Hz, 1H), 8.11-8.07 (m, 1H), 7.90-7.87 (m, 3H), 7.67 (d, J = 8 Hz, 1H), 5.22 (s, 2H), 4.12-3.95 (m, 2H), 3.59 (s, 2H), 3.36 (s, 3H), 3.28 (s, 2H), 3.17 (s, 1H), 2.02-1.92 (m, 2H), 1.13 (d, J = 6.4 Hz, 2H), 0.99 (s, 2H); ESI m/z 445.1 [M + 1]$^+$ |
| 23 | methyl 1-(2-(6-(4-cyclopropyl-4H-1,2,4-triazol-3-yl)pyridin-2-yl)-1-oxoisoindoline-5-carbonyl)piperidine-4-carboxylate | 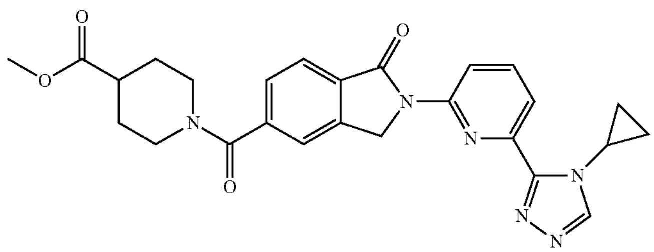 [SMILES: COC(=O)C1CCN(C(=O)c2ccc3c(c2)CN(c2cccc(-c4nncn4C4CC4)n2)C3=O)CC1] | $^1$H NMR (400 MHz, CDCl$_3$) δ 8.78 (d, J = 8 Hz, 1H), 8.43 (s, 1H), 8.02-7.93 (m, 3H), 7.61 (s, 1H), 7.52 (d, J = 8 Hz, 1H), 5.12 (s, 2H), 4.55 (s, 1H), 4.01-3.92 (m, 1H), 3.72 (s, 2H), 3.11-2.82 (s, 3H), 2.67-2.60 (m, 1H), 2.11-1.73 (m, 4H), 1.22-1.16 (m, 2H), 1.01 (s, 2H); ESI m/z 487.1[M + 1]$^+$ |
| 24 | 2-(6-(4-cyclopropyl-4H-1,2,4-triazole-3-yl)pyridin-2-yl)-5-(thiomorpholine-4-carbonyl)isoindolin-1-one | 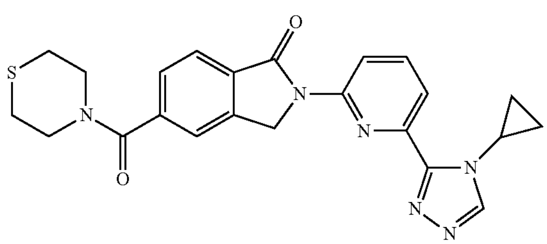 [SMILES: O=C(c1ccc2c(c1)CN(c1cccc(-c3nncn3C3CC3)n1)C2=O)N1CCSCC1] | $^1$H NMR (400 MHz, DMSO-d$_6$) δ 8.70 (s, 1H), 8.64 (d, J = 8.4 Hz, 1H), 8.09 (t, J = 8 Hz, 1H), 7.91-7.89 (m, 2H), 7.75 (s, 1H), 7.57 (d, J = 7.6 Hz, 1H), 5.22 (s, 2H), 4.13-4.06 (m, 1H), 3.97-3.85 (m, 2H), 3.61-3.50 (m, 2H), 2.70-2.62 (m, 4H), 1.14-1.09 (m, 2H), 1.00-0.96 (m, 2H); ESI m/z 447.0 [M + 1]$^+$ |
| 25 | 2-(6-(4-cyclopropyl-4H-1,2,4-triazol-3-yl)pyridin-2-yl)-5-(4-(methylthio)piperidine-1-carbonyl)isoindolin-1-one | 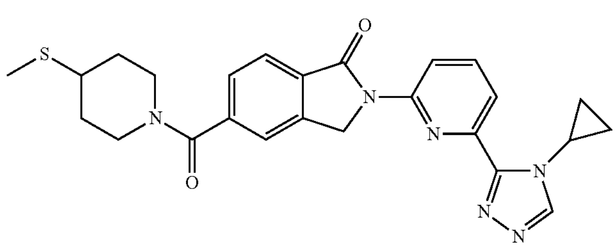 [SMILES: CSC1CCN(C(=O)c2ccc3c(c2)CN(c2cccc(-c4nncn4C4CC4)n2)C3=O)CC1] | $^1$H NMR (400 MHz, CDCl$_3$) δ 7.50 (d, J = 8 Hz, 1H), 8.25 (s, 1H), 8.01-7.94 (m, 3H), 7.60 (s, 1H), 7.51 (d, J = 7.6 Hz, 1H), 5.11 (s, 2H), 4.48 (br, 1H), 3.94 (t, 6.8 Hz, 1H), 3.67 (br, 1H), 3.17 (t, J = 10.8 Hz, 2H), 2.88-2.83 (m, 1H), 2.13-1.95 (m, 5H), 1.68-1.54 (m, 2H), 1.16-1.12 (m, 2H), 0.99-0.95 (m, 2H); ESI m/z 475.0[M + 1]$^+$ |

Example 3: Preparation of 6-chloro-2-(6-(4-cyclopropyl-4H-1,2,4-triazol-3-yl)pyridin-2-yl)-5-(morpholine-4-carbonyl)isoindolin-1-one (compound 26)

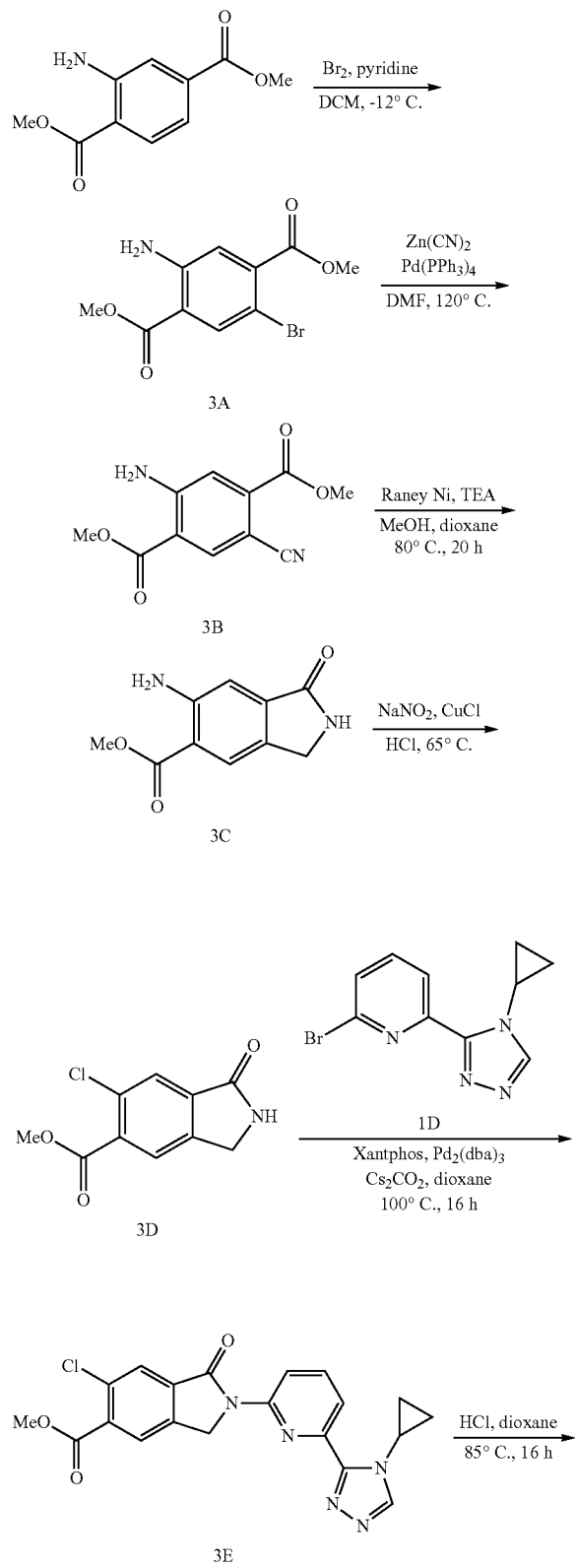

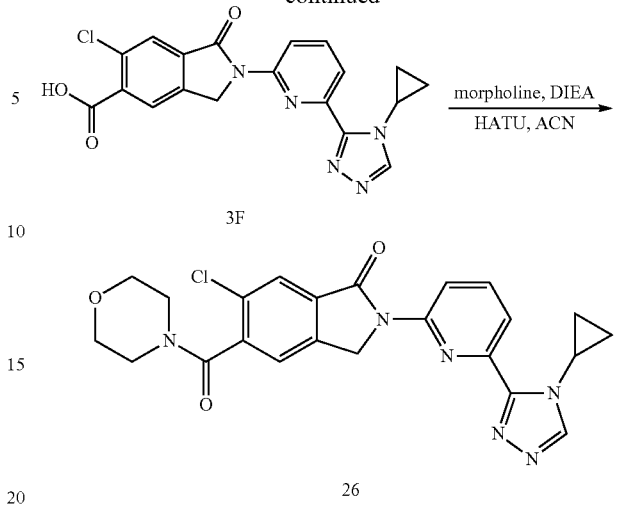

Bromine (7.43 mL, 0.14 mol) was added dropwise to a −12° C. suspension of dimethyl 2-aminoterephthalate (25.0 g, 0.12 mol) and pyridine (19 mL, 0.24 mol) in dichloromethane (500 mL) over 1 hour. After the addition, the reaction mixture was allowed to warm to ambient temperature and stirred overnight. The mixture was concentrated and the residue was recrystallized from 95% ethanol to give compound 3A (20 g, 58% yield) as a yellow solid: $^1$H NMR (400 MHz, CDCl$_3$) δ 8.09 (s, 1H), 7.05 (s, 1H), 3.90 (d, J 10.8 Hz, 6H), 1.59 (s, 2H); ESI m/z 289.2, 291.2 [M+1]$^+$.

A mixture of 3A (20.0 g, 69.4 mmol), zinc (II) cyanide (9.37 g, 83.3 mmol) and tetrakis(triphenylphosphine)palladium(0) (4.0 g, 3.47 mmol) was suspended in DMF (200 mL) and the reaction mixture was degassed and purged with argon. The reaction mixture was heated at 120° C. for 1 hour and then concentrated under vacuum. The residue was triturated with hot water (200 mL) and the product was collected by filtration to give intermediate 3B (11.2 g, 70% yield) as a yellow solid: $^1$H NMR (400 MHz, CDCl$_3$) δ 8.11 (s, 1H), 7.63 (s, 2H), 7.52 (s, 1H), 3.88 (s, 3H), 3.84 (s, 3H); ESI m/z 235.2 [M+1]$^+$.

Raney Ni (1 g) was added to a mixture of 3B (4 g, 17.1 mmol) in MeOH (150 mL), TEA (20 mL) and dioxane (100 mL). The reaction mixture was stirred under 0.5 MPa of H$_2$ at 80° C. for 20 hours. The reaction mixture was filtered and the filtrate was concentrated under vacuum. The product was purified by flash chromatography on silica gel (1-2% MeOH in DCM) to give 3C (2.9 g, 82% yield) as a yellow solid: $^1$H NMR (400 MHz, DMSO-d$_6$) δ 8.61 (s, 1H), 7.87 (s, 1H), 7.07 (s, 1H), 6.78 (s, 2H), 4.21 (s, 2H), 3.82 (s, 3H); ESI m/z 207.3 [M+H]$^+$.

A solution of sodium nitrite (1.94 g, 28.1 mmol) in water (40 mL) was added to a suspension of 3C (2.9 g, 14.06 mmol) in conc. HCl (100 mL) at 0° C. After stirring at 0° C. for 10 minutes, copper(I) chloride (2.88 g, 28.1 mmol) in conc. HCl (100 mL) was added and the reaction mixture was stirred at 65° C. for 1 hour. The reaction mixture was cooled to room temperature, diluted with water (100 mL) and the mixture was extracted with ethyl acetate (3×200 mL). The combined organic fractions were washed with brine (20 mL), dried with sodium sulfate and concentrated under vacuum. The residue was purified by chromatography on silica gel (3% MeOH in DCM) to give 3D (723 mg, 23% yield) as a yellow solid: $^1$H NMR (400 MHz, CDCl$_3$) δ 7.94 (s, 1H), 7.89 (s, 1H), 4.48 (s, 2H), 3.98 (s, 3H); ESI m/z 226.0, 228.0 [M+H]$^+$.

A mixture of 3D (400 mg, 1.77 mmol), intermediate 1D (470 mg, 1.77 mmol), cesium carbonate (1.15 g, 3.54 mmol), Xantphos (1.02 g, 0.09 mmol) and $Pd_2(dba)_3$ (49 mg, 0.05 mmol) in dioxane (40 mL) was stirred at 100° C. overnight under a nitrogen atmosphere. The mixture was concentrated under reduced pressure and purified by chromatography on silica gel (0.5%-1.5% MeOH in DCM) to give 3E (354 mg, 49% yield) as a white solid: ESI m/z 410.1, 412.1 $[M+H]^+$.

A suspension of 3E (150 mg, 0.37 mmol) in HCl (6M, 10 mL) and dioxane (10 mL) was stirred at 85° C. overnight. The reaction mixture was concentrated under reduced pressure to give carboxylate 3F (120 mg, 83% yield) as a yellow solid: $^1$H NMR (400 MHz, DMSO-$d_6$) δ 8.72 (dd, J=7.6 Hz, 1.2 Hz), 8.25 (s, 1H), 8.03-8.01 (m, 2H), 7.97 (s, 1H), 5.10 (s, 2H), 3.94-3.88 (m, 1H), 1.12 (q, J=6.4 Hz, 2H), 0.99-0.95 (m, 2H); ESI m/z 396.0, 397.0 $[M+H]^+$.

A mixture of 3F (60 mg, 0.15 mmol), morpholine (26 mg, 0.30 mmol), HATU (86 mg, 0.23 mmol) and DIEA (1 mL) in ACN (6 mL) was stirred at room temperature overnight. The reaction mixture was concentrated under vacuum and purified by chromatography on silica gel (1-2% MeOH in DCM) to give compound 25 (45 mg, 64% yield) as a white solid: $^1$H NMR (400 MHz, DMSO-$d_6$) δ 8.71 (s, 1H), 8.61 (d, J=8 Hz, 1H), 8.10 (t, J=8 Hz, 1H), 7.96 (s, 1H), 7.91 (d, J=6.8 Hz, 1H), 7.78 (s, 1H), 5.25-5.15 (m, 2H), 4.10-4.05 (m, 1H), 3.68 (s, 4H), 3.57-3.54 (m, 2H), 3.19-3.16 (m, 2H), 1.12-1.11 (m, 2H), 0.99-0.98 (m, 2H); ESI m/z 465.0, 466.0 $[M+H]^+$.

Example 4: Preparation of 6-chloro-2-(6-(4-cyclopropyl-4H-1,2,4-triazol-3-yl)pyridin-2-yl)-5-(morpholine-4-carbonyl)isoindolin-1-one (compound 27)

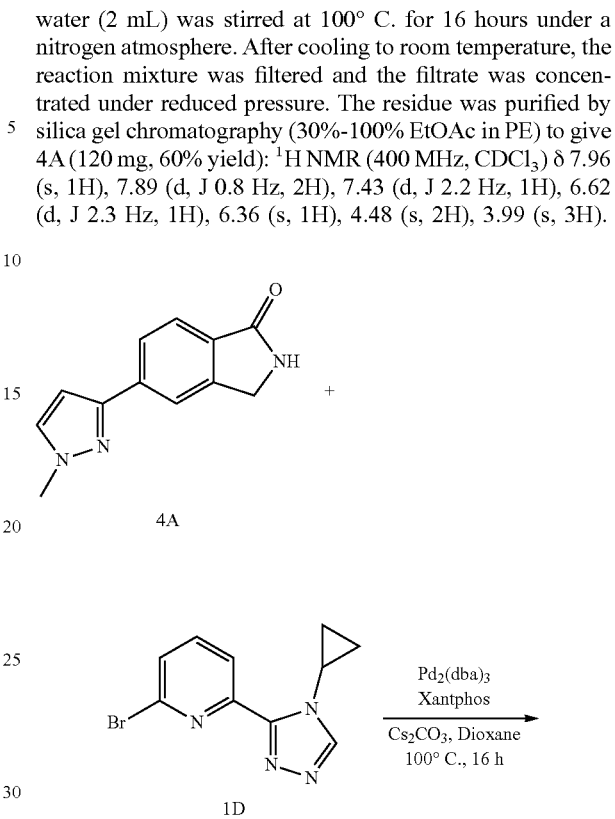

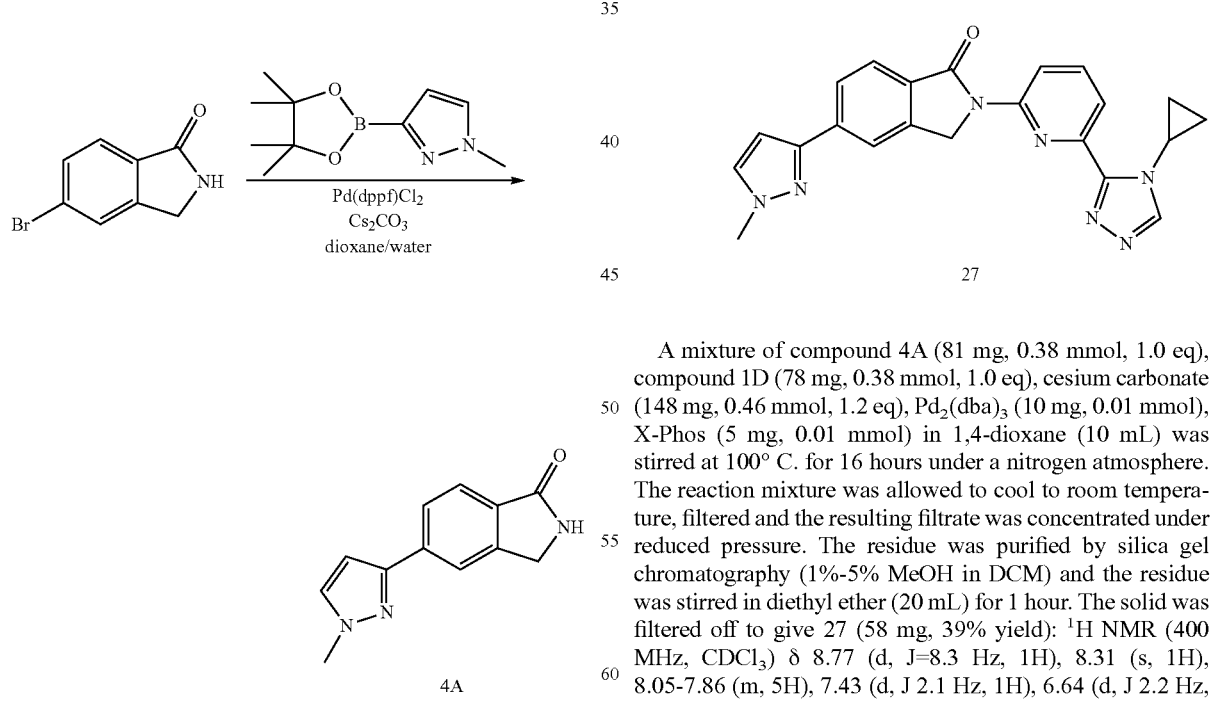

A mixture of compound 5-bromoisoindolin-1-one (200 mg, 0.94 mmol, 1.0 eq), 1-methyl-3-(4,4,5,5-tetramethyl-1,3,2-dioxaborolan-2-yl)-1H-pyrazole (215 mg, 1.04 mmol, 1.1 eq), cesium carbonate (922 mg, 2.83 mmol, 1.2 eq), and Pd(dppf)Cl$_2$ (21 mg, 0.03 mmol) in 1,4-dioxane (15 mL) and water (2 mL) was stirred at 100° C. for 16 hours under a nitrogen atmosphere. After cooling to room temperature, the reaction mixture was filtered and the filtrate was concentrated under reduced pressure. The residue was purified by silica gel chromatography (30%-100% EtOAc in PE) to give 4A (120 mg, 60% yield): $^1$H NMR (400 MHz, CDCl$_3$) δ 7.96 (s, 1H), 7.89 (d, J 0.8 Hz, 2H), 7.43 (d, J 2.2 Hz, 1H), 6.62 (d, J 2.3 Hz, 1H), 6.36 (s, 1H), 4.48 (s, 2H), 3.99 (s, 3H).

A mixture of compound 4A (81 mg, 0.38 mmol, 1.0 eq), compound 1D (78 mg, 0.38 mmol, 1.0 eq), cesium carbonate (148 mg, 0.46 mmol, 1.2 eq), Pd$_2$(dba)$_3$ (10 mg, 0.01 mmol), X-Phos (5 mg, 0.01 mmol) in 1,4-dioxane (10 mL) was stirred at 100° C. for 16 hours under a nitrogen atmosphere. The reaction mixture was allowed to cool to room temperature, filtered and the resulting filtrate was concentrated under reduced pressure. The residue was purified by silica gel chromatography (1%-5% MeOH in DCM) and the residue was stirred in diethyl ether (20 mL) for 1 hour. The solid was filtered off to give 27 (58 mg, 39% yield): $^1$H NMR (400 MHz, CDCl$_3$) δ 8.77 (d, J=8.3 Hz, 1H), 8.31 (s, 1H), 8.05-7.86 (m, 5H), 7.43 (d, J 2.1 Hz, 1H), 6.64 (d, J 2.2 Hz, 1H), 5.09 (s, 2H), 3.99 (s, 4H), 1.16 (d, J 6.8 Hz, 2H), 1.00 (d, J 3.7 Hz, 2H); ESI m/z 398.1$[M+1]^+$.

Compounds 28-30 in Table 3 were synthesized according to the procedure for compound 27 substituting the appropriate boronate in place of 1-methyl-3-(4,4,5,5-tetramethyl-1,3,2-dioxaborolan-2-yl)-1H-pyrazole.

TABLE 3

| Compound | Name | Structure | Characterization |
|---|---|---|---|
| 28 | 2-(6-(4-cyclopropyl-4H-1,2,4-triazol-3-yl)pyridin-2-yl)-5-(1H-pyrazol-3-yl)isoindolin-1-one | 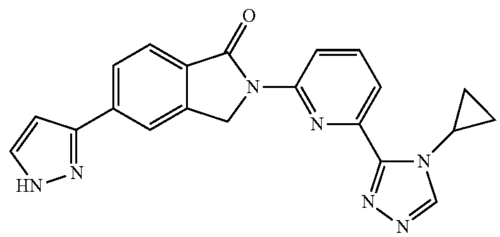 [SMILES: O=C1c2ccc(-c3cc[nH]n3)cc2CN1c1cccc(-c2nncn2C2CC2)n1] | $^1$H NMR (400 MHz, DMSO-$d_6$) δ 13.12 (s, 1H), 8.71 (s, 1H), 8.66 (d, J = 5.2 Hz, 1H), 8.18-7.87 (m, 6H), 6.88 (s, 1H), 5.22 (s, 2H), 4.13 (s, 1H), 1.14 (d, J = 6 Hz, 4H); ESI m/z 384.1 [M + 1]$^+$ |
| 29 | 2-(6-(4-cyclopropyl-4H-1,2,4-triazol-3-yl)pyridin-2-yl)-5-(1-methyl-1H-pyrazol-5-yl)isoindolin-1-one | 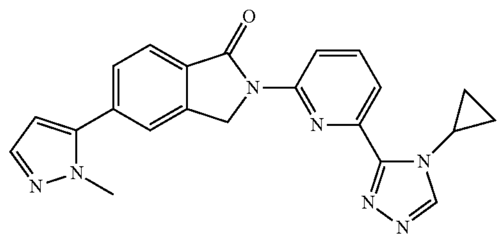 [SMILES: Cn1nccc1-c1ccc2c(c1)CN(c1cccc(-c3nncn3C3CC3)n1)C2=O] | $^1$H NMR (400 MHz, CDCl$_3$) δ 8.77 (dd, J = 8.4 Hz, 0.4 Hz, 1H), 8.24 (s, 1H), 8.04 (d, J = 8 Hz, 1H), 7.98 (m, 1H), 7.95 (d, J = 8 Hz, 1H), 7.60-7.58 (m, 2H), 7.56 (d, J = 2 Hz, 1H), 6.40 (d, J = 2 Hz, 1H), 5.14 (s, 2H), 3.95 (s, 4H), 1.16-1.11 (m, 2H), 0.99-0.95 (m, 2H); ESI m/z 398.2[M + 1]$^+$ |
| 30 | 2-(6-(4-cyclopropyl-4H-1,2,4-triazol-3-yl)pyridin-2-yl)-5-(1-methyl-1H-imidazol-4-yl)isoindolin-1-one | 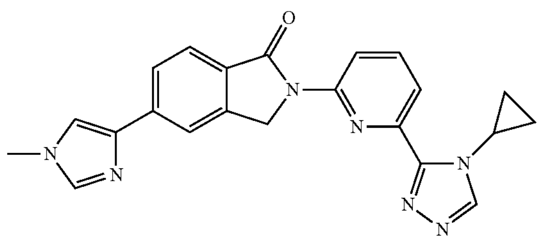 [SMILES: Cn1cnc(-c2ccc3c(c2)CN(c2cccc(-c4nncn4C4CC4)n2)C3=O)c1] | $^1$H NMR (400 MHz, DMSO-$d_6$) δ 9.08 (s, 1H), 8.81 (s, 1H), 8.62 (d, J = 8.4 Hz, 1H), 8.24 (s, 1H), 8.08-8.05 (m, 2H), 7.94-7.88 (m, 3H), 5.19 (s, 2H), 5.23 (s, 2H), 4.10-4.09 (m, 4H), 1.14-1.12 (m, 2H), 1.03 (br, 2H); ESI m/z 397.9 [M + 1]$^+$ |

Example 5: Preparation of 5-amino-2-(6-(4-cyclopropyl-4H-1,2,4-triazol-3-yl)pyridin-2-yl)isoindolin-1-one (compound 31)

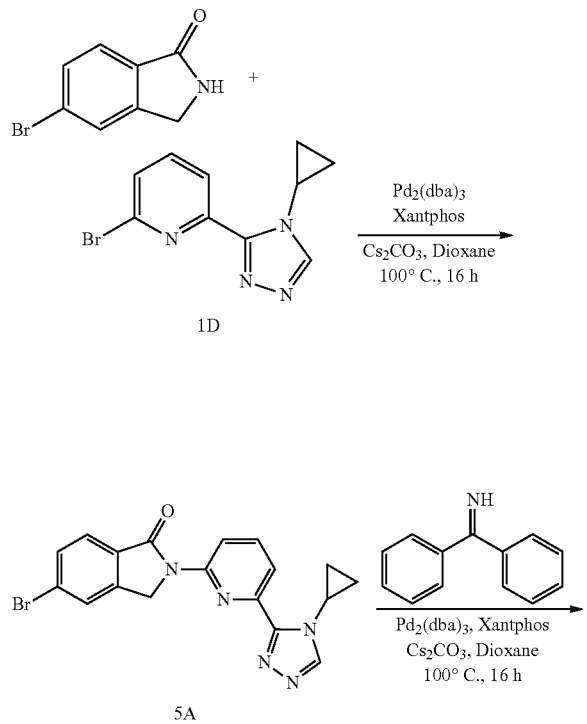

A mixture of 5-bromoisoindolin-1-one (636 mg, 3.0 mmol), 1D (800 mg, 3.0 mmol), Pd$_2$(dba)$_3$ (82 mg, 0.09 mmol), Xantphos (52 mg, 0.09 mmol) and Cs$_2$CO$_3$ (1.17 g, 3.6 mmol) in dioxane (60 mL) was heated to 100° C. for 4 h. After that time, the mixture was allowed to cool to room temperature and filtered. The filtrate was concentrated under vacuum and purified by column chromatography on silica gel (1%-10% EtOAc in pet. ether) to afford 5A (400 mg, 34%) as a yellow solid: $^1$H NMR (400 MHz, DMSO-$d_6$) δ 8.71 (s, 1H), 8.61 (d, J=8.4 Hz, 1H), 8.07 (t, J=8.4 Hz, 1H), 8.0 (d, J=7.6 Hz, 1H), 7.89 (d, J=8 Hz, 1H), 7.76 (d, J=3.2 Hz, 2H), 5.17 (s, 2H), 4.11-4.04 (m, 1H), 1.14-1.11 (m, 2H), 1.0-0.95 (m, 2H); ESI m/z 396.1, 398.1 [M+1]$^+$.

A mixture of 5A (400 mg, 1.01 mmol), diphenylmethanimine (550 mg, 3.03 mmol), Pd$_2$(dba)$_3$ (28 mg, 0.03 mmol), Xantphos (29 mg, 0.05 mmol) and Cs$_2$CO$_3$ (987 mg, 3.03 mmol) in dioxane (40 mL) was heated to 100° C. for 16 h. After cooling to room temperature, HCl (1.0 M, 50 mL) was added and the mixture was stirred at room temperature for 4 h. After that time, the mixture was extracted with ethyl acetate. The aqueous phase was neutralized with a saturated solution of sodium bicarbonate and extracted with ethyl acetate. The organic layer was dried with sodium sulfate, concentrated under vacuum and purified by column chromatography on silica gel (2%-50% EtOAc in pet. ether) to give compound 31 (30 mg, 9% yield) as a white solid: $^1$H NMR (400 MHz, DMSO-$d_6$) δ 8.72 (s, 1H), 8.61 (d, J=8.4 Hz, 1H), 7.99 (t, J=8 Hz, 1H), 7.78 (d, J=7.6 Hz, 1H), 7.48 (d, J=8.4 Hz, 1H), 6.71-6.67 (m, 2H), 4.97 (s, 2H), 4.12-4.07 (m, 1H), 1.12-1.07 (m, 2H), 0.98-0.94 (m, 2H); ESI m/z 333.2 [M+1]$^+$.

Example 6: Preparation of N-(2-(6-(4-cyclopropyl-4H-1,2,4-triazol-3-yl)pyridin-2-yl)-1-oxoisoindolin-5-yl)acetamide (compound 32)

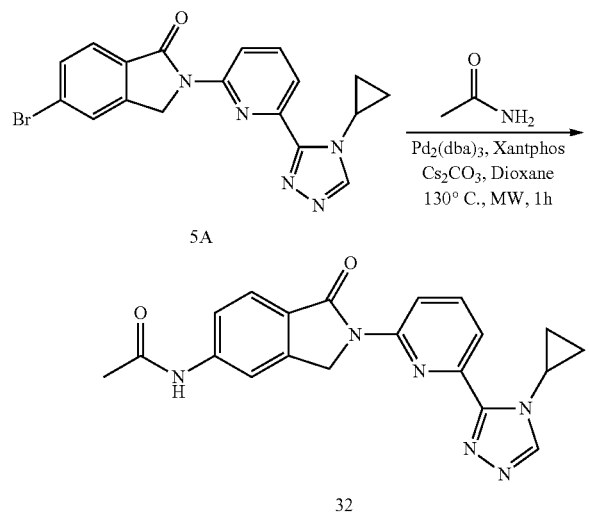

A mixture of 5A (100 mg, 0.25 mmol), acetamide (45 mg, 0.76 mmol), Pd$_2$(dba)$_3$ (7 mg, 0.0076 mmol), Xantphos (8 mg, 0.013 mmol) and Cs$_2$CO$_3$ (100 mg, 0.31 mmol) in dioxane (5 mL) was heated to 130° C. for 1 h in the microwave. After cooling, the reaction mixture was concentrated under reduced pressure and purified by column chromatography on silica gel (1%-5% MeOH in DCM) to afford compound 32 (5 mg, 5%) as a white solid: $^1$H NMR (400 MHz, DMSO-$d_6$) δ 10.37 (s, 1H), 8.71 (s, 1H), 8.63 (d, J=8 Hz, 1H), 8.72 (s, 1H), 8.07-8.03 (m, 1H), 7.85 (d, J=6.8 Hz, 1H), 7.77 (d, J=8 Hz, 1H), 7.53 (d, J=8 Hz, 1H), 5.14 (s, 2H), 4.13 (br, 1H), 2.12 (s, 3H), 1.12-1.11 (m, 2H), 0.95 (s, 2H); ESI m/z 375.2 [M+1]$^+$.

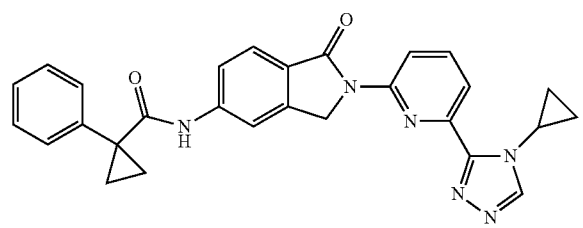

N-(2-(6-(4-Cyclopropyl-4H-1,2,4-triazol-3-yl)pyridin-2-yl)-1-oxoisoindolin-5-yl)-1-phenylcyclopropane-1-carboxamide (compound 33) was prepared according to the procedure for compound 32 substituting 1-phenylcyclopropane-1-carboxamide in place of acetamide. $^1$H NMR (400 MHz, DMSO-$d_6$) δ 9.49 (s, 1H), 8.70 (s, 1H), 8.61 (d, J=8.4 Hz, 1H), 8.08-8.02 (m, 2H), 7.86 (d, J=7.6 Hz, 1H), 7.73 (d, J=8.4 Hz, 1H), 7.62 (dd, J=7.6 Hz, 6.8 Hz, 1H), 7.43-7.36 (m, 4H), 7.32-7.28 (m, 1H), 5.11 (s, 2H), 4.14-4.09 (m, 1H), 1.50-1.48 (m, 2H), 1.19-1.16 (m, 2H), 1.14-1.09 (m, 2H), 1.0-0.95 (m, 2H); ESI m/z 477.1 [M+1]$^+$.

Example 7: Preparation of N-(2-(6-(4-cyclopropyl-4H-1,2,4-triazol-3-yl)pyridin-2-yl)-1-oxoisoindolin-5-yl)acetamide (compound 34)

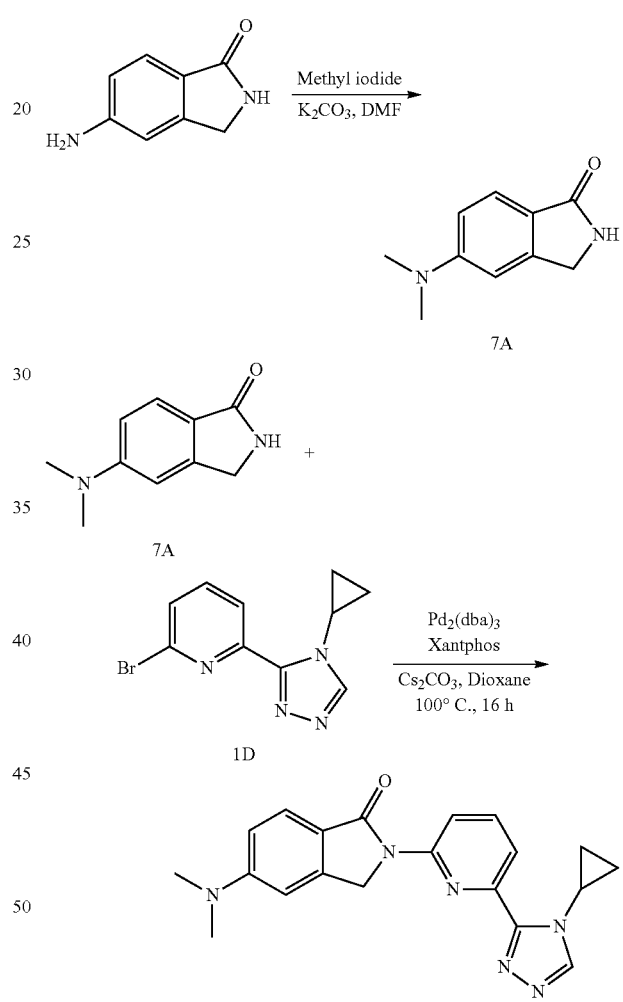

A stirred mixture of 7A (250 mg, 1.42 mmol), 1D (376 mg, 1.42 mmol), Pd$_2$(dba)$_3$ (91 mg, 0.099 mmol), Cs$_2$CO$_3$ (1.39 g, 4.26 mmol) and Xantphos (82 mg, 0.142 mmol) in 1,4-dioxane (30 mL) was heated to 100° C. overnight. The reaction mixture was allowed to cool to room temperature and filtered. The resulting filtrate was concentrated under reduced pressure and the residue was purified by silica column chromatography (1%-5% MeOH in DCM) to give compound 34 (60 mg, 12% yield) as a white solid: $^1$H NMR (400 MHz, CDCl$_3$) δ 8.69 (s, 1H), 8.61 (d, J=8.4 Hz, 1H), 8.0 (t, J=7.6 Hz, 1H), 7.80 (d, J=7.6 Hz, 1H), 7.60 (d, J=8.8

Hz, 1H), 6.88 (s, 1H), 6.84 (dd, J=8.4 Hz, 2.0 Hz, 1H), 5.02 (s, 2H), 4.11-4.07 (m, 1H), 3.05 (s, 6H), 1.14-1.09 (m, 2H), 1.0-0.97 (m, 2H); ESI m/z 361.0 [M+1]$^+$.

Example 8: Preparation of 2-(6-(4-cyclopropyl-4H-1,2,4-triazol-3-yl)pyridin-2-yl)-5-(ethylamino)isoindolin-1-one (compound 35)

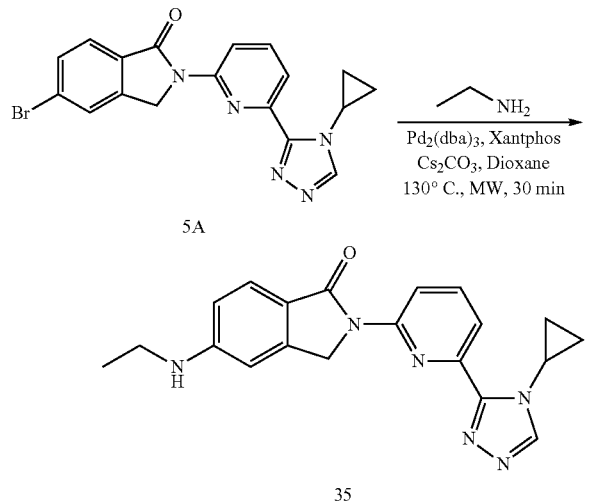

A mixture of 5A (400 mg, 1.0 mmol), ethylamine in THF (2.0M, 8 mL), Pd$_2$(dba)$_3$ (27 mg, 0.03 mmol), Xantphos (29 mg, 0.05 mmol) and Cs$_2$CO$_3$ (391 mg, 1.2 mmol) in dioxane (4 mL) was heated to 130° C. for 30 min in the microwave. After cooling, the reaction mixture was concentrated under reduced pressure and purified by column chromatography on silica gel (1%-10% MeOH in DCM) to afford compound 35 (50 mg, 14%) as a white solid: $^1$H NMR (400 MHz, CDCl$_3$) δ 8.66 (dd, J=7.6 Hz, 1.2 Hz, 1H), 8.15 (s, 1H), 7.84-7.71 (m, 2H), 7.63 (d, J=8.4 Hz, 1H), 7.19 (s, 1H), 6.58 (dd, J=8.4 Hz, 2 Hz, 1H), 6.52 (s, 1H), 4.86 (s, 2H), 3.91-3.86 (m, 1H), 3.21-3.15 (m, 2H), 1.24 (t, J=7.2 Hz, 3H), 1.08-1.03 (m, 2H), 0.90-0.86 (m, 2H); ESI m/z 361.1 [M+1]$^+$.

Example 9: Preparation of 2-(6-(4-cyclopropyl-4H-1,2,4-triazol-3-yl)pyridin-2-yl)-6-(1-methyl-1H-imidazol-5-yl)isoindolin-1-one (compound 36)

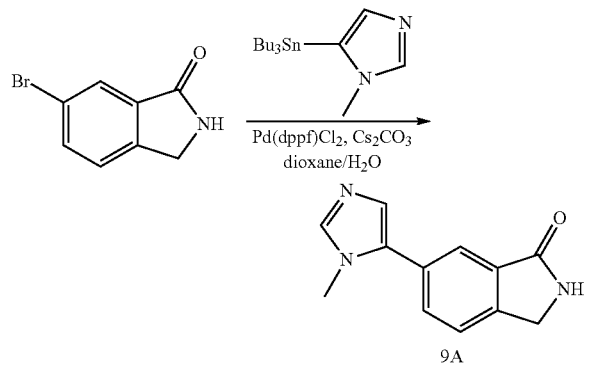

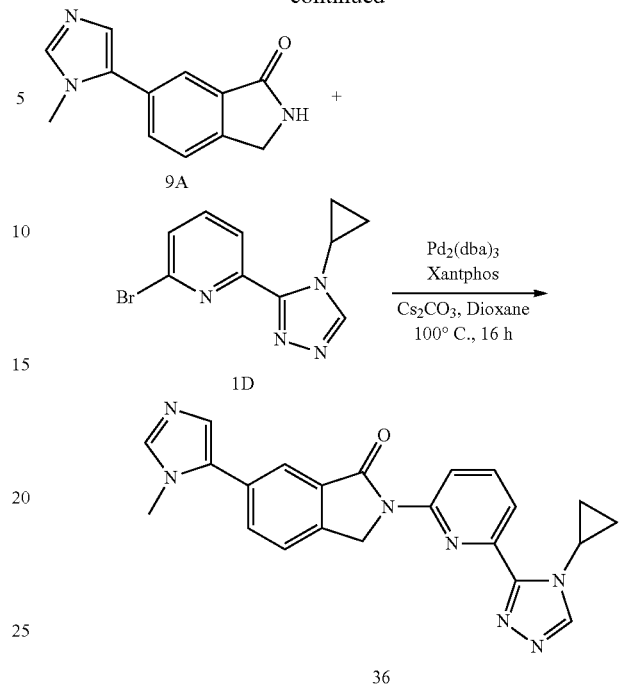

A mixture of 6-bromoisoindolin-1-one (287 mg, 1.35 mmol), 1-methyl-5-(tributylstannyl)-1H-imidazole (500 mg, 1.35 mmol), Pd(dppf)Cl$_2$ (33 mg, 0.041 mmol) and Cs$_2$CO$_3$ (1.32 g, 4.05 mmol) in dioxane (50 mL) and water (8 mL) was heated to 100° C. overnight. After cooling, the mixture was concentrated under vacuum and purified by column chromatography on silica gel ((1%-3% MeOH in DCM) to afford 9A (220 mg, 76% yield) as a brown solid: $^1$H NMR (400 MHz, DMSO-d$_6$) δ 8.66 (s, 1H), 7.76-7.15 (m, 4H), 7.15 (s, 1H), 4.43 (s, 2H), 3.72 (s, 3H); ESI m/z 214.1 [M+1]$^+$.

A stirred mixture of 9A (220 mg, 1.03 mmol), 1D (273 mg, 1.03 mmol), Pd$_2$(dba)$_3$ (28 mg, 0.03 mmol), Cs$_2$CO$_3$ (404 mg, 1.24 mmol) and Xantphos (18 mg, 0.03 mmol) in dioxane (50 mL) was heated to 100° C. overnight. The reaction mixture was allowed to cool to room temperature and filtered. The resulting filtrate was concentrated under reduced pressure and the residue was purified by silica column chromatography (1%-3% MeOH in DCM) to give compound 36 (100 mg, 24% yield) as a light yellow solid: 1H NMR (400 MHz, DMSO-d$_6$) δ 8.73 (s, 1H), 8.66 (d, J=8.4 Hz, 1H), 8.08 (t, J=8 Hz, 1H), 7.90-7.80 (m, 5H), 7.24 (s, 1H), 5.23 (s, 2H), 4.14-4.08 (m, 1H), 3.76 (s, 3H), 1.16-1.11 (m, 2H), 1.0-0.97 (m, 2H); ESI m/z 398.2 [M+1]$^+$.

Example 10: Preparation of 2-(6-(4-cyclopropyl-4H-1,2,4-triazol-3-yl)pyridin-2-yl)-6-(1H-imidazol-1-yl)isoindolin-1-one (compound 37)

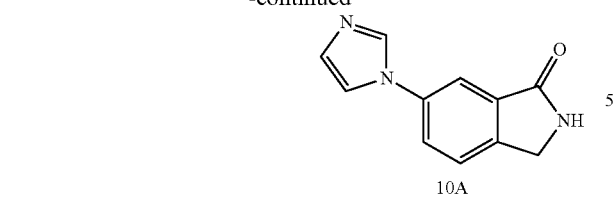

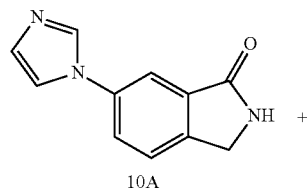

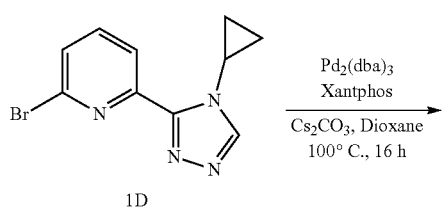

A mixture of 6-bromoisoindolin-1-one (1.0 g, 4.72 mmol), 1H-imidazole (1.28 g, 18.87 mmol), CuI (179 mg, 0.94 mmol), L-proline (108 mg, 0.94 mmol) and K$_2$CO$_3$ (1.30 g, 9.44 mmol) in NMP (6 mL) was heated to 200° C. for 1 h in the microwave. The mixture was poured into water and extracted with EtOAc (3×100 mL). The organic layer was washed with water and dried with sodium sulfate and concentrated. The residue was purified by silica gel column (2%-7% MeOH in DCM) to give 10A (150 mg, 16% yield) as a yellow solid: $^1$H NMR (400 MHz, DMSO-d$_6$) δ 8.75 (br, 1H), 8.38 (s, 1H), 7.92-7.88 (m, 3H), 7.71 (d, J=8.4 Hz, 1H), 7.12 (s, 1H), 4.42 (s, 2H); ESI m/z 200.1 [M+1]$^+$.

Compound 37 was synthesized according to the procedure for compound 36 substituting intermediate 10A for 9A. $^1$H NMR (400 MHz, DMSO-d$_6$) δ 9.76 (s, 1H), 8.76 (s, 1H), 8.64 (d, J=8 Hz, 1H), 8.40 (s, 1H), 8.29 (d, J=2 Hz, 1H), 8.15-8.07 (m, 2H), 8.97 (d, J=8 Hz, 1H), 7.90 (d, J=7.2 Hz, 2H), 5.27 (s, 2H), 4.13-4.08 (m, 1H), 1.16-1.11 (m, 2H), 1.01-0.97 (m, 2H); ESI m/z 384.2 [M+1]$^+$.

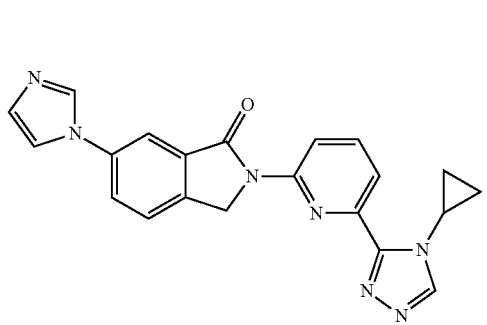

6-(1H-Benzo[d]imidazol-1-yl)-2-(6-(4-cyclopropyl-4H-1,2,4-triazol-3-yl)pyridin-2-yl)isoindolin-1-one (compound 38) was prepared according to the procedure for compound 37 substituting 1H-benzimidazole in place of 1H-imidazole. $^1$H NMR (400 MHz, DMSO-d$_6$) δ 8.72-8.66 (m, 3H), 8.13-8.05 (m, 3H), 7.98 (d, J=8 Hz, 1H), 7.92 (d, J=7.6 Hz, 1H), 7.81 (d, J=7.2 Hz, 1H), 7.66 (d, J=7.6 Hz, 1H), 7.40-7.33 (m, 2H), 5.30 (s, 2H), 4.16-4.10 (m, 1H), 1.17-1.12 (m, 2H), 1.02-0.98 (m, 2H); ESI m/z 434.0 [M+H]$^+$.

Example 11: Preparation of 2-(6-(4-cyclopropyl-4H-1,2,4-triazol-3-yl)pyridin-2-yl)-6-(1-methyl-1H-pyrazol-3-yl)isoindolin-1-one (compound 39)

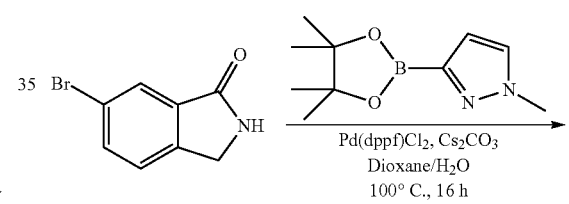

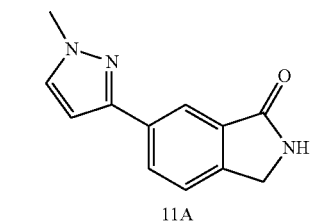

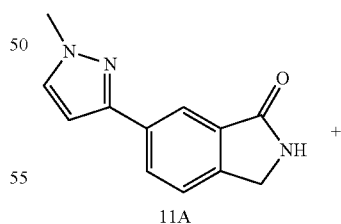

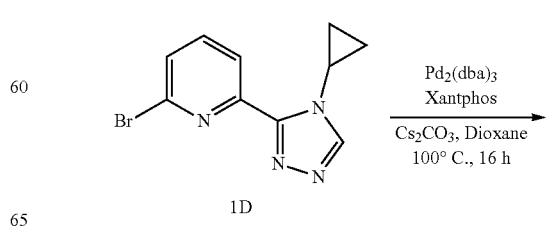

-continued

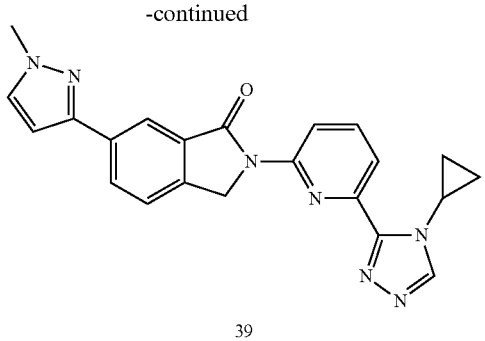

39

A mixture of 6-bromoisoindolin-1-one (509 mg, 2.4 mmol), 1-methyl-3-(4,4,5,5-tetramethyl-1,3,2-dioxaborolan-2-yl)-1H-pyrazole (500 mg, 2.4 mmol), Pd(dppf)Cl$_2$ (59 mg, 0.072 mmol) and Cs$_2$CO$_3$ (2.3 g, 7.2 mmol) in dioxane (50 mL) and water (8 mL) was heated to 100° C. overnight. After that time, the mixture was cooled to room temperature and filtered. The filtrate was concentrated under reduced pressure and purified by column chromatography on silica gel (1%-3% MeOH in DCM) to give 11A (390 mg, 76% yield) as a yellow solid: $^1$H NMR (400 MHz, DMSO-d$_6$) δ 8.57 (s, 1H), 8.03-8.01 (m, 2H), 7.75 (d, J=2.4 Hz, 1H), 7.58 (d, J=8 Hz, 1H), 8.79 (d, J=2.4 Hz, 1H), 4.38 (s, 2H), 3.90 (s, 3H); ESI m/z 214.1 [M+H]$^+$.

Compound 39 was synthesized according to the procedure for compound 36 substituting intermediate 11A for 9A. $^1$H NMR (400 MHz, DMSO-d$_6$) δ 8.71 (s, 1H), 8.65 (d, J=7.6 Hz, 1H), 8.17 (s, 1H), 8.14 (d, J=8 Hz, 1H), 8.07 (t, J=8 Hz, 1H), 7.88 (d, J=7.2 Hz, 1H), 7.76 (d, J=1.2 Hz, 1H), 7.71 (d, J=7.6 Hz, 1H), 6.85 (d, J=2 Hz, 1H), 5.17 (s, 2H), 4.13-4.08 (m, 1H), 3.91 (s, 3H), 1.16-1.11 (m, 2H), 1.02-0.96 (m, 2H); ESI m/z 398.2 [M+1]$^+$.

Compounds 40-55 in Table 4 were synthesized according to the procedure for compound 39 substituting the appropriate boronate in place of 1-methyl-3-(4,4,5,5-tetramethyl-1,3,2-dioxaborolan-2-yl)-1H-pyrazole.

TABLE 4

| Compound | Name | Structure | Characterization |
|---|---|---|---|
| 40 | 2-(6-(4-cyclopropyl-4H-1,2,4-triazol-3-yl)pyridin-2-yl)-6-(pyridin-3-yl)isoindolin-1-one | 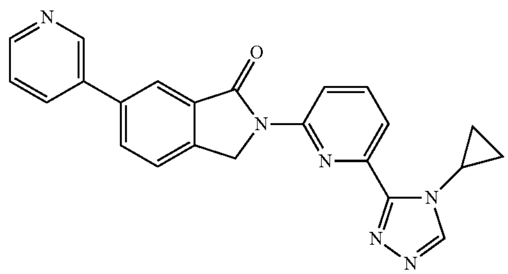 | $^1$H NMR (400 MHz, DMSO-d$_6$) δ 9.0 (s, 1H), 8.72 (s, 1H), 8.68 (d, J = 8.4 Hz, 1H), 8.63 (d, J = 4 Hz, 1H), 8.22 (d, J = 8 Hz, 1H), 8.15 (s, 1H), 8.12-8.08 (m, 2H), 7.91-7.85 (m, 2H), 7.55-7.53 (m, 1H), 5.25 (s, 2H), 4.15-4.09 (m, 1H), 1.16-1.11 (m, 2H), 1.01-0.96 (m, 2H); ESI m/z 395.2 [M + 1]$^+$ |
| 41 | 2-(6-(4-cyclopropyl-4H-1,2,4-triazol-3-yl)pyridin-2-yl)-6-(4-methylpyridin-3-yl)isoindolin-1-one | 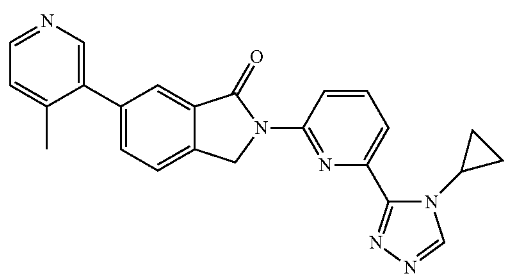 | $^1$H NMR (400 MHz, DMSO-d$_6$) δ 8.71 (s, 1H), 8.65 (d, J = 8.4 Hz, 1H), 8.48 (d, J = 5.2 Hz, 1H), 8.4.1 (s, 1H), 8.10-8.06 (m, 1H), 7.89 (d, J =7.6 Hz, 1H), 7.84-7.81 (m, 2H), 7.75 (dd, J = 7.6 Hz, 0.8 Hz, 1H), 7.37 (d, J = 5.2 Hz. 1H), 5.25 (s, 2H), 4.14-4.09 (m, 1H), 2.29 (s, 3H), 1.16-1.11 (m, 2H), 1.00-0.96 (m, 2H); ESI m/z 409.2 [M + 1]$^+$ |
| 42 | 2-(6-(4-cyclopropyl-4H-1,2,4-triazol-3-yl)pyridin-2-yl)-6-(6-methylpyridin-3-yl)isoindolin-1-one | 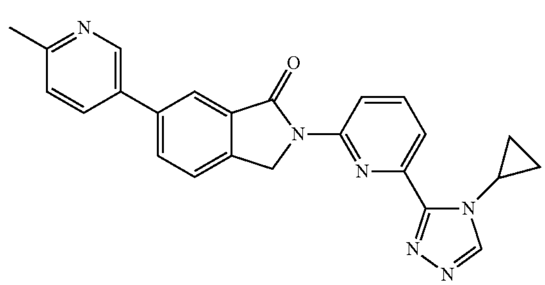 [SMILES: Cc1ccc(-c2ccc3c(c2)C(=O)N(c2cccc(-c4nncn4C4CC4)n2)C3)cn1] | $^1$H NMR (400 MHz, CDCl$_3$) δ 9.18 (s. 1H), 8.81 (dd, J = 6.4 Hz, 2.8 Hz, 1H), 8.42-8.39 (m, 2H), 8.18 (s, 1H), 8.00-7.92 (m, 3H), 7.75-7.68 (m, 2H), 5.18 (s, 2H), 4.01-3.96 (m, 1H), 2.89 (s, 3H), 1.23-1.18 (m, 2H), 1.04-1.0 (m, 2H); ESI m/z 409.1 [M + 1]$^+$ |

TABLE 4-continued

| Compound | Name | Structure | Characterization |
|---|---|---|---|
| 43 | 2-(6-(4-cyclopropyl-4H-1,2,4-triazol-3-yl)pyridin-2-yl)-6-(pyrimidin-5-yl)isooindolin-1-one | 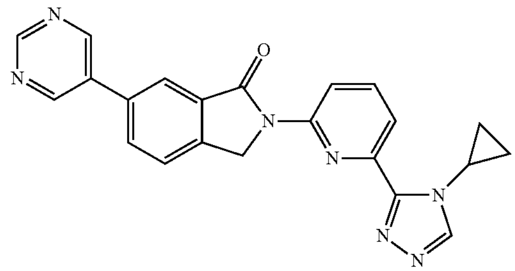 [SMILES: O=C1c2cc(-c3cncnc3)ccc2CN1c1cccc(-c2nncn2C2CC2)n1] | $^1$H NMR (400 MHz, CDCl$_3$) δ 8.27 (s, 1H), 9.03 (s, 1H), 8.78 (dd, J = 8 Hz, 1.2 Hz, 1H), 7.72 (d, J = 8 Hz, 1H), 5.17 (s, 2H), 3.98-3.93 (m, 1H), 1.18-1.13 (m, 2H), 1.0-0.96 (m, 2H); ESI m/z 396.1 [M + 1]$^+$ |
| 44 | 2-(6-(4-cyclopropyl-4H-1,2,4-triazol-3-yl)pyridin-2-yl)-6-(2-methylpyrimidin-5-yl)isoindolin-1-one | 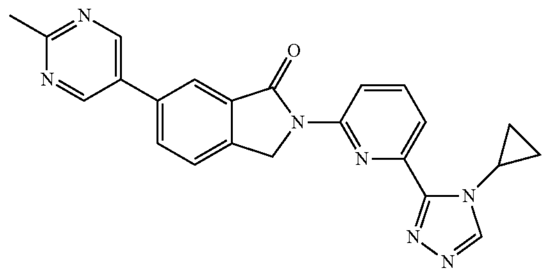 [SMILES: Cc1ncc(-c2ccc3c(c2)C(=O)N(c2cccc(-c4nncn4C4CC4)n2)C3)cn1] | $^1$H NMR (400 MHz, CDCl$_3$) δ 8.93 (s, 2H), 8.78 (d, J = 8 Hz, 1H), 8.25 (s, 1H), 8.16 (s, 1H), 8.01-7.93 (m, 2H), 7.84 (dd, J = 7.6 Hz, 1.2 Hz, 1H), 7.70 (d, J = 7.6 Hz, 1H), 5.16 (s, 2H), 3.98-3.93 (m, 1H), 2.82 (s, 3H), 1.18-1.13 (m, 2H), 1.0-0.96 (m, 2H); ESI m/z 410.1 [M + 1]$^+$ |
| 45 | 2-(6-(4-cyclopropyl-4H-1,2,4-triazol-3-yl)pyridin-2-yl)-6-(6-methoxypyridin-3-yl)isoindolin-1-one | 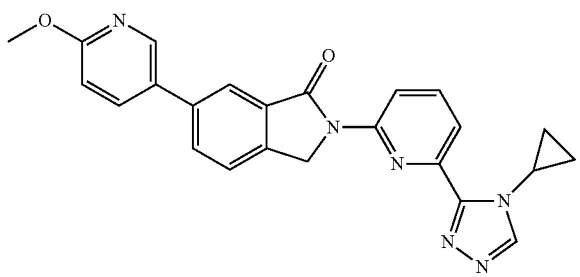 [SMILES: COc1ccc(-c2ccc3c(c2)C(=O)N(c2cccc(-c4nncn4C4CC4)n2)C3)cn1] | $^1$H NMR (400 MHz, CDCl$_3$) δ 8.78 (d, J = 8 Hz, 1H), 8.45 (s, 1H), 8.25 (s, 1H), 8.10 (s, 1H), 8.0-7.87(m, 2H), 7.86 (d, J = 8 Hz, 1H), 7.80 (d, J = 7.2 Hz, 1H), 7.62 (d, J = 7.6 Hz, 1H), 6.87 (d, J = 8.4 Hz, 1H), 5.12 (s, 2H), 4.0 (s, 3H), 4.0-3.92 (m, 1H), 1.16-1.14 (m, 2H), 1.0-0.96 (m, 2H); ESI m/z 425.0 [M + 1]$^+$ |
| 46 | 2-(6-(4-cyclopropyl-4H-1,2,4-triazol-3-yl)pyridin-2-yl)-6-(6-cyclopropylpyridin-3-yl)isoindolin-1-one | 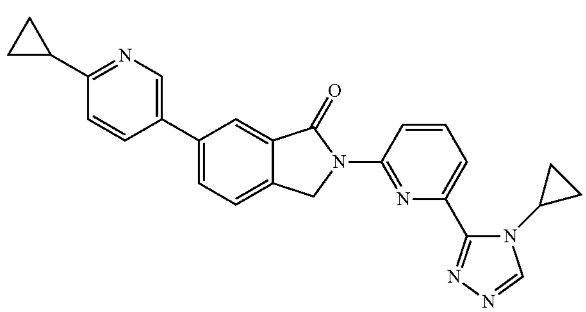 [SMILES: O=C1c2cc(-c3ccc(C4CC4)nc3)ccc2CN1c1cccc(-c2nncn2C2CC2)n1] | $^1$H NMR (400 MHz, DMSO-d$_6$) δ 8.78 (d, J = 1.2 Hz, 1H), 8.71 (s, 1H), 8.65 (d, J = 7.6 Hz, 1H), 8.08 (t, J = 8 Hz, 2H), 8.04-8.01 (m, 2H), 7.89 (d, J = 7.6 Hz, 1H), 7.81 (d. J = 8 Hz, 1H), 7.40 (d, J = 8.4 Hz, 1H), 5.20 (s, 2H), 4.11 (m, 1H), 2.19-2.13 (m, 1H), 1.16-1.11 (m, 2H), 1.0-0.96 (m, 6H); ESI m/z 435.1 [M + 1]$^+$ |
| 47 | 6-(1-cyclopropyl-1H-pyrazol-4-yl)-2-(6-(4-cyclopropyl-4H-1,2,4-triazol-3-yl)pyridin-2-yl)isoindolin-1-one | 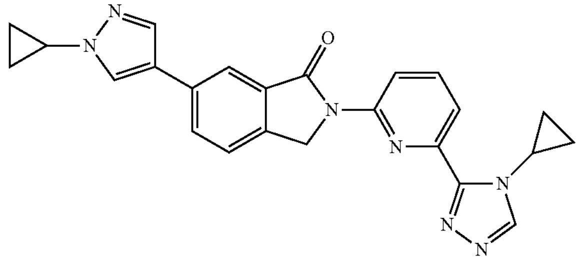 [SMILES: O=C1c2cc(-c3cnn(C4CC4)c3)ccc2CN1c1cccc(-c2nncn2C2CC2)n1] | $^1$H NMR (400 MHz, CDCl$_3$) δ 8.76 (d, J = 8.4 Hz, 1H), 8.23 (s, 1H), 8.0-7.98 (m, 2H), 7.91 (t, 8.4 Hz, 1H), 7.81 (d, J = 6 Hz, 2H), 7.73 (dd, J = 8 Hz, 1.6 Hz, 1H), 7.51 (d, J = 8 Hz, 1H), 5.06 (s, 2H), 3.97-3.94 (m, 1H), 3.68-3.63 (m, 1H), 1.21-1.05 (m, 6H), 0.98-0.94 (m, 2H); ESI m/z 424.1 [M + 1]$^+$ |

TABLE 4-continued

| Compound | Name | Structure | Characterization |
|---|---|---|---|
| 48 | 2-(6-(4-cyclopropyl-4H-1,2,4-triazol-3-yl)pyridin-2-yl)-6-(4-fluoropyridin-3-yl)isoindolin-1-one | 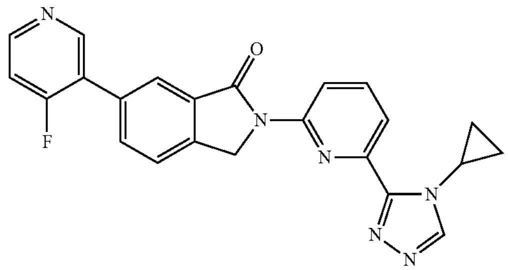 [SMILES: O=C1c2cc(-c3cnccc3F)ccc2CN1c1cccc(-c2nncn2C2CC2)n1] | $^1$H NMR (400 MHz, CDCl$_3$) δ 8.76 (t, J = 8 Hz, 2H), 8.63-8.60 (m, 1H), 8.25 (s, 1H), 8.14 (s, 1H), 8.00-7.92 (m, 2H), 7.82 (d, J = 8 Hz, 1H), 7.68 (d, J = 8 Hz, 1H), 7.20-7.16 (m, 1H), 5.51 (s, 2H), 3.99-3.93 (m, 1H), 1.17-1.12 (m, 2H), 1.00-0.95 (m, 2H); ESI m/z 413.0 [M + H]$^+$ |
| 49 | 6-(4-chloropyridin-3-yl)-2-(6-(4-cyclopropyl-4H-1,2,4-triazol-3-yl)pyridin-2-yl)isoindolin-1-one | 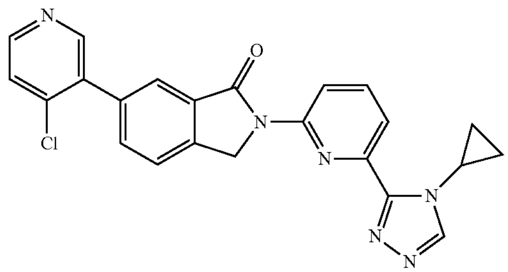 [SMILES: O=C1c2cc(-c3cnccc3Cl)ccc2CN1c1cccc(-c2nncn2C2CC2)n1] | $^1$H NMR (400 MHz, CDCl$_3$) δ 8.77 (d, J = 8.4 Hz, 1H), 8.60 (s, 1 H), 8.54 (d, J = 5.2 Hz, 1H), 8.25 (s, 1H), 8.05 (s, 1H), 8.0-7.94 (m, 2H), 7.74-7.66 (m, 2H), 7.48 (d, J = 5.2 Hz, 1H), 5.16 (s, 2H), 3.98-3.95 (m, 1H), 1.18-1.11 (m, 2H), 1.01-0.93 (m, 2H); ESI m/z 429.0 [M + 1]$^+$ |
| 50 | 2-(6-(4-cyclopropyl-4H-1,2,4-triazol-3-yl)pyridin-2-yl)-6-(pyridin-4-yl)isoindolin-1-one | 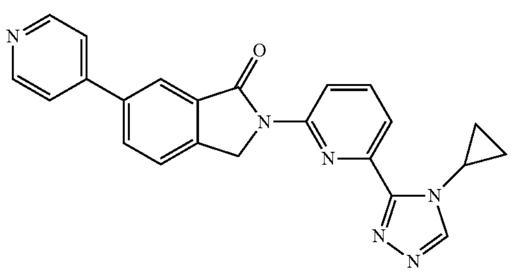 [SMILES: O=C1c2cc(-c3ccncc3)ccc2CN1c1cccc(-c2nncn2C2CC2)n1] | $^1$H NMR (400 MHz, CDCl$_3$) δ 8.79 (dd, J = 8 Hz, 0.8 Hz, 1H), 8.73-8.72 (m, 2H), 8.25 (s, 1H), 8.24 (d, J = 0.6 Hz, 1H), 8.01-7.91 (m, 3H), 7.68 (d, J = 8 Hz, 2H), 7.59-7.58 (m, 2H), 5.16 (s, 2H), 3.99-3.93 (m, 1H), 1.18-1.23 (m, 2H), 1.0-0.98 (m, 2H); ESI m/z 395.0 [M + 1]$^+$ |
| 51 | 2-(6-(4-cyclopropyl-4H-1,2,4-triazol-3-yl)pyridin-2-yl)-6-(2-methylthiazol-5-yl)isoindolin-1-one | 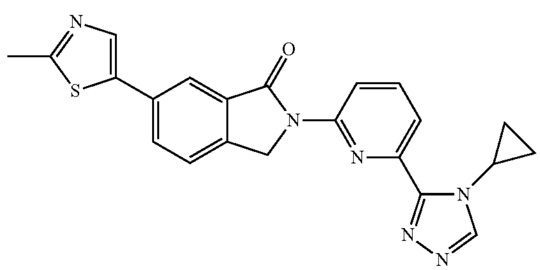 [SMILES: Cc1ncc(-c2ccc3c(c2)C(=O)N(c2cccc(-c4nncn4C4CC4)n2)C3)s1] | $^1$H NMR (400 MHz, CDCl$_3$) δ 8.76 (d, J = 8.4 Hz, 1H), 8.25 (s, 1H), 8.07 (s, 1H), 8.00-7.90 (m, 3H), 7.79 (dd, J = 8 Hz, 1.2 Hz, 1H), 7.57 (d, J = 8 Hz, 1H), 5.10 (s, 2H), 3.98-3.92 (m, 1H), 2.76 (s, 3H), 1.14 (q, J = 6.8 Hz, 2H), 0.99-0.95 (m, 2H); ESI m/z 415.0 [M + 1]$^+$ |
| 52 | 2-(6-(4-cyclopropyl-4H-1,2,4-triazol-3-yl)pyridin-2-yl)-6-(2-methylpyridin-3-yl)isoindolin-1-one | 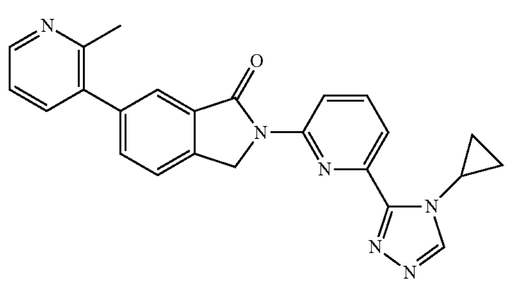 [SMILES: Cc1ncccc1-c1ccc2c(c1)C(=O)N(c1cccc(-c3nncn3C3CC3)n1)C2] | $^1$H NMR (400 MHz, DMSO-d$_6$) δ 8.71 (s, 1H), 8.65 (d, J = 8.4 Hz, 1H), 8.50 (dd, J = 4.8 Hz, 1.2 Hz, 1H), 8.09 (t, J = 8 Hz, 1H), 7.89 (d, J = 7.2 Hz, 1H), 7.83-7.80 (m, 2H), 7.75 (dd, J = 8 Hz, 1.6 Hz, 1H), 7.69 (dd, J = 7.6 Hz, 1.2 Hz, 1H), 7.34 (dd, J = 7.6 Hz, 4.8 Hz, 1H), 5.25 (s, 2H), 4.14-4.08 (m, 1H), 2.45 (s, 3H), 1.13 (q, J = 5.6 Hz, 2H), 0.98-0.96 (m, 2H); ESI m/z 409.1 [M + 1]$^+$ |

TABLE 4-continued

| Compound | Name | Structure | Characterization |
|---|---|---|---|
| 53 | 2-(6-(4-cyclopropyl-4H-1,2,4-triazol-3-yl)pyridin-2-yl)-6-(2-fluoropyridin-3-yl)isoindolin-1-one | 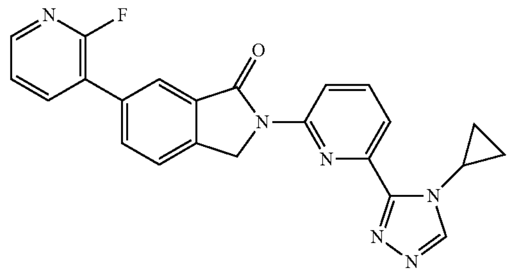 [SMILES: O=C1c2cc(-c3cccnc3F)ccc2CN1c1cccc(-c2nncn2C2CC2)n1] | $^1$H NMR (400 MHz, DMSO-d$_6$) δ 8.71 (s, 1H), 8.65 (d, J = 8.4 Hz, 1H), 8.50 (dd, J = 4.8 Hz, 1.2 Hz, 1H), 8.09 (t, J = 8 Hz, 1H), 7.89 (d, J = 7.2 Hz, 1H), 7.83-7.80 (m, 2H), 7.75 (dd, J = 8 Hz, 1.6 Hz, 1H), 7.69 (dd, J = 7.6 Hz, 1.2 Hz, 1H), 7.34 (dd, J = 7.6 Hz, 4.8 Hz, 1H), 5.25 (s, 2H), 4.14-4.08 (m, 1H), 2.45 (s, 3H), 1.13 (dd, J = 12.8 Hz, 7.2 Hz, 2H), 0.98-0.96 (m, 2H); ESI m/z 413.0 [M + 1]$^+$ |
| 54 | 2-(6-(4-cyclopropyl-4H-1,2,4-triazol-3-yl)pyridin-2-yl)-6-(5-methylpyridin-3-yl)isoindolin-1-one | 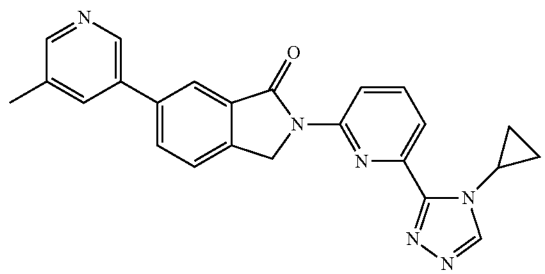 [SMILES: Cc1cncc(-c2ccc3c(c2)C(=O)N(c2cccc(-c4nncn4C4CC4)n2)C3)c1] | $^1$H NMR (400 MHz, CDCl$_3$) δ 8.78 (d, J = 8 Hz, 1H), 8.71 (d, J = 1.6 Hz, 1H), 8.48 (s, 1H), 8.25 (s, 1H), 8.15 (s, 1H), 8.00-7.91 (m, 2H), 7.86 (dd, J = 8 Hz, 1.6 Hz, 1H), 7.76 (s, 1H), 7.65 (d, J = 8 Hz, 1H), 5.14 (s, 2H), 4.00-3.94 (m, 1H), 2.44 (s, 3H), 1.15 (q, J = 6.4 Hz, 1H), 1.00-0.95 (m, 2H); ESI m/z 409.1 [M + 1]$^+$ |
| 55 | 2-(6-(4-cyclopropyl-4H-1,2,4-triazol-3-yl)pyridin-2-yl)-6-(5-fluoropyridin-3-yl)isoindolin-1-one | 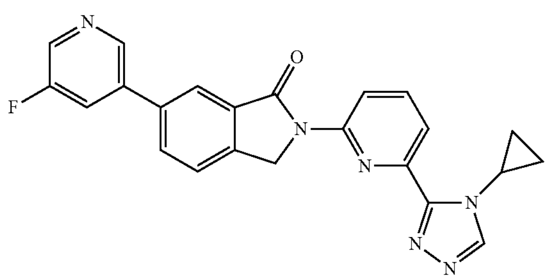 [SMILES: O=C1c2cc(-c3cncc(F)c3)ccc2CN1c1cccc(-c2nncn2C2CC2)n1] | $^1$H NMR (400 MHz, CDCl$_3$) δ 8.79 (m, 1H), 8.53 (d, J = 2.4 Hz, 1H), 8.25 (s, 1H), 8.17 (d, J = 0.8 Hz, 1H), 8.01-7.93 (m, 2H), 7.86 (dd, J = 8 Hz, 1.6 Hz 1H), 7.70-7.66 (m, 2H), 5.16 (s, 2H), 3.99-3.93 (m, 1H), 7.15 (q, J = 6.8 Hz, 2H), 1.00-0.96 (m, 2H); ESI m/z 413.0 [M + 1]$^+$ |

Example 12: Preparation of 2-(6-(4-cyclopropyl-4H-1,2,4-triazol-3-yl)pyridin-2-yl)-6-(2-cyclopropylpyrimidin-5-yl)isoindolin-1-one (compound 56)

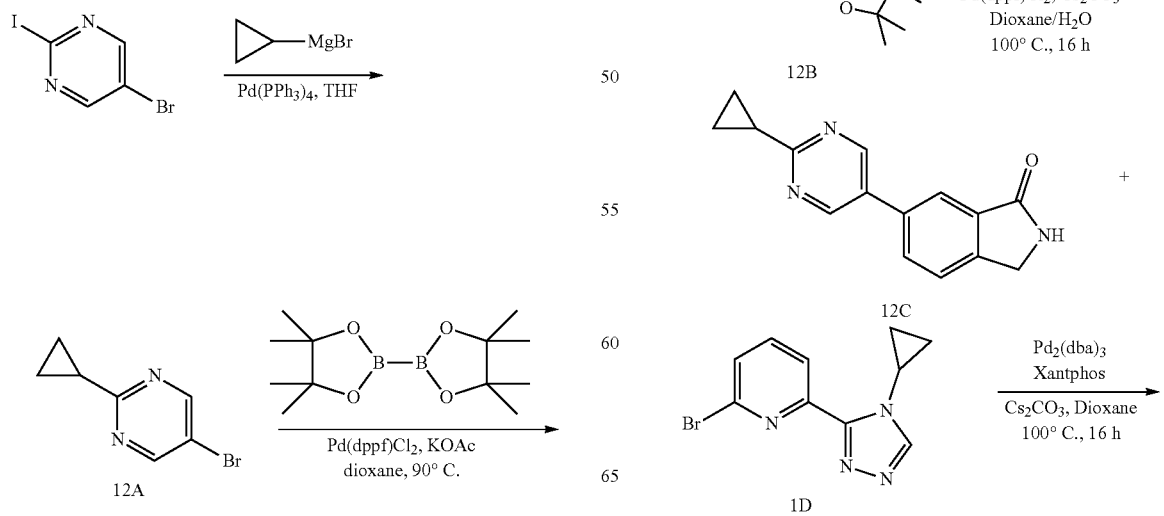

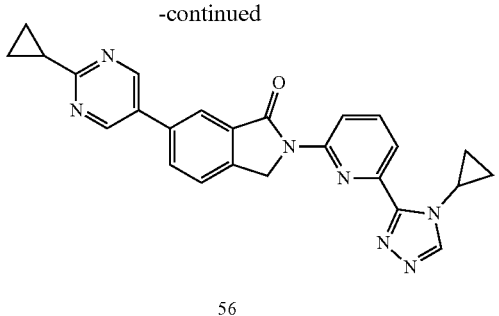

56

5-Bromo-2-iodo-pyrimidine (5.0 g, 17.6 mmol) and Pd(PPh$_3$)$_4$ (1.02 g, 0.88 mmol) were suspended in THF (80 mL), and cyclopropylmagnesium bromide (1.0 M in THF, 35 ml, 35 mmol) was added dropwise under a nitrogen atmosphere. After stirring at 70° C. for 2 h, the reaction was diluted with water (20 ml). The mixture was extracted with ethyl acetate (100 mL×3) and the combined organic fractions were dried over sodium sulfate. The solvent was removed under reduced pressure and the residue was purified by silica gel column chromatography (1:50 ethyl acetate/pet. ether) to obtain 12A (0.8 g, 23% yield): $^1$H NMR (400 MHz, CDCl$_3$) δ 8.53 (s, 2H), 2.18-2.13 (m, 1H), 1.06-1.04 (m, 4H); ESI m/z 199.1, 201.1 [M+1]$^+$.

A mixture of 12A (0.8 g, 4.02 mmol), Pd(dppf)Cl$_2$ (147 mg, 0.20 mmol), KOAc (592 mg, 6.03 mmol) and bis(pinacolato)diboron (1.16 g, 4.82 mmol) in dioxane (20 mL) was heated to 90° C. overnight. After cooling, the reaction mixture was concentrated and the residue was purified by silica gel column chromatography (1/50 to 1/10 ethyl acetate/pet. ether) to give 12B (0.38 g, 39% yield) as a yellow solid: ESI m/z 247.1 [M+H]$^+$.

Compound 56 was synthesized according to the procedure for compound 39 substituting intermediate 12B in place of 1-methyl-3-(4,4,5,5-tetramethyl-1,3,2-dioxaborolan-2-yl)-1H-pyrazole. $^1$H NMR (400 MHz, CDCl$_3$) δ 8.83 (s, 2H), 8.77 (d, J=8 Hz, 1H), 8.25 (s, 1H), 8.12 (s, 1H), 8.0-7.92 (m, 1H), 7.80 (dd, J=8 Hz, 1.6 Hz, 1H), 7.68 (d, J=7.6 Hz, 1H), 5.14 (s, 2H), 3.98-3.93 (m, 1H), 1.23-1.19 (m, 2H), 1.17-1.13 (m, 4H), 0.99-0.95 (m, 2H); ESI m/z 436.1 [M+1]$^+$.

Example 13: Preparation of 2-(6-(4-cyclopropyl-4H-1,2,4-triazol-3-yl)pyridin-2-yl)-6-(1-methyl-1H-imidazol-2-yl)isoindolin-1-one (compound 57)

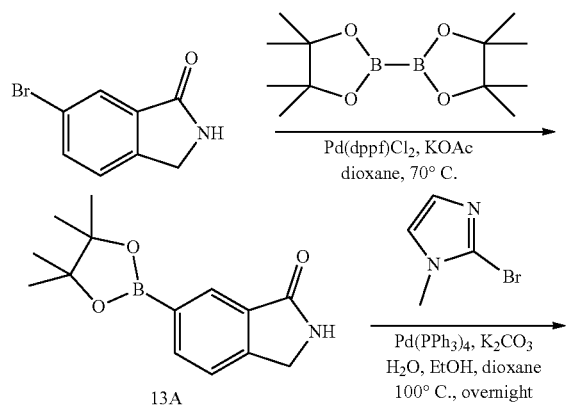

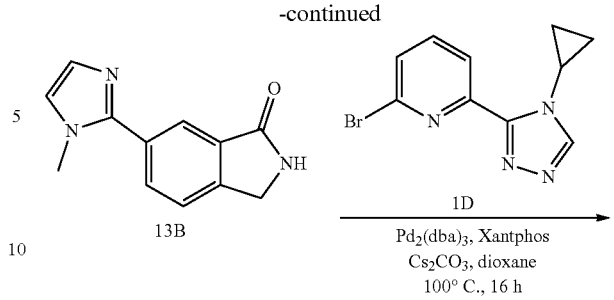

A mixture of 6-bromoisoindolin-1-one (2.0 g, 9.44 mmol), bis(pinacolato)diboron (2.41 g, 9.7 mmol), KOAc (1.86 g, 18.66 mmol) and Pd(dppf)$_2$Cl$_2$ (0.39 g, 0.49 mmol) in dioxane (50 mL) was stirred at 100° C. overnight under a nitrogen atmosphere. The mixture was poured into water and extracted with EtOAc (100 mL×3). The combined organic fractions were washed with brine, dried over sodium sulfate and concentrated under vacuum. The residue was purified by chromatography on silica gel (1/10 to 1/5 EtOAc in pet. ether) to give compound 13A (600 mg, 25% yield) as a white solid. ESI m/z 260.0 [M+1]$^+$.

A mixture of 13A (321 mg, 1.98 mmol), 2-bromo-1-methyl-1H-imidazole (626 mg, 2.41 mmol), K$_2$CO$_3$ (1.10 g, 7.92 mmol) and Pd(PPh$_3$)$_4$ (114 mg, 0.098 mmol) in dioxane (20 mL), ethanol (10 mL) and water (10 mL) was stirred at 100° C. overnight under a nitrogen atmosphere. The mixture was poured into water and extracted with EtOAc (100 mL×3). The combined organic fractions were washed with brine, dried over sodium sulfate and concentrated under vacuum. The residue was purified by chromatography on silica gel (1%-2% MeOH in DCM) to give compound 13B (200 mg, 47% yield) as a yellow solid. ESI m/z 214.0 [M+1]$^+$.

A mixture of 13B (200 mg, 0.82 mmol), intermediate 1D (212 mg, 0.82 mmol), Cs$_2$CO$_3$ (834 mg, 2.56 mmol), Xantphos (30 mg, 0.041 mmol) and Pd(dba)$_3$ (30 mg, 0.024 mmol) in dioxane (20 mL) was stirred at 100° C. overnight under a nitrogen atmosphere. The reaction mixture was concentrated under vacuum and purified by chromatography on silica gel (1%-3% MeOH in DCM) to give compound 57 (60 mg, 19% yield) as a white solid: $^1$H NMR (400 MHz, CDCl$_3$) δ 8.77 (d, J=8.4 Hz, 1H), 8.25 (s, 1H), 8.12 (s, 1H), 8.08 (d, J=8 Hz, 1H), 8.01-7.92 (m, 2H), 7.66 (d, J=8 Hz, 1H), 7.17 (s, 1H), 7.03 (s, 1H), 5.14 (s, 2H), 3.99-3.93 (m, 1H), 3.84 (s, 3H), 1.15 (q, J 6.8 Hz, 2H), 0.99-0.95 (m, 2H); ESI m/z 398.1 [M+1]$^+$.

Compounds 58-60 in Table 5 were synthesized according to the procedure for compound 57 substituting the appropriate heteroaryl halide in place of 2-bromo-1-methyl-1H-imidazole.

TABLE 5

| Compound | Name | Structure | Characterization |
|---|---|---|---|
| 58 | 2-(6-(4-cyclopropyl-4H-1,2,4-triazol-3-yl)pyridin-2-yl)-6-(pyridin-2-yl)isoindolin-1-one | 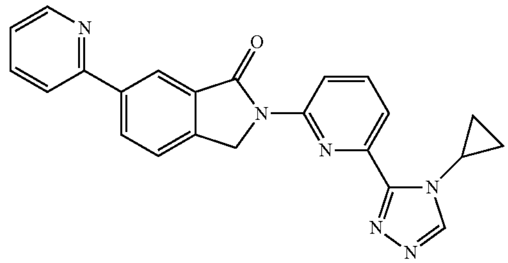 [SMILES: O=C1c2cc(-c3ccccn3)ccc2CN1c1cccc(-c2nncn2C2CC2)n1] | $^1$H NMR (400 MHz, CDCl$_3$) δ 8.78 (d, J = 8 Hz, 1H), 8.72 (d, J = 5.2 Hz, 1H), 8.49 (s, 1H), 8.41 (dd, J = 8 Hz, 2.4 Hz, 1H), 8.24 (s, 1H), 7.99 (d, J = 6.4 Hz, 1H), 7.95-7.91 (m, 1H), 7.85-7.81 (m, 2H), 7.65 (d, J = 8 Hz, 1H), 7.31-7.28 (m, 1H), 5.13 (s, 2H), 4.0-3.94 (m, 1H), 1.18-1.13 (m, 2H), 1.0-1.95 (m, 2H); ESI m/z 395.0 [M + 1]$^+$ |
| 59 | 2-(6-(4-cyclopropyl-4H-1,2,4-triazol-3-yl)pyridin-2-yl)-6-(pyridazin-3-yl)isoindolin-1-one | 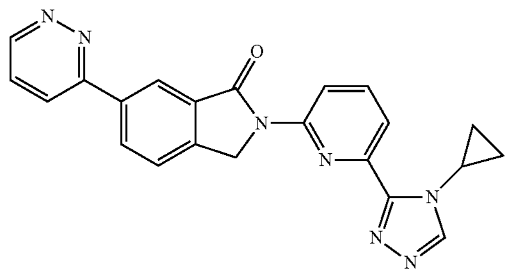 [SMILES: O=C1c2cc(-c3cccnn3)ccc2CN1c1cccc(-c2nncn2C2CC2)n1] | $^1$H NMR (400 MHz, CDCl$_3$) δ 9.23 (dd, J = 4.8 Hz, 1.2 Hz, 1H), 8.80 (d, J = 8.8 Hz, 1H), 8.63 (dd, J = 8 Hz, 1.6 Hz, 1H), 8.50 (s, 1H), 8.26 (s, 1H), 8.02-7.93 (m, 3H), 7.74 (d, J = 8 Hz, 1H), 7.63 (m, 1H), 5.18 (s, 2H), 4.01-3.94 (m, 1H), 1.17-1.12 (m, 2H), 1.01-0.95 (m, 2H); ESI m/z 396.0 [M + 1]$^+$ |
| 60 | 2-(6-(4-cyclopropyl-4H-1,2,4-triazol-3-yl)pyridin-2-yl)-6-(5-cyclopropylpyrazin-2-yl)isoindolin-1-one | 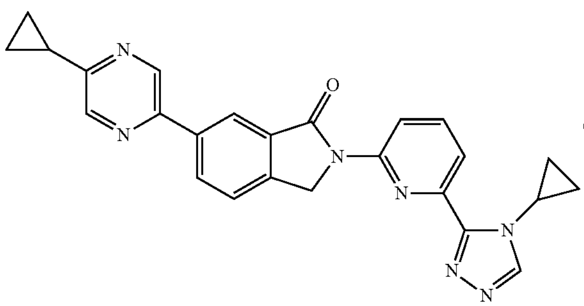 | $^1$H NMR (400 MHz, CDCl$_3$) δ 8.90 (s, 1H), 8.76 (d, J = 8 Hz, 1H), 8.54 (s, 1H), 8.49 (s, 1H), 8.30 (d, J = 8 Hz, 1H), 8.24 (s, 1H), 7.99-7.90 (m, 2H), 7.65 (d, J = 8 Hz, 1H), 5.12 (s, 2H), 3.99-3.93 (m, 1H), 2.14-2.11 (m 1H), 1.17-1.08 (m, 6H), 0.99-0.95 (m, 2H); ESI m/z 436.1 [M + 1]$^+$ |

Example 14: Preparation of 2-(6-(4-cyclopropyl-4H-1,2,4-triazol-3-yl)pyridin-2-yl)-6-(6-cyclopropylpyridazin-3-yl)isoindolin-1-one (compound 61)

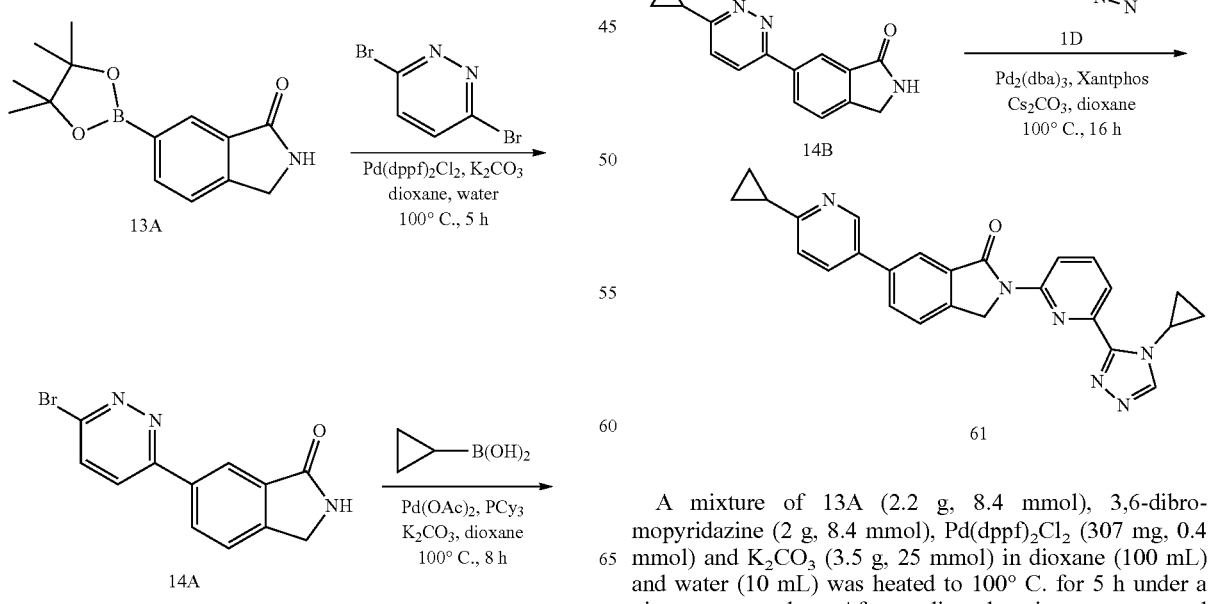

A mixture of 13A (2.2 g, 8.4 mmol), 3,6-dibromopyridazine (2 g, 8.4 mmol), Pd(dppf)$_2$Cl$_2$ (307 mg, 0.4 mmol) and K$_2$CO$_3$ (3.5 g, 25 mmol) in dioxane (100 mL) and water (10 mL) was heated to 100° C. for 5 h under a nitrogen atmosphere. After cooling, the mixture was poured into water and extracted with EtOAc (150 mL×3). The combined organic layers were washed with water and brine and dried with sodium sulfate. The solvent was evaporated and the residue was purified by column chromatography on silica gel (1%-2% MeOH in DCM) to afford compound 14A (660 mg, 28% yield) as an off-white solid. ESI m/z 291.9, 289.9 [M+1]$^+$.

A mixture of 14A (370 mg, 1.3 mmol) cyclopropylboronic acid (329 mg, 3.8 mmol), palladium diacetate (29 mg, 0.10 mmol), K$_2$CO$_3$ (1.1 g, 7.7 mmol) and tricyclohexylphosphine (72 mg, 0.3 mmol) in dioxane (17 mL) and water (2 mL) was heated to 100° C. for 8 hours under nitrogen. The reaction mixture was concentrated under vacuum and the residue was purified by column chromatography on silica gel (1%-2% MeOH in DCM) to give 14B (125 mg, 39% yield) as a white solid. ESI m/z 252.1 [M+1]$^+$.

A mixture of 14B (125 mg, 0.5 mmol), 1D (158 mg, 0.6 mmol), Pd$_2$(dba)$_3$ (23 mg, 0.02 mmol), Xantphos (20 mg, 0.03 mmol) and Cs$_2$CO$_3$ (486 mg, 1.5 mmol) in dioxane (25 mL) was heated to 100° C. overnight under nitrogen. The reaction mixture was concentrated under vacuum and the residue was purified by column chromatography on silica gel (1%-2% MeOH in DCM) to afford compound 61 (12 mg, 5% yield) as a yellow solid: $^1$H NMR (400 MHz, CDCl$_3$) δ 8.59 (dd, J=7.6 Hz, 1.6 Hz 1H), 8.44 (s, 1H), 8.25 (s, 1H), 8.01-7.92 (m, 2H), 7.84 (d, J=8.8 Hz, 1H), 7.69 (d, J=8 Hz, 1H), 7.38 (d, J=8.8 Hz, 1H), 5.15 (s, 2H), 4.00-3.94 (m, 1H), 2.25-2.18 (m, 1H), 1.31-1.29 (m, 2H), 1.21-1.15 (m, 4H), 1.00-0.95 (m, 2H); ESI m/z 436.1 [M+1]$^+$.

Example 15: Preparation of 6-(4-cyclopropyl-1H-1,2,3-triazol-1-yl)-2-(6-(4-cyclopropyl-4H-1,2,4-triazol-3-yl)pyridin-2-yl)isoindolin-1-one (compound 62)

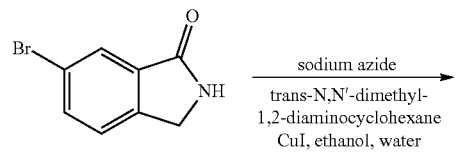

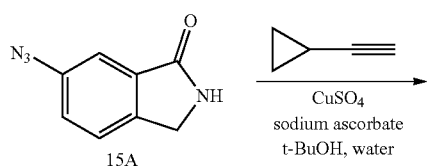

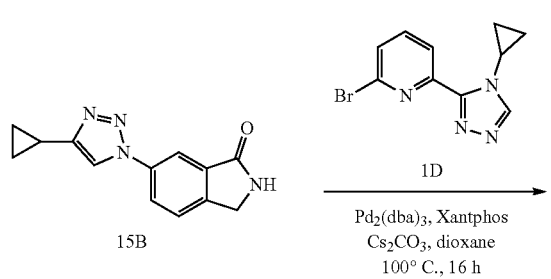

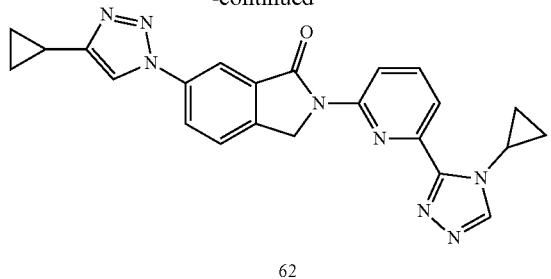

62

A mixture of 6-bromoisoindolin-1-one (5 g, 23.6 mmol), sodium azide (3.07 g, 47.2 mmol), sodium ascorbate (234 mg, 1.18 mmol), CuI (450 mg, 2.36 mmol) and trans-N,N-dimethyl-1,2-diaminocyclohexane (504 mg, 3.54 mmol) in ethanol (35 mL) and water (15 mL) was stirred at reflux for 5.5 h under nitrogen. The reaction mixture was allowed to cool to room temperature and extracted with EtOAc (100 mL×3). The combined organic fractions were washed with brine and dried with anhydrous sodium sulfate. The solvent was evaporated under reduced pressure and the residue was purified by chromatography on silica gel (10-50% EtOAc in pet. ether) to give 15A (1.2 g, 29% yield) as an off-white solid. ESI m/z 175.0 [M+1]$^+$.

A mixture of 15A (100 mg, 0.57 mmol), sodium ascorbate (12 mg, 0.06 mmol), ethynylcyclopropane (46 mg, 0.69 mmol), CuSO$_4$.5H$_2$O (11 mg, 0.06 mmol) in 3 mL of a 1:1 solution of t-BuOH/H$_2$O was stirred at room temperature overnight. The mixture was concentrated under vacuum and the residue was purified by silica gel column chromatography (1%-50% EtOAc in pet. ether) to afford 15B (30 mg, 22% yield) as an off-white solid: $^1$H NMR (400 MHz, DMSO-d$_6$) δ 8.77 (br, 1H), 8.68 (s, 1H), 8.13-8.08 (m, 2H), 7.77 (d, J=8.4 Hz, 1H), 4.45 (s, 2H), 2.06-2.0 (m, 1H), 1.0-0.95 (m, 2H), 0.83-0.80 (m, 2H); ESI m/z 241.0 [M+1]$^+$.

A mixture of 15B (240 mg, 1.0 mmol), 1D (265 mg, 1.0 mmol), Pd$_2$(dba)$_3$ (28 mg, 0.03 mmol), Xantphos (29 mg, 0.05 mmol) and K$_2$CO$_3$ (276 mg, 2.0 mmol) in dioxane (45 mL) was heated to 100° C. overnight under a nitrogen atmosphere. The mixture was allowed to cool to room temperature and filtered. The filtrate was concentrated under reduced pressure and the residue was purified by column chromatography on silica gel (1%-5% MeOH in DCM) to give compound 62 (100 mg, 23% yield) as a white solid: $^1$H NMR (400 MHz, DMSO-d$_6$) δ 8.76 (s, 1H), 8.72 (s, 1H), 8.66 (d, J=8.4 Hz, 1H), 8.26-8.25 (m, 2H), 8.11 (t, J=8 Hz, 1H), 7.93-7.90 (m, 2H), 5.26 (s, 2H), 4.14-4.08 (m, 1H), 2.08-2.01 (m, 1H), 1.18-1.13 (m, 2H), 1.0-0.98 (m, 4H), 0.85-0.82 (m, 2H); ESI m/z 425.1 [M+1]$^+$.

Example 16: Preparation of 2-(6-(4-cyclopropyl-4H-1,2,4-triazol-3-yl)pyridin-2-yl)-5-fluoro-6-(pyridin-3-yl)isoindolin-1-one (compound 63)

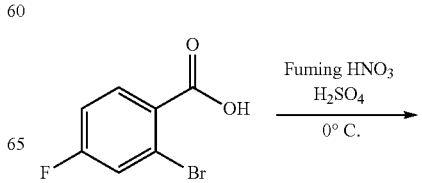

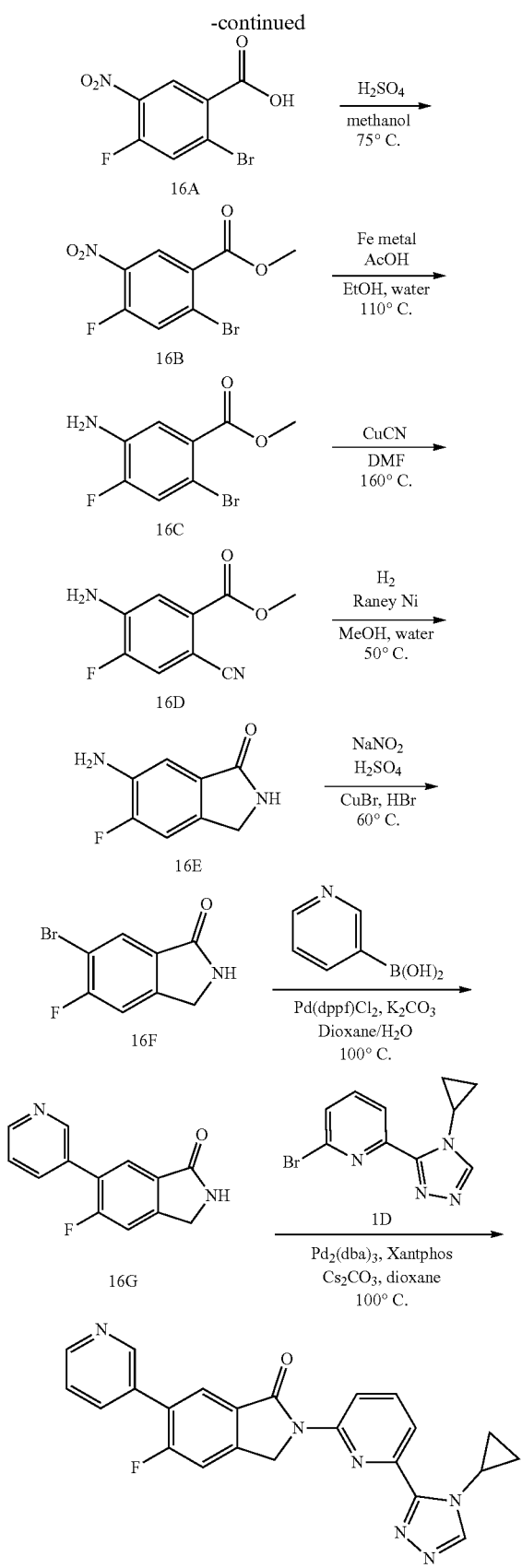

Fuming nitric acid (8 mL) was added dropwise to a mixture of 2-bromo-4-fluorobenzoic acid (20 g, 91.2 mmol) in concentrated sulfuric acid (68 mL) at 0° C. After stirring at room temperature for 3 h, the mixture was poured into ice water and stirred rapidly for 1 hour. The solid was collected by filtration, washed with water and dried to give compound 16A (17.59 g, 73% yield) as a white solid: $^1$H NMR (400 MHz, CDCl$_3$) δ 8.81 (d, J=8 Hz, 1H), 7.73 (d, J=10 Hz, 1H).

A mixture of 16A (11.5 g, 43.7 mmol) in methanol (230 mL) and H$_2$SO$_4$ (1.7 mL) was heated to 75° C. overnight. The reaction mixture was taken up in ethyl acetate and washed with saturated sodium bicarbonate. The organic fraction was dried over anhydrous sodium sulfate, concentrated and purified by column chromatography (1/30 to 1/5 EtOAc in pet. ether) to give the compound 16B (3.5 g, 29% yield) as a white solid: $^1$H NMR (400 MHz, CDCl$_3$) δ 8.63 (d, J=7.6 Hz, 1H), 7.67 (d, J=10 Hz, 1H), 3.98 (s, 3H).

A mixture of 16B (10 g, 36.1 mmol) and Fe (10.1 g, 180.5 mmol) in acetic acid (10 mL), EtOH (240 mL) and water (60 mL) was heated to 110° C. for 5 h. After cooling to room temperature, the reaction mixture was filtered. The filtrate was poured into water and extracted with EtOAc (3×300 mL). The combined organic fractions were washed with water and brine and dried with sodium sulfate. The solvent was removed under vacuum and the residue was purified by silica column chromatography (1/10 to 1/2 EtOAc in pet. ether) to afford 16C (7.5 g, 84% yield) as an off-white solid: ESI m/z 248.0, 250.0 [M+H]$^+$.

A mixture of 16C (8.5 g, 34.4 mmol), and CuCN (4.6 g, 51.6 mmol) in DMF (120 mL) was heated to 160° C. for 1 h under nitrogen. After cooling to room temperature, the mixture was partitioned between EtOAc and water. The organic layer was washed with water and brine and dried with sodium acetate. The solvent was evaporated and the residue was purified by column chromatography on silica gel (1/100 to 1/1 EtOAc in pet. ether) to give 16D (4.0 g, 60% yield) as a brown solid: $^1$H NMR (400 MHz, DMSO-d$_6$) δ 7.66 (d, J=11.6, 1H), 7.45 (d, J=8 Hz, 1H), 6.53 (s, 2H), 3.86 (s, 3H); ESI m/z 195.0 [M+H]$^+$.

A mixture of 16D (2.0 g, 10.2 mmol) and Raney Nickel (1.0 g) in water (15 mL) and methanol (70 mL) was heated to 50° C. under 1 atm of H$_2$ for 8 h. The reaction mixture was filtered and the filtrate was poured into water and extracted with EtOAc (50 mL×3). The combined organic fractions were washed with brine and dried with sodium sulfate. The solvent was evaporated and the residue was purified by column chromatography (1/4 to 1/1 EtOAc in pet. ether) to afford compound 16E (1.1 g, 65% yield) as a white solid: ESI m/z 167.1 [M+H]$^+$.

A solution of NaNO$_2$ (126 mg, 1.8 mmol) in water (2 mL) was added dropwise to a mixture of 16E (200 mg, 1.2 mmol) in water (8 mL) and H$_2$SO$_4$ (3 mL) at 0° C. After the addition, the mixture was stirred at 0° C. for 1 hour. Then CuBr (516 mg, 3.6 mmol) in HBr (25 mL) was added dropwise to the reaction mixture. The reaction was then heated to 60° C. for 5 h. The resulting mixture was poured into water and extracted with EtOAc (3×50 mL). The combined organic fractions were washed with water and brine and dried over sodium sulfate. The solvent was concentrated under reduced pressure and the residue was purified by column chromatography (1%-2.5% MeOH in DCM) to give 16F (130 mg, 47% yield) as a white powder: ESI m/z 231.9, 229.9 [M+H]$^+$.

A mixture of 16F (260 mg, 1.1 mmol), pyridin-3-ylboronic acid (139 mg, 1.1 mmol), Pd(dppf)$_2$C$_1$ (25 mg, 0.03 mmol) and K$_2$CO$_3$ (469 mg, 3.4 mmol) in dioxane (25 mL) and water (2.5 mL) was heated to 100° C. overnight under nitrogen. The resulting mixture was concentrated under reduced pressure and purified by column chromatography on silica gel (1%-2% MeOH in DCM) to afford compound 16G (110 mg, 43% yield) as a white solid: ESI m/z 229.0 [M+H]+.

A mixture of 16G (110 mg, 0.48 mmol), 1D (153 mg, 0.6 mmol), Pd$_2$(dba)$_3$ (22 mg, 0.02 mmol), Xantphos (20 mg, 0.03 mmol) and Cs$_2$CO$_3$ (471 mg, 1.4 mmol) in dioxane (20 mL) was heated to 100° C. overnight under nitrogen. The reaction mixture was concentrated and purified by column chromatography on silica gel (1%-2% MeOH in DCM) to afford compound 63 (35 mg, 18% yield) as a white solid: $^1$H NMR (400 MHz, CDCl$_3$) δ 8.85 (s, 1H), 8.75 (dd, J=8.4 Hz, 1.2 Hz, 1H), 8.68 (s, 1H), 8.25 (s, 1H), 8.05 (d, J=7.2 Hz, 1H), 8.01-7.90 (m, 3H), 7.45-7.38 (m, 2H), 5.13 (s, 2H), 3.97-3.91 (s, 1H), 1.17-1.12 (m, 2H); ESI m/z 413.1 [M+H]+.

Example 17: Preparation of 2-(6-(4-cyclopropyl-4H-1,2,4-triazol-3-yl)pyridin-2-yl)-5-methyl-6-(pyridin-3-yl)isoindolin-1-one (compound 64)

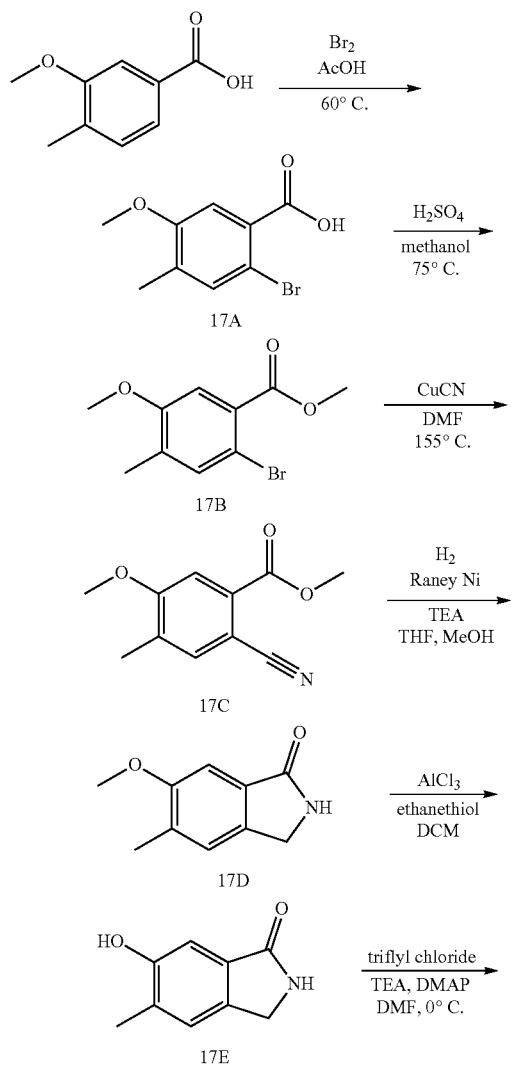

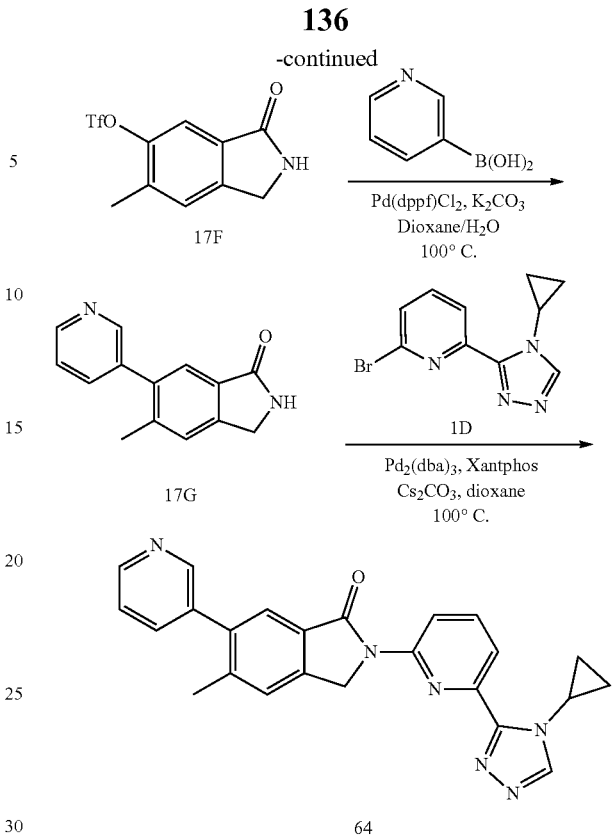

Bromine (23 g, 144 mmol) was added dropwise to a suspension of 3-methoxy-4-methylbenzoic acid (20 g, 120 mmol) in acetic acid (153 mL) and water (153 mL) at room temperature. The reaction mixture was heated to 60° C. for 2 h. After cooling to room temperature, the reaction mixture was filtered and rinsed with cold water (400 mL) to afford product 17A (28 g, 95% yield) as a white solid: $^1$H NMR (400 MHz, DMSO-d$_6$) δ 13.26 (br, 1H), 7.48 (s, 1H), 7.28 (s, 1H), 3.82 (s, 3H), 2.16 (s, 3H); ESI m/z 268.9, 266.9 [M+Na].

A mixture of 17A (30 g, 122.4 mmol) in methanol (600 mL) and H$_2$SO$_4$ (3 mL) was heated to 75° C. overnight. The reaction mixture was taken up in ethyl acetate and washed with saturated sodium bicarbonate. The organic fraction was dried over anhydrous sodium sulfate and concentrated under reduced pressure to give 17B (20 g, 59% yield) as a white solid: $^1$H NMR (400 MHz, DMSO-d$_6$) δ 7.52 (d, 0.8 Hz, 1H), 7.29 (s, 1H), 3.84 (s, 3H), 3.82 (s, 3H), 2.17 (s, 3H); ESI m/z 282.9, 280.9 [M+Na]+.

A mixture of 17B (9.6 g, 37.1 mmol) and CuCN (5 g, 55.8 mmol) in DMF (120 mL) was heated to 155° C. for 2 hours under nitrogen. After cooling to room temperature, the mixture was partitioned between EtOAc and water. The organic layer was washed with water and brine and dried with sodium acetate. The solvent was evaporated and the residue was purified by column chromatography on silica gel (1/100 to 1/1 EtOAc in pet. ether) to give 17C (6 g, 67% yield) as an off-white solid: ESI m/z 206.0 [M+H]+.

A mixture of 17C (4.5 g, 21.9 mmol), Raney Nickel (1 g) in Et$_3$N (25 mL), THF (45 mL) and methanol (100 mL) was shaken under a hydrogen atmosphere of 55 psi at room temperature overnight. The reaction mixture was filtered and the filtrate was concentrated under reduced pressure. The residue was purified by column chromatography on silica gel (1/10 to 1/1 EtOAc in pet. ether) to afford compound 17D (2.9 g, 74% yield) as an off-white solid: $^1$H NMR (400 MHz, DMSO-$d_6$) δ 8.39 (s, 1H), 7.32 (s, 1H), 7.13 (s, 1H), 4.24 (s, 2H), 3.84 (s, 3H), 2.23 (s, 3H); ESI m/z 178.0 [M+H]$^+$.

A mixture of 17D (1.85 g, 10.4 mmol) and AlCl$_3$ (4.2 g, 31.3 mmol) in DCM (80 mL) was stirred at room temperature for 5 min under nitrogen. Ethanethiol (1.9 g, 31.3 mmol) was added and the reaction mixture was stirred for 3 h at room temperature. A precipitate formed as the mixture was poured into water. The solid was collected by filtration, washed with water and dried under vacuum. The product was further purified by column chromatography (2%-10% MeOH in DCM) to give 17E (1.35 g, 80%) as a white solid: $^1$H NMR (400 MHz, DMSO-$d_6$) δ 9.70 (s, 1H), 8.31 (s, 1H), 7.23 (s, 1H), 7.04 (s, 1H), 4.19 (s, 2H), 2.19 (s, 3H); ESI m/z 164.0 [M+H].

Trifluoromethanesulfonyl chloride (1.2 g, 7.4 mmol) was added dropwise to a mixture of 17E (600 mg, 3.7 mmol), triethylamine (2.2 g, 22.1 mmol) and DMAP (449 mg, 3.7 mmol) in DMF (20 mL) at 0° C. over a period of 10 min. The reaction mixture was warmed to room temperature and stirred for 3 hours under a nitrogen atmosphere. The resulting mixture was poured into water and extracted with EtOAc (100 mL×3). The organic fractions were washed with water and brine and dried over sodium sulfate. The solvent was removed under vacuum and the residue was purified by column chromatography on silica gel (1%-2% MeOH in DCM) to afford 17F (600 mg, 55%) as a white solid: $^1$H NMR (400 MHz, DMSO-$d_6$) δ 8.79 (s, 1H), 7.70 (s, 1H), 7.56 (s, 1H), 4.40 (s, 2H), 2.43 (s, 3H); ESI m/z 295.9 [M+H]$^+$.

A mixture of 17F (400 mg, 1.4 mmol), pyridin-3-ylboronic acid (217 mg, 1.8 mmol), Pd(dppf)$_2$Cl$_2$ (50 mg, 0.06 mmol) and K$_2$CO$_3$ (562 mg, 4.1 mmol) in dioxane (35 mL) and water (5 mL) was heated to 100° C. overnight under nitrogen. The resulting mixture was concentrated under reduced pressure and purified by column chromatography on silica gel (1%-3% MeOH in DCM) to afford compound 17G (210 mg, 70%) as a white solid: ESI m/z 225.0 [M+H]$^+$.

A mixture of 17G (210 mg, 0.9 mmol), 1D (248 mg, 0.9 mmol), Pd$_2$(dba)$_3$ (43 mg, 0.05 mmol), Xantphos (38 mg, 0.07 mmol) and Cs$_2$CO$_3$ (915 mg, 2.8 mmol) in dioxane (25 mL) was heated to 100° C. overnight under nitrogen. The reaction mixture was concentrated and purified by column chromatography on silica gel (1%-3% MeOH in DCM) to give compound 64 (95 mg, 25% yield) as a white solid: $^1$H NMR (400 MHz, DMSO-$d_6$) δ 8.71 (s, 1H), 8.64-8.62 (m, 3H), 8.07 (t, J=7.6 Hz, 1H), 7.89-7.86 (m, 2H), 7.70 (s, 1H), 7.64 (s, 1H), 7.52 (dd, 7.6 Hz, 4.8 Hz, 1H), 5.20 (s, 2H), 4.14-4.08 (m, 1H), 2.35 (s, 3H), 1.15-1.10 (m, 2H), 1.01-0.97 (m, 2H); ESI m/z 409.0 [M+H]$^-$.

Example 18: Preparation of 5-chloro-2-(6-(4-cyclopropyl-4H-1,2,4-triazol-3-yl)pyridin-2-yl)-6-(pyridin-3-yl)isoindolin-1-one (compound 65)

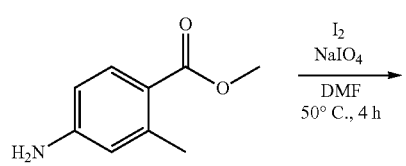

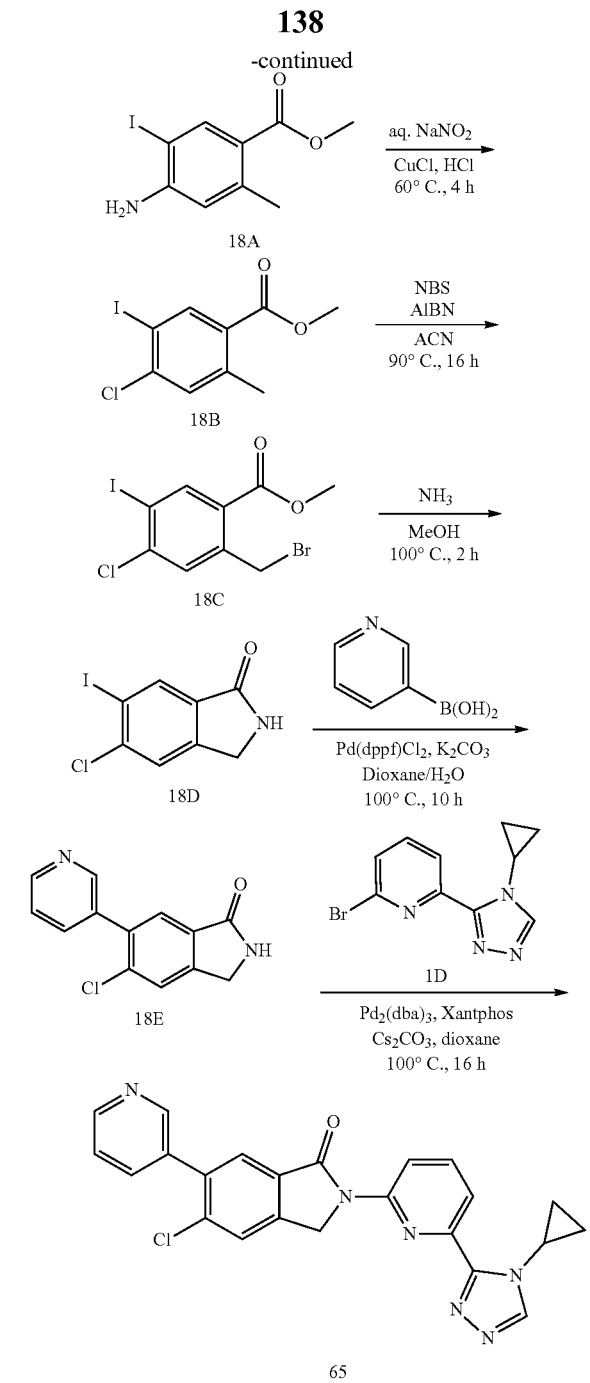

To a mixture of methyl 4-amino-2-methylbenzoate (15.0 g, 85.86 mmol) in DMF (80 mL) was added sodium periodate (7.36 g, 34.42 mmol) and iodine (17.6 g, 68.84 mmol). The reaction mixture was stirred at 50° C. for 3 hours. The mixture was poured into a solution of NaHSO$_3$ (2.6 g) in water (200 mL). After stirring for 3 h, the mixture was extracted with DCM (300 mL×3). The organic layer was dried over sodium sulfate, concentrated under reduced pressure and purified by chromatography on silica gel (2%-30% EtOAc in pet. ether) to give 18A (16.15 g, 65% yield) as a yellow solid: $^1$H NMR (400 MHz, CDCl$_3$) δ 8.20 (s, 1H), 6.47 (s, 1H), 3.75 (s, 3H), 2.42 (s, 3H); ESI m/z 292.0 [M+H]$^+$.

A solution of NaNO$_2$ (5.33 g, 77.25 mmol) in water (150 mL) was added dropwise to a solution of 18A (15.0 g, 51.53 mmol) in conc. HCl (150 mL) at −5° C. over a period of 20 min. The reaction mixture was stirred at −5° C. for 1 hour, then a solution of CuCl (7.72 g, 0.078 mmol) in conc. HCl (150 mL) was added. The reaction mixture was stirred at 60° C. for 4 hours. After cooling, the resulting mixture was extracted with EtOAc (400 mL×3). The combined organic fractions were washed with water and brine and dried over sodium sulfate. The solvent was concentrated under reduced pressure and the residue was purified by chromatography on silica gel (4% EtOAc in pet. ether) to provide 18B (9.69 g, 60% yield) as yellow oil: ESI m/z 311, 313.0 [M+H]$^+$.

A mixture of 18B (5.0 g, 16.10 mmol) AIBN (530 mg, 3.23 mmol) and NBS (5.73 g, 32.19 mmol) in ACN (80 mL) was stirred at 90° C. overnight. The reaction mixture was concentrated and the residue was purified by chromatography on silica gel (1% EtOAc in pet. ether) to give 18C (4.43 g, 71% yield) as yellow oil: ESI m/z 391.2 [M+H]$^+$.

A solution of 18C (5 g, 12.84 mmol) in NH$_3$/MeOH (7.0 M, 100 mL) was stirred in a sealed tube at 100° C. for 2 h. The mixture was concentrated under reduced pressure and purified by chromatography on silica gel (2%-50% EtOAc in pet. ether) to afford 18D (3 g, 80% yield) as an off-white solid: ESI m/z 293.8, 295.8 [M+H]$^+$.

A mixture of 18D (3.0 g, 10.22 mmol), pyridin-3-ylboronic acid (1.5 g, 12.27 mmol), K$_2$CO$_3$ (4.24 g, 30.66 mmol) and Pd(dppf)$_2$Cl$_2$ (0.37 g, 0.51 mmol) in dioxane (160 mL) and H$_2$O (40 mL) was stirred at 90° C. for 10 hours under nitrogen. The mixture was poured into water and extracted with EtOAc (100 mL×3). The combined organic fractions were washed with water and brine and dried over sodium sulfate. The solvent was removed under reduced pressure and the residue was purified by chromatography on silica gel (1%-2% MeOH in DCM) to provide compound 18E (1.0 g, 41% yield) as a yellow solid: $^1$H NMR (400 MHz, CDCl$_3$) δ 8.71 (d, J=1.6 Hz, 1H), 8.67 (dd, J=7.6 Hz, 1.2 Hz, 1H), 7.85 (s, 1H), 7.79 (tt, J=1.6 Hz, 1H), 7.65 (s, 1H), 7.42-7.39 (m, 1H), 6.96 (s, 1H), 4.52 (s, 2H); ESI m/z 245.0, 247.0 [M+H]$^+$.

A mixture of 18E (200 mg, 0.82 mmol), 1D (217 mg, 0.82 mmol), Cs$_2$CO$_3$ (533 mg, 1.64 mmol), Xantphos (24 mg, 0.041 mmol) and Pd(dba)$_3$ (22 mg, 0.025 mmol) in dioxane (40 mL) was stirred at 90° C. overnight under a nitrogen atmosphere. The reaction mixture was concentrated under reduced pressure and purified by chromatography on silica gel (1%-2% MeOH in DCM) to give compound 65 (70 mg, 20% yield) as a white solid: $^1$H NMR (400 MHz, DMSO-d$_6$) δ 8.72-8.62 (m, 4H), 8.10 (t, J=8.4 Hz, 1H), 8.03 (s, 1H), 7.97-7.90 (m, 2H), 7.87 (s, 1H), 7.57-7.54 (m, 1H), 5.24 (s, 2H), 4.12-4.07 (m, 1H), 1.16-1.11 (m, 2H), 1.02-0.98 (m, 2H); ESI m/z 429.0, 431.0 [M+H]$^+$.

Example 19: Preparation of 2-(6-(4-cyclopropyl-4H-1,2,4-triazol-3-yl)pyridin-2-yl)-5-methoxy-6-(pyridin-3-yl)isoindolin-1-one (compound 66)

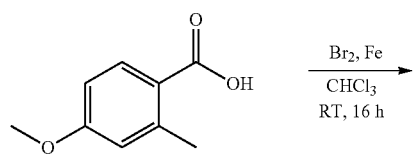

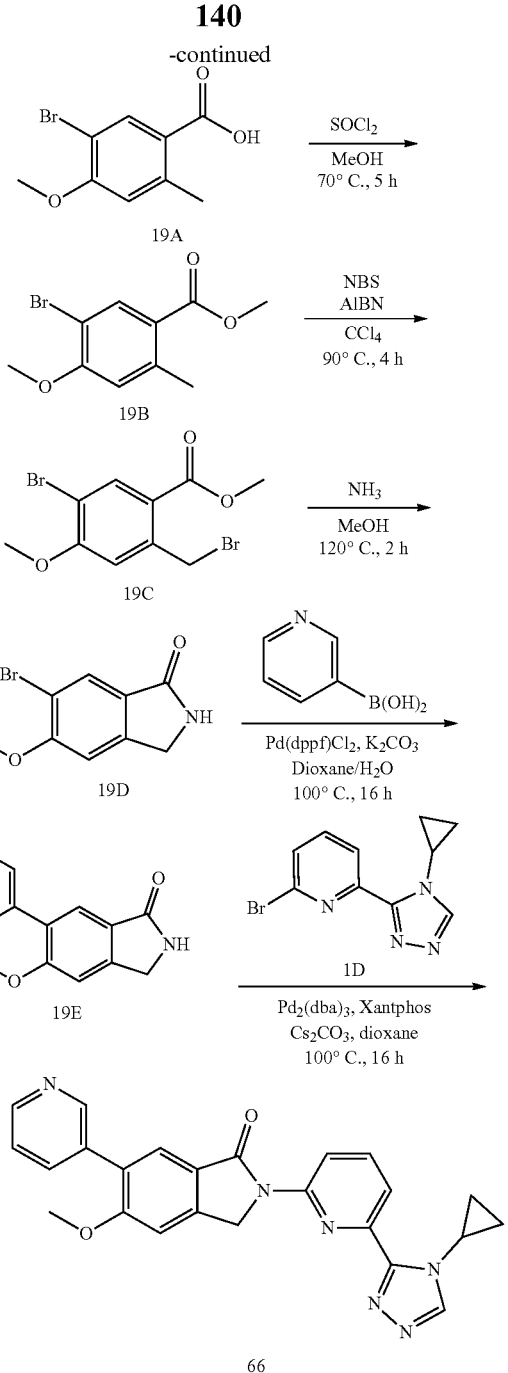

Bromine (14.3 g, 90.3 mmol) was added dropwise at 5° C. to a mixture of 4-methoxy-2-methylbenzoic acid (15 g, 90.3 mmol), Fe (3.51 g, 62.8 mmol) in chloroform (90 mL). The reaction mixture was warmed to room temperature and stirred overnight. The reaction mixture was diluted with chloroform (600 mL) and washed with 10% sodium hydrogen sulfate (200 mL×2) and brine. The organic fraction was dried with sodium sulfate and solvent was removed under reduced pressure. The residue was purified by chromatography on silica gel (1%-10% EtOAc in pet. ether) to afford 19A (4 g, 18% yield) as a yellow solid: ESI m/z 266.9, 268.9[M+Na]$^+$.

Thionyl chloride (11.4 mL) was slowly added to a solution of 19A (4 g, 16.3 mmol) in methanol (30 mL). The mixture was refluxed for 3 h then cooled to room temperature. After the bulk of solvent was evaporated, the residue was diluted with water and extracted with EtOAc (100 mL×3). The combined organic fractions were dried over sulfate and concentrated under vacuum. The residue was purified by silica gel column chromatography (1%-5% EtOAc in pet. ether) to afford 19B (3.0 g, 71% yield) as a white solid: ESI m/z 258.9, 260.9[M+H]$^+$.

A mixture of 19B (2.8 g, 10.8 mmol), NBS (2.02 g, 11.3 mmol) and AIBN (177 mg, 1.08 mmol) in CCl$_4$ (50 mL) was heated to 90° C. for 4 h. After that time, the mixture was cooled to room temperature and concentrated under reduced pressure. The residue was purified by column chromatography (1%-5% EtOAc in pet. ether) to give the 19C (3.1 g, 86% yield) as a white solid: ESI m/z 338.8, 340.8 [M+H]$^+$.

A mixture of 19C (2.8 g, 8.28 mmol) in NH$_3$/MeOH (7.0 M, 30 mL) was heated to 120° C. for 2 h in a sealed tube. After that time, the mixture was cooled to room temperature and concentrated under reduced pressure. The residue was purified by column chromatography (1%-50% EtOAc in pet. ether) to provide 19D (1.4 g, 65% yield) as a yellow solid: $^1$H NMR (400 MHz, DMSO-d$_6$) δ 8.47 (s, 1H), 7.77 (s, 1H), 7.33 (s, 1H), 4.31 (s, 2H), 3.92 (s, 3H); ESI m/z 241.9, 243.9 [M+H]$^+$.

A mixture of 19D (700 mg, 2.9 mmol), Pd(dppf)Cl$_2$ (110 mg, 0.15 mmol), K$_2$CO$_3$ (1.2 g, 8.7 mmol) and 3-pyridylboronic acid (355 mg, 2.9 mmol) in dioxane (40 mL) and water (5 mL) was heated to 100° C. overnight. The mixture was poured into water and extracted with EtOAc (50 mL×3). The combined organic fractions were washed with brine and dried over sodium sulfate.

The solvent was removed under vacuum and the residue was purified by column chromatography on silica gel (1%-2% MeOH in DCM) to give 19E (270 mg, 38% yield) as a brown solid: $^1$H NMR (400 MHz, DMSO-d$_6$) δ 8.69 (s, 1H), 8.55 (d, J=4 Hz, 1H), 8.41 (s, 1H), 7.91 (d, J=7.6 Hz, 1H), 7.55 (s, 1H), 7.47-7.44 (m, 1H), 7.35 (s, 1H), 4.39 (s, 2H), 3.86 (s, 3H); ESI m/z 241.0 [M+H]$^+$.

A mixture of 19E (258 mg, 1.08 mmol), 1D (285 mg, 1.08 mmol), Pd$_2$(dba)$_3$ (31 mg, 0.03 mmol), Xantphos (32 mg, 0.05 mmol) and Cs$_2$CO$_3$ (420 mg, 1.29 mmol) in dioxane (45 mL) was heated to 100° C. overnight under a nitrogen atmosphere. After that time, the mixture was cooled to room temperature and filtered. The filtrate was concentrated under reduced pressure and the residue was purified by column chromatography on silica gel (1%-5% MeOH in DCM) to afford compound 66 (260 mg, 57% yield) as a white solid: $^1$H NMR (400 MHz, DMSO-d$_6$) δ 8.72 (br, 1H), 8.71 (s, 1H), 8.63 (d, J=8.4 Hz, 1H), 8.57 (d, J=4 Hz, 1H), 8.06 (t, J=7.6 Hz, 1H), 7.95 (tt, J=1.6 Hz, 1H), 7.87 (d, J=7.6 Hz, 1H), 7.73 (s, 1H), 7.50-7.46 (m, 2H), 5.19 (s, 2H), 4.14-4.09 (m, 1H), 3.92 (s, 3H), 1.17-1.12 (m, 2H), 1.03-0.99 (m, 2H); ESI m/z 425.1 [M+H]$^+$.

Example 20: Preparation of 2-(6-(4-cyclopropyl-4H-1,2,4-triazol-3-yl)pyridin-2-yl)-5-(dimethylamino)-6-(pyridin-3-yl)isoindolin-1-one (compound 67)

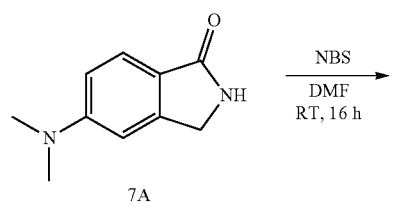

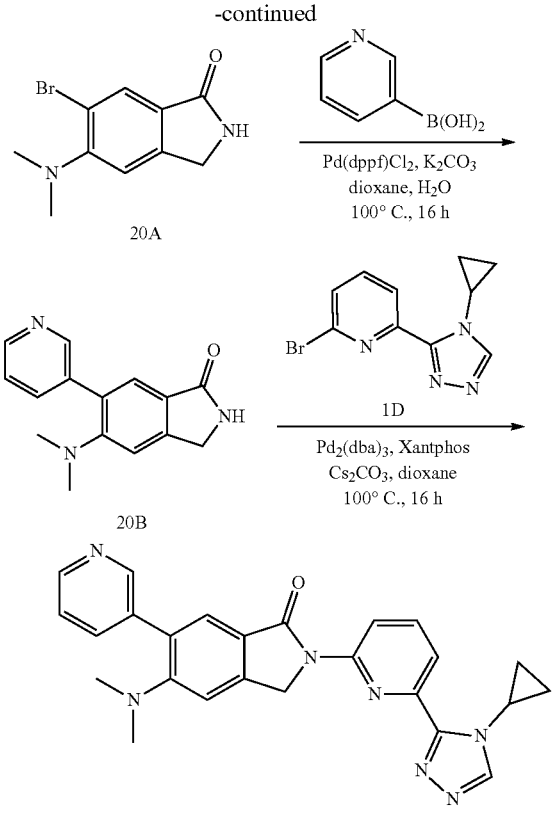

A mixture of 7A (425 mg, 2.41 mmol) and NBS (429 mg, 2.41 mmol) in DMF (15 mL) was stirred at RT overnight. The mixture was poured into water and extracted with EtOAc (3×80 mL). The combined organic fractions were washed with water and brine and dried over sodium sulfate. The solvent was concentrated under vacuum and the residue was purified by column chromatography on silica gel (1%-2% MeOH in DCM) to give 20A (200 mg, 33% yield) as a yellow solid: $^1$H NMR (400 MHz, DMSO-d$_6$) δ 8.54 (s, 1H), 7.60 (d, J=8.4 Hz, 1H), 7.23 (d, J=8.4 Hz, 1H), 4.24 (s, 2H), 2.81 (s, 6H); ESI m/z 254.9, 256.9 [M+H]$^+$.

A mixture of 20A (250 mg, 1.0 mmol) pyridin-3-ylboronic acid (181 mg, 1.5 mmol), Pd(dppf)$_2$C$_1$ (36 mg, 0.05 mmol) and K$_2$CO$_3$ (406 mg, 3.0 mmol) in dioxane (20 mL), methanol (1 mL) and water (1 mL) was heated to 100° C. overnight under a nitrogen atmosphere. The reaction mixture was concentrated under vacuum and the residue was purified by column chromatography (1%-2% MeOH in DCM) to afford 20B (160 mg, 64% yield) as a brown solid: ESI m/z 254.0 [M+H]$^+$.

A mixture of 20B (160 mg, 0.6 mmol), 1D (167 mg, 0.6 mmol), Pd$_2$(dba)$_3$ (29 mg, 0.03 mmol), Xantphos (26 mg, 0.04 mmol) and Cs$_2$CO$_3$ (617 mg, 1.9 mmol) in dioxane (20 mL) was heated to 100° C. overnight. The reaction mixture was concentrated under vacuum and the residue was purified by column chromatography (1%-2% MeOH in DCM) to provide compound 67 (110 mg, 40% yield) as a yellow solid: $^1$H NMR (400 MHz, DMSO-d$_6$) δ 8.67 (d, J=2.8 Hz, 1H), 8.63-8.60 (m, 2H), 8.56 (d, J=8.4 Hz, 1H), 8.01 (t, J=8 Hz, 1H), 7.95-7.92 (m, 1H), 7.87 (d, J=7.6 Hz, 1H), 7.76 (d, J=8.4 Hz, 1H), 7.52 (dd, J=7.6 Hz, 2.4 Hz, 1H), 7.22 (d, J=8.4 Hz, 1H), 4.86 (s, 2H), 3.88-3.82 (m, 1H), 2.62 (s, 6H), 0.96-0.95 (m, 2H), 0.77 (q, J=6 Hz, 2H); ESI m/z 438.0 [M+H]$^+$.

Example 21: Preparation of 2-(6-(4-cyclopropyl-4H-1,2,4-triazol-3-yl)pyridin-2-yl)-5-isopropoxy-6-(pyridin-3-yl)isoindolin-1-one (compound 68)

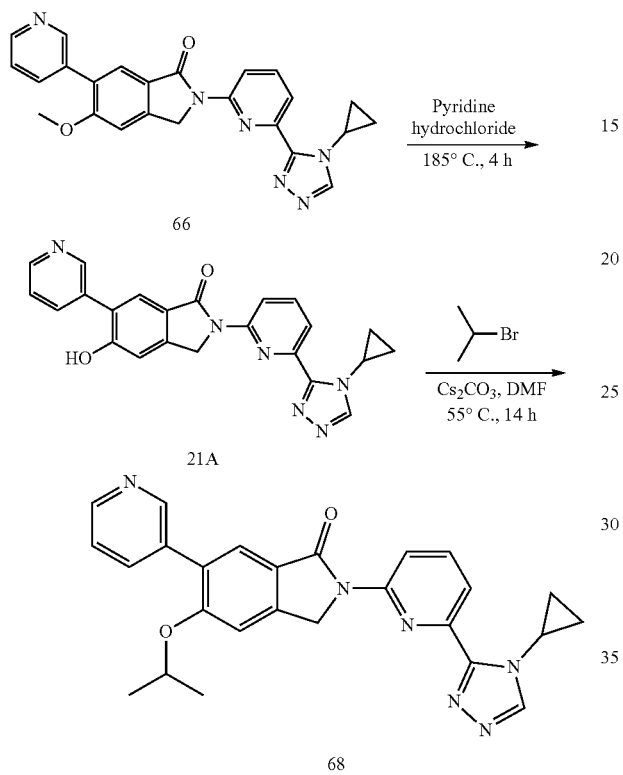

A mixture of compound 66 (250 mg, 0.59 mmol) and pyridine hydrochloride was heated at 185° C. for 4 h. After cooling to room temperature, the mixture was dissolved into water and extracted with EtOAc (50 mL×3). The combined organic fractions were washed with brine and dried with sodium sulfate. The solvent was concentrated under vacuum and the residue was purified by silica gel column chromatography (1%-5% MeOH in DCM) to afford 21A (130 mg, 54% yield) as a yellow solid: $^1$H NMR (400 MHz, DMSO-d$_6$) δ 11.73 (s, 1H), 9.19 (s, 1H), 9.15 (s, 1H), 8.94 (d, J=5.2 Hz, 1H), 8.89 (d, J=5.2 Hz, 1H), 8.85 (d, J=8.4 Hz, 1H), 8.68 (d, J=8.4 Hz, 1H), 7.99 (s, 1H), 7.88 (d, J=7.6 Hz, 1H), 7.32 (s, 1H), 7.20 (s, 1H), 5.17 (s, 2H), 4.21-4.14 (m, 1H), 1.18-1.34 (m, 2H), 1.05-1.01 (m, 2H); ESI m/z 411.0 [M+H]$^+$.

A mixture of 21A (100 mg, 0.24 mmol), 2-bromopropane (90 mg, 0.73 mmol) and Cs$_2$CO$_3$ (238 mg, 0.73 mmol) in DMF (8 mL) was heated at 55° C. for 14 h. The mixture was poured into water and extracted with EtOAc (50 mL×3 The combined organic fractions were washed with brine and dried with sodium sulfate. The solvent was concentrated under vacuum and the residue was purified by silica gel column chromatography (1%-5% MeOH in DCM) to provide compound 68 (25 mg, 23% yield) as a yellow solid: $^1$H NMR (400 MHz, CDCl$_3$) δ 8.82 (s, 1H), 8.75 (d, J=7.6 Hz, 1H), 8.59 (d, J=3.6 Hz, 1H), 8.25 (s, 1H), 7.96-7.87 (m, 4H), 7.40-7.37 (m, 1H), 7.10 (s, 1H), 5.08 (s, 2H), 4.74-4.68 (m, 1H), 3.96-3.94 (m, 1H), 1.36 (d, J=5.6 Hz, 6H), 1.17-1.12 (m, 2H), 1.0-0.95 (m, 2H); ESI m/z 453.1 [M+H]$^+$.

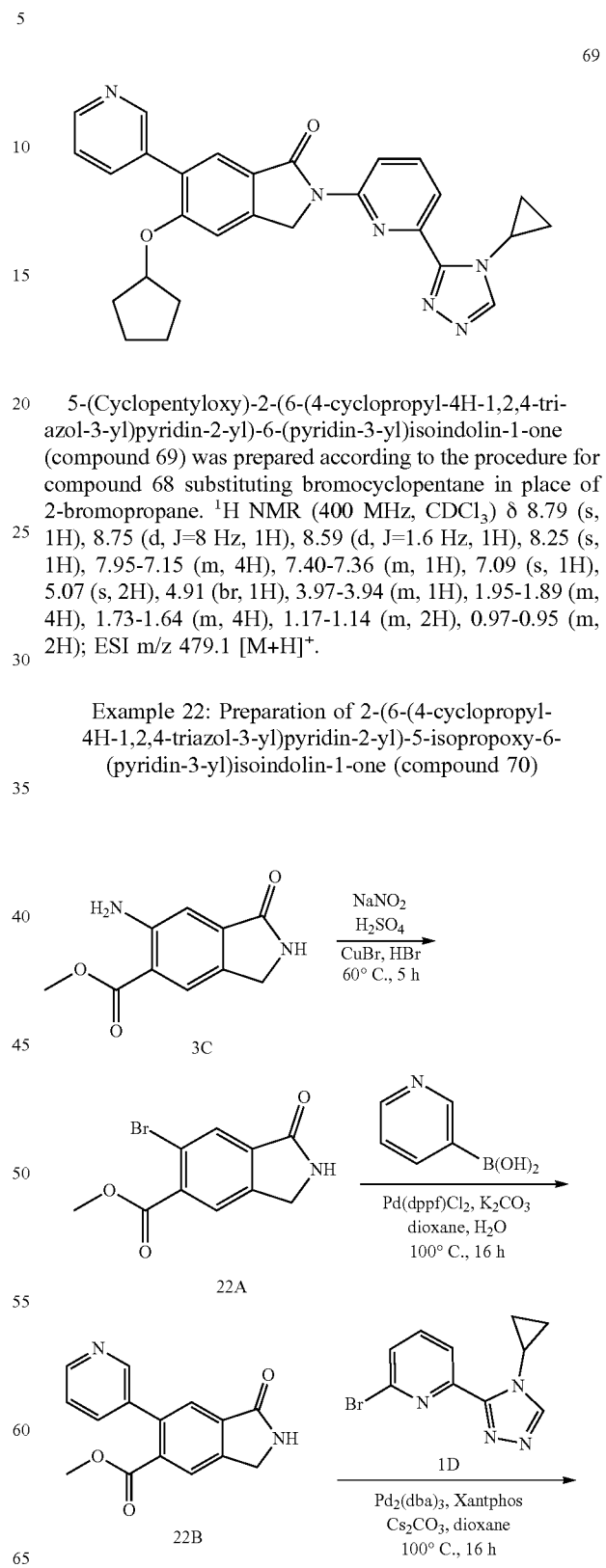

5-(Cyclopentyloxy)-2-(6-(4-cyclopropyl-4H-1,2,4-triazol-3-yl)pyridin-2-yl)-6-(pyridin-3-yl)isoindolin-1-one (compound 69) was prepared according to the procedure for compound 68 substituting bromocyclopentane in place of 2-bromopropane. $^1$H NMR (400 MHz, CDCl$_3$) δ 8.79 (s, 1H), 8.75 (d, J=8 Hz, 1H), 8.59 (d, J=1.6 Hz, 1H), 8.25 (s, 1H), 7.95-7.15 (m, 4H), 7.40-7.36 (m, 1H), 7.09 (s, 1H), 5.07 (s, 2H), 4.91 (br, 1H), 3.97-3.94 (m, 1H), 1.95-1.89 (m, 4H), 1.73-1.64 (m, 4H), 1.17-1.14 (m, 2H), 0.97-0.95 (m, 2H); ESI m/z 479.1 [M+H]$^+$.

Example 22: Preparation of 2-(6-(4-cyclopropyl-4H-1,2,4-triazol-3-yl)pyridin-2-yl)-5-isopropoxy-6-(pyridin-3-yl)isoindolin-1-one (compound 70)

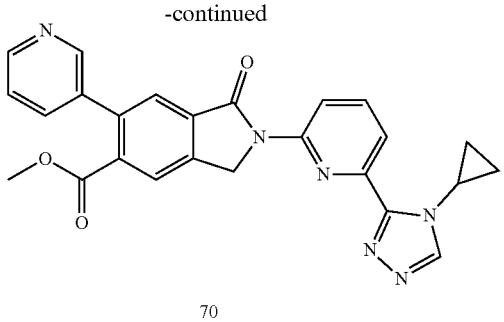

70

A solution of NaNO₂ (953 mg, 11 mmol) in water (15 mL) was added dropwise to a mixture of 3C (1.5 g, 7.3 mmol) in water (55 mL) and H₂SO₄ (20 mL) at 0° C. over a period of 10 min. After stirring at 0° C. for 1 hour, CuBr (3.1 g, 22 mmol) in HBr (150 mL) was added dropwise to the reaction mixture for 10 min, then the reaction was heated to 60° C. for 5 h. After cooling, the reaction mixture was poured into water, neutralized with NaHCO₃, and extracted with EtOAc (3×300 mL). The combined organic fractions were washed with brine and dried with sodium sulfate. The solvent was evaporated and the residue was purified by column chromatography on silica gel (1% MeOH in DCM) to give bromide 22A (400 mg, 18% yield) as a yellow powder: ¹H NMR (400 MHz, CDCl₃) δ 7.98 (s, 1H), 7.91 (s, 1H), 4.48 (s, 2H), 3.98 (s, 3H); ESI m/z 271.9, 269.9 [M+H]⁺.

A mixture of 22A (300 mg, 1.1 mmol), pyridin-3-ylboronic acid (273 mg, 2.2 mmol), Pd(dppf)₂Cl (41 mg, 0.06 mmol) and K₂CO₃ (461 mg, 3.3 mmol) in dioxane (20 mL), methanol (1 mL) and water (1 mL) was heated to 100° C. overnight. The resulting mixture was concentrated and purified by column chromatography on silica gel (1%-2% MeOH in DCM) to afford 22B (200 mg, 67% yield) as a pink solid: ESI m/z 269.0 [M+H]⁺.

A mixture of 22B (200 mg, 0.75 mmol), 1D (198 mg, 0.75 mmol), Pd₂(dba)₃ (34 mg, 0.04 mmol), Xantphos (30 mg, 0.05 mmol) and Cs₂CO₃ (729 mg, 2.2 mmol) in dioxane (20 mL) was heated to 100° C. overnight. The mixture was concentrated and purified by column chromatography on silica gel (1%-2% MeOH in DCM) to provide compound 70 (90 mg, 27% yield) as a yellow solid: ¹H NMR (400 MHz, DMSO-d₆) δ 8.73 (s, 1H), 8.65-8.58 (m, 3H), 8.24 (s, 1H), 8.10 (t, J=7.6 Hz, 1H), 7.93 (d, J=7.6 Hz, 1H), 7.86-7.83 (m, 2H), 7.51 (dd, J=7.6 Hz, 2.4 Hz, 1H), 5.29 (s, 2H), 4.15-4.09 (m, 2H), 3.68 (s, 3H), 1.15 (q, J=6 Hz, 2H), 1.01-0.97 (m, 2H); ESI m/z 453.0 [M+H]⁺.

Example 23: Preparation of 2-(6-(4-cyclopropyl-4H-1,2,4-triazol-3-yl)pyridin-2-yl)-6-(pyridin-3-yl)-5-(pyrrolidine-1-carbonyl)isoindolin-1-one (compound 71)

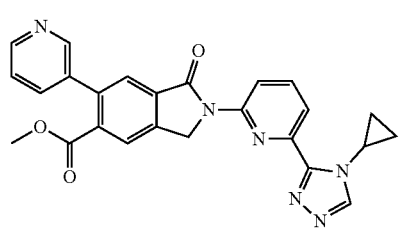

70

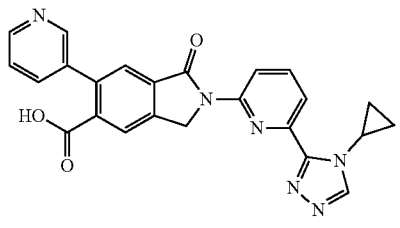

23A

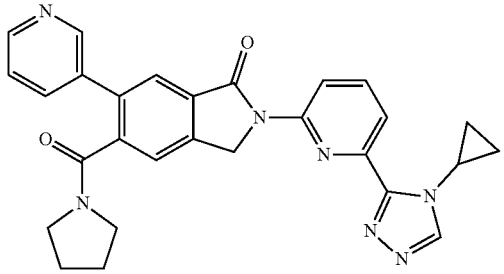

71

A mixture of compound 70 (100 mg, 0.2 mmol) in 6M HCl (8 mL) and dioxane (7 mL) was heated to 95° C. overnight. The reaction mixture was concentrated under reduced pressure to give 23A (90 mg, 93% yield) as a yellow solid: ESI m/z 439.0 [M+H]⁺.

A mixture of 23A (90 mg, 0.2 mmol), pyrrolidine (44 mg, 0.6 mmol), HATU (156 mg, 0.4 mmol) and DIEA (159 mg, 1.2 mmol) in ACN (10 mL) was stirred at room temperature overnight. The reaction mixture was concentrated under reduced pressure and purified by column chromatography (1%-2% MeOH in DCM) to afford compound 71 (88 mg, 87% yield) as a white solid: ¹H NMR (400 MHz, DMSO-d₆) δ 8.72 (s, 1H), 8.68-8.62 (m, 3H), 8.10 (t, J=8 Hz, 1H), 7.93-7.89 (m, 3H), 7.81 (s, 1H), 7.50 (dd, J=7.6 Hz, 4.8 Hz, 1H), 5.27 (s, 2H), 4.13-4.08 (m, 1H), 3.30-3.27 (m, 2H), 2.87 (s, 2H), 1.68-1.62 (m, 2H), 1.55-1.52 (m, 2H), 1.16-1.11 (m, 2H), 1.02-0.98 (m, 2H); ESI m/z 492.1 [M+H]⁺.

Example 24: Preparation of methyl 2-(6-(4-cyclopropyl-4H-1,2,4-triazol-3-yl)pyridin-2-yl)-3-oxoisoindoline-5-carboxylate (compound 72)

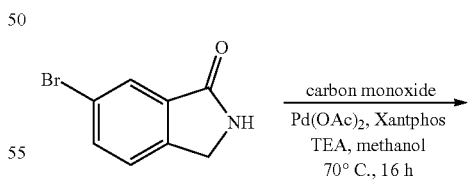

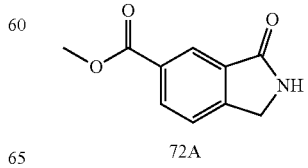

72A

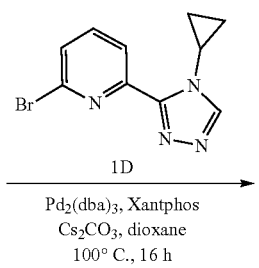

1D

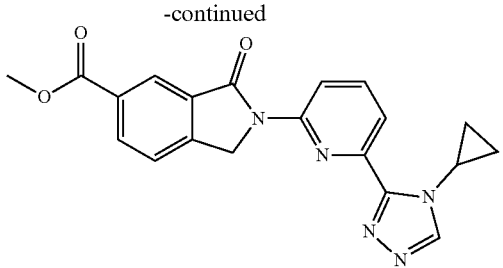

72

A mixture of 6-bromoisoindolin-1-one (5.0 g, 23.58 mmol), Pd(AcO)$_2$ (528 mg, 2.30 mmol), Xantphos (1.36 g, 2.36 mmol) and TEA (1.19 g, 117.9 mmol) in methanol (100 mL) was heated to 70° C. under 1 atm of CO (gas) overnight. The reaction mixture was filtered and the filtrate was concentrated under vacuum. The residue was purified by silica column chromatography (1%-2% MeOH in DCM) to give 72A (500 mg, 11% yield) as a white solid: ESI m/z 192.1 [M+H]$^+$.

A stirred mixture of 72A (66 mg, 0.35 mmol), 1D (80 mg, 0.30 mmol), Pd$_2$(dba)$_3$ (28 mg, 0.03 mmol), Cs$_2$CO$_3$ (196 mg, 0.60 mmol) and Xantphos (20 mg, 0.03 mmol) in 1,4-dioxane (5 mL) was heated to 100° C. overnight under a nitrogen atmosphere. The reaction mixture was allowed to cool to room temperature and filtered. The filtrate was concentrated under reduced pressure and the residue was purified by silica column chromatography (1%-2% MeOH in DCM) to provide compound 72 (50 mg, 44% yield) as a white solid: $^1$H NMR (400 MHz, CDCl$_3$) δ 8.76 (d, J=8.4 Hz, 1H), 8.62 (s, 1H), 8.34 (d, J=7.6 Hz, 1H), 8.26 (br, 1H), 8.01-7.92 (m, 2H), 7.64 (d, J=8 Hz, 1H), 5.14 (s, 2H), 3.98 (s, 3H), 3.96-3.90 (m, 3H), 1.15-1.13 (m, 2H), 1.0-0.95 (m, 2H); ESI m/z 376.1 [M+H]$^+$.

Example 25: Preparation of 2-(6-(4-cyclopropyl-4H-1,2,4-triazol-3-yl)pyridin-2-yl)-3-oxoisoindoline-5-carboxylic acid (compound 73)

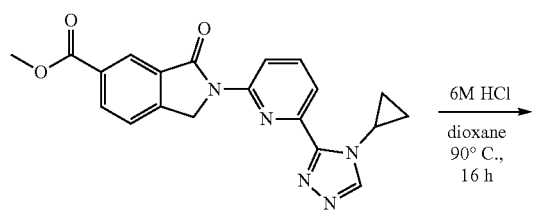

72

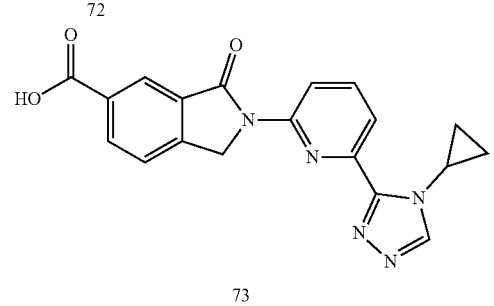

73

A suspension of compound 72 (100 mg, 0.26 mmol) in dioxane (5 mL) and HCl (6M, 5 mL) was heated to 90° C. overnight. The solvent was concentrated and the addition of water (5 mL) caused a precipitate to form. The solid was collected by filtration and dried to give compound 73 (70 mg, 73% yield) as a white solid: $^1$H NMR (400 MHz, DMSO-d$_6$) δ 9.01 (s, 1H), 8.67 (d, J=8.4 Hz, 1H), 8.28-8.25 (m, 2H), 8.10 (t, J=8 Hz, 1H), 7.91 (d, J=7.2 Hz, 1H), 7.85 (d, J=7.6 Hz, 1H), 5.25 (s, 2H), 4.16-4.10 (m, 1H), 1.17-1.12 (m, 2H), 1.01-1.0 (m, 2H); ESI m/z 362.1 [M+H]$^+$.

Example 26: Preparation of 2-(6-(4-cyclopropyl-4H-1,2,4-triazol-3-yl)pyridin-2-yl)-N,N-dimethyl-3-oxoisoindoline-5-carboxamide (compound 74)

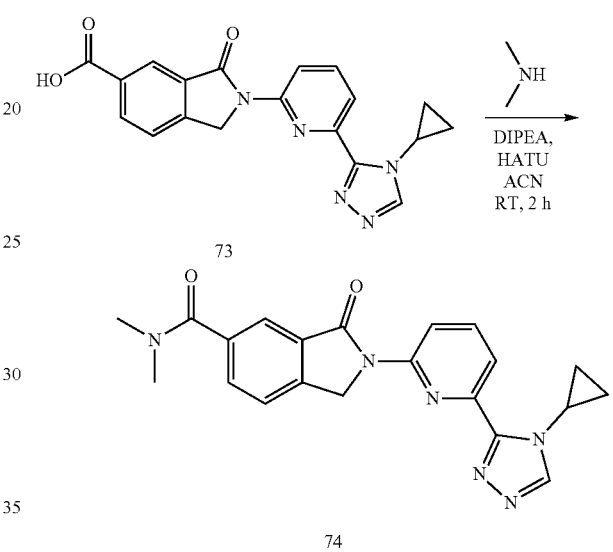

A mixture of compound 73 (80 mg, 0.22 mmol), dimethylamine hydrochloride (36 mg, 0.44 mmol), HATU (167 mg, 0.44 mg) and triethylamine (111 mg, 1.10 mmol) in MeCN (6 mL) was stirred at room temperature for 2 h. The solid was collected by filtration, washed with water and dried to provide compound 74 (30 mg, 35% yield) as a white solid: $^1$H NMR (400 MHz, DMSO-d$_6$) δ 8.71 (s, 1H), 8.64 (d, J=8.4 Hz, 1H), 8.09 (t, J=8 Hz, 1H), 7.89 (d, J=7.6 Hz, 1H), 7.82 (s, 1H), 7.77 (q, J=7.6 Hz, 2H), 5.22 (s, 2H), 3.0 (d, J=7.2 Hz, 1H), 1.14-1.09 (m, 2H), 0.99-0.95 (m, 2H); ESI m/z 389.2 [M+H]$^+$.

Example 27: Preparation of N-(2-(6-(4-cyclopropyl-4H-1,2,4-triazol-3-yl)pyridin-2-yl)-6-fluoro-3-oxoisoindolin-5-yl)cyclopropanecarboxamide (compound 75)

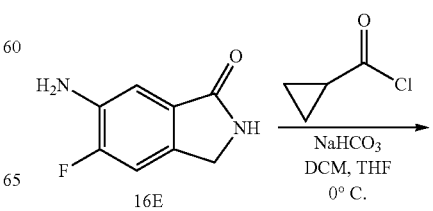

16E

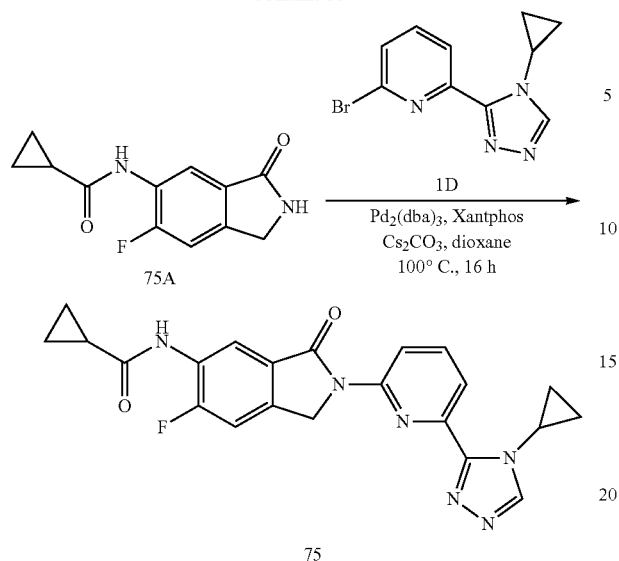

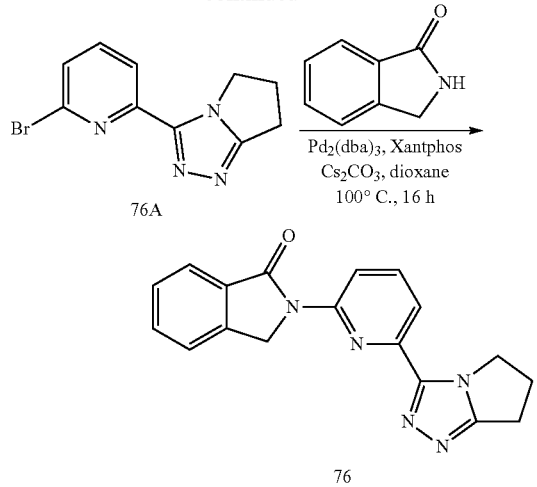

To a mixture of 16E (200 mg, 1.2 mmol) and NaHCO₃ (1.0 g, 12.0 mmol) in DCM (15 mL) and THF (15 mL) was added cyclopropanecarbonyl chloride (377 mg, 3.6 mmol) in three portions at 0° C. After stirring at room temperature for 4 h, the mixture was poured into water and extracted with EtOAc (50 mL×3). The combined organic fractions were washed with water and brine and dried over sodium sulfate. The solvent was removed under vacuum and the residue was purified by column chromatography on silica gel (1%-2% MeOH in DCM) to afford 75A (70 mg, 25% yield) as an off-white solid: ESI m/z 235.0 [M+H]⁺.

A mixture of 75A (70 mg, 0.3 mmol), 1D (79 mg, 0.3 mmol), Pd₂(dba)₃ (14 mg, 0.015 mmol), Xantphos (12 mg, 0.02 mmol), and Cs₂CO₃ (195 mg, 0.6 mmol) in dioxane (15 mL) was heated to 100° C. overnight. The reaction mixture was allowed to cool to room temperature and filtered. The filtrate was concentrated under reduced pressure and the residue was purified by silica column chromatography (1%-2% MeOH in DCM) to provide compound 75 (20 mg, 20% yield) as a yellow powder: ¹H NMR (400 MHz, CDCl₃) δ 8.76 (dd, J=0.8 Hz, 1H), 8.25 (s, 1H), 8.01-7.92 (m, 3H), 7.60 (s, 1H), 7.52-7.50 (m, 1H), 5.11 (s, 2H), 3.96-3.91 (m, 1H), 3.75 (br, 2H), 3.36 (br, 2H), 1.71 (s, 4H), 1.31 (s, 2H), 1.16-1.10 (m, 2H), 0.98-0.94 (m, 2H); ESI m/z 429.1 [M+H]⁺.

Example 28: Preparation of 2-(6-(6,7-dihydro-5H-pyrrolo[2,1-c][1,2,4]triazol-3-yl)pyridin-2-yl)isoindolin-1-one (compound 76)

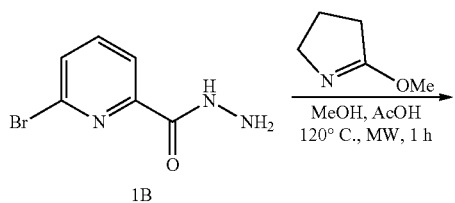

A mixture of 1B (2.1 g, 10 mmol), 5-methoxy-3,4-dihydro-2H-pyrrole (1.49 g, 15 mmol) and acetic acid (5 drops) in methanol (12 mL) was heated by microwave at 100° C. for 2 hours. The mixture was concentrated and the residue was purified by column chromatography on silica gel (EtOAc/Pet. Ether, 1/4 to 4/1, v/v) to give 76A (2 g, 76% yield) as a white solid: ESI m/z 266.9, 264.9 [M+H]⁺.

A mixture of 76A (500 mg, 1.89 mmol), isoindolin-1-one (504 mg, 3.79 mmol), Pd₂(dba)₃ (52 mg, 0.06 mmol), Xantphos (55 mg, 0.10 mmol) and Cs₂CO₃ (2.47 g, 7.57 mmol) in dioxane (20 mL) was heated to 100° C. overnight. The reaction mixture was concentrated under vacuum and the residue was purified by column chromatography on silica gel (1%-5% MeOH in DCM) to afford compound 76 (50 mg, 8% yield) as a white solid: ¹H NMR (400 MHz, CDCl₃) δ 8.67 (d, J=8.4 Hz, 1H), 8.05 (d, J=7.6 Hz, 1H), 7.94 (d, J=7.6 Hz, 1H), 7.85 (t, J=8 Hz, 1H), 7.66-7.51 (m, 3H), 5.08 (s, 2H), 4.51 (t, J=7.2 Hz, 2H), 3.05 (t, J=8 Hz, 2H), 2.92-2.85 (m, 2H); ESI m/z 318.0 [M+H]⁺.

2-(6-(5,6,7,8-Tetrahydro-[1,2,4]triazolo[4,3-a]pyridin-3-yl)pyridin-2-yl)isoindolin-1-one (compound 77) was prepared according to the procedure for compound 76 substituting 6-methoxy-2,3,4,5-tetrahydropyridine in place of 5-methoxy-3,4-dihydro-2H-pyrrole. ¹H NMR (400 MHz, DMSO-d₆) δ 8.55 (d, J=8 Hz, 1H), 8.00 (t, J=8 Hz, 1H), 7.90 (d, J=7.6 Hz, 1H), 7.83 (d, J=7.6 Hz, 1H), 7.73-7.70 (m, 2H), 7.58-7.54 (m, 1H), 5.15 (s, 2H), 4.53 (t, J=6 Hz, 2H), 2.96-2.93 (m, 2H), 2.02-1.99 (m, 2H), 1.92-1.89 (m, 2H); ESI m/z 332.1 [M+H]⁺.

Example 29: Preparation of 2-(6-(5-methyl-6,7-dihydro-5H-pyrrolo[2,1-c][1,2,4]triazol-3-yl)pyridin-2-yl)isoindolin-1-one (compound 78)

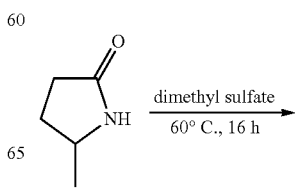

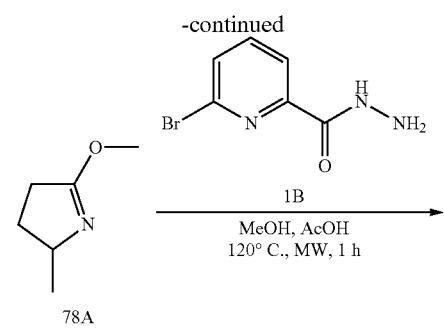

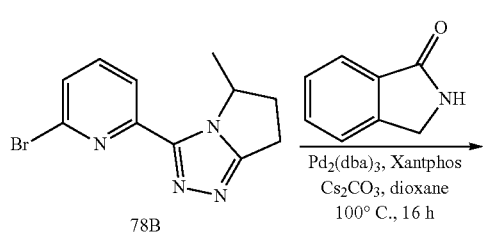

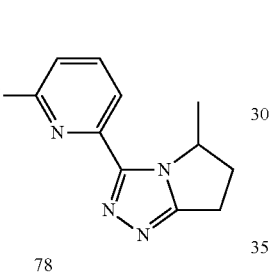

78

A mixture of 5-methylpyrrolidin-2-one (3.0 g, 30.3 mmol) and dimethyl sulfate (5.2 g, 31.8 mmol) was heated at 60° C. for 16 h. The reaction mixture was then cooled and added to a saturated aqueous solution of potassium carbonate (30 mL). The mixture was extracted with ether and the organic layer was dried over sodium sulfate. The solvent was evaporated to afford the 78A (860 mg, 25% yield) as a brown oil.

A mixture of 78A (100 mg, 0.57 mmol) and 1B (1.09 mg, 5.1 mmol) in methanol (10 mL) and acetic acid (8 drops) was heated at 120° C. by microwave for 2 h. The mixture was then cooled and concentrated under vacuum. The residue was purified by silica gel column chromatography (1%-50% EtOAc in pet. ether) to give 78B (125 mg, 9% yield) as a yellow oil: ESI m/z 279.0, 280.9 [M+H]$^+$.

A mixture of 78B (125 mg, 0.45 mmol), isoindolin-1-one (60 mg, 0.45 mmol), Pd$_2$(dba)$_3$ (13 mg, 0.014 mmol), Xantphos (14 mg, 0.023 mmol) and Cs$_2$CO$_3$ (176 mg, 0.54 mmol) in dioxane (45 mL) was heated to 100° C. overnight. After that time, the mixture was cooled to room temperature and filtered. The filtrate was concentrated under reduced pressure and purified by column chromatography on silica gel (1%-50% EtOAc in pet. ether) to provide compound 78 (50 mg, 34% yield) as a light yellow solid: $^1$H NMR (400 MHz, DMSO-d$_6$) δ 8.59 (d, J=7.2 Hz, 1H), 8.02 (d, J=7.2 Hz, 1H), 7.94 (d, J=4.2 Hz, 1H), 7.85 (d, J=5.6 Hz, 1H), 7.75 (d, J=11.2 Hz, 2H), 7.58 (s, 1H), 5.29-5.08 (m, 3H), 3.04 (br, 2H), 2.91 (d, J=4 Hz, 1H), 2.40 (s, 1H), 1.49 (s, 3H); ESI m/z 332.1 [M+H]$^+$.

Example 30: Preparation of (R)-2-(6-(5-(hydroxymethyl)-6,7-dihydro-5H-pyrrolo[2,1-c][1,2,4]triazol-3-yl)pyridin-2-yl)isoindolin-1-one (compound 79)

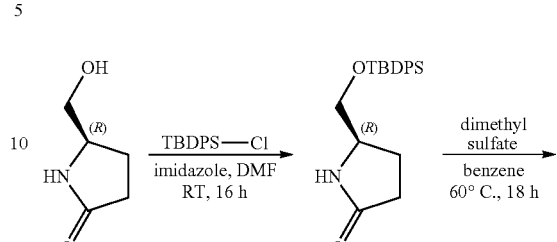

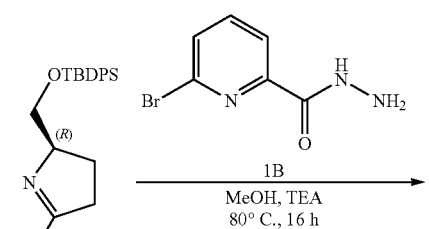

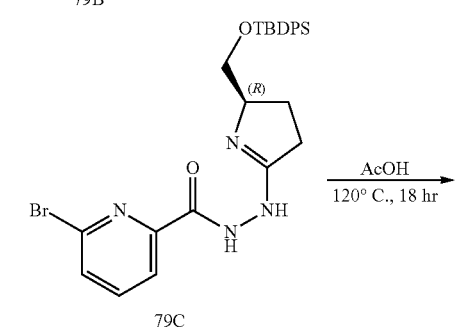

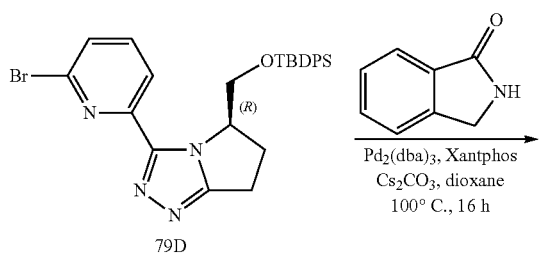

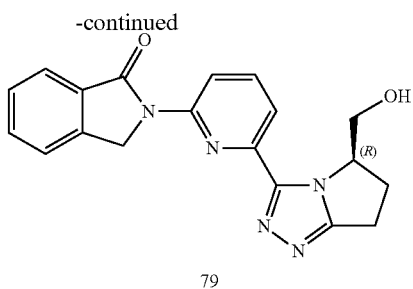

79 tert-Butylchlorodiphenylsilane (25.8 g, 93.83 mmol) was added to a solution of (R)-5-(hydroxymethyl)pyrrolidin-2-one (9 g, 78.19 mmol) and 1H-imidazole (6.4 g, 93.83 mmol) in DMF (180 mL). After stirring at room temperature overnight, the reaction mixture was poured into water and extracted with EtOAc. The organic fraction was washed with water and brine and dried over sodium sulfate. The solvent was concentrated under vacuum and the residue was purified by chromatography on silica gel (1%-2% MeOH in DCM) to afford silyl ether 79A (22 g, 80% yield) as a colorless oil: $^1$H NMR (400 MHz, CDCl$_3$) δ 7.65-7.62 (m, 4H), 7.46-7.37 (m, 6H), 5.86 (br, 1H), 3.84-3.77 (m, 1H), 3.64-3.61 (m, 1H), 3.53-3.49 (m, 1H), 2.35-2.31 (m, 2H), 2.18-2.11 (m, 1H), 1.76-1.61 (m, 2H), 1.05 (s, 9H); ESI m/z 354.1 [M+H]$^+$.

A mixture of 79A (22.0 g, 62.27 mmol) and dimethyl sulfate (7.85 g, 7.93 mmol) in benzene (73 mL) was heated to 60° C. for 18 h. The mixture was cooled to room temperature and the reaction mixture was stirred with hexane (73 mL). The upper layer was removed and then the reaction mixture was stirred with ether (140 mL). After removing the ether layer, the residual oil was diluted with DCM (100 mL) and washed with aqueous NaOH (1 M, 2×50 mL) and brine. The organic layer was dried over sodium sulfate and concentrated under reduced pressure to give 79B (15 g, 62% yield) as yellow oil: $^1$H NMR (400 MHz, DMSO-d$_6$) δ 7.64-7.60 (m, 5H), 7.50-7.44 (m, 5H), 4.18 (s, 2H), 3.76 (t, J=4.4 Hz, 2H), 3.59 (s, 1H), 3.04 (t, J=8.4 Hz, 2H), 1.03 (s, 3H), 1.00 (s, 9H); ESI m/z 368.1 [M+H]$^+$.

A mixture of 79B (12.3 g, 33.3 mmol), 1B (6.0 g, 27.8 mmol) and triethylamine (10 mL) in methanol (300 mL) was stirred at 80° C. overnight. The mixture was concentrated under vacuum and purified by chromatography on silica gel (1%-3% MeOH in DCM) to afford 79C as yellow solid (12 g, 81% yield): ESI m/z 551.0, 553.0 [M+H]$^+$.

A solution of 79C (9.0 g, 16.3 mmol) in AcOH (300 mL) was stirred at 120° C. overnight. The mixture was concentrated under vacuum and purified by chromatography on silica gel (1%-2% MeOH in DCM) to provide triazole 79D (6.8 g, 60% yield) as yellow oil: $^1$H NMR (400 MHz, CDCl$_3$) δ 8.14 (d, J=8 Hz, 1H), 7.56-7.52 (m, 2H), 7.46 (d, J=6.4 Hz, 2H), 7.33-7.25 (m, 3H), 7.20 (d, J=7.2 Hz, 2H), 7.14 (t, J=7.2 Hz, 1H), 7.03 (t, J=8 Hz, 2H), 4.15 (dd, J=2.8 Hz, 1H), 3.84 (dd, J=2.6 Hz, 1H), 2.96-2.86 (m, 2H); ESI m/z 533.0, 535.0 [M+H]$^+$.

A stirred mixture of 79D (4.6 g, 8.64 mmol), isoindolin-1-one (1.15 g, 8.64 mmol), Pd$_2$(dba)$_3$ (791 mg, 0.864 mmol), Cs$_2$CO$_3$ (8.44 g, 25.92 mmol) and Xantphos (700 mg, 1.21 mmol) in 1,4-dioxane (150 mL) was heated to 100° C. overnight. The reaction mixture was allowed to cool to room temperature and filtered. The filtrate was concentrated under reduced pressure and the residue was purified by silica column chromatography (1%-5% MeOH in DCM) to give 79E (2.6 g, 56% yield) as a white solid: $^1$H NMR (400 MHz, DMSO-d$_6$) δ 8.54 (d, J=8 Hz, 1H), 8.05 (t, J=7.6 Hz, 1H), 7.99 (d, J=6.8 Hz, 1H), 7.79 (d, J=7.6 Hz, 1H), 7.66 (t, J=7.2 Hz, 1H), 7.57-7.48 (m, 3H), 7.22 (t, J=7.6 Hz, 1H), 7.13-7.04 (m, 4H), 5.19 (d, J=7.2 Hz, 1H), 5.03 (d, J=17.6 Hz, 1H), 4.56 (d, J=17.6 Hz, 1H), 4.11 (dd, J=10.4 Hz, 3 Hz, 1H), 3.95 (d, J=9.2 Hz, 1H), 3.12-2.93 (m, 3H), 2.81-2.75 (m, 1H), 0.80 (s, 9H); ESI m/z 586.1 [M+H]$^+$.

TBAF (1.0 M in THF, 3 mL, 3.0 mmol) was added dropwise to a solution of 79E (600 mg, 1.02 mmol) in THF (15 mL) at room temperature. After stirring at room temperature overnight, the mixture was concentrated and purified by silica gel chromatography (1%-5% MeOH in DCM) to provide compound 79 (260 mg, 73% yield) as a white solid: $^1$H NMR (400 MHz, CDCl$_3$) δ 8.58 (d, J=8.4 Hz, 1H), 8.03 (t, J=8 Hz, 1H), 7.94 (d, J=7.2 Hz, 1H), 7.85 (d, J=8.4 Hz, 1H), 7.74 (d, J=4 Hz, 2H), 7.59-7.55 (m, 1H), 5.21 (d, J=17.6 Hz, 1H), 5.07-5.02 (m, 3H), 3.82-3.80 (m, 2H), 3.82-2.80 (m, 3H), 2.74-2.67 (m, 1H); ESI m/z 348.0 [M+H]$^+$.

Example 31: Preparation of (S)-2-(6-(5-methyl-6,7-dihydro-5H-pyrrolo[2,1-c][1,2,4]triazol-3-yl)pyridin-2-yl)isoindolin-1-one (compound 80)

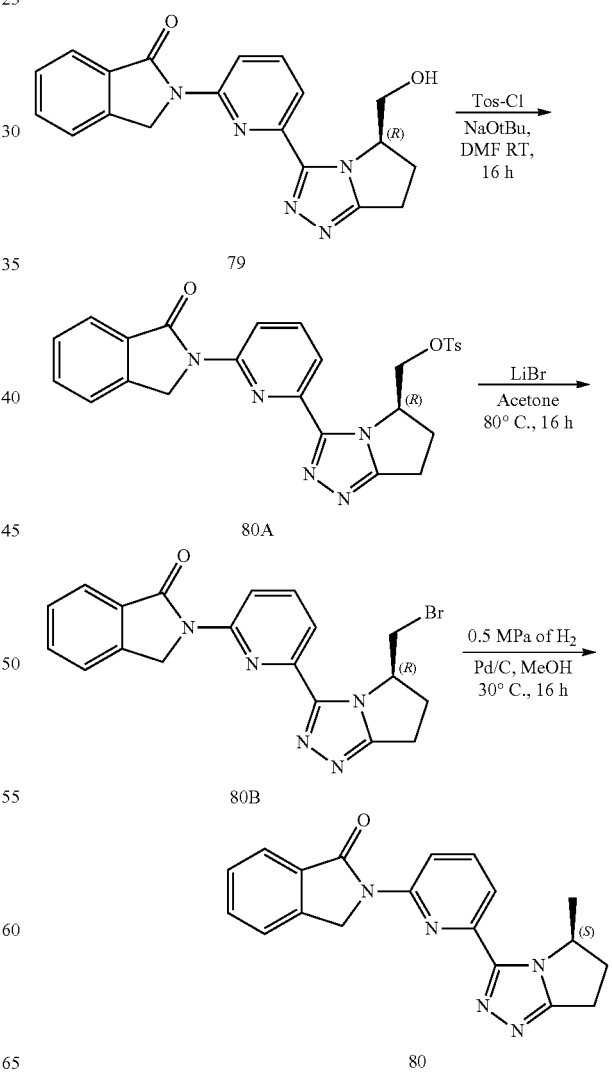

Sodium t-butoxide (415 mg, 4.32 mmol) was added in portions to a solution of compound 79 (600 mg, 1.73 mmol) in DMF (20 mL) at room temperature. After 30 min, 4-toluenesulfonyl chloride (660 mg, 3.46 mmol) was added and the reaction mixture was stirred at room temperature overnight. The mixture was poured into water and extracted with EtOAc (3×100 mL). The combined organic fractions were washed with water and brine and dried over sodium sulfate. The solvent was removed under vacuum and the residue was purified by silica gel chromatography (3% MeOH in DCM) to give 80A (260 mg, 30% yield) as a white solid: $^1$H NMR (400 MHz, DMSO-$d_6$) δ 8.55 (d, J=8.4 Hz, 1H), 8.01 (t, J=8.4 Hz, 1H), 7.86 (d, J=7.6 Hz, 1H), 7.80-7.71 (m, 3H), 7.59 (t, J=7.2 Hz, 1H), 7.42 (d, J=8.4 Hz, 2H), 7.13 (d, J=8 Hz, 2H), 5.27 (d, J=8 Hz, 1H), 5.11 (d, J=17.6 Hz, 1H), 4.79 (d, J=17.6 Hz, 1H), 4.61-4.52 (m, 2H), 3.10-2.99 (m, 1H), 2.92-2.89 (m, 2H), 2.62-2.68 (m, 1H), 2.27 (s, 3H); ESI m/z 502.0 [M+H]$^+$.

A mixture of 80A (200 mg, 0.40 mmol) and LiBr (695 mg, 0.80 mmol) in acetone (50 mL) was heated to 80° C. overnight. After cooling, the reaction mixture was concentrated and purified by silica gel chromatography (1% MeOH in DCM) to afford bromide 80B (140 mg, 85% yield) as a white solid: $^1$H NMR (400 MHz, DMSO-$d_6$) δ 8.62 (d, J=8.4 Hz, 1H), 8.06 (t, J=7.6 Hz, 1H), 7.97 (d. J=7.6 Hz, 1H), 7.86 (d, J=7.6 Hz, 1H), 7.77-7.71 (m, 2H), 7.58 (t, J=7.2 Hz, 1H), 5.41 (s, 1H), 5.29-5.13 (m, 2H), 4.14-4.04 (m, 2H), 3.16-3.04 (m, 2H), 2.95-2.87 (m, 1H), 2.71-2.64 (m, 1H); ESI m/z 409.9, 411.9 [M+H]$^+$.

A mixture of 80B (100 mg, 0.24 mmol) and Pd/C (wet, 10%, 100 mg) in triethylamine (10 mL) and methanol (30 mL) was stirred at 30° C. under 0.5 Mpa of H$_2$ overnight. The mixture was filtered and the filtrate was concentrated under vacuum. The residue was purified by silica gel chromatography (3% MeOH in DCM) to provide compound 80 (40 mg, 50% yield) as a white solid: $^1$H NMR (400 MHz, CDCl$_3$) δ 8.70 (d, J=8.4 Hz, 1H), 8.11 (d, J=7.6 Hz, 1H), 7.96 (d, J=7.6 Hz, 1H), 7.89 (t, 8 Hz, 1H), 7.66 (t, 7.2 Hz, 7.2 Hz, 1H), 7.59-7.52 (m, 2H), 5.15-5.04 (m, 3H), 3.11-3.03 (m, 3H), 2.51-2.44 (m, 1H), 1.55 (d, J=6.8 Hz, 3H); ESI m/z 332.0 [M+H]$^+$.

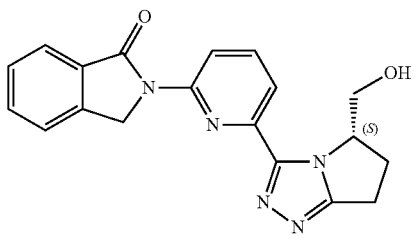

81

(S)-2-(6-(5-(Hydroxymethyl)-6,7-dihydro-5H-pyrrolo[2,1-c][1,2,4]triazol-3-yl)pyridin-2-yl)isoindolin-1-one (compound 81) was prepared according to the procedure for compound 79 substituting (S)-5-(hydroxymethyl)pyrrolidin-2-one in place of (R)-5-(hydroxymethyl)pyrrolidin-2-one. $^1$H NMR (400 MHz, DMSO-$d_6$) δ 8.59 (d, J=8 Hz, 1H), 8.03 (t, J=8 Hz, 1H), 7.94 (d, J=7.6 Hz, 1H), 7.85 (d, J 7.6 Hz, 1H), 7.74 (d, J=4 Hz, 2H), 7.59-7.55 (m, 1H), 5.21 (d, J=18 Hz, 1H), 5.07-5.03 (m, 3H), 3.83-3.82 (m, 2H), 2.98-2.82 (m, 3H), 2.73-2.67 (m, 1H); ESI m/z 348.0 [M+H]$^+$.

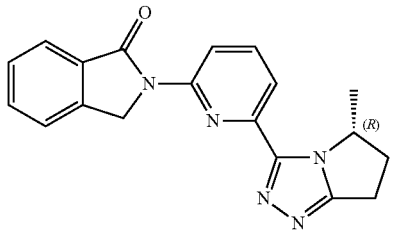

82

(R)-2-(6-(5-methyl-6,7-dihydro-5H-pyrrolo[2,1-c][1,2,4]triazol-3-yl)pyridin-2-yl)isoindolin-1-one (compound 82) was prepared according to the procedure for compound 80 substituting compound 81 in place of compound 79. $^1$H NMR (400 MHz, DMSO-$d_6$) δ 8.60 (d, J=8.4 Hz, 1H), 8.04 (t, J=8 Hz, 1H), 7.85 (d, J=7.6 Hz, 1H), 7.79-7.72 (m, 2H), 7.58 (t, J=7.2 Hz, 1H), 5.28 (d, J=17.6 Hz, 1H), 5.12 (t, J=6.8 Hz, 1H), 5.11 (d, J=17.6 Hz, 1H), 3.09-2.87 (m, 3H), 2.42-2.37 (m, 1H), 1.48 (d, J=6.4 Hz, 3H); ESI m/z 332.0 [M+H]$^+$.

Example 32: Preparation of 2-(6-(5-cyclopropyl-1H-1,2,3-triazol-1-yl)pyridin-2-yl)isoindolin-1-one (compound 83)

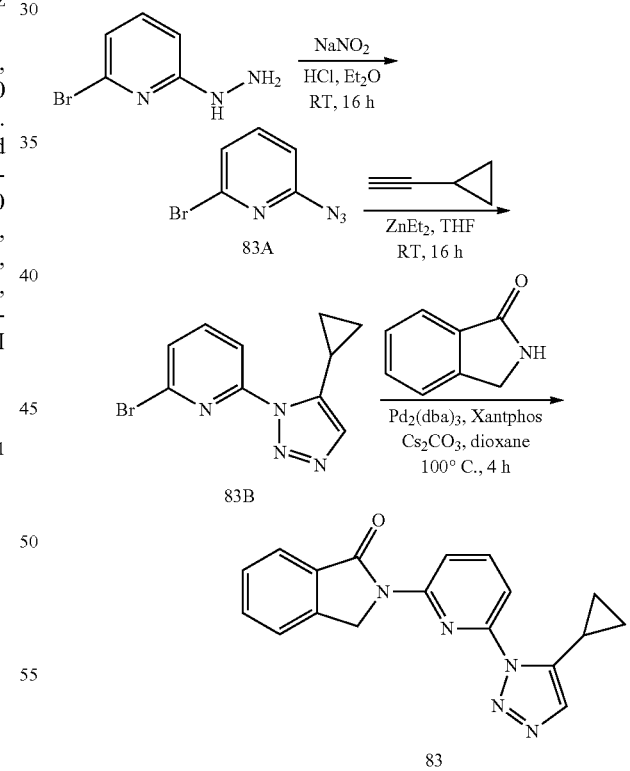

A mixture of 2-bromo-6-hydrazinylpyridine (10 g, 53.2 mmol), NaNO$_2$ (4.1 g, 58.5 mmol) in conc. HCl (20 mL), H$_2$O (70 mL) and ether (32 mL) was stirred at room temperature overnight. The reaction mixture was extracted with ether and the organic fractions were washed with brine and dried over sodium sulfate. The solvent was evaporated and the residue was purified by column chromatography on silica gel (1%-5% EtOAc in pet. ether) to afford 83A (4.2 g, 40% yield) as a yellow solid: ¹H NMR (400 MHz, DMSO-d₆) δ 7.76 (t, J=8 Hz, 1H), 7.46 (d, J=7.6 Hz, 1H), 7.01 (d, J=8 Hz, 1H); ESI m/z 199.9, 201.9 [M+H]⁺.

A mixture of 83A (500 mg, 2.51 mmol), ZnEt₂ in THF (1.0 M, 3.8 mL), ethynylcyclopropane (200 mg, 3.02 mmol) and 1-methyl-1H-imidazole (21 mg, 0.25 mmol) was stirred at room temperature overnight under nitrogen. The mixture was poured into water and extracted with EtOAc (100 mL×3). The combined organic fractions were washed with water and brine and dried over sodium sulfate. The solvent was removed under vacuum and the residue was purified by column chromatography on silica gel (1%-10% EtOAc in pet. ether) to give the 83B (200 mg, 30% yield) as a yellow solid: ¹H NMR (400 MHz, DMSO-d₆) δ 8.09 (t, J=8 Hz, 1H), 8.00 (d, J=7.2 Hz, 1H), 7.86 (d, J=8 Hz, 1H), 7.64 (s, 1H), 2.40-2.33 (m, 1H), 1.07-1.02 (m, 2H), 0.81-0.77 (m, 2H); ESI m/z 265.0, 267.0 [M+H]⁺.

A mixture of 83B (200 mg, 0.8 mmol), isoindolin-1-one (107 mg, 0.8 mmol), Pd₂(dba)₃ (22 mg, 0.024 mmol), Xantphos (23 mg, 0.04 mmol) and Cs₂CO₃ (313 mg, 0.96 mmol) in dioxane (50 mL) was heated to 100° C. for 4 h. After cooling to room temperature, the reaction mixture was filtered. The filtrate was concentrated and the residue was purified by column chromatography on silica gel (1%-5% EtOAc in pet. ether) to provide compound 83 (180 mg, 31% yield) as an off-white solid: ¹H NMR (400 MHz, DMSO-d₆) δ 8.66 (d, J=8.4 Hz, 1H), 8.19 (t, J=8 Hz, 1H), 7.85 (d, J=7.6 Hz, 1H), 7.73-7.69 (m, 3H), 7.63 (s, 1H), 7.59-7.55 (m, 1H), 5.14 (s, 2H), 2.62-2.56 (m, 1H), 1.13-1.09 (m, 2H), 0.83-0.79 (m, 2H); ESI m/z 318.0 [M+H]⁺.

Example 33: Preparation of 2-(6-(1H-1,2,3-triazol-1-yl)pyridin-2-yl)isoindolin-1-one (compound 84)

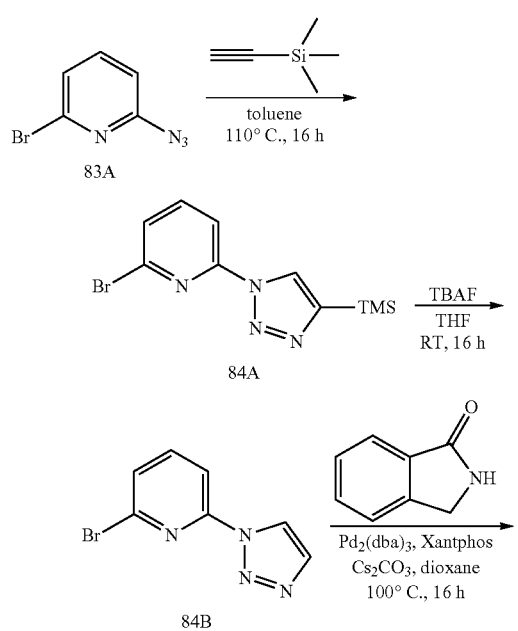

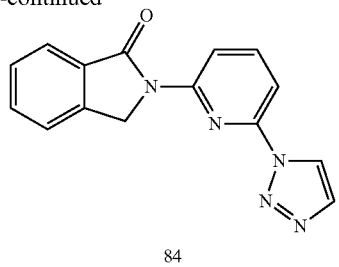

A mixture of 83A (600 mg, 3.02 mmol) and ethynyltrimethylsilane (890 mg, 9.06 mmol) in toluene (20 mL) was heated to 110° C. overnight in a sealed tube. After cooling, the mixture was concentrated under vacuum and the residue was purified by column chromatography on silica gel (1%-5% EtOAc in pet. ether) to give 84A (600 mg, 58% yield) as a white solid: ESI m/z 298.9, 296.9 [M+H]⁺.

TBAF (1.0 M in THF, 3.1 mL, 3.03 mmol) was added to a solution of 84A (300 mg, 1.01 mmol) in THF (2 mL). After stirring at room temperature overnight the reaction mixture was diluted with water and extracted with EtOAc. The combined organic fractions were washed with brine, dried over sodium sulfate and evaporated. The residue was purified by flash chromatography (10%-30% EtOAc in pet. ether) to afford 84B as a white solid: ¹H NMR (400 MHz, DMSO-d₆) δ 8.83 (s, 1H), 8.15 (d, J=8 Hz, 1H), 8.08-8.04 (m, 1H), 8.01 (s, 1H), 7.81 (d, J=8 Hz, 1H); ESI m/z 224.9, 226.9 [M+H]⁺.

A mixture of 84B (225 mg, 1.0 mmol), isoindolin-1-one (133.1 mg, 1.0 mmol), Pd₂(dba)₃ (28 mg, 0.03 mmol), Xantphos (29 mg, 0.05 mmol) and Cs₂CO₃ (391 mg, 1.2 mmol) in dioxane (45 mL) was heated to 100° C. overnight. After cooling to room temperature, the reaction mixture was filtered. The filtrate was concentrated under vacuum and the residue was purified by column chromatography on silica gel (1%-30% EtOAc in pet. ether) to provide compound 84 (170 mg, 61% yield) as a white solid: ¹H NMR (400 MHz, CDCl₃) δ 8.72 (dd, J=7.6 Hz, 6.4 Hz, 1H), 8.57 (d, J=1.2 Hz, 1H), 8.01-7.94 (m, 3H), 7.86 (d, J=0.8 Hz, 1H), 7.69-7.65 (m, 1H), 7.59-7.52 (m, 2H), 5.14 (s, 2H); ESI m/z 278.0 [M+H]⁺.

Example 34: Preparation of 2-(6-(4-isopropyl-4H-1,2,4-triazol-3-yl)pyridin-2-yl)-6-(pyridin-3-yl)isoindolin-1-one (compound 85)

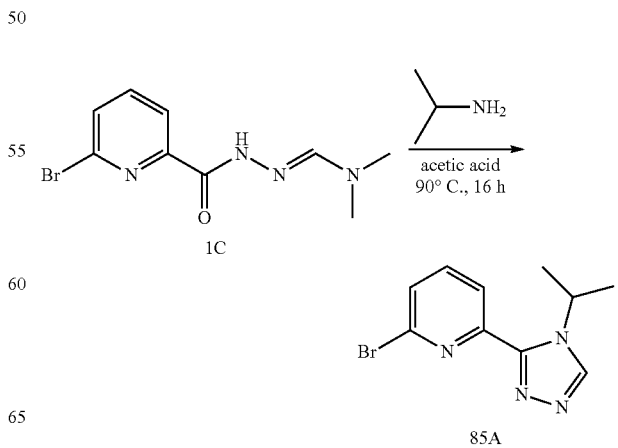

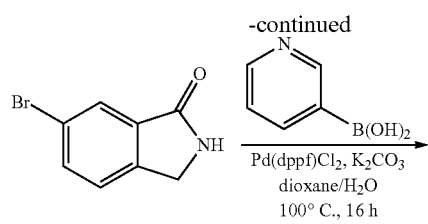

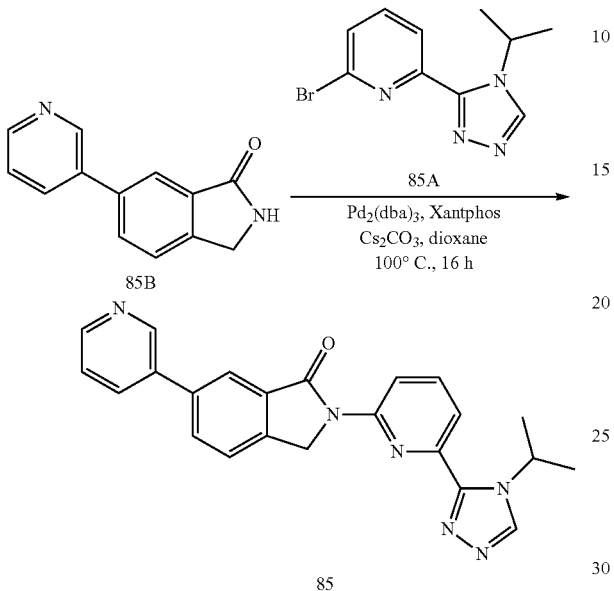

A mixture of 1C (2.1 g, 7.75 mmol), propan-2-amine hydrochloride (3.71 g, 38.8 mmol) and DIPEA (5.0 g, 38.8 mmol) in acetonitrile (32 mL) and acetic acid (8 mL) was heated to 90° C. overnight. After cooling, the reaction mixture was concentrated under vacuum and purified by column chromatography on silica gel (1%-50% EtOAc in pet. ether) to give triazole 85A (1.7 g, 82% yield) as a white solid: $^1$H NMR (400 MHz, DMSO-$d_6$) δ 8.92 (s, 1), 8.15 (d, J=8 Hz, 1H), 7.96-7.92 (m, 1H), 7.77 (d, J=8 Hz, 1H), 5.34-5.24 (m, 1H), 1.48 (d, J=6.8 Hz, 6H); ESI m/z 266.9, 268.9 [M+H]$^+$.

A mixture of 6-bromoisoindolin-1-one (1.0 g, 4.72 mmol), Pd(dppf)Cl$_2$ (104 mg, 0.14 mmol), K$_2$CO$_3$ (1.96 g, 14.2 mmol) and 3-pyridylboronic acid (580 mg, 4.72 mmol) in dioxane (45 mL) and water (5 mL) was heated to 100° C. overnight. After cooling, the mixture was poured into water and extracted with EtOAc (3×100 mL). The combined organic fractions were washed with brine and dried over sodium sulfate. The solvent was evaporated and the residue was purified by column chromatography on silica gel (1%-50% EtOAc in pet. ether) to afford 85B (500 mg, 50% yield) as an off-white solid: $^1$H NMR (400 MHz, DMSO-$d_6$) δ 8.94 (d, J=2 Hz, 1H), 8.67 (s, 1H), 8.60 (dd, J=4.8 Hz, 1.2 Hz, 1H), 8.16-8.13 (m, 1H), 7.96-7.94 (m, 2H), 7.71 (d, J=8.8 Hz, 1H), 7.52-7.49 (m, 1H), 4.44 (s, 2H); ESI m/z 211.0 [M+H]$^+$.

A mixture of 85B (210 mg, 1.0 mmol), 85A (267 mg, 1.0 mmol), Pd$_2$(dba)$_3$ (28 mg, 0.03 mmol), Xantphos (29 mg, 0.05 mmol) and Cs$_2$CO$_3$ (391 mg, 1.2 mmol) in dioxane (45 mL) was heated to 100° C. overnight. After cooling to room temperature, the reaction was filtered. The filtrate was concentrated under reduced pressure and purified by column chromatography on silica gel (1%-5% MeOH in EtOAc) to provide compound 85 (220 mg, 55% yield) as a white solid:

$^1$H NMR (400 MHz, DMSO-$d_6$) δ 9.0 (s, 1H), 8.93 (s, 1H), 8.66-8.61 (m, 2H), 8.19 (d, J=8 Hz, 1H), 8.13 (s, 1H), 8.10-8.06 (m, 2H), 7.92 (d, J=7.6 Hz, 1H), 7.87 (d, J=8 Hz, 1H), 7.54-7.51 (m, 1H), 5.57-5.51 (m, 1H), 5.21 (s, 2H), 1.59 (d, J=6.8 Hz, 6H); ESI m/z 397.0 [M+H]$^+$.

Example 35: Preparation of 2-(4-(4-cyclopropyl-4H-1,2,4-triazol-3-yl)pyrimidin-2-yl)isoindolin-1-one (compound 86)

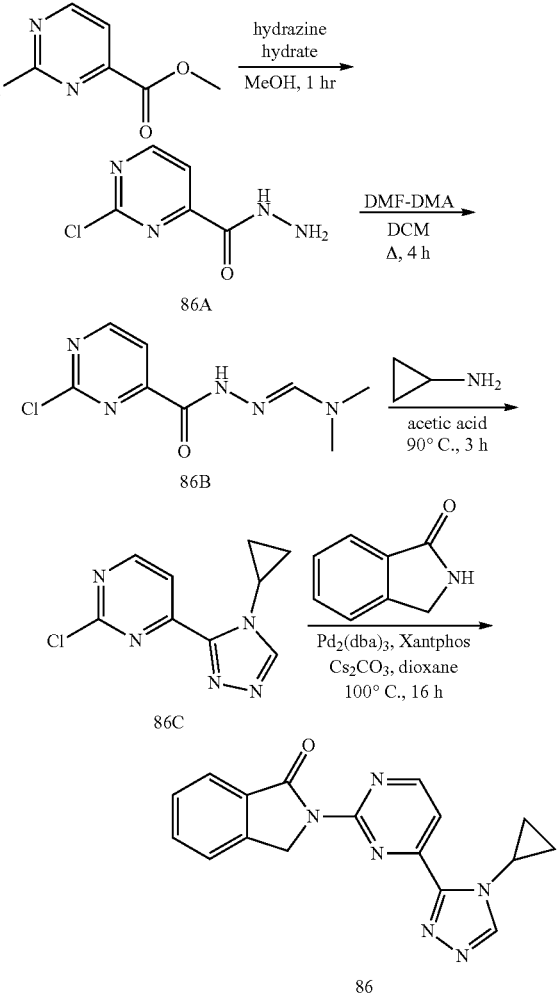

A mixture of methyl 2-chloropyrimidine-4-carboxylate (2.8 g, 16.2 mmol) and hydrazine hydrate (0.80 g, 16.2 mmol) in methanol (50 mL) was stirred at 0° C. for 1 hour. The solid was collected by filtration and washed with hexane to give 86A (1.71 g, 61% yield) as a yellow solid: ESI m/z 173.0 [M+H]$^+$.

A mixture of 86A (1.5 g, 8.70 mmol) and DMF-DMA (5.1 g, 43.4 mmol) in DCM (100 mL) was heated to reflux for 4 hours. The mixture was concentrated under vacuum and triturated with pet. ether to afford 86B (1.9 g, 96% yield) as a yellow solid: ESI m/z 228.1 [M+H]$^+$. Cyclopropylamine (1.44 g, 25.2 mmol) was added to a solution of 86B (1.9 g, 8.40 mmol) in acetic acid (60 mL). The reaction mixture was stirred at 90° C. for 3 hours. The mixture was concentrated under reduced pressure and purified by chromatography on silica gel (1%-3% MeOH in DCM) to give 86C (1.2 g, 65% yield) as a yellow solid: ESI m/z 222.1 [M+H]+.

A mixture of 86C (150 mg, 0.68 mmol), isoindolin-1-one (90 mg, 0.68 mmol), Cs$_2$CO$_3$ (265 mg, 0.82 mmol), Xantphos (19 mg, 0.034 mmol) and Pd(dba)$_3$ (18 mg, 0.02 mmol) in dioxane (8 mL) was stirred at 100° C. overnight under a nitrogen atmosphere. The mixture was poured into water and extracted with EtOAc (100 mL×3). The combined organic fractions were dried over sodium sulfate, concentrated under reduced pressure and purified by chromatography on silica gel (1%-3% MeOH in DCM) to provide compound 86 (15 mg, 7% yield) as a white solid: $^1$H NMR (400 MHz, DMSO-d$_6$) δ 8.94 (d, J=5.2 Hz, 1H), 8.80 (s, 1H), 7.91 (d, J=4.8 Hz, 1H), 7.84 (d, J=8 Hz, 1H), 7.74-7.72 (m, 2H), 7.58-7.54 (m, 1H), 5.18 (s, 2H), 4.65-4.62 (m, 1H), 1.14-1.11 (m, 2H), 1.08-1.06 (m, 2H); ESI m/z 319.1 [M+H]+.

Example 36: Preparation of 2-(6-(4-cyclopropyl-4H-1,2,4-triazol-3-yl)pyridin-2-yl)-1,2-dihydro-3H-indazol-3-one (compound 87)

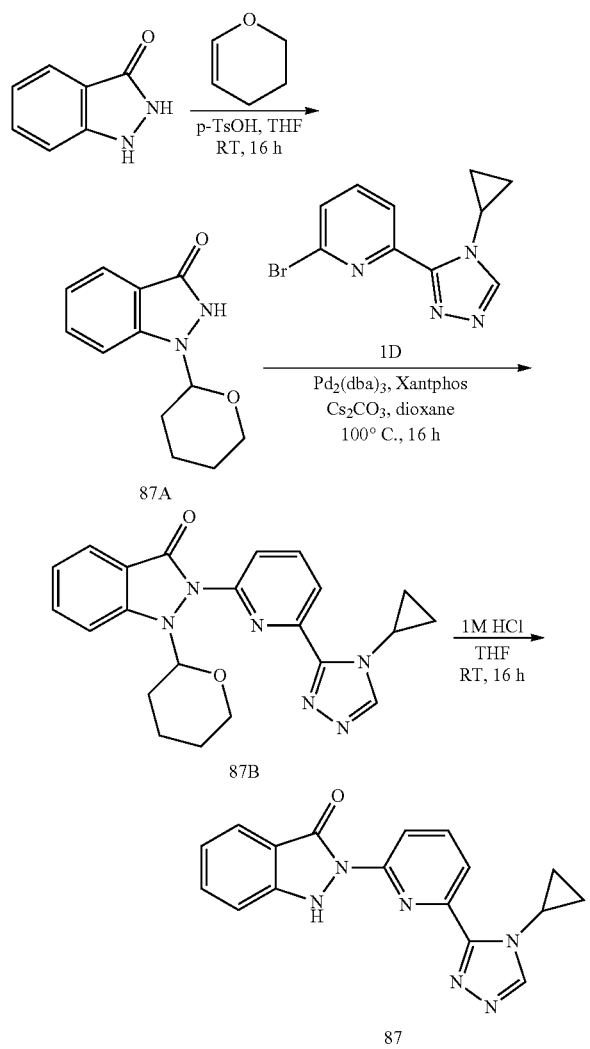

A mixture of 3,4-dihydro-2H-pyran (2.1 g, 24.6 mmol), 1H-indazol-3(2H)-one (3 g, 22.4 mmol), toluene-4-sulfonic acid (775 mg, 4.5 mmol) in THF (25 mL) was stirred at RT overnight. The mixture was concentrated under vacuum and purified by silica gel column chromatography (1%-5% EtOAc in pet. ether) to afford 87A (2 g, 41% yield) as a white solid: $^1$H NMR (400 MHz, DMSO-d$_6$) δ 10.79 (s, 1H), 7.62 (d, J=8 Hz, 1H), 7.52 (d, J=8.4 Hz, 1H), 7.36 (t, J=7.6 Hz, 1H), 7.07-7.03 (m, 1H), 5.58 (dd, J=10 Hz, 1 Hz, 1H), 3.87-3.84 (m, 1H), 3.69-3.62 (m, 1H), 2.34-2.24 (m, 1H), 2.01-1.98 (m, 1H), 1.91-1.87 (m, 1H), 1.76-1.65 (m, 1H), 1.55-1.48 (m, 2H); ESI m/z 219.1 [M+H]+.

A mixture of 87A (550 mg, 2.52 mmol), 1D (668 mg, 2.52 mmol) Pd$_2$(dba)$_3$ (74 mg, 0.08 mmol), Xantphos (75 mg, 0.13 mmol) and Cs$_2$CO$_3$ (985 mg, 3.0 mmol) in dioxane (50 mL) was heated to 100° C. overnight. After cooling to room temperature, the reaction mixture was filtered. The filtrate was concentrated under reduced pressure and purified by column chromatography (1%-50% EtOAc in pet. ether) to give 87B (600 mg, 60% yield) as a yellow solid: ESI m/z 403.1 [M+H]+.

A mixture of 87B (600 mg, 1.49 mmol) and HCl (1.0 M, 20 mL) in THF (10 mL) was stirred at room temperature overnight. The mixture was poured into water and extracted with EtOAc (100 mL×3). The combined organic fractions were washed with water and brine and dried over sodium sulfate. The solvent was removed under vacuum and the residue was purified by column chromatography on silica gel (1%-5% MeOH in DCM) to provide compound 87 (230 mg, 48% yield) as a white solid: $^1$H NMR (400 MHz, DMSO-d$_6$) δ 12.69 (s, 1H), 8.42 (s, 1H), 8.13-8.09 (m, 1H), 7.91 (d, J=7.2 Hz, 1H), 7.51 (d, J=8.4 Hz, 1H), 7.44-7.36 (m, 3H), 7.06 (t, J=7.2 Hz, 1H), 2.85-2.79 (m, 1H), 0.65-0.60 (m, 2H), 0.15-0.10 (m, 2H); ESI m/z 319.0 [M+H]+.

Example 37: Preparation of 2-(6-(4-cyclopropyl-4H-1,2,4-triazol-3-yl)pyridin-2-yl)-1-methyl-1,2-dihydro-3H-indazol-3-one (compound 88)

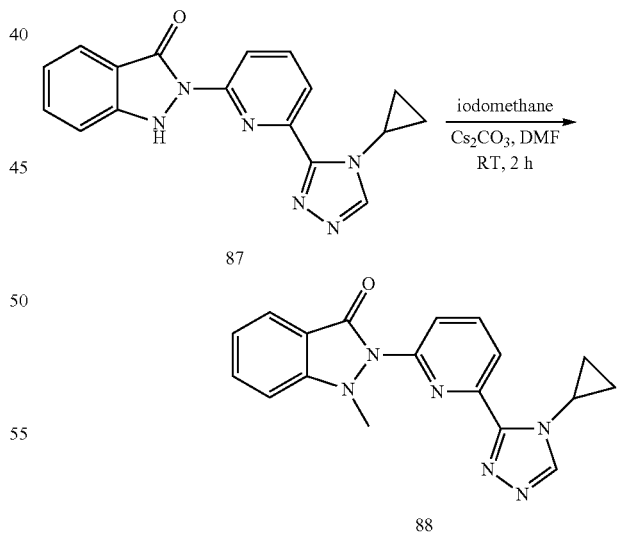

To a mixture of compound 87 (100 mg, 0.31 mmol) and Cs$_2$CO$_3$ (206 mg, 0.63 mmol) in DMF (10 mL) was added iodomethane (67 mg, 0.47 mmol). After stirring at room temperature for 2 h, the mixture was poured into water and extracted with EtOAc (50 mL×3), the organic layer was washed with water and brine, dried over Na$_2$SO$_4$, filtered, concentrated and purified by silica gel column chromatography (MeOH/DCM=1/100 to 1/30, v/v) and Prep-TLC (MeOH/DCM=1/15, v/v) to afford the product (13 mg, 13% yield) as a white solid: $^1$H NMR (400 MHz, DMSO-d$_6$) δ 8.43 (s, 1H), 8.11 (t, J=8 Hz, 1H), 7.91 (d, J=7.6 Hz, 1H), 7.64 (d, J=8.8 Hz, 1H), 7.45-7.38 (m, 3H), 7.11-7.07 (m, 1H), 3.97 (s, 3H), 2.87-2.81 (m, 1H), 0.66-0.62 (m, 2H), 0.17-0.12 (m, 2H); ESI m/z 333.0 [M+H]$^+$.

Example 38: Preparation of 2-(6-(4-cyclopropyl-4H-1,2,4-triazol-3-yl)pyridin-2-yl)benzo[d]isothiazol-3(2H)-one (compound 89)

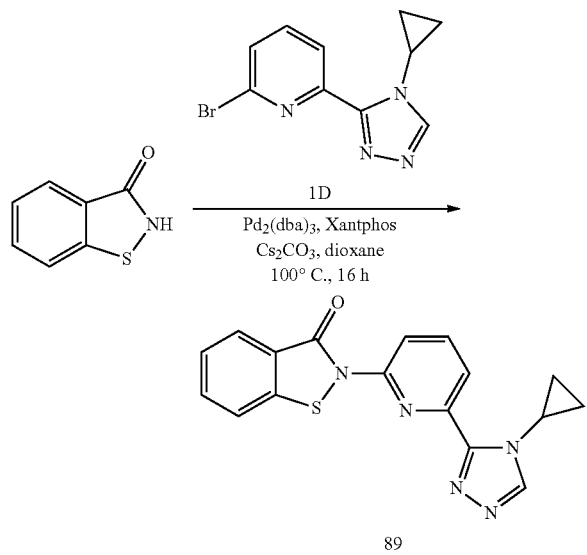

A stirred mixture of benzo[d]isothiazol-3(2H)-one (113 mg, 0.75 mmol), 1D (200 mg, 0.75 mmol), Pd$_2$(dba)$_3$ (34 mg, 0.0375 mmol), Cs$_2$CO$_3$ (733 mg, 2.25 mmol) and Xantphos (30 mg, 0.0525 mmol) in 1,4-dioxane (20 mL) was heated to 100° C. overnight. The reaction mixture was allowed to cool to room temperature and filtered. The filtrate was concentrated under reduced pressure and the residue was purified by silica column chromatography (1%-5% MeOH in DCM) to afford compound 89 (20 mg, 8% yield) as a yellow solid: $^1$H NMR (400 MHz, CDCl$_3$) δ 8.86 (d, J=8.4 Hz, 1H), 8.27 (s, 1H), 8.10 (dd, J=7.6 Hz, 3.2 Hz, 1H), 7.97 (t, J=8 Hz, 1H), 7.68 (t, J=7.6 Hz, 1H), 7.57 (d, J=8 Hz, 1H), 7.44 (t, J=7.6 Hz, 1H), 4.16-4.11 (m, 1H), 1.28-1.23 (m, 2H), 0.96-0.92 (m, 2H); ESI m/z 336.0 [M+H]$^+$.

Example 39: ASK1 Kinase Assay

The ASK1 enzymatic assay was run following Promega ASK1 Kinase Enzyme System (Cat #V3881). The kit provides the protocol, enzymes and all reagents necessary to run an assay. Firstly, the compounds, enzyme, substrate and ATP were diluted in provided assay buffer. The final concentration of the enzyme was 50 nM, substrate (Myelin basic protein) 1 μg/ml and ATP 10 μM. The compound and the enzyme were pre-incubated in a 384 well white solid bottom plate (Greiner, Cat#784075) for 10 minutes. After incubation, the substrate and ATP were added and incubated for further 60 minutes. After 60 minutes, ADP-Glo™ was added and plate was incubated for another 40 minutes. After 40 minutes, Kinase Detection Reagent was added and the plate was incubated for 45 minutes. After 45 minutes, plate was read on Perkin Elmer EnVision using luminescence read (0.5 seconds/well). IC50 data for compounds are shown in Table 6.

Example 40: Inhibition of LPS-induced TNFalpha in Human PBMCs

Cryopreserved human PBMCs were obtained from AllCells (cat# PB003F). After thawing/dilution protocols using RPMI medium supplemented with 5% FBS (heat inactivated), 100 ul/well of 1×10$^6$ cells/ml were plated into 96 well tissue culture plates (Corning). Cells were then pre-incubated for 1 hr at 37° C. in humidified 5% CO2 and 95% air with test compounds diluted in DMSO (final DMSO concentration 0.3%). Each compound was tested at 10 concentrations in duplicate wells. After the pre-incubation, 100 ng/ml LPS (E. Coli; Sigma) in RPMI media with 5% FBS was added for a 6 hr incubation at 37° C. in humidified 5% CO2 and 95% air. Controls on each plate included cells and LPS only, cells and media only (no LPS), and media only. After the 6 hr incubation, plates were centrifuged and the supernatants transferred to a new plate and frozen for subsequent TNFalpha analysis. Human TNFalpha was analyzed by ELISA according to the manufacturer's instructions (BD Sciences, BD OptEIA™ Cat#550610) and analyzed on a SpectraMax M series (Molecular Devices) microplate reader at OD 450 nm. IC50s were calculated using XLFit4 curve fitting software (IDBS) and a 4-parameter one-site sigmoid dose response fit. IC50 data for compounds are shown in Table 6.

Example 41: MYLK/MLCK Assay

MYLK dissociation constants (Kd) for compounds were determined using the DiscoverX KdELECT platform. The MYLK kinase (accession number NP_444254.3) was labeled with a DNA tag for subsequent qPCR readout while a known active site binding ligand (staurosporine) was immobilized on a solid support (beads). Test compounds were prepared as 111X stocks in 100% DMSO and Kds were determined using an 11-point 3-fold compound dilution series with three DMSO control points. The compounds were then diluted directly into the assays such that the final concentration of DMSO was 0.9%. The assay plates were incubated at room temperature with shaking for 1 hour to equilibrate. The affinity beads were washed (lx PBS, 0.05% Tween 20) to remove unbound kinase and quantify MYLK captured on solid support by qPCR. The Kd was determined by measuring the amount of MYLK captured on the solid support as a function of the test compound concentration. The Kd values were calculated by fitting dose-response curves to the Hill binding equation using the Levenberg-Marquardt algorithm. The Kd data for compounds are shown in Table 6.

For the myosin light chain kinase (MLCK) IC50 determinations, the Reaction Biology Corporation radioactive kinase platform (CAT#: MLCK) was utilized. The MLCK peptide substrate (KKLNRTLSFAEPG, 20 uM) was freshly prepared in base reaction buffer (20 mM Hepes (pH 7.5), 10 mM MgCl2, 1 mM EGTA, 0.02% Brij35, 0.02 mg/ml BSA, 0.1 mM Na3VO4, 2 mM DTT, 1% DMSO) with 1 uM calmodulin and 30 uM ATP (Km). Test compounds were tested in 10-dose IC50 mode with a 3-fold serial dilution starting at 60 uM. The control compound, staurosporine, was tested in 10-dose IC50 mode with 4-fold serial dilution starting at 20 uM.

Compounds were incubated for 20 minutes with the peptide substrate and the MLCK kinase enzyme (UniProtKB Q15746 (MYLK_HUMAN)) prior to the addition of $^{33}$P-ATP (specific activity 10 μCi/μl), to initiate the reaction, resulting in $^{33}$P-Substrate+ADP. After 2 hr incubation at room temperature the reactions are spotted onto P81 ion exchange paper and the kinase activity detected by a filter-binding method. IC50 values and curve fits were obtained using Prism GraphPad Software. IC50 data for compounds are shown in Table 6.

Example 42: hERG QPatchHTX Assay

The hERG QPatchHTX assay was conducted at room temperature. The whole-cell protocols, voltage protocols and application protocols were established with QPatch Assay Software 5.2 (Sophion Bioscience). Chinese hamster ovary (CHO) cells stably expressing hERG potassium channels (Aviva Bioscience) were cultured at more than 75% confluent. Cells were harvested using TrypLE and resuspended in the extracellular solution at the room temperature.

Test compounds described herein, commercial compound GS-4997 and positive control Amitriptyline were dissolved in 100% DMSO to obtain stock solutions and were further diluted into extracellular solution to achieve final concentrations for testing. Visual check for precipitation was conducted before testing. Final DMSO concentration in extracellular solution was not more than 0.30% for the test compounds and Amitriptyline (positive) control. Three additions of 5 l of the vehicle were applied, followed by 30 runs of voltage protocol for a baseline period. Then the ascending doses of each compound were added with three repetitions (5 l*3). The exposure of test compound at each concentration was no less than 5 minutes. The recording for the whole process had to pass the quality control or the well was abandoned and the compound was retested, all automatically set by QPatch Assay Software. Two concentrations (10 M and 30 μM) were tested for each compound. Minimum 2 replicates per concentration were obtained.

Voltage command protocol: From this holding potential of −80 mV, the voltage was first stepped to −50 mV for 80 ms for leak subtraction, and then stepped to +20 mV for 4800 ms to open hERG channels. After that, the voltage was stepped back down to −50 mV for 5000 ms, causing a "rebound" or tail current, which was measured and collected for data analysis. Finally, the voltage was stepped back to the holding potential (−80 mV, 3100 ms). This voltage command protocol was repeated every 15000 msec. This command protocol was performed continuously during the test (vehicle control and test compounds described herein).

Compound 2 and Compound 27 did not have a significant effect on hERG current up to 30 μM (FIG. 1). In contrast, the ASK1 inhibitor GS-4997 and the positive control compound both had significant effect on hERG current. Activity data for compounds are shown in Table 6.

TABLE 6

| Compound | ASK1 Kinase Avg $IC_{50}$ | TNFa Inhibition $IC_{50}$ | MYLK/MLCK Kinase $IC_{50}$ or $K_d$ | hERG Inhibition at 10 μM |
| --- | --- | --- | --- | --- |
| 1 | +++ | | +++ | |
| 2 | +++ | ++ | + | + |
| 3 | +++ | | | |
| 4 | +++ | | | |
| 5 | +++ | | | |
| 6 | +++ | | | |
| 7 | +++ | + | + | ++ |
| 8 | +++ | | | ++ |
| 9 | +++ | | | ++ |
| 10 | +++ | ++ | | + |
| 11 | +++ | ++ | | + |
| 12 | +++ | + | | |
| 13 | +++ | + | | |
| 14 | +++ | ++ | | + |
| 15 | +++ | ++ | | + |
| 16 | +++ | + | | + |
| 17 | +++ | + | | |
| 18 | +++ | | | |
| 19 | +++ | | | |
| 20 | +++ | | | |
| 21 | +++ | | | |
| 22 | +++ | | | |
| 23 | +++ | | | |
| 24 | +++ | | | |
| 25 | +++ | | | |
| 26 | +++ | | | |
| 27 | +++ | | | ++ |
| 28 | +++ | | ++ | |
| 29 | +++ | | | |
| 30 | +++ | | ++ | ++ |
| 31 | +++ | | | |
| 32 | ++ | | ++ | |
| 33 | ++ | | | |
| 34 | +++ | | | |
| 35 | +++ | | | |
| 36 | +++ | | | |
| 37 | +++ | | | |
| 38 | +++ | | | |
| 39 | +++ | | | |
| 40 | +++ | +++ | +++ | +++ |
| 41 | +++ | +++ | +++ | +++ |
| 42 | +++ | | | |
| 43 | +++ | ++ | | ++ |
| 44 | +++ | ++ | | + |
| 45 | +++ | | | |
| 46 | +++ | +++ | +++ | +++ |
| 47 | +++ | | | |
| 48 | +++ | | | |
| 49 | +++ | | | |
| 50 | +++ | | | |
| 51 | +++ | | | + |
| 52 | +++ | | | |
| 53 | +++ | | | |
| 54 | +++ | | | |
| 55 | ++ | | | |
| 56 | +++ | | | |
| 57 | +++ | | | |
| 58 | +++ | | | |
| 59 | +++ | | | |
| 60 | +++ | + | +++ | |
| 61 | +++ | | | |
| 62 | +++ | | | |
| 63 | +++ | | + | |
| 64 | +++ | | +++ | ++ |
| 65 | +++ | | + | |
| 66 | +++ | +++ | +++ | |
| 67 | +++ | | | |
| 68 | +++ | +++ | ++ | |
| 69 | +++ | +++ | ++ | |
| 70 | +++ | | | |
| 71 | +++ | ++ | ++ | |
| 72 | +++ | | | |
| 73 | +++ | | | |
| 74 | ++ | | | |
| 75 | ++ | | | |
| 76 | ++ | | | |
| 77 | + | | | |
| 78 | +++ | | +++ | |
| 79 | +++ | | | |
| 80 | ++ | | | |
| 81 | + | | | |
| 82 | +++ | | | |

TABLE 6-continued

| Compound | ASK1 Kinase Avg IC$_{50}$ | TNFa Inhibition IC$_{50}$ | MYLK/MLCK Kinase IC$_{50}$ or K$_d$ | hERG Inhibition at 10 µM |
|---|---|---|---|---|
| 83 | +++ | | | |
| 84 | ++ | | | |
| 85 | +++ | | | |
| 86 | + | | | |
| 87 | + | | | |
| 88 | + | | | |
| 89 | + | | | |

For ASK1 Kinase Assay: +++ = IC$_{50}$ < 200 nM; ++ = IC$_{50}$ 200 nM-<1 µM; + = IC$_{50}$ 1-10 µM.
For TNFa Inhibition Assay: +++ = IC$_{50}$ < 2 µM; ++ = IC$_{50}$ 2-10 µM; + = IC$_{50}$ > 10 nM.
For MYLK/MLCK Kinase Assay: +++ = Kd or IC$_{50}$ < 1 µM; ++ = Kd or IC$_{50}$ 1-10 µM; + = Kd or IC$_{50}$ > 10 µM.
For hERG Inhibition Assay: +++ >20% inhibition; ++ = 10-20% inhibition; + = <%10 inhibition.

Example 43: Clinical Trial of ASK1 Inhibitors in Human NASH

Patient Selection/Management

Patient inclusion criteria are: age 18-75, greater than 60 U/L serum alanine transaminase (ALT), ultrasound-documented fatty liver, biopsy-consistent NASH without cirrhosis, platelet count >75,000/mm$^3$, absolute neutrophil count >1500/mm$^3$, hemoglobin >11.0 g/dL, and creatinine clearance >70 mL/min as calculated with the Cockcroft-Gault equation.

Histological criteria used for NASH in biopsy analysis are: steatosis (>5% of hepatocytes containing liver fat), hepatocyte ballooning, and lobular inflammation, regardless of the amount of fibrosis.

Patients are required to have a stable weight (within 4%) before screening, and to maintain their existing diets and physical activity levels over the course of the study.

Patient exclusion criteria are: any other cause of liver disease (e.g., viral hepatitis, autoimmune hepatitis, hemochromatosis, and others), hepatocellular carcinoma (HCC), daily alcohol consumption higher than 30 g in males and 20 g in females, or drug-induced/secondary NASH.

Cohort Design/Drug Administration

The study is randomized, double-blind, parallel-group, and placebo-controlled. Patients successfully meeting selection criteria are stratified by comorbid conditions that may exacerbate liver injury (e.g. type-2 diabetes). After stratification, subjects are randomly assigned to one of five parallel treatment groups: placebo or 4 escalating doses of any of the ASK-1 inhibitors of Formula I, Formula II, or Formula III described herein. The inhibitor is administered orally once daily for 4 weeks. On completion of treatment, subjects are followed for 4 weeks.

Measures of Drug Efficacy

Serum ALT and AST (liver function markers) are measured from weekly blood samples collected during the treatment and follow-up periods. Normal levels are defined as 43 U/L ALT and 36 U/L AST for males, and 34 U/L ALT and 34 U/L AST for females.

Cytokeratin-18 fragments (resulting from caspase-3 cleavage and apoptotic activity, liver damage markers) are measured using ELISA from blood samples collected at week 2 and week 4 of the treatment period.

Concentrations of ASK-1 inhibitors are determined in plasma by using a validated bioanalytical assay to assess drug concentration. Steady state analysis of pharmacokinetic parameters (e.g. (C$_{max}$), time of C$_{max}$ (T$_{max}$), half-life (T$_{1/2}$), and area under the plasma concentration versus time curve over the dosing interval (AUC$_{tau}$)) occurs between weeks 2 and 4.

Safety Analysis

Safety monitoring includes clinical laboratory tests, physical examinations, vital signs measurements, 12-lead electrocardiograms, and documentation of adverse events (AEs).

Efficacy Endpoints

Absolute and percent change from baseline in ALT levels, AST levels, and CK-18 fragment levels at week 4 are assessed by an analysis of covariance (ANCOVA) model with adjustment for baseline values.

Plasma concentration-time data for each subject are analyzed using standard noncompartmental methods to compute pharmacokinetic parameters. Exposure/response relationships for ASK-1 inhibitors are determined by fitting C$_{max}$ or AUC$_{au}$ to time-weighted absolute changes in CK-18 fragment, AST, or ALT levels.

The examples and embodiments described herein are for illustrative purposes only and various modifications or changes suggested to persons skilled in the art to be included within the spirit and purview of this application and scope of the appended claims.

What is claimed is:

1. A compound of Formula II, or a pharmaceutically acceptable salt or solvate thereof:

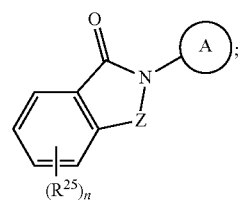

Formula II wherein

is

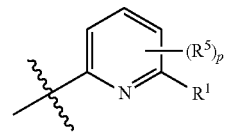

R$^1$ is

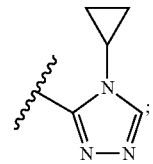 [SMILES: *c1nncn1C1CC1]

Z is C(R⁹)₂;
  each R⁵ is independently selected from a group consisting of halogen and C₁₋₆alkyl;
  R²⁵ is selected from a group consisting of halogen, —N(R⁶)₂, —C(=O)OR⁶, —C(=O)N(R⁶)₂, —NR⁶C(=O)N(R⁶)₂, and C₁₋₉heteroaryl selected from pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl; wherein the C₁₋₉heteroaryl is optionally substituted with one, two, or three substituents selected from the group consisting of halo, C₁₋₆alkyl, C₁₋₆haloalkyl, and C₃₋₈cycloalkyl;
  each R⁶ is independently selected from the group consisting of hydrogen, C₁-C₆alkyl, —C₁-C₆alkyl-O—C₁-C₆alkyl, —C₁-C₆alkyl-pyrazole, and C₃-C₈cycloalkyl; or two R⁶ on the same heteroatom are taken together with that heteroatom to which they are attached to form a C₂₋₉heterocycle or a C₂₋₉heteroaryl selected from imidazolyl, pyrazolyl, and pyrrolyl, wherein the C₂₋₉heterocycle or C₂₋₉heteroaryl are optionally substituted with one, two, or three substituents selected from the group consisting of halo, —OR⁸, —N(R⁸)₂, —C₁₋₆alkyl, —C(=O)R¹⁴, —C(=O)OR¹³, and —N(R¹³)C(=O)R¹⁴;
  R⁸ is selected from the group consisting of hydrogen and C₁-C₆alkyl;
  each R⁹ is hydrogen;
  each R¹³ is independently selected from the group consisting of hydrogen and C₁-C₆alkyl;
  each R¹⁴ is independently selected from the group consisting of C₁-C₆alkyl;
  n is 0, 1, or 2; and
  p is 0.

2. The compound of claim 1, or a pharmaceutically acceptable salt or solvate thereof, wherein n is 1.

3. The compound of claim 2, or a pharmaceutically acceptable salt or solvate thereof, wherein
  R²⁵ is —C(=O)N(R⁶)₂ and each R⁶ is independently selected from the group consisting of hydrogen, C₁-C₆alkyl, —C₁₋₆alkyl-O—C₁-C₆alkyl, —C₁-C₆alkyl-pyrazole, and C₃-C₈cycloalkyl.

4. The compound of claim 2, or a pharmaceutically acceptable salt or solvate thereof, wherein
  R²⁵ is —C(=O)N(R⁶)₂ and two R⁶ on the same heteroatom are taken together with that heteroatom to which they are attached to form a C₂₋₉heterocycle or a C₂₋₉heteroaryl selected from imidazolyl, pyrazolyl, and pyrrolyl, wherein the C₂₋₉heterocycle or C₂₋₉heteroaryl are optionally substituted with one substituent selected from the group consisting of —OR⁸, —SR⁸, —N(R⁸)₂, —C₁₋₆alkyl, —C(=O)R¹⁴, —C(=O)OR¹³, and —N(R¹³)C(=O)R¹⁴.

5. The compound of claim 4, or a pharmaceutically acceptable salt or solvate thereof, wherein
  R²⁵ is

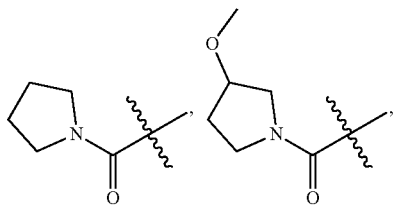

-continued

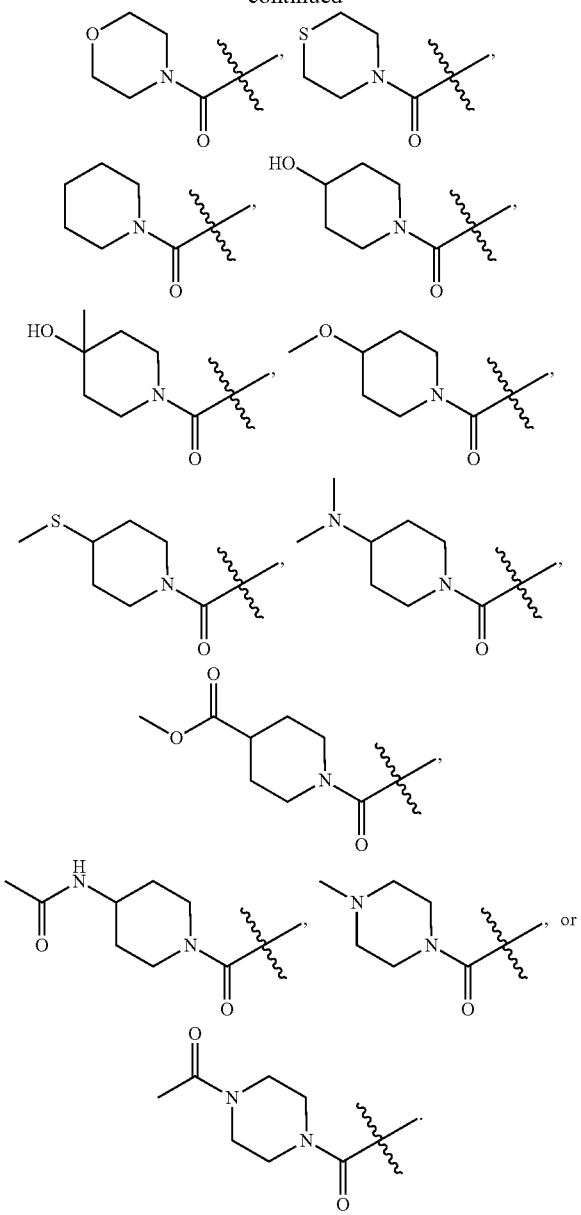

6. The compound of claim 5, or a pharmaceutically acceptable salt or solvate thereof, wherein
  R²⁵ is

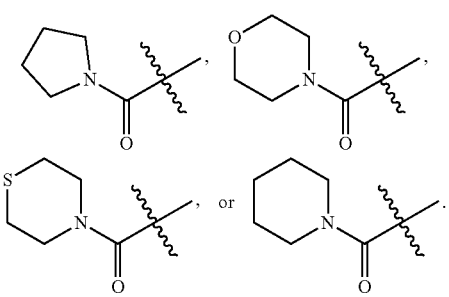

7. The compound of claim 1, or a pharmaceutically acceptable salt or solvate thereof, wherein the compound is

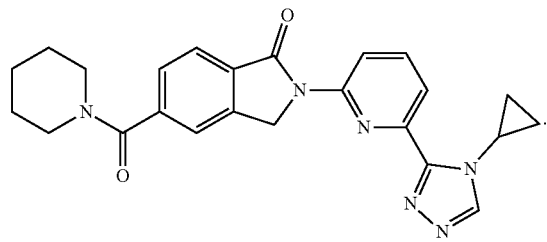 [SMILES: O=C(c1ccc2c(c1)CN(c1cccc(-c3nncn3C3CC3)n1)C2=O)N1CCCCC1]

8. The compound of claim 1, or a pharmaceutically acceptable salt or solvate thereof, wherein the compound is

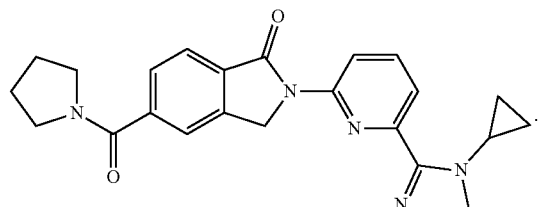

9. The compound of claim 1, or a pharmaceutically acceptable salt or solvate thereof, wherein the compound is

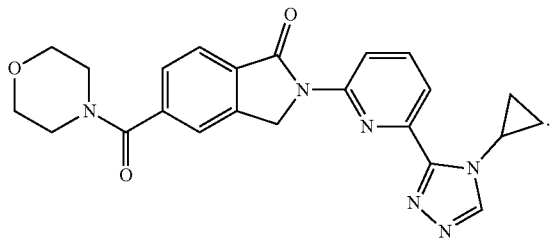

10. The compound of claim 1, or a pharmaceutically acceptable salt or solvate thereof, wherein the compound is

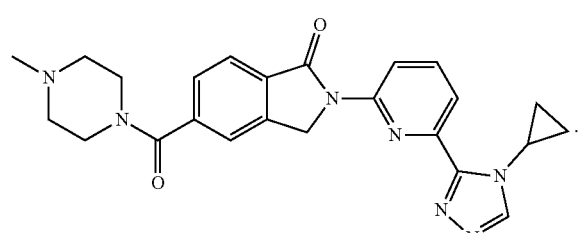

11. The compound of claim 1, or a pharmaceutically acceptable salt or solvate thereof, wherein the compound is

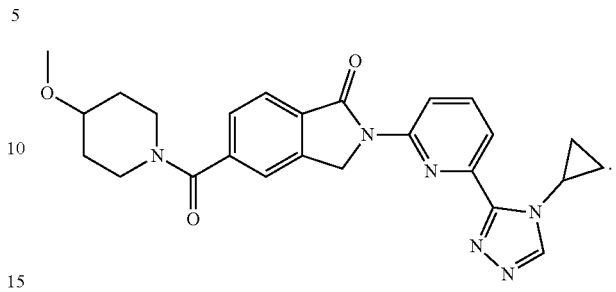

12. A compound or a pharmaceutically acceptable salt or solvate thereof, selected from:

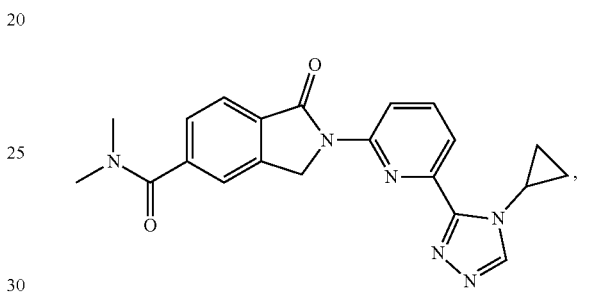

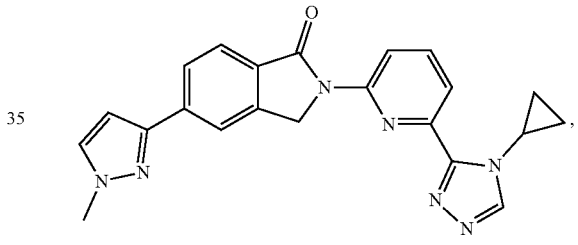

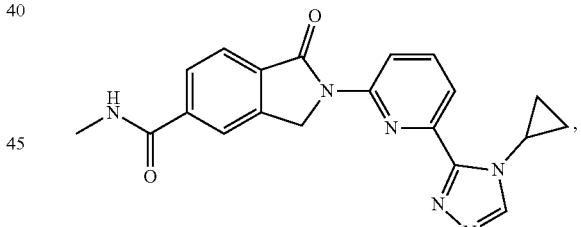

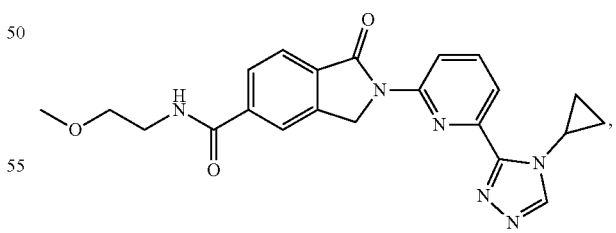

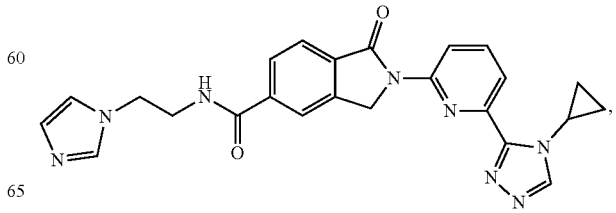

173
-continued
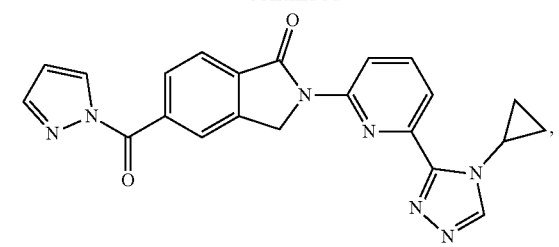 [SMILES: O=C(c1ccc2c(c1)CN(c1cccc(-c3nncn3C3CC3)n1)C2=O)N1CCCC1]
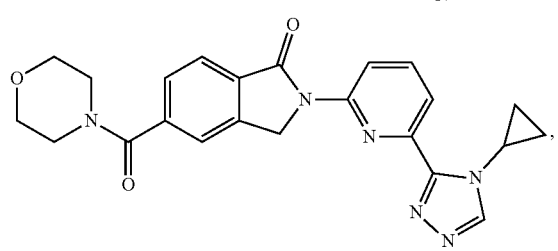
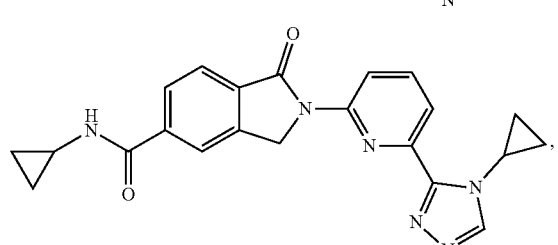
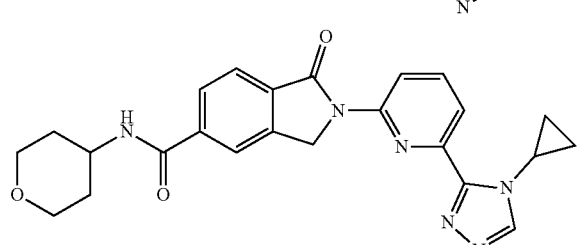
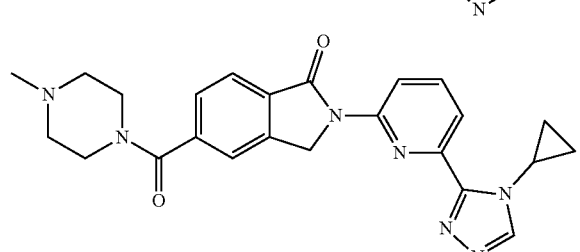
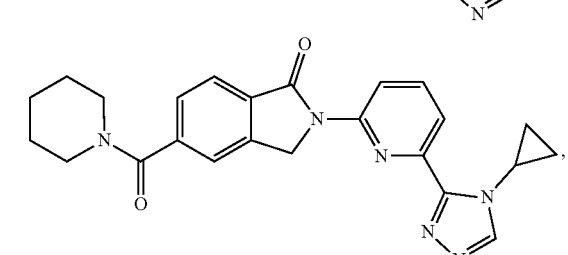
174
-continued
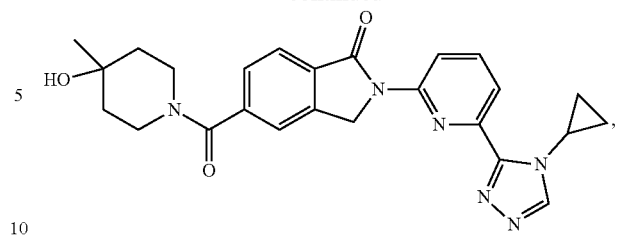
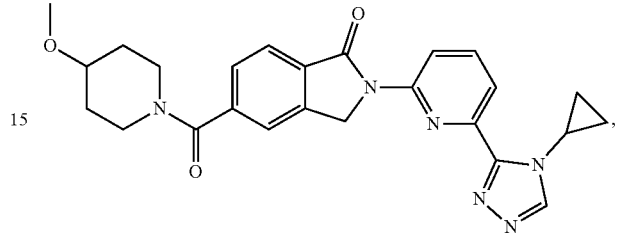
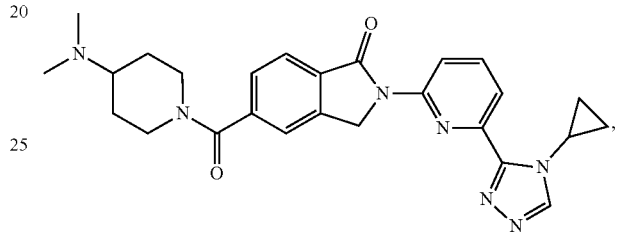
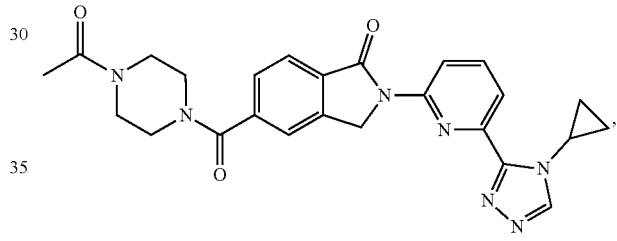
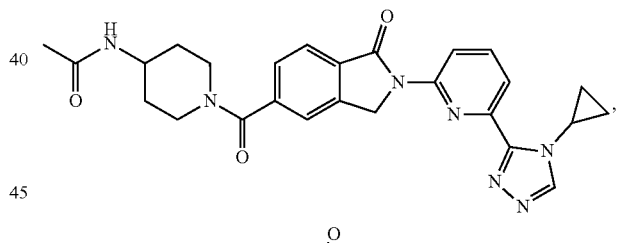
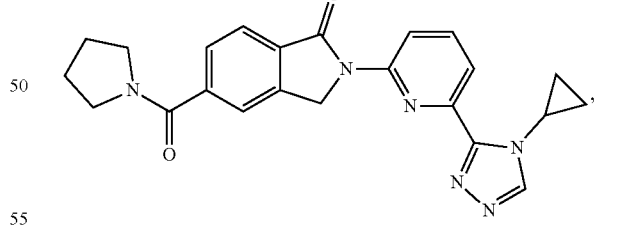

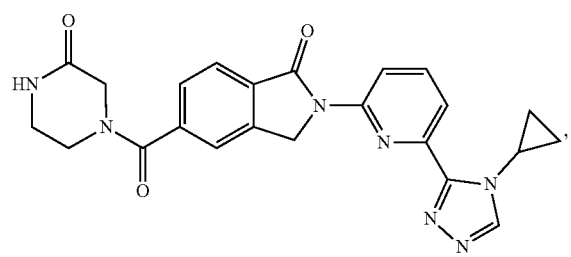
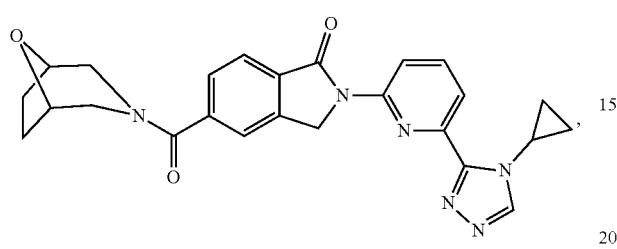
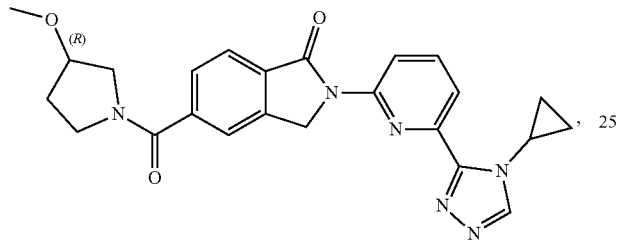
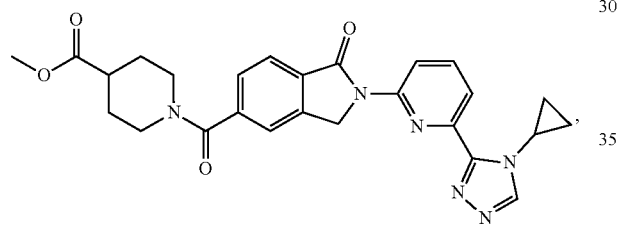
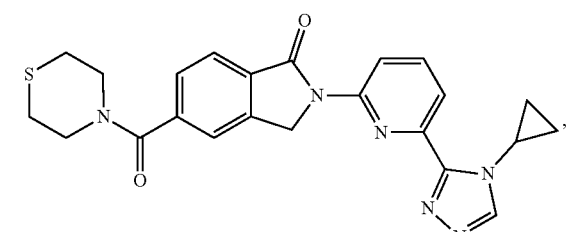
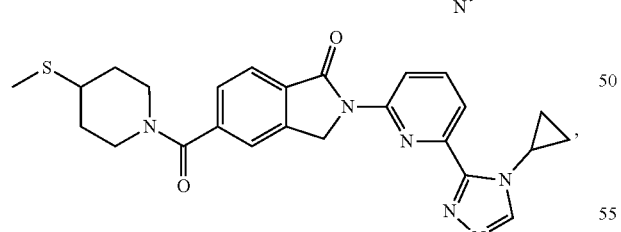
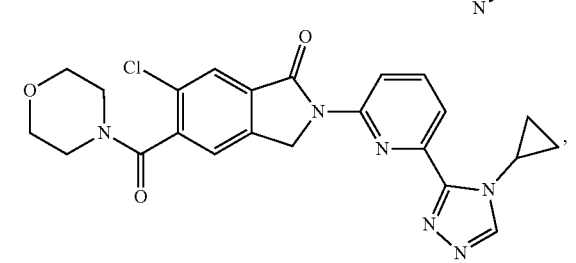
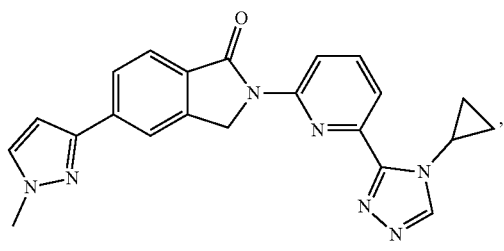
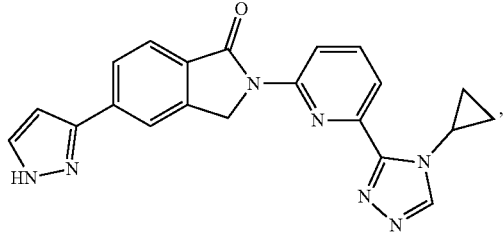
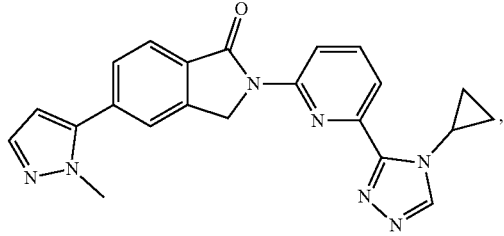
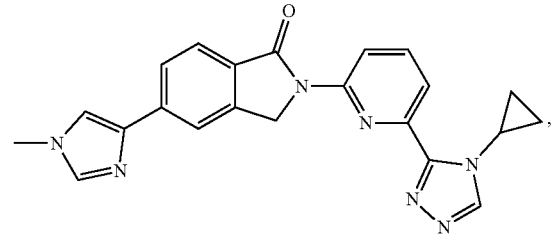
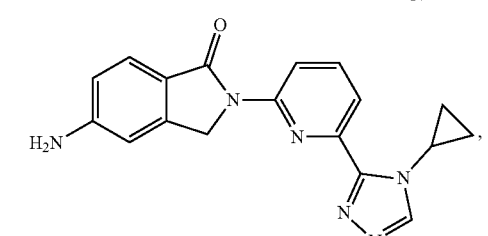
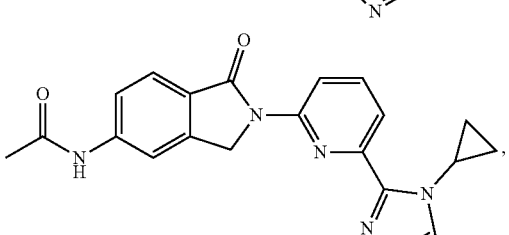
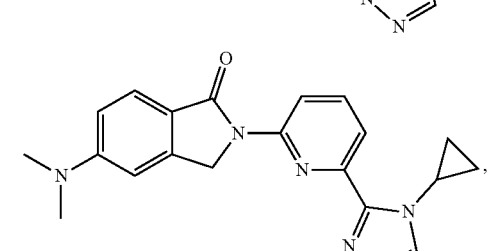

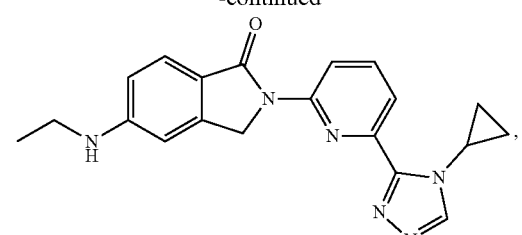,
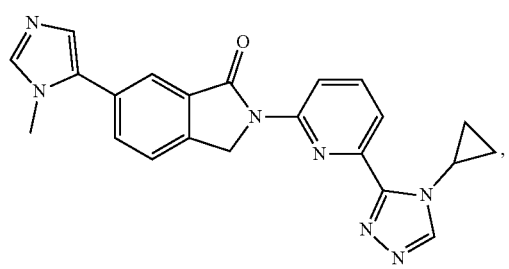,
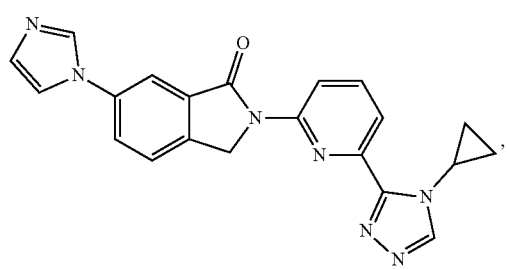,
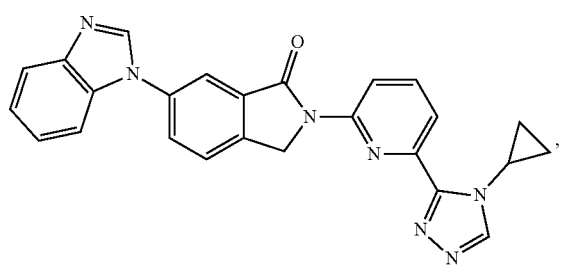,
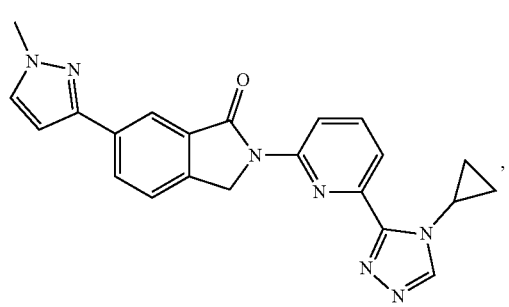,
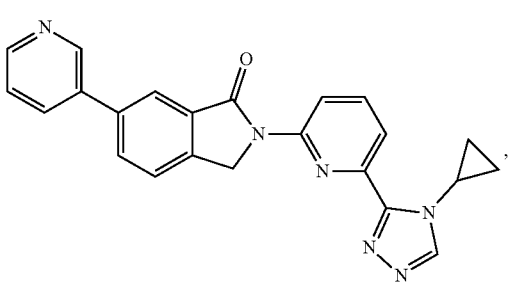,
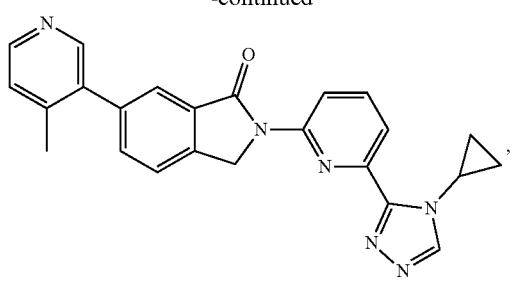,
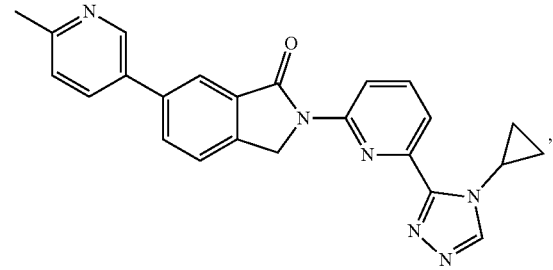,
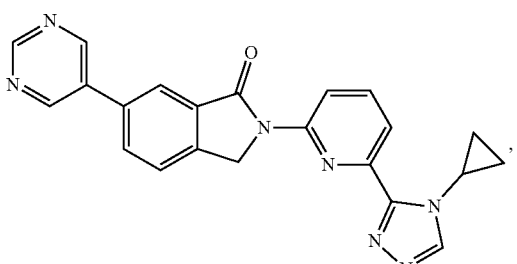,
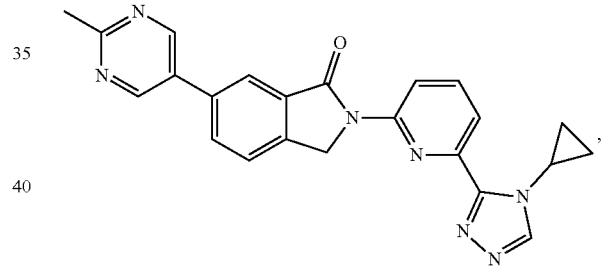,
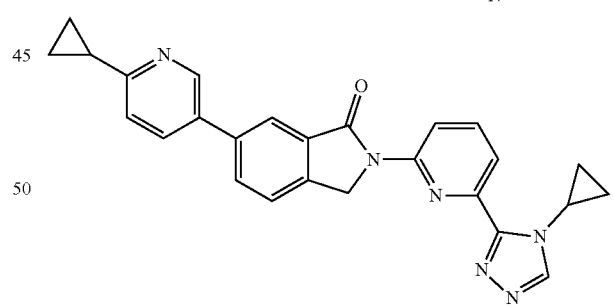,
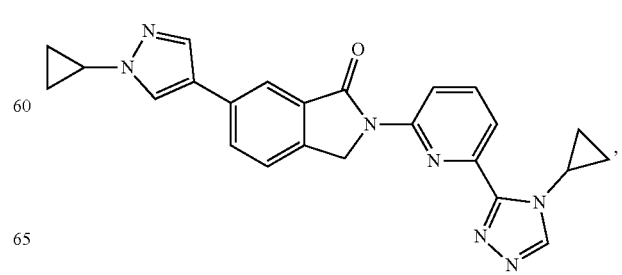, -continued
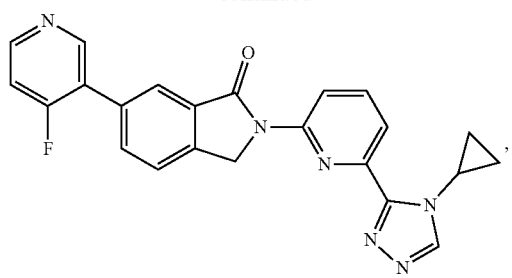
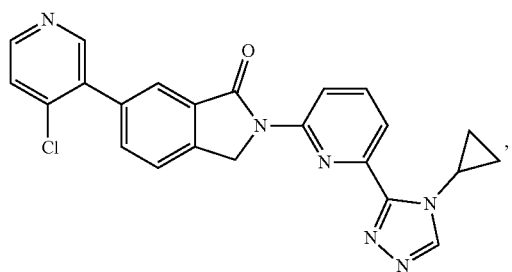
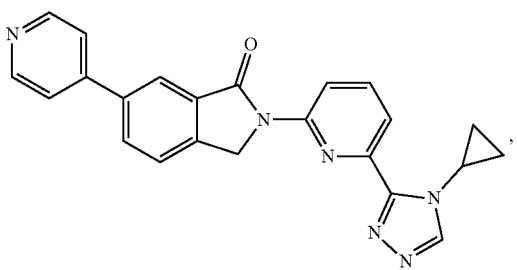
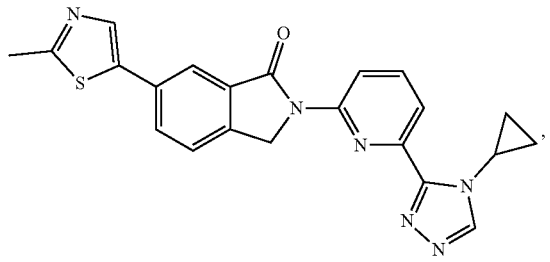
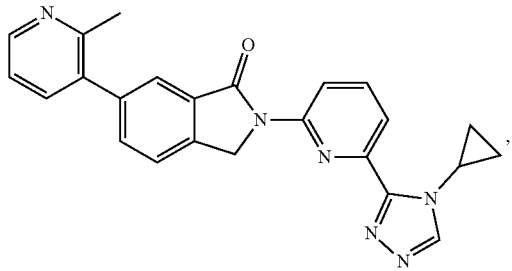
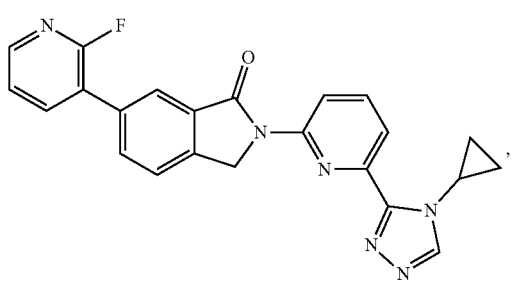
-continued
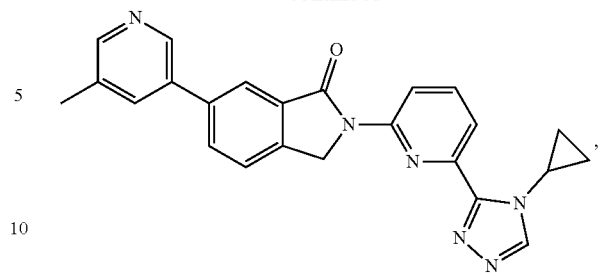
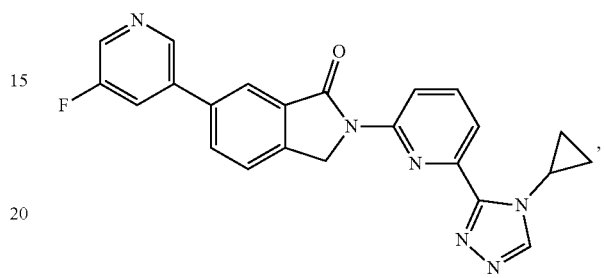
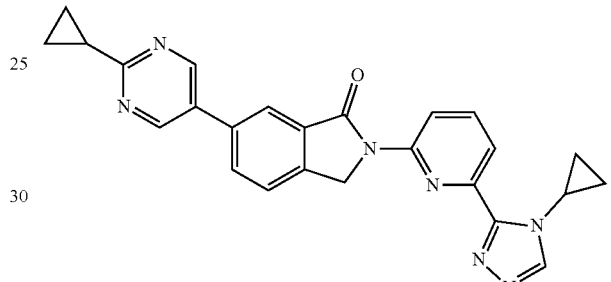
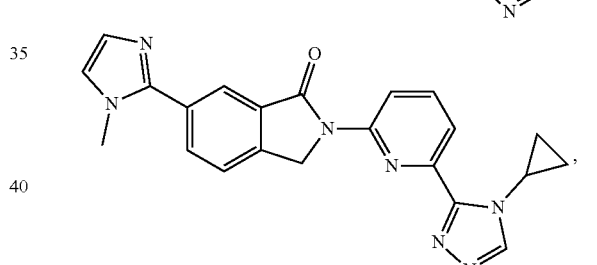
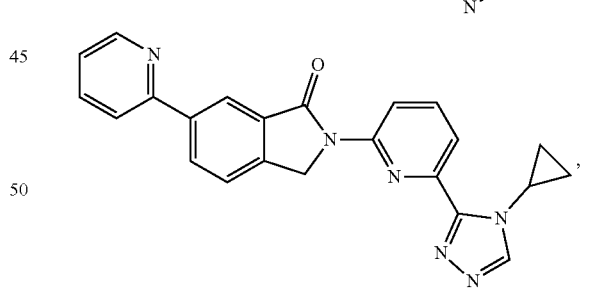
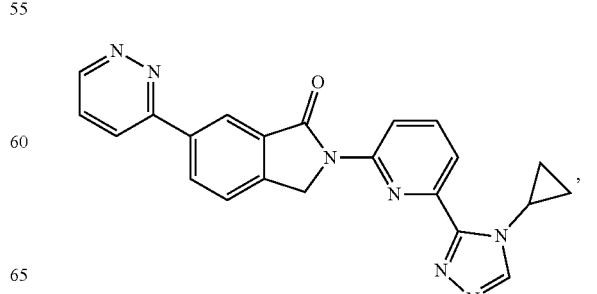

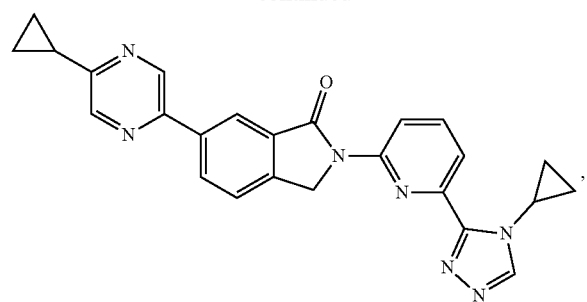
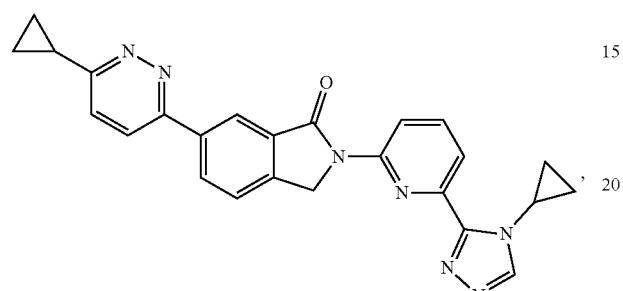
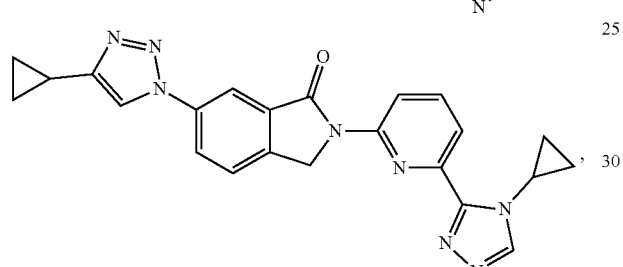
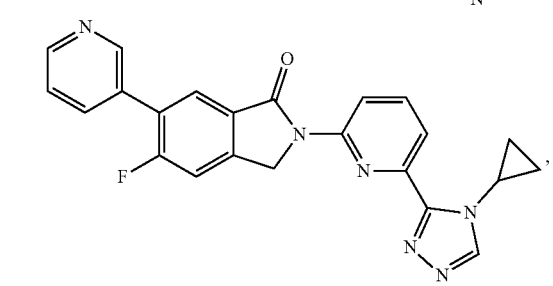
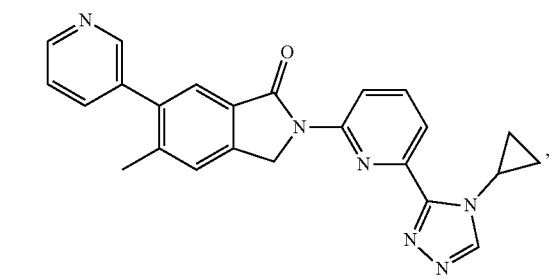
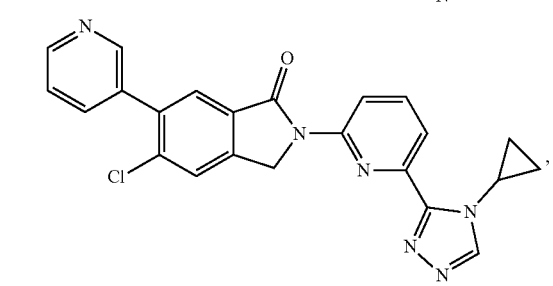
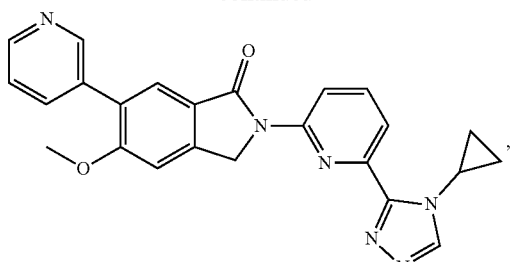
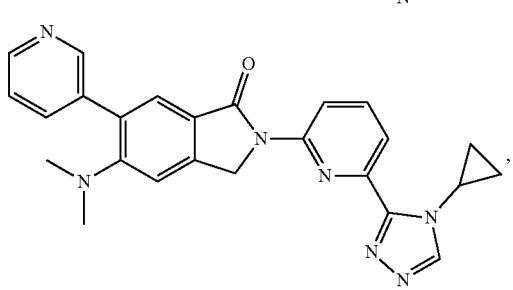
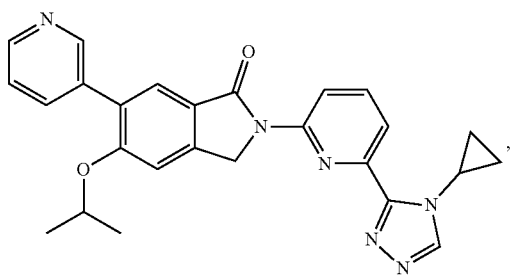
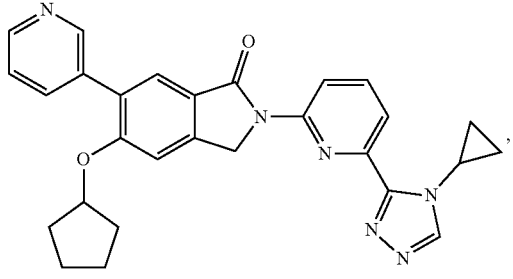
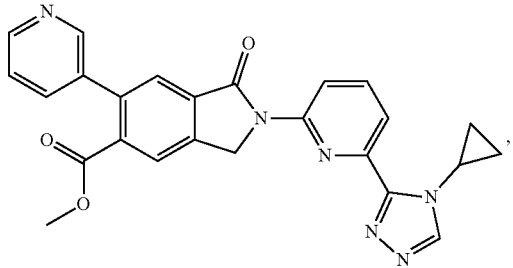
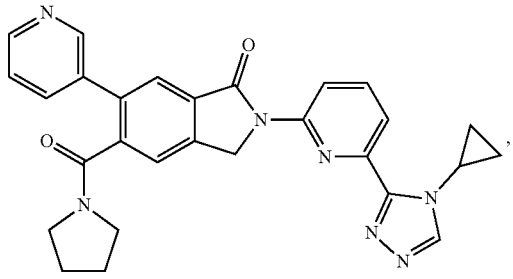

183
-continued
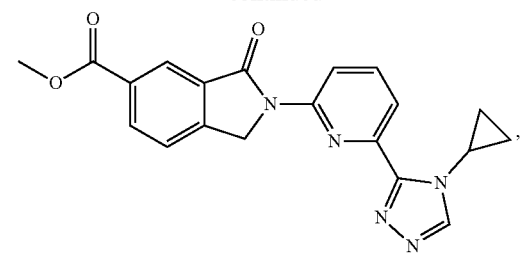
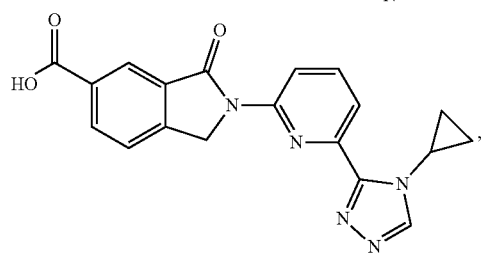
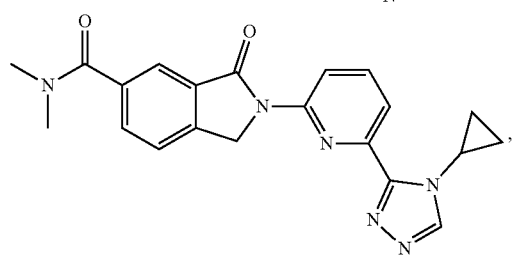
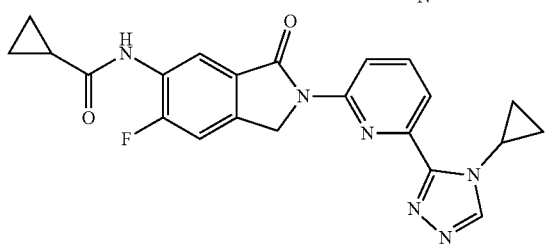
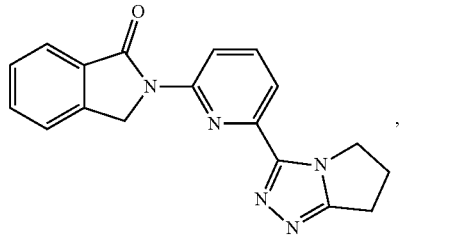
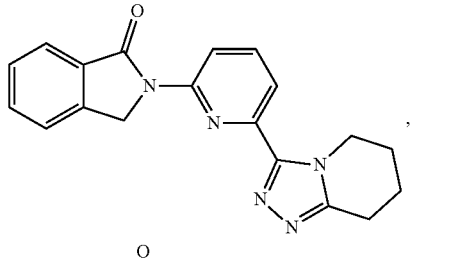
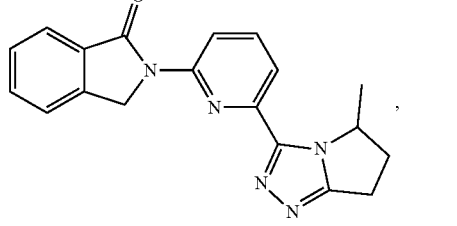
184
-continued
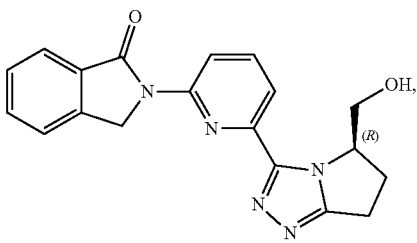
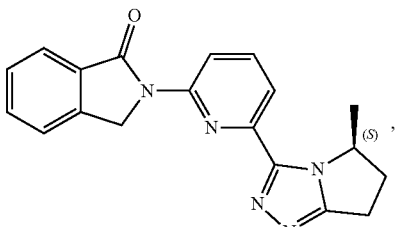
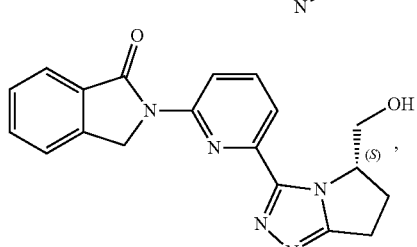
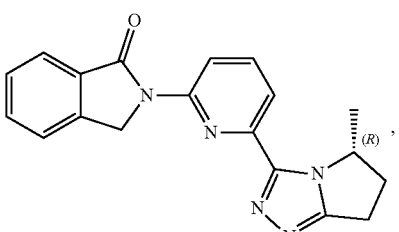
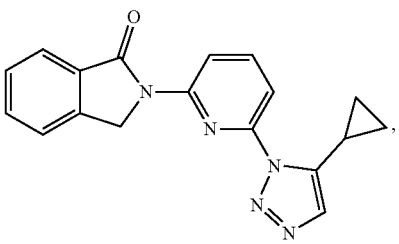
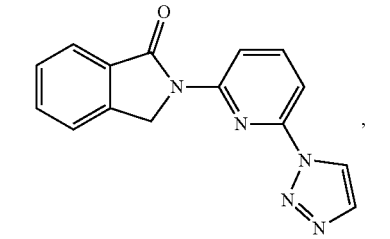
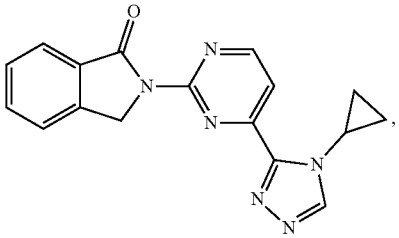

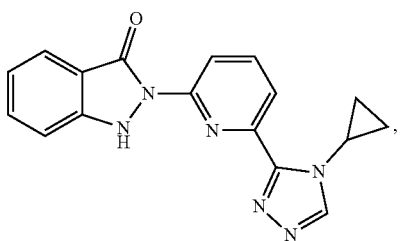

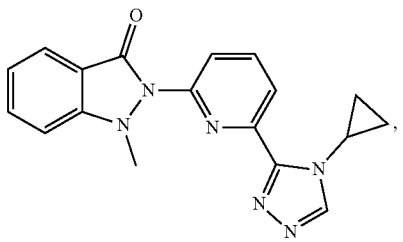

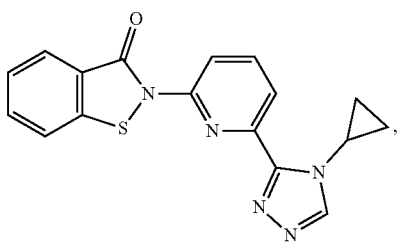

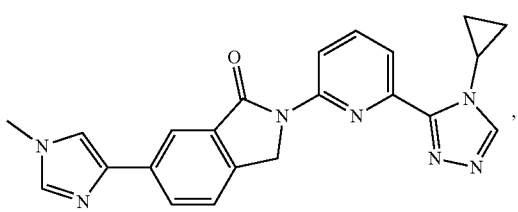

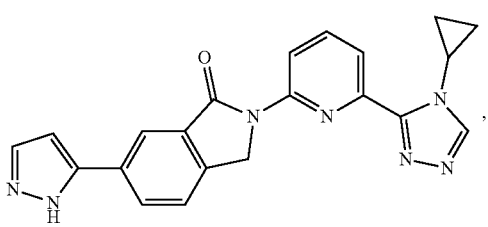

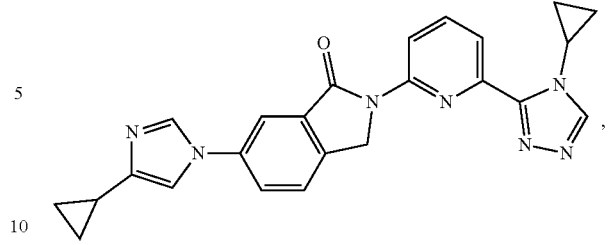

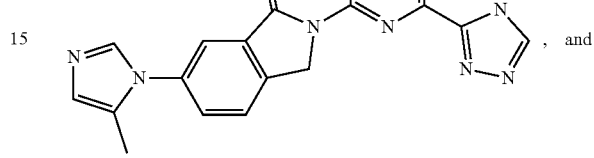, and

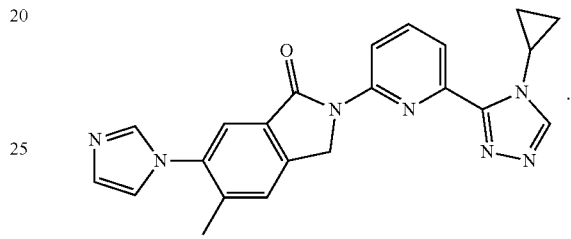.

13. A pharmaceutical composition comprising a compound of claim 1, or a pharmaceutically acceptable salt or solvate thereof, and at least one pharmaceutically acceptable excipient.

14. A method of treating non-alcoholic steatohepatitis in a subject in need thereof, comprising administering to the subject a therapeutically effective amount of a compound of claim 1, or a pharmaceutically acceptable salt or solvate thereof.

15. A pharmaceutical composition comprising a compound of claim 12, or a pharmaceutically acceptable salt or solvate thereof, and at least one pharmaceutically acceptable excipient.

16. A method of treating non-alcoholic steatohepatitis in a subject in need thereof, comprising administering to the subject a therapeutically effective amount of a compound of claim 12, or a pharmaceutically acceptable salt or solvate thereof.

* * * * *

UNITED STATES PATENT AND TRADEMARK OFFICE
CERTIFICATE OF CORRECTION

PATENT NO. : 10,150,755 B2  
APPLICATION NO. : 15/970587  
DATED : December 11, 2018  
INVENTOR(S) : Samuel David Brown Page 1 of 1

It is certified that error appears in the above-identified patent and that said Letters Patent is hereby corrected as shown below:

In the Claims

Column 175, Lines 21-29 In Claim 12, delete:

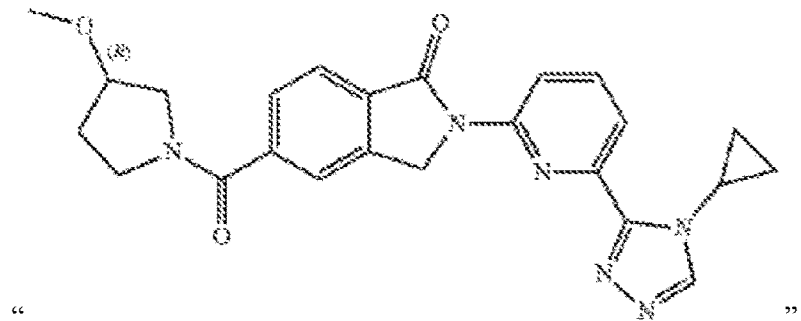

" "

And replace with:

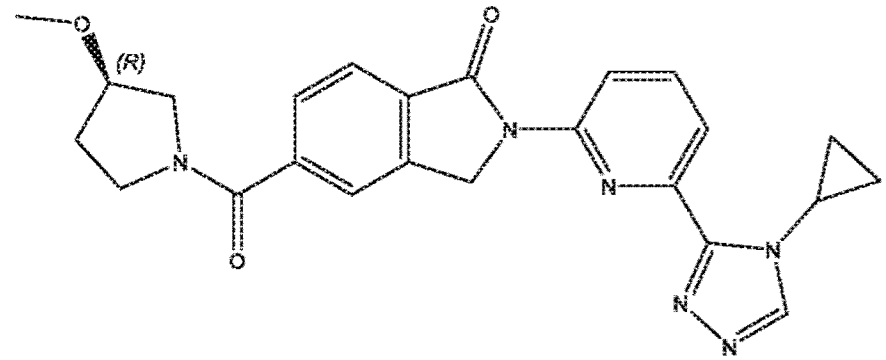

.

Signed and Sealed this  
Eighteenth Day of June, 2019

Andrei Iancu  
*Director of the United States Patent and Trademark Office*